US009000188B2

(12) United States Patent
Honda et al.

(10) Patent No.: US 9,000,188 B2
(45) Date of Patent: *Apr. 7, 2015

(54) MONOCYCLIC CYANOENONES AND METHODS OF USE THEREOF

(71) Applicant: Trustees of Dartmouth College, Hanover, NH (US)

(72) Inventors: Tadashi Honda, Port Jefferson Station, NY (US); Emilie David, Kingston (CA); Dale Mierke, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/645,187

(22) Filed: Oct. 4, 2012

(65) Prior Publication Data

US 2013/0274480 A1    Oct. 17, 2013

Related U.S. Application Data

(63) Continuation of application No. 13/055,418, filed as application No. PCT/US2009/051447 on Jul. 22, 2009, now Pat. No. 8,314,137.

(60) Provisional application No. 61/082,550, filed on Jul. 22, 2008.

(51) Int. Cl.

| C07F 7/10 | (2006.01) |
|---|---|
| C07C 255/46 | (2006.01) |
| C07C 255/47 | (2006.01) |
| C07D 233/64 | (2006.01) |
| C07D 215/48 | (2006.01) |
| C07D 217/02 | (2006.01) |
| C07D 217/24 | (2006.01) |
| C07D 235/12 | (2006.01) |
| C07D 235/14 | (2006.01) |
| C07F 7/08 | (2006.01) |
| C07F 7/18 | (2006.01) |

(52) U.S. Cl.
CPC ................ *C07F 7/10* (2013.01); *C07C 255/46* (2013.01); *C07D 215/48* (2013.01); *C07D 217/02* (2013.01); *C07D 217/24* (2013.01); *C07D 235/12* (2013.01); *C07D 235/14* (2013.01); *C07F 7/0818* (2013.01); *C07F 7/1856* (2013.01); *C07C 255/47* (2013.01); *C07D 233/64* (2013.01); *C07C 2101/16* (2013.01)

(58) Field of Classification Search
USPC ................................................ 558/303–480
See application file for complete search history.

(56) References Cited

U.S. PATENT DOCUMENTS

| 2,875,201 | A | 2/1959 | Johns ........................ 260/239.55 |
|---|---|---|---|
| 4,395,423 | A | 7/1983 | Neumann ...................... 424/304 |
| 4,808,614 | A | 2/1989 | Hertel .............................. 514/45 |
| 4,871,652 | A | 10/1989 | Normandin ................... 430/387 |
| 5,013,649 | A | 5/1991 | Wang et al. .................. 435/69.1 |
| 5,064,823 | A | 11/1991 | Lee et al. ...................... 514/198 |
| 5,401,838 | A | 3/1995 | Chou ............................ 536/281 |
| 5,426,183 | A | 6/1995 | Kjell .......................... 536/285.5 |
| 5,443,826 | A | 8/1995 | Borody ........................ 424/93.3 |
| 5,464,826 | A | 11/1995 | Grindey et al. ................ 514/50 |
| 5,506,361 | A | 4/1996 | Koh et al. ..................... 548/253 |
| 5,521,294 | A | 5/1996 | Wildfeur ...................... 536/187 |
| 5,565,408 | A | 10/1996 | Hagen et al. .................. 504/104 |
| 5,597,124 | A | 1/1997 | Kessel et al. .................... 241/30 |
| 5,599,795 | A | 2/1997 | McCann et al. ............. 424/93.4 |
| 5,603,958 | A | 2/1997 | Morein et al. ................ 424/489 |
| 5,606,048 | A | 2/1997 | Chou et al. .................. 536/271.1 |
| 5,629,295 | A | 5/1997 | Deninno et al. ................ 514/26 |
| 5,849,403 | A | 12/1998 | Aoki et al. .................... 428/220 |
| 5,972,703 | A | 10/1999 | Long et al. .................... 435/372 |
| 6,025,395 | A | 2/2000 | Breitner et al. ............... 514/570 |
| 6,303,569 | B1 | 10/2001 | Greenwald et al. ............... 514/2 |
| 6,326,507 | B1 | 12/2001 | Gribble et al. ................ 558/415 |
| 6,485,756 | B1 | 11/2002 | Aust et al. ..................... 424/725 |
| 6,552,075 | B2 | 4/2003 | Gribble et al. ................ 514/522 |
| 6,649,654 | B1 | 11/2003 | Karin et al. ................... 514/530 |
| 6,727,070 | B2 | 4/2004 | Thomas et al. ................ 435/7.1 |
| 6,974,801 | B2 | 12/2005 | Honda et al. .................... 514/25 |
| 7,053,119 | B2 | 5/2006 | Karin et al. ................... 514/530 |
| 7,176,237 | B2 | 2/2007 | Honda et al. .................. 514/519 |
| 7,202,033 | B2 | 4/2007 | Prescott et al. .................... 435/6 |
| 7,265,096 | B2 | 9/2007 | Gallop et al. ................... 514/49 |
| 7,288,568 | B2 | 10/2007 | Gribble et al. ................ 514/519 |
| 7,399,606 | B2 | 7/2008 | Karin et al. ..................... 435/15 |

(Continued)

FOREIGN PATENT DOCUMENTS

| CN | 102 070 697 A | 5/2011 |
|---|---|---|
| CN | 102 250 189 A | 11/2011 |

(Continued)

OTHER PUBLICATIONS

Schultz et al. "Photochemical and Acid-Catalyzed Dienone-Phenol Rearrangements. The Effect of Substituents on the Regioselectivity of 1,4-Sigmatropic Rearrangements of the Type A Intermediate" J. Org. Chem. 1991, 56(3), 1105-1111.*
Liu et al. "An Efficacious Synthetic Strategy for cis-Clerodane Diterpenoids. Application to the Total Synthesis of 6-beta-Acetoxy-2-oxokolavenool." Synlett 2001, 11, 1805-1807.*
Kung et al. "Palladium(II) acetate mediated oxidative cyclization of w-unsaturated a-cyano ketones. A facile methylenecyclopentane annulation process." Chem. Commun. 2003, 19, 2490-2491.*
Liu et al. "Diels-Alder Reactions of 4,4-Disubstituted 2-Cyano-2,5-cyclohexadienones. A Facile Approach to the Angularly Substituted cis-Decalin System." Synlett 2000, 8, 1119-1122.*

(Continued)

*Primary Examiner* — Joseph Kosack
*Assistant Examiner* — Amanda L Aguirre
(74) *Attorney, Agent, or Firm* — Parker Highlander PLLC

(57) ABSTRACT

The present invention features monocyclic cyanoenone compositions and methods for using the same in the treatment of diseases such as cancer, inflammatory diseases and neurodegenerative diseases.

14 Claims, 15 Drawing Sheets

(56) References Cited

U.S. PATENT DOCUMENTS

| | | |
|---|---|---|
| 7,435,755 B2 | 10/2008 | Konopleva et al. ............ 514/510 |
| 7,455,978 B2 | 11/2008 | Thomas et al. ................ 435/7.1 |
| 7,635,569 B2 | 12/2009 | Thomas et al. ................ 435/7.1 |
| 7,678,830 B2 | 3/2010 | Honda et al. ................... 514/519 |
| 7,714,012 B2 | 5/2010 | Honda et al. ................... 514/396 |
| 7,915,402 B2 | 3/2011 | Anderson et al. ............ 540/519 |
| 7,943,778 B2 | 5/2011 | Jiang et al. .................... 548/247 |
| 8,034,955 B2 | 10/2011 | Gribble et al. ................ 548/241 |
| 8,067,394 B2 | 11/2011 | Honda et al. |
| 8,067,465 B2 | 11/2011 | Honda et al. |
| 8,071,632 B2 | 12/2011 | Jiang et al. |
| 8,088,824 B2 | 1/2012 | Walling et al. |
| 8,124,656 B2 | 2/2012 | Anderson et al. |
| 8,124,799 B2 | 2/2012 | Anderson et al. |
| 8,129,429 B2 | 3/2012 | Sporn et al. |
| 8,258,329 B2 | 9/2012 | Anderson et al. |
| 8,299,046 B2 | 10/2012 | Sporn et al. |
| 2002/0042535 A1 | 4/2002 | Gribble et al. ................ 558/429 |
| 2003/0119732 A1 | 6/2003 | Konopleva et al. |
| 2003/0232786 A1 | 12/2003 | Honda et al. ................... 514/63 |
| 2003/0236303 A1 | 12/2003 | Gribble et al. |
| 2004/0002463 A1 | 1/2004 | Honda et al. ................... 514/25 |
| 2005/0276836 A1 | 12/2005 | Wilson et al. ................. 424/434 |
| 2005/0288363 A1 | 12/2005 | Gribble et al. ................ 558/303 |
| 2006/0258752 A1 | 11/2006 | Vander Jagt et al. ......... 514/475 |
| 2007/0155742 A1 | 7/2007 | Honda et al. .................. 514/519 |
| 2007/0232577 A1 | 10/2007 | Xu et al. |
| 2008/0220057 A1 | 9/2008 | Gribble et al. ................ 514/522 |
| 2008/0233195 A1 | 9/2008 | Sporn et al. .................... 514/63 |
| 2008/0261985 A1 | 10/2008 | Honda et al. ................... 548/400 |
| 2009/0048204 A1 | 2/2009 | Walling et al. |
| 2009/0048205 A1 | 2/2009 | Meyer et al. .................... 514/49 |
| 2009/0060873 A1 | 3/2009 | Sporn et al. ................... 424/85.6 |
| 2009/0093447 A1 | 4/2009 | Konopleva et al. ........... 514/510 |
| 2009/0326063 A1 | 12/2009 | Sporn et al. .................... 514/529 |
| 2010/0048887 A1 | 2/2010 | Anderson et al. ............... 540/8 |
| 2010/0048892 A1 | 2/2010 | Anderson et al. |
| 2010/0048911 A1 | 2/2010 | Jiang et al. |
| 2010/0056777 A1 | 3/2010 | Anderson et al. |
| 2010/0261930 A1 | 10/2010 | Honda et al. .................. 558/429 |
| 2011/0009363 A1 | 1/2011 | Honda et al. ................... 514/63 |
| 2011/0196007 A1 | 8/2011 | Honda et al. |
| 2011/0245206 A1 | 10/2011 | Jiang et al. |
| 2011/0245233 A1 | 10/2011 | Anderson et al. |
| 2011/0281955 A1 | 11/2011 | Meyer et al. |
| 2012/0022156 A1 | 1/2012 | Zhang et al. |
| 2012/0071684 A1 | 3/2012 | Walling et al. |
| 2012/0101149 A1 | 4/2012 | Honda et al. |
| 2012/0214814 A1 | 8/2012 | Anderson et al. |
| 2012/0220652 A1 | 8/2012 | Sporn et al. |
| 2012/0238767 A1 | 9/2012 | Jiang et al. |
| 2012/0245374 A1 | 9/2012 | Anderson et al. |
| 2012/0283450 A1 | 11/2012 | Anderson et al. |

FOREIGN PATENT DOCUMENTS

| | | |
|---|---|---|
| DE | 10 2005 041613 | 3/2007 |
| JP | 55 055153 | 4/1980 |
| JP | 2006 248909 A | 9/2006 |
| JP | 2008 110962 | 5/2008 |
| JP | 2008 247898 | 10/2008 |
| WO | WO 98/32762 | 7/1998 |
| WO | WO 99/65478 | 12/1999 |
| WO | WO 00/73253 | 12/2000 |
| WO | WO 01/01135 | 1/2001 |
| WO | WO 01/82923 | 11/2001 |
| WO | WO 02/03996 | 1/2002 |
| WO | WO 03/015761 | 2/2002 |
| WO | WO 02/32410 | 4/2002 |
| WO | WO 02/47611 | 6/2002 |
| WO | WO 03/059339 | 7/2003 |
| WO | WO 2004/105517 | 12/2004 |
| WO | WO 2005/020932 | 3/2005 |
| WO | WO 2005/042002 | 5/2005 |
| WO | WO 2005/046732 | 5/2005 |
| WO | WO 2004/064723 | 8/2005 |
| WO | WO 2006/089406 | 8/2006 |
| WO | WO 2006/102097 | 9/2006 |
| WO | WO 2007/005879 | 1/2007 |
| WO | WO 2007/112043 | 10/2007 |
| WO | WO 2008/000068 | 1/2008 |
| WO | WO 2008/000070 | 1/2008 |
| WO | WO 2008/016095 | 2/2008 |
| WO | WO 2008/029294 | 3/2008 |
| WO | WO 2008/064132 | 5/2008 |
| WO | WO 2008/064133 | 5/2008 |
| WO | WO 2008/097596 | 8/2008 |
| WO | WO 2008/111497 | 9/2008 |
| WO | WO 2008/136838 | 11/2008 |
| WO | WO 2009/023232 | 2/2009 |
| WO | WO 2009/023845 | 2/2009 |
| WO | WO 2009/058849 | 5/2009 |
| WO | WO 2009/089545 | 7/2009 |
| WO | WO 2009/129545 | 10/2009 |
| WO | WO 2009/129546 | 10/2009 |
| WO | WO 2009/129548 | 10/2009 |
| WO | WO 2009/146216 | 12/2009 |
| WO | WO 2009/146218 | 12/2009 |
| WO | WO 2010/011782 | 1/2010 |
| WO | WO 2010/053817 | 5/2010 |
| WO | WO 2010/093944 | 8/2010 |
| WO | WO 2011/130302 | 10/2011 |
| WO | WO 2011/140078 | 11/2011 |
| WO | WO 2012/125488 | 9/2012 |

OTHER PUBLICATIONS

Liu et al. "A modified Robinson annulation process to alpha,alpha-disubstituted-beta-gamma-unsaturated cyclohexanone system. Application to the total synthesis of nanaimoal." Tetrahedron 2003, 59(8), 1209-1226.*

Andresen and Margaretha, "Preparation of Dialkyl 2-cyanocycloalk-2-en-1-ones," *J. Chem. Research (S)*, 1:332, 1994.

Abad et al., "Diastereoselective synthesis of antiquorin and related polyoxygenated atisene-type diterpenes," *Tetrahedron*, 63 (7): 1664-1679, 2007.

Abraham and Kappas, "Heme oxygenase and the cardiovascular-renal system," *Free Radical Biol. Med.*, 39:1-25, 2005.

Agarwal and Mehta, "Possible involvement of Bcl-2 pathway in resinoid X receptor alpha-induced apoptosis of HL-60 cells," *Biochem Biophys Res Commun.*, 230(2):251-253, 1997.

Ahmad et al., "Triterpenoid CDDO-Me blocks the NF-kappaB pathway by direct inhibition of IKKbeta on Cys-179," *J. Biol. Chem.*, 281:35764-35769, 2006.

Ahmad et al., "Triterpenoid CDDO-methyl ester inhibits the Janus-activated kinase-1 (JAK1)—>signal transducer and activator of transcription-3 (STAT3) pathway by direct inhibition of JAK1 and STAT3," *Cancer Res.*, 68:2920-2926, 2008.

Akisanya et al., "West african timbers. XII. The interrelation of gedunin and khivorin," *J. Chem. Soc. Org.*, 5: 506-509, 1966.

Akiyama et al., "Cell mediators of inflammation in the Alzheimer disease brain," *Alzheimer Dis. Assoc. Disord.*, 14(1): S47-S53, 2000.

Ambs et al., "p53 and vascular endothelial growth factor regulate tumor growth of NOS2-expressing human carcinoma cells," *Nat. Med.*, 4(12):1371-1376, 1998.

Amstutz et al., "Die position 5 im oxotremorin-gerust: eine zentrale stelle fur die steuerung der aktivitat am muscarinischen rezeptor," *Helv. Chim. Acta.*, 70:2232-2244, 1987.

Andreef et al., "PPARgamma nuclear resceptor as a novel molecular target in leukemias," *2002 Keystone Symposia*, Abstract 501:149, 2002.

Andreeff et al., "Expression of bcl-2-related genes in normal and AML progenitors: Changes induced by chemotherapy and cationic acid," *Leukemia*, 13:1881-1892, 1999.

Andreeff, "Acute myeloid leukemia," In: *Cancer Treatment*, Haskell (Ed.), W. B. Saunders, 911-922, 1995.

Anjaneyulu et al., "ent-Kaurane and beyerane diterpenoids from Excoecaria agallocha," *J. of Natural Products*, 65 (3): 382-385, 2002.

(56) References Cited

OTHER PUBLICATIONS

Appendino et al., "Polycyclic diterpenoids from *Euphorbia characias*," *Fitoterapia*, 71 (2): 134-142, 2000.
Araujo et al., "Systemic rather than local heme oxygenase-1 overexpression improves cardiac allograft outcomes in a new transgenic mouse," *J. Immunol.*, 171(3):1572-1580, 2003.
Ardestani et al., "Effects of dexamethasone and betamethasone as COX-2 gene expression inhibitors on rigidity in a rat model of Parkinson's disease," *Indian J. Pharmacol.*, 39:235-9, 2007.
Awale et al., "Inhibition of NO production by highly-oxygenated diterpenes of orthosiphon stamineus and their structure-activity relationship," *Biological and Pharmaceutical Bulletin*, 26 (4): 468-473, 2003.
Awale et al., "Norstaminane- and isopimarane-type diterpenes of *Orthosiphon stamineus* from Okinawa," *Tetrahedron*, 58 (27): 5503-5512, 2002.
Baarschers et al., "The structure of some diterpenes from tambooti wood, *Spirostachys africana sond*," *J. of the Chemical Society*, 4046-4055, 1962.
Baeuerle, "NF-κB: ten years after," *Cell*, 87:13-20, 1996.
Bagasra et al., "Activation of the inducible form of nitric oxide synthase in the brains of patients with multiple sclerosis," *Proc. Natl. Acad. Sci.*, 92(26): 12041-12045, 1995.
Baldwin, Jr., "The NF-κB and IκB proteins: new discoveries and insights," *Annu. Rev. Immunol.*, 14:649-681, 1996.
Balkwill et al., "Smoldering and polarized inflammation in the initiation and promotion of malignant disease," *Cancer Cell*, 7 (3): 211-217, 2005.
Bargou et al., "Constitutive nuclear factor κB-RelA activation is required for proliferation and survival of Hodgkin's disease tumor cells," *J Clin. Invest.*, 100:2961-2969, 1997.
Barkett and Gilmore, "Control of apoptosis by Rel/NF-κB transcription factors," *Oncogene*, 18:6910-6924, 1999.
Barnes and Karin, "Nuclear factor-κB—a pivotal transcription factor in chronic inflammation diseases," *N. Engl. J. Med.*, 336:1066-1071, 1997.
Barrero et al., "Ring A functionalization of terpenoids by the unusual Baeyer-Villiger rearrangement of aliphatic aldehydes," *Synlett*, 6: 713-716, 1999.
Beal, "Mitochondria, free radicals, and neurodegeneration," *Curr. Opin. Neurobiol.*, 6:661-666, 1996.
Berge et al., "Addition of vinylketenes to enamines. A method for the preparation of 6,6-dialkylcyclohexa-2,4-dienones and 4,4-dialkyl-2-vinylcyclobutenones," *Helvetica Chimica Acta*, 65 (7): 2230-2341, 1982.
Bollag and Holdener, "Retinoids in cancer prevention and therapy," *Annals of Oncology*, 3:513-526, 1992.
Boolbol et al., "Cyclooxygenase-2 overexpression and tumor formation are blocked by sulindac in a murine model of familial adenomatous polyposis," *Cancer Res.*, 56(11):2556-2560, 1996.
Bore et al., "The anti-inflammatory triterpenoid methyl 2-cyano-3,12-dioxoolean 1,9(11)-dien-28-oate methanol solvate hydrate," *Acta Crystallorg C.*, 58(Pt 3):o199-o200, 2002.
Bronte et al., "L-arginine metabolism in myeloid cells controls T-lymphocyte functions," *Hum. Immunol.*, 24:302-306, 2003.
Brookes et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore," *Cancer Res.*, 67:1793-1802, 2007.
Brown and DuBois, "Cyclooxygenase as a target in lung cancer," *Clin. Cancer Res.*, 10:4266s-4269s, 2005.
Buzoni-Gatel et al., "Murine ileitis after intracellular parasite infection is controlled by TGF-beta-producing intraepithelial lymphocytes," *Gastroenterolog*, 120:914-924, 2001.
Cai and Vasella, "A new protecting group for alkynes: orthogonally protected dialkynes," *Helv. Chim. Acta.*, 78:732-757, 1995.
Cai et al., "Local and systemic insulin resistance resulting from hepatic activation of IKK-beta and NF-kappaB," *Nat. Med.*, 11(2): 183-190, 2005.

Cambie et al., "Chemistry of the podocarpaceae. LXXVI. 8,13-Epoxy-3-β-hydroxylabd-14-en-2-one and 8,13-Epoxy-2-hydroxylabda-1,14-dien-3-one, new diterpenoids from *Lagarostrobus colensoi*," *Australian Journal of Chemistry*, 43 (4): 791-794, 1990.
Campbell and Cromwell, "Endocyclic α,β-Unsaturated Ketones. VI.1 Ultraviolet and Infrared Absorption Spectra and Resonance Stabilizations," *J. Am. Chem. Soc.*, 79:3456-3463, 1957.
Cassady and Suffness, In *Anticancer Agents Based on Natural Product Models*; Academic Press, NY, 254-269, 1980.
Castaigne et al., "All-trans retinoic acid as a differentiation therapy for acute promyelocytic leukemia," *Blood*, 76(9):1704-1709, 1990.
Chauhan and Chauhan, "Oxidative stress in autism," *Pathophysiology*, 13(3): 171-181, 2006.
Chauhan et al., "The bortezomib/proteasome inhibitor PS-341 and triterpenoid CDDO-Im induce synergistic anti-multiple myeloma (MM) activity and overcome bortezomib resistance," *Blood*, 103:3158-3166, 2004.
Cheng et al., "Differentiation of human bone marrow osteogenic stromal cells in vitro: induction of the osteoblast phenotype by dexamethasone," *Endocrinology*, 134:277-86, 1994.
Chintharlapalli et al., "2-Cyano-3,12-dioxoolean-1,9-dien-28-oic acid and related compounds inhibit growth of colon cancer cells through peroxisome proliferator-activated receptor gamma-dependent and -independent pathways," *Mol. Pharmacol.*, 68:119-128, 2005.
Choi et al., "Nitric oxide synthase variants and disease-free survival among treated and untreated breast cancer patients in a Southwest Oncology Group clinical trial," 15:5258-5266, 2009.
Chou et al., "Sterospecific Synthesis of 2-Deoxy-2,2-difluororibonolactone and its Use in the Preparation of 2'-Deoxy-2', 2'-difluoro-B—D-ribofuranosyl Pyrimidine Nucleosides: The Key Role of Selective Crystallization," *Synthesis*, 565-570, 1992.
Chow and Erdtman, "The chemistry of the natural order cupressales. 43. The structure and configuration of hinokiol and hinokione," *Acta Chemica Scandinavica*, 16: 1296-1300, 1962.
Chung and Wasicak, "Synthesis of chiral ∀-acetylenic cyclic amines from ∀-amino acids: App.s to differentially constrained oxotremorine analogues as muscarinic agents," *Tetrahedron Lett.*, 31:3957-3960, 1990.
Clarke et al., "Full and partial differentiation of tris-1,1,1-(hydroxymethyl)ethane via direct and indirect methodology," *Tetrahedron*, 60:3625-3636, 2004.
Corey et al., "Stereoselective methods for the synthesis of terminal cis and trans enyne units," *Tetrahedron Letters*, 14(17): 1495-1499, 1973.
Cromwell et al., "Endocyclic α,β-unsaturated ketones. V.[1] Synthesis and reaction of 3-bromo-1,1-dimethyl-2-keto-1,2-dihydronaphthalene with morpholine," *J. of Organic Chemistry*, 22: 520-523, 1957.
Crowell et al., "Is inducible nitric oxide synthase a target for chemoprevention," *Mol. Cancer. Thera.*, 2:815-823, 2003.
Cui, "A material science perspective of pharmaceutical solids," *Int. J. Pharmceutics*, 339 (1-2): 3-18, 2007.
Danishefsky et al., "Diels-Alder reactions of trans-l-methoxy-3-trimethylsilyloxy-1,3-butadiene," *J. Am. Chem. Soc.*, 101: 6996-7000, 1979.
De Mico et al., "A Versatile and Highly Selective Hypervalent Iodine (III)/2,2,6,6-Tetramethyl-1-piperidinyloxyl-Mediated Oxidation of Alcohols to Carbonyl Compounds," *J. Org. Chem.*, 62: 6974, 1997.
Deng and Snyder, "Preparation of a 24-Nor-1,4-dien-3-one triterpene derivative from betulin: a new route to 24-nortriterpene analogues," *J. of Organic Chemistry*, 67 (9): 2864-2873, 2002.
Dezube et al., "Interim results of a phase I trial with a novel orally administered synthetic triterpenoid RTA 402 (CDDO-Me) in patients with solid tumors and lymphoid malignancies," *J. Clin. Oncol.*, 2007 ASCO Annual Meeting Proceedings, 25(185):14101, 2007.
Dickereson et al., "Elevated serum levels of C-reactive protein are associated with mania symptoms in outpatients with bipolar disorder," *Prog. Neuropschopharmacol Biol. Psychiatry*, 31(4):952-955, 2007.

(56) References Cited

OTHER PUBLICATIONS

Ding et al., "Macrophage deactivating factor and transforming growth factors-$\beta_1$ $\beta_2$ and $\beta_3$, inhibit induction of macrophage nitrogen oxide synthesis by IFN$\gamma^1$," *J. Immunol.*, 145:940-944, 1990.

Dinkova-Kostova et al., "Direct evidence that sulfhydryl groups of Keap1 are the sensors regulating induction of phase 2 enzymes that protect against carcinogens and oxidants," *Proc. Natl. Acad. Sci.*, 99(18): 11908-11913, 2002.

Dinkova-Kostova et al., "Extremely potent triterpenoid inducers of the phase 2 response: correlations of protection against oxidant and inflammatory stress," *Proc. Natl. Acad. Sci.*, 102(12): 4584-4589, 2005.

Drach et al., "Induction of differentiation in myeloid leukemia cell lines and acute promyelocytic leukemia cells by liposomal all-trans-retinoic acid," *Cancer Research*, 53:2100-2104, 1993.

Dragnev et al., "The retinoids and cancer prevention mechanisms," *The Oncologist*, 5:361-368, 2000.

Duan et al., "Immunosuppressive terpenoids from extracts of *Tripterygium wilfordii*," *Tetrahedron*, 57 (40): 8413-8424, 2001.

DuBois et al., "$G_1$ delay in cells overexpressing prostaglandin endoperoxide synthase-$2^1$," *Cancer Res.*, 56(4):733-737, 1996.

Dutcher et al., "Pentacyclic triterpene synthesis. 5. Synthesis of optically pure ring AB precursors," *J. Org. Chem.*, 41:2663-2669, 1976.

Eikelenboom et al., "Neuroinflammation in Alzheimer's disease and prion disease," *Glia*, 40(2): 232-239, 2002.

Eistert et al., "Reaktionen von diazoalkanen mit $\alpha$a-diketonen and chinonen, XII. ringerweiterung von 1.1-dimethyl-indandion-(2.3)," *Chemische Berichte*, 102 (7): 2429-2439, 1969.

Ekmekcioglu et al., "Tumor iNOS predicts poor survival for stage III melanoma patients," *Int. J. Cancer*, 119:861-866, 2006.

Ekong and Olagbemi, "West african timbers. Part XVII. Correlation of gedunin, methyl angolensate, and andirobin," *J. of the Chemical Society*, [Section] C: Organic, 10: 944-966, 1966.

Ellies et al., "Mammary tumor latency is increased in mice lacking the inducible nitric oxide synthase," *Int. J. Cancer*, 106:1-7, 2003.

Elliot et al., "The triterpenoid CDDO inhibits expression of matrix metalloproteinase-1, matrix metalloproteinase-13 and Bcl-3 in primary human chondrocytes," *Arthritis Res. Ther.*, 5:R285-R291, 2003.

Elsawa et al., "Preferential Inhibition of Malignant Cell Growth by CDDO in Waldenstrom Macroglobulinemia," *Blood*, 108(11):2528, 2006.

Elstner et al., "Ligands for peroxisome proliferator-activated receptorgamma and retinoic acid receptor inhibit growth and induce apoptosis of human breast cancer cells in vitro and in BNX mice," *Proc. Natl. Acad. Sci. USA*, 95:8806-8811, 1998.

Estey et al., "Molecular remissions induced by liposomal-encapsulated all-trans retinoic acid in newly diagnosed acute promyelocytic leukemia," *Blood*, 94:2230-2235, 1999.

Estey et al., "Randomized phase II study of fludarabine + cytosine arabinoside + idarubicin + all-trans retinoic acid + granulocyte-colony stimulating factor in poor prognosis newly diagnosed acute myeloid leukemia and myelodysplastic syndrom," *Blood*, 93(8):2478-2484, 1999.

Ettehadi et al., "Elevated tumour necrosis factor-alpha (TNF-alpha) biological activity in psoriatic skin lesions," *Clin. Exp. Immunol.*, 96(1): 146-151, 1994.

Favaloro et al., "Design and synthesis of tricyclic compounds with enone functionalities in rings A and C: a novel class of highly active inhibitors of nitric oxide production in mouse macrophages," *J. Med. Chem.*, 45:4801-4805, 2002.

Finlay et al., "Novel A-ring cleaved analogs of oleanolic and ursolic acids which affect growth regulation in NRP.152 prostate cells," *Biorg. Med. Chem. Lett.*, 7(13): 1769-1772, 1997.

Forstermann, "Janus-faced role of endothelial NO synthase in vascular disease: uncoupling of oxygen reduction from NO synthesis and its pharmacological reversal," *Biol. Chem.*, 387:1521-1533, 2006.

Fraga et al., "Partial synthesis of a colensenone isomer," *Anales de Quimica*, 90 (7-8): 513-516, 1994.

Gehrmann et al., "Amyloid precursor protein (APP) expression in multiple sclerosis lesions," *Glia*, 15(2): 141-151, 1995.

Genain and Nauser, "Creation of a model for multiple sclerosis in *Callithrix jacchus* marmosets," *J. Mol. Med. (Berl)*, 75:187-197, 1997.

Graeber et al., "Microglia in brain tumors," *Glia*, 40(2): 252-259, 2002.

Granger et al. "Stereospecificity in 2,3-diethylindanone syntheses. II. Synthesis 2-ethyl -5-hydroxy (or 5-methoxy) -3-methylindanones," *Bulletin de la Societe Chimique de France*, 815-819, 1957.

Grant and Carman, "Colensenone," *J. of the Chemical Society*, 3740-3746, 1962.

Grant et al., "Boron trifluoride catalyzed rearrangements of novel expoxide derivatives of manool and manoyl oxide," *Australian Journal of Chemistry*, 46 (8): 1125-1145, 1993.

Greten et al., "IKKbeta links inflammation and tumorigenesis in a mouse model of colitis-associated cancer," *Cell*, 118:285-296, 2004.

Griffin et al., "Brain interleukin 1 and S-100 immunoreactivity are elevated in Down syndrome and Alzheimer disease," *Proc. Natl. Acad. Sci, USA*, 86(19): 7611-7615, 1989.

Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 279:11179-11187, 2004.

Hanson et al., "Theories of schizophrenia: a genetic-inflammatory-vascular synthesis," *BMC Medical Genetics*, 6:7, 2005.

Hansson and Anton, "Function and morphology of the antennal lobe: new developments," *Annu. Rev. Entomol.*, 45:203-231, 2006.

Hemmert et al., "Nuclear magnetic response. II. Methyl groups of lanostane," *Bulletin de la Societe Chimique de France*, 3: 976-982, 1966.

Hemmert et al., "Nuclear magnetic response. III. Methyl groups of 4,4-dimethylcholestane," *Bulletin de la Societe Chimique de France*, 3: 982-987, 1966.

Herzon and Meyers, "Enantioselective Synthesis of Stephacidin B," *J. of the American Chemical Society*, 127 (15): 5342-5344, 2005.

Hirota et al., "Stereoselective total synthesis of ($\pm$)-epemane-8$\beta$,15-diol$^1$," *Bull. Chem. Soc. Jpn.*, 61:4023-4028, 1988.

Honda et al., "A novel dicyanotriterpenoid, 2-cyano-3,12-dioxooleana-1,9(11)-dien-28-onitrile, active at picomolar concentrations for inhibition of nitric oxide production," *Bioorg. Med. Chem. Lett.*, 12:1027-1030, 2002.

Honda et al., "An efficient synthesis of tricyclic compounds ($\pm$)—(4a$\beta$, 8a$\beta$, 10a$\alpha$)—1,2,3,4,4a,6,7,8,8a,9,1-,10a-Dodecahydro-1,1,4a-Trimethyl-2-Oxophenanthrene-8a-Carboxolic acid, its methyl ester, and ($\pm$)-(4a$\beta$,8a$\beta$,10a$\alpha$)-3,4,4a,6,7,8,8a,9,10,10a-Decahydro-8a-Hydroxymethyl-1,1,4a-Trimethylphenanthren-2(1H)-one," *Org. Prep. Proced. Int.*, 37 (6):546-550, 2005.

Honda et al., "Design and synthesis of 23,24-dinoroleanolic acid derivatives, novel triterpenoid—steroid hybrid molecules," *J. Org. Chem.*, 63:4846-4849, 1998.

Honda et al., "Design and synthesis of 2-cyano-3,12-dioxoolean-1,9-dien-28-oic acid, a novel and highly active inhibitor of nitric oxide production in mouse macrophages," *Bioorg. Med. Chem. Lett.*, 8(19):2711-2714, 1998.

Honda et al., "Design, synthesis, and biological evaluation of biotin conjugates of 2-cyano-3,12-dioxooleana-1,9(11)-dien-28-oic acid for the isolation of the protein targets," *J. Med. Chem.*, 47 (20): 4923-4932, 2004.

Honda et al., "Efficient synthesis of (−)- and (+)-tricyclic compounds with enome functionalities in rings A and C. A novel class of orally active anti-inflammatory and cancer chemopreventive agents," *Org Biomol Chem.*, 1:4384-4391, 2003.

Honda et al., "New enone derivatives of oleanolic acid and ursolic acid as inhibitors of nitric oxide production in mouse macrophages," *Bioorg. Med. Chem. Lett.*, 7:1623-1628, 1997.

Honda et al., "Novel synthetic oleanane and ursane triterpenoids with various enone functionalities in ring A as inhibitors of nitric oxide production in mouse macrophages," *J. Med. Chem.*, 43:1866-1877, 2000.

Honda et al., "Novel synthetic oleanane triterpenoids: A series of highly active inhibitors of nitric oxide production in mouse macrophages," *Bioorg. Med. Chem. Lett.*, 9(24): 3429-3434, 1999.

(56) References Cited

OTHER PUBLICATIONS

Honda et al., "Novel tricyclic compounds having acetylene groups at C-8a and cyano enones in rings A and C: highly potent anti-inflammatory and cytoprotective agents," *J. Med. Chem.*, 50:1731-1734, 2007.
Honda et al., "Synthesis of (±)-3,3-ethylenedioxy-14α-hydroxy-5-picrasene-11,16-dione, a 14αH-picrasane derivative," *Chem. Lett.*, 299-302, 1981.
Honda et al., "Synthesis of a novel dicyano abietane analogue: a potential antiinflammatory agent," *J. Org. Chem.*, 71:3314-3316, 2006.
Honda et al., "Synthetic oleanane and ursane triterpenoids with modified rings A and C: A series of highly active inhibitors of nitric oxide production in mouse macrophages," *J. Med. Chem.*, 43:4233-4246, 2000.
Hong et al., "Phase I trial of a novel oral NF-κB/pSTAT3 inhibitor Rta-402 in patients with solid tumors and lymphoid malignancies," 44$^{th}$ Annual Meeting of the American Society of Clinical Oncology, 2008.
Hotamisligil, "Inflammation and metabolic disorders," *Nature*, 444(7121): 860-867, 2006.
Hyer et al., "Synthetic triterpenoids cooperate with tumor necrosis factor-related apoptosis-inducing ligand to induce apoptosis of breast cancer cells," *Cancer Res.*, 65:4799-4808, 2005.
Iddon et al., "Synthesis and reactions of 1,2,3,4,5,6-hexahydro-3,6-dimethyl-2,6-methano-3-benzazocin-11-one (2,5-dimethyl-9-oxo-6,7-benzomorphan); a new route to 3-benzazocines," *J. of the Chemical Society, Perkin Transactions 1: Organic and bio-Organic Chemistry*, 10: 2583-2593, 1983.
Ikeda et al., "Induction of redox imbalance and apoptosis in multiple myeloma cells by the novel triterpenoid 2-cyano-3,12-dioxoolean-1,9-dien-28-oic acid," *Mol. Cancer Ther.*, 3:39-45, 2004.
Ikeda et al., "The novel triterpenoid CDDO and its derivatives induce apoptosis by disruption of intracellular redox balance," *Cancer Res.*, 63:5551-5558, 2003.
International Preliminary Report on Patentability issued in PCT/US2009/051447 dated Jan. 25, 2011.
International Search Report issued in PCT/US2009/051447 dated Sep. 8, 2009.
International Search Report issued in PCT/US2009/041177 dated Jan. 21, 2010.
Ishizawa and Dickson, "Microglial activation parallels system degeneration in progressive supranuclear palsy and corticobasal degeneration," *J. Neuropathol. Exp. Neuro.*, 60(6): 647-657, 2001.
Ito et al., "Involvement of caspase-8 in the induction of osteosarcoma cell apoptosis by the novel triterpenoid CDDO," 47$^{th}$ Annual Meeting, Orthopaedic Research Society, Feb. 25-28, 2001, San Francisco, California, p. 0863, Poster Session, 2001.
Ito et al., "The novel triterpenoid 2-cyano-3, 12-dioxoolean-1,9-dien-28-oic acid induces apoptosis of human myeloid leukemia cells by a caspase-8-dependent mechanism," *Cell Growth & Differentiation*, 11(5):261-267, 2000.
Ito et al., "The novel triterpenoid CDDO induces apoptosis and differentiation of human osteosarcoma cells by a caspase-8 dependent mechanism," *Mol. Pharmacol.*, 59:1094-1099, 2001.
Johansen et al., "Pharmacology and preclinical pharmacokinetics of the triterpenoid CDDO methyl ester," *Proc. Amer. Assoc. Cancer Res.*, 44:1728, 2003.
Johnson et al., "A plan for distinguishing between some five- and six-membered ring ketones," *J. Am Chem. Soc.*, 67:1745-1754, 1945.
Kahne and Collum, "Kinetic cyanations of ketone enolates," *Tetrahedron Lett.*, 22:5011-5014, 1981.
Karin et al, "NF-κB in cancer: From innocent bystander to major culprit," *Nat. Rev.*, 2:301-303, 2002.
Karin et al., "Nuclear factor-κB in cancer development and progression," *Nature*, 441(7092):431-436, 2006.
Kasinski et al., "Inhibition of IkappaB kinase-nuclear factor-kappaB signaling pathway by 3,5-bis(2-flurobenzylidene)piperidin-4-one (EF24), a novel monoketone analog of curcumin," *Mol. Pharmacology*, 74 (3): 654-661, 2008.

Kawakami et al., "A comparative study of nitric oxide, glutathione, and glutathione peroxidase activities in cerebrospinal fluid from children with convulsive diseases/children with aseptic meningitis," *Brain Dev.*, 28(4): 243-246, 2006.
Kendall-Tackett, "Inflammation, cardiovascular disease, and metabolic syndrome as sequelae of violence against women: the role of depression, hostility, and sleep disturbance," *Trauma, Violence Abuse*, 8(2): 117-126, 2007.
Kim et al., "Capasase-3 activation is involved in apoptosis induced by a synthetic triterpenoid in Non-small cell lung cancer (NSCLC) cells," *Proc. Amer. Assoc. Cancer Res.*, 41:770, Abstract #4894, 2000.
Kim et al., "Identification of a novel synthetic triterpenoid, methyl-2-cyano-3,12-dioxooleana-1,9-dien-28-oate, that potently induces caspace-mediated apoptosis in human lung cancer cells," Molecular Cancer Therapeutics, 1:177-184, 2002.
Kokpol et al., "Structure of trigonostemone, a new phenanthrenone from the thai plant *Trigonostemon reidioide*," *Journal of Natural Products*, 53 (5): 1148-1151, 1990.
Konishi et al., "Anti-tumor-promoting activity of diterpenes from *Excoecaria agallocha*," *Biological and Pharmaceutical Bulletin*, 21 (9): 993-996, 1998.
Konishi et al., "Five new labdane-type diterpenes from *Excoecaria agallocha* IV," *Chemical and Pharmaceutical Bulletin*, 46 (9): 1393-1398, 1998.
Konopleva et al., "Activation of nuclear transcription factor PPARgamma by the novel triterpenoid CDDO as targeted therapy in breast cancer," 2002 Keystone Symposium, Abstract No. 539, 2002.
Konopleva et al., "Mechanisms and Activity of PPARgamma-Active Triterpenoids CDDO and CDDO-Me in Leukemias," *Blood*, 106:2460, 2005.
Konopleva et al., "Novel synthetic triterpenoid CDDO-Me: potent antiproliferative, proapoptotic and differentiating agent in AML," *Blood*, 96(11), Part 1: 121A, abstract # 522, 2000.
Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.
Konopleva et al., "Novel triterpenoid CDDO-Me is a potent inducer of apoptosis and differentiation in acute myelogenous leukemia," *Blood*, 99(1):326-335, 2002.
Konopleva et al., "Peroxisome proliferator-activated receptor gamma and retinoid X receptor ligands are potent inducers of differentiation and apoptosis in leukemias," *Mol. Cancer Ther.*, 3:1249-1262, 2004.
Konopleva et al., "PPARγ nuclear receptor as a novel therapeutic target in AML," Blood, 96(11):460a, Abstract #1982, 2000.
Konopleva et al., "PPARgamma Ligand CDDO Induces Apoptosis in Leukemias via Multiple Apoptosis Pathways," *Abstracts of the 44$^{th}$ Annual Meeting of the American Society of Hematology*, Abstract No. 2209, 2002.
Konopleva et al., "PPARgamma Ligands Are Potent Inducers of Apoptosis in Leukemias and Lymphomas," *American Society of Hematology 43$^{rd}$ Annual Meeting and Exposition*, Abstract No. 501, 2001.
Konopleva et al., "PPARgamma Nuclear Receptor as a Novel Molecular Target in Leukemia Therapy," *Proc. Amer. Assoc. Cancer Res.*, 43:4730, 2002.
Konopleva et al., "Suppression of ERK Activation is Required for Triterpenoid Methyl-CDDO-Induced Apoptosis in AML," *Blood*, 102(11):1404, 2003.
Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.
Konopleva et al., "Synthetic triterpenoid CDDO as a novel therapy for resistant breast cancer," *Proc. Amer. Assoc. Cancer Res.*, 44:2726, 2003.
Konopleva et al., "The novel triterpenoid CDDO-Me suppresses MAPK pathways and promotes p38 activation in acute myeloid leukemia cells," *Leukemia*, 19:1350-1354, 2005.
Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.

(56) References Cited

OTHER PUBLICATIONS

Konopleva et al., "Triterpenoid methyl-CDDO s a potent inducer of apoptosis in CD34+ AML progenitor cells via activation of SAPK pathways and inhibition of MAPK cascades," *Blood*, 104:2533, 2004.
Kortylewski et al., "Inhibiting Stat3 signaling in the hematopoietic system elicits multi-component antitumor immunity," *Nature Med.*, 11:1314-1321, 2005.
Kress et al., "Triterpenoids display single agent activity in a mouse model of CLL/SBL," *Blood*, 108(11):2530, 2006.
Kress et al., "Triterpenoids display single agent anti-tumor activity in a transgenic mouse model of chronic lymphocytic leukemia and small B cell lymphoma," *PLOS One*, 6(e559):1-11, 2007.
Kurinna et al., "The novel triterpenoid CDDO-Me promotes apoptosis in Gleevec-resistant chronic myeloid leukemia cells by caspase-independent mechanisms," *Proc. Amer. Assoc. Cancer Res.*, 46:2240, 2005.
Laing et al., "The x-ray crystal and molecular structure of a tetracyclic diterpenoid-benzaldehyde reaction product and the long range protective influence of its benzene ring," *Tetrahedron Letters*, 32: 3043-3046, 1973.
Langille et al., "Differential effects of physiological concentrations of retinoic acid in vitro on chondrogenesis and myogenesis in chick craniofacial mesenchyme," *Differentiation*, 40:84, 1989.
Lapillonne et al., "Activation of peroxisome proliferator-activated receptor gamma by a novel synthetic triterpenoid 2-cyano-3,12-dioxooleana-1,9-dien-28-oic acid induces growth arrest and apoptosis in breast cancer cells," *Cancer Res.*, 63:5926-5939, 2003.
Larock et al., "Carbocycle synthesis via carbopalladation of nitriles," *J. of the American Chemical Society*, 121 (13): 3238-3239, 1999.
Lee et al., "Double-stranded RNA induces iNOS gene expression in Schwann cells, sensory neuronal death, and peripheral nerve demyelination," *Glia*, 55(7): 712-722, 2007.
Lemieux, "Acylglycosyl Halides. [55] tetra-O-acetyl-α-D-glucopyranosyl bromide," *Methods Carbohydr. Chem.*, 2:221-222, 1963.
Lencz et al., "Converging evidence for a pseudoautosomal cytokine receptor gene locus in schizophrenia," *Mol. Psychiatry*, 12(6): 572-580, 2007.
Levy and Lavie, "Attempted skeletal rearrangements in the lanostane series," *Israel J. of Chemistry*, 8 (4): 677-684, 1970.
Li and Nel, "Role of the Nrf2-mediated signaling pathway as a negative regulator of inflammation: implications for the impact of particulate pollutants on asthma," *Antioxidants & Redox Signaling*, 8:88-98, 2006.
Liby et al., "A novel acetylenic tricyclic bis-(cyano enone) potently induces phase 2 cytoprotective pathways and blocks liver carcinogenesis induced by aflatoxin," *Cancer Res.*, 68:6727-6733, 2008.
Liby et al., "Novel semisynthetic analogues of betulinic acid with diverse cytoprotective, antiproliferative, and proapoptotic activities," *Mol. Cancer. Ther.*, 6(7): 2113-2119, 2007.
Liby et al., "The rexinoid LG100268 and the synthetic triterpenoid CDDO-methyl amide are more potent than erlotinib for prevention of mouse lung carcinogenesis," *Mol. Cancer Ther.*, 7:1251-1257, 2008.
Liby et al., "The synthetic triterpenoids, CDDO and CDDO-imidazolide, are potent inducers of heme oxygenase-1 and Nrf2/ARE signaling," *Cancer Res.*, 65:4789-4798, 2005.
Ling et al., "The novel triterpenoid C-28 methyl ester of 2-cyano-3, 12-dioxoolen-1, 9-dien-28-oic acid inhibits metastatic murine breast tumor growth through inactivation of STAT3 signaling," *Cancer Res.*, 67:4210-4218, 2007.
Ling et al., "The novel triterpenoid CDDO-Me inhibits metastatic murine breast tumor through inhibition of Stat3 signaling," 2007 AACR Annual Meeting, Abstract No. 301, 2007.
Liotta et al., "A simple method for the efficient sysnthesis of unsaturated ∃-dicarbonyl compunds," *J. Org. Chem.*, 46:2920-2923, 1981.
Liu et al., "An efficacious synthetic strategy for cis-clerodane diterpenoids. Application to the total synthetis of (+x)-6beta-acetoxy-2-oxokolavenool," *Synlett*, 11:1805-1807, 2001.

Liu et al., "Diels-Alder reactions of 4,4-disubstituted 2-cyano-2,5-cyclohexadienones. A facile approach to the angularly substituted cis-decalin system," *Synlett*, 8:1119-1122, 2000.
Luo et al., "IKK/NF-kappaB signaling: balancing life and death—a new approach to cancer therapy," *J. Clin. Invest.*, 115 (10): 2625-2631, 2005.
Ma et al., "Two pimarane diterpenoids from *Ephemerantha lonchophylla* and their evaluation as modulators of the multidrug resistance phenotype," *J. of Natural Products*, 61 (1): 112-115, 1998.
Mai et al., "Epigenetic multiple ligands: mixed histone/protein mathyltransferase, acetyltransferase, and class III deacetylase (sirtuin) inhibitors," *J. Med. Chem.*, 51:2279-2290, 2008.
Marples and Spilling, "Facile intramolecular ene reactions of steroidal unsaturated acyloins," *Tetrahedron*, 48 (19): 4017-4026, 1992.
Maruyama et al., "Co(salen)-catalyzed tert-butyl hydroperoxide oxidation of tert-butylphenols bearing an unsaturated side chain," *J. Org. Chem.*, 61(1):3342-3349, 1996.
Matsumoto et al., "Synthesis of pygmaeocine E, a linear abietane diterpene from *pygmaeopremna herbacea* (Roxb.) moldenke," *Chemical and Pharmaceutical Bulletin*, 44 (7): 1318-1325, 1996.
McIver et al., "NO-mediated alterations in skeletal muscle nutritive blood flow and lactate metabolism in fibromyalgia," *Pain*, 120(1-2): 161-169, 2005.
Mease et al., "Etanercept in the treatment of psoriatic arthritis and psoriasis: a randomised trial," *Lancet*, 356:385-390, 2000.
Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-gamma expression," *Gynecologic Oncology*, 93:149-154, 2004.
Meng et al., "A diterpenoid with a new carbon skeleton from *Pygmaeopremna herbacea*," *Phytochemistry*, 27 (4): 1151-1152, 1988.
Meng et al., "RV09, a novel resveratrol analogue, inhibits NO and TNF-α production by LPS-activated microglia," *Int. Immunopharmacology*, 8: 1074-1082, 2008.
Miller and Shi, "Formation of 2,3-dehydro-1,2-dihydro-1,1-dimethylnaphthalene, 'isoaromatic' molecule," *J. of the American Chemical Society*, 109 (2): 578-579, 1987.
Miller and Shi, "Novel rearrangement and cyclization processes resulting from bromination of 1,1-dibenzyltetralin derivatives," *Journal of Organic Chemistry*, 57 (6): 1677-1681, 1992.
Minghetti et al., "Production of diterpenoids by *Euphorbia calyptrata* cell cultures," *Phytochemistry*, 42 (6): 1587-1589, 1996.
Minns et al., "A novel triterpenoid induces transforming growth factor beta production by intraepithelial lymphocytes to prevent ileitis," *Gastroenterology*, 127:119-126, 2004.
Mix et al., "A synthetic triterpenoid selectively inhibits the induction of matrix metalloproteinases 1 and 13 by inflammmatory cytokines," *Arthritis Rheum.*, 44:1096-1104, 2001.
Mix et al., "Peroxisome proliferator-activated receptor-gamma-independent repression of collagenase gene expression by 2-cyano-3,12-dioxooleana-1,9-dien-28-oic acid and prostaglandin 15-deoxy-delta(12,14) J2: a role for Smad signaling," *Mol. Pharmacol.*, 65:309-318, 2004.
Moncada et al., "Nitric oxide: physiology, pathophysiology, and pharmacology," *Pharmacol. Rev.*, 43:109-142, 1991.
Morris et al., "Association of a functional inducible nitric oxide synthase promoter variant with complications in type 2 diabetes," *J. Mol. Med.*, 80(2):96-104, 2002.
Morse and Choi, "Heme oxygenase-1: from bench to bedside," *Am. J. Respir. Crit. Care Med.*, 172(6): 660-670, 2005.
Morse and Choi, "Heme oxygenase-1: the 'emerging molecule' has arrived," *Am. J. Respir. Crit. Care Med.*, 27(1):8-16, 2002.
Morse and Choi, "Improving tuberculin skin testing in HIV-infected individuals," *Am. J. Respir. Cell Mol. Biol.*, 27(1):8-16, 2002.
Murphy et al, "Immunomodulatory Effects of the Triterpenoid CDDO after Allogeneic Bone Marrow Transplantation in Mice: Reduction of Acute Graft-Versus-Host Disease Lethality," *Blood*, 106:1316, 2005.
Murray and Zweifel, "Preparation of Phenyl Cyanate and Its Utilization for the Synthesis of α, β-Unsaturated Nitriles," *Synthesis*, 150-151, 1980.*Synthesis*, 150-151, 1980.

(56) References Cited

OTHER PUBLICATIONS

Muzart, "Synthesis of unsaturated carbonyl compounds via a chromium-mediated allylic oxidation by 70% tert.butylhydroperoxide," *Tetrahedron Lett.*, 28:4665-4668, 1987.
Na and Surh et al., "Transcriptional regulation via cysteine thiol modification: a novel molecular strategy for chemoprevention and cytoprotection," *Mol. Carcinog.*,45 (6): 368-380, 2006.
Naik et al., "Role of oxidative stress in pathophysiology of peripheral neuropathy and modulation by N-acetyl-L-cysteine in rats," *Eur. J. Pain*, 10(7):573-579, 2006.
Nath et al., "Progression of progressive multifocal leukoencephalopathy despite treatment with beta-interferon," *Neurology*, 66(1): 149-150, 2006.
Nathan and Xie, "Nitric oxide synthases: roles, tolls, and controls," *Cell*, 78:915-918, 1994.
Nathan, "Points of control in inflammation," *Nature*, 420:846-852, 2002.
Nichols, "NF-kappaB and reperfusion injury," *Drug News Perpect.*, 17(2): 99-104, 2004.
Notice of Allowance issued in U.S. Appl. No. 13/055,418, dated Jul. 11, 2012.
Office Communication issued in U.S. Appl. No. 13/055,418, dated Feb. 3, 2012.
Office Communication issued in U.S. Appl. No. 13/055,418, dated Oct. 21, 2011.
Orr et al, "Steroids. CCLXV. Studies in cyano steroids. 3. Unsaturated 2-cyano steroids," *J. Org. Chem.*, 29(11): 3300-3303, 1964.
Osburn et al., "Genetic of pharmacologic amplification of Nrf2 signaling inhibits acute inflammatory liver injury in mice," *Toxicological Sciences*, 104:218-227, 2008.
Overnell and Whitehurts, "Reactions of steroid A-ring lactones with Grignard reagents," *J. of the Chemical Society [Section] C: Organic*, 2: 378-384, 1971.
Pall, "Nitric oxide synthase partial uncoupling as a key switching mechanism for the NO/ONOO- cycle," *Med. Hypoth.*, 69:821-825, 2007.
Pappas et al., "Photoisomerization of phenalen-1-one oxide. New course of light-induced alpha beta-epoxy ketone rearrangement," *J. of the American Chemical Society*, 92 (19): 5797-5798, 1970.
Partsch et al., "Highly increased levels of tumor necrosis factor-alpha and other proinflammatory cytokines in psoriatic arthritis synovial fluid," *J. Rheumatol.*, 24:518-523, 1997.
Pedersen et al., "The triterpenoid CDDO induces apoptosis in refractory CLL B cells," *Blood*, 100:2965-2972, 2002.
Piacenza et al., "A new atisane diterpene: ent-16ß-hydroxyatis-13-en-3-one from *Androstachys johnsonii* prain," *J. of the Chemical Society, Perkins Transactions 1: Organic and Bio-Organic Chemistry*, 4: 703-709, 1985.
Piacenza et al., "Beyerane diterpenes: structure and reactivity of the α-ketol ent-3β-hydroxybeyer-15-ene-2,12-dione, its corresponding diosphenol, and synthesis of the isomeric α-ketol acetates," *J. of the Chemical Society, Perkin Transactions 1: Organic and Bio-Organic Chemistry*, 4: 1004-1012, 1979.
Pica et al., "Delta(12)-prostaglandin J(2) is a potent inhibitor of influenza A virus replication," *Antimicrob. Agents Chemother.*, 44(1): 200-204, 2000.
Place et al., "The novel synthetic triterpenoid, CDDO-imidazolide, inhibits inflammatory response and tumor growth in vivo," *Clin. Cancer Res.*, 9:2798-2806, 2003.
Pletnev et al., "Carbopalladation of nitriles: Synthesis of 2,3-diarylindenones and polycyclic aromatic ketones by the Pd-catalyzed annulation of alkynes and bicyclic alkenes by 2-iodoarenenitriles," *J. of Organic Chemistry*, 67 (26): 9276-9287, 2002.
Rasmusson et al., "Azasteroids: structure-activity relationships for inhibition of 5 alpha-reductase and of androgen receptor binding," *J. Med. Chem.*, 29 (11): 2298, 1986.
Response to Office Communication issued in U.S. Appl. No. 13/055,418, dated Nov. 21, 2011.
Response to Office Communication issued in U.S. Appl. No. 13/055,418, dated May 3, 2012.

Rogers et al., "Expression of immune system-associated antigens by cells of the human central nervous system: relationship to the pathology of Alzheimer's disease," *Neurobiol. Aging*, 9(4): 339-349, 1988.
Ross et al., "Breast cancer biomarkers and molecular medicine," *Expert Rev. Mol. Diagn.*, 3(5): 573-585, 2003.
Rossi et al., "Anti-inflammatory cyclopentenone prostaglandins are direct inhibitors of IkappaB kinase," *Nature*, 403:103-108, 2000.
Rostom et al., "Nonsteroidal anti-inflammatory drugs and cyclooxygenase-2 inhibitors for primary prevention of colorectal cancer: a systematic review prepared for the U.S. Preventive Services Task Force," *Ann. Intern. Med.*, 146(5): 376-389, 2007.
Ruster et al., "Detection of elevated N epsilon-carboxymethyllysine levels in muscular tissue and in serum of patients with fibromyalgia," *Scand. J. Rheumatol.*, 34(6): 460-463, 2005.
Ruvolo et al., "The novel triterpenoid methyl-CDDO inhibits Bcl2 phosphorylation and potently kolls U937 cells," *Blood*, 94(10), Suppl. 1, Part 1: 280A, abstract #1251, 1999.
Salvemini et al., "Nitric oxide activates cyclooxygenase enzymes," *Proc. Natl. Acad. Sci. USA*, 90(15):7240-7244, 1993.
Samudio et al., "2,cyano-3,12 dioxoolean-1,9 diene-28-imidazolide induces apoptosis in pancreatic cancer via redox-dependent cytoplasmic stress," *Proc. Amer. Assoc. Cancer Res.*, 46: Abstract No. 5899, 2005.
Samudio et al., "2-Cyano-3,12-dioxooleana-1,9-dien-28-imidazolide (CDDO-Im) directly targets mitochondrial glutathione to induce apoptosis in pancreatic cancer," *J. Biol. Chem.*, 280:36273-36282, 2005.
Samudio et al., "A novel mechanism of action of methyl-2-cyano-3,12 dioxoolean-1,9 diene-28-oate: direct permeabilization of the inner mitochondrial membrane to inhibit electron transport and induce apoptosis," *Mol. Pharmacol.*, 69:1182-1193, 2006.
Samudio et al., "A novel mechanism of action of methyl-2-cyano-3,12 dioxoolean-1,9 diene28-oate (CDDO-Me): Direct permeabilization of the inner mitochondrial membrane to inhibit electron transport and induce apoptosis," *Proc. Am. Assoc. Cancer Res.*, 47: Abstract No. 4693, 2006.
Samudio et al., "The novel triterpenoid CDDOme potently synergizes with inhibition of bcl-2 function to induce apoptosis in AML via disruption of intracellular redox homeostasis," *Proc. Amer. Assoc. Cancer Res.*, 46: Abstract No. 4955, 2005.
Scholz et al., "Sensitive and specific methods for the determination of CDDO methyl ester in mouse, rat, dog, monkey, and human plasma by LC-tandem mass spectrometry," *Proc. Amer. Assoc. Cancer Res.*, 4: Abstract No. 6321, 2003.
Schulz et al., "Nitric oxide, tetrahydrobiopterin, oxidative stress, and endothelial dysfunction in hypertension," *Antioxid. Redox. Sig.*, 10:1115-1126, 2008.
Serhan et al., "Resolving inflammation: dual anti-inflammatory and pro-resolution lipid mediators," *Nat. Rev.*, 8:349-361, 2008.
Shishodia et al., "A synthetic triterpenoid, CDDO-Me, inhibits IkappaBalpha kinase and enhances apoptosis induced by TNF and chemotherapeutic agents through down-regulation of expression of nuclear factor kappaB-regulated gene products in human leukemic cells," *Clin. Cancer Res.*, 12:1828-1838, 2006.
Singh and Evans, "Nitric oxide, the biological mediator of the decade: fact or fiction?" *Eur. Respir. J.*, 10:699-707, 1997.
Singh et al., "Anti-inflammatory activity of oleanolic acid in rats and mice," *J. Pharm.Pharmacol.*, 44:456-458, 1992.
Sinha et al., "Prostaglandin E2 promotes tumor progression by inducing myeloid-derived suppressor cells," *Cancer Res.*, 67:4507-4513, 2007.
Snitman et al., "Synthetic approaches to taxodione synthesis of methyl 12-oxopodocarpa-5,9(11)-diene-8β-carboxylate," *Synth. Comm.*, 8:187-194, 1978.
Sonogashira et al., "A convenient synthesis of acetylenes: catalytic substitutions of acetylenic hydrogen with bromoalkenes, iodoarenes and bromopyridines," *Tetrahedron Lett.*, 16(50): 4467-4470, 1975.
Stadheim et al., "The novel triterpenoid 2-cyano-3,12-dioxooleana-1,9-dien-28-oic acid (CDDO) potently enhances apoptosis induced by tumor necrosis factor in human leukemia cells," *J. Biol. Chem.*, 277:16448-16455, 2002.

(56) References Cited

OTHER PUBLICATIONS

Stork et al., "A stereospecific total synthesis of 18-substituted steroids. Application to the synthesis of dl-conessine," *J. of the American Chemical Society*, 84: 2018-2020, 1962.
Suginome et al., "The photochemistry of steroidal 6-membered cyclic a-nitro ketones," *Bulletin of the Chemical Society of Japan*, 61 (11): 4005-4014, 1988.
Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59:336-341, 1999.
Suh et al., "A novel synthetic oleanane triterpenoid, 2-cyano-3,12-dioxoolean-1,9-dien-28-oic acid (CDDO), induces cell differentiation in human myeloid leukemias," *Proceedings of the American Association for Cancer Research Annual Meeting*, 40:300, abstract # 1988, 1999.
Suh et al., "New triterpenoids as cancer preventive and anti-inflammatory agents," *Proceedings of the American Association for Cancer Research*, Abstract No. 1457, 38: 216, 1997.
Suh et al., "Novel triterpenoids suppress inducible nitric oxide synthase (iNOS) and inducible cyclooxygenase (COX-2) in mouse macrophages," *Cancer Res.*, 58:717-723, 1998.
Suh et al., "Novel triterpenoids suppress inducible nitric oxide synthase (iNOS) and inducible cyclooxygenase (COX-2)," *Proceedings of the American Association for Cancer Research Annual Meeting*, 39: Abstract No. 1821, 1998.
Suh et al., "Synthetic triterpenoids activate a pathway for apoptosis in AML cells involving downregulation of FLIP and sensitization to TRAIL," *Leukemia*, 17:2122-2129, 2003.
Suh et al., "Synthetic triterpenoids enhance transforming growth factor β/Smad signaling," *Cancer Res.*, 63:1371-1376, 2003.
Suh et al., "Triterpenoids CDDO and CDDO-Me Down-Regulate FLIP Expression and Sensitize AML Cells to Trail-Induced Apoptosis," *American Society of Hematology 43$^{rd}$ Annual Meeting and Exposition*, Abstract No. 498, 2001.
Sun et al., "Structure-activity relationships of oleanan- and ursane-type triterpenoids," *Botanical Studies*, 47:339-368, 2006.
Sun et al., "The synthetic triterpenoid, CDDO, suppresses alloreactive T cell responses and reduces murine early acute graft-versus-host disease mortality," *Biology of Blood and Marrow Transplantation*, 13:521-529, 2007.
Supplemental European Search Report issued in European Patent Application No. 09800964, dated Mar. 28, 2012.
Sussan et al., "Disruption of Nrf2, a key inducer of antioxidant defenses, attenuates ApoE-mediated atherosclerosis in mice," *PLoS One*, 3 (11): 1-9, 2008.
Szabo et al., "Peroxynitrite: biochemistry, pathophysiology and development of therapeutics," *Nature Rev. Drug Disc.*, 6:662-680, 2007.
Tabe et al., "Chromatin-Mediated Transcriptional Activation with Novel Peroxisome Proliferator—Activated Receptor gamma(P-PARgamma) Ligand 2-cyano-1,9-dien-28-oic Acid (CDDO) in Acute Promyelocytic Leukemia Cells," *Abstracts of the 44$^{th}$ Annual Meeting of the American Society of Hematology*, Abstract No. 2191, 2002.
Takeda et al., "Orthosiphol D and E, minor diterpenes from *Orthosiphon stamineus*," *Phytochemistry* , 33 (2): 411-415, 1993.
Tamm et al., "Expression and prognostic significance of IAP-family genes in human cancers and leukemias," *Blood*, 94(Suppl. 1):69a, Abstract # 298, 1999.
Thimmulappa et al., "Nrf2-dependent protection from LPS induced inflammatory response and mortality by CDDO-imidazolide," *Biochem. Biophys. Res. Commun.*, 351:883-889, 2006.
Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," *Antioxidants & Redox Signaling*, 9:1-8, 2007.
Tian et al., "Carbopalladation of nitriles: synthesis of 3,4-disubstituted 2-aminonaphthalenes and 1,3-benzoxazine derivatives by the palladium-catalyzed annulation of alkynes by (2-Iodophenyl)acetonitrile," *J. of Organic Chemistry*, 68 (2): 339-347, 2003.
Tinto et al., "Terpenoid constituents of *Oxandra asbeckii*," *Journal of Natural Products*, 55 (6): 701-706, 1992.
Touzani et al., "Potential mechanisms of interleukin-1 involvement in cerebral ischaemia," *J. Neuroimmunol.*, 100(1-2): 203-215, 1999.
Tran et al., "The synthetic triterpenoid CDDO-methyl ester modulates microglial activities, inhibits TNF production, and provides dopaminergic neuroprotection," *Journal of Neuroinflammation*, 5:1-14, 2008.
Tsao et al., "DRIP205 co-activator overexpression enhances PPARgamma-mediated differentiation of leukemia cells by CDDO," *Proc. Amer. Assoc. Cancer Res.*, 46: Abstract No. 1855, 2005.
Tsao et al., "Targeted Induction of Apoptosis in Leukemias by PPARgammma Ligation," *American Society of Hematology 43$^{rd}$ Annual Meeting and Exposition*, Abstract No. 2381, 2001.
Tumlin et al., "Pathophysiology of contrast-induced nephropathy," *Am. J. Cardiol.*, 98(6A): 14K-20K, 2006.
Urban et al., "Influence of esterification and modification of A-ring in a group of lupane acids on their cytotoxicity ," *Bioorganic and Medicinal Chemistry*, 13 (19): 5527-5535, 2005.
Wada and Tanaka, "Synthetic lanostane-type triterpenoids as inhibitors of DNA topoisomerase II ," *Bioorganic and Medicinal Chemistry Letters*, 15 (12): 2966-2969, 2005.
Wang et al., "A novel synthetic triterpenoid, 2-cyano-3,12-dioxoolean-1,9-dien-28-oic acid (CDDO) induces adipocyte differentiation in 3T3-L1 cells," *Proceedings of the American Association for Cancer Research Annual Meeting*, 40:300, abstract # 1989, 1999.
Wang et al., "A synthetic triterpenoid, 2-cyano-3,12-dioxooleana-1,9-dien-28-oic acid (CDDO), is a ligand for the peroxisome proliferator-activated receptor γ," *Mol. Endocrin.*, 14(10):1550-1556, 2000.
Wang et al., "Diterpenoids from roots of *Euphorbia wallichii*," *Zhongcaoyao*, 35 (6): 611-614, 2004.
Wang et al., "Synthetic triterpenoid CDDO and its derivatives increase ceramides and are cytotoxic to pediatric acute lymphoblastic leukemia cell lines," *Proc. Am. Assoc. Cancer Res.*, 47: 4643, 2006.
Wardle, "Nuclear factor kappaB for the nephrologist," *Nephrol. Dial. Transplant*, 16(9): 1764-1768, 2001.
Williams et al., "Immunology of multiple sclerosis," *Clin. Neurosci.*, 2(3-4):229-245, 1994.
Wu et al., "An improvedgeneralsyntheticapproach to cis-clerodane diterpenoids. A more efficient total synthesis of (±)-6β-acetoxy-2-oxokolavenool," *Tetrahedron*, 42(25): 4207-4209, 2001.
Wulff et al., "The Natural Product Avrainvillamide Binds to the Oncoprotein Nucleophosmin," *J. of the American Chemical Society*, 129 (46): 14444-14451, 2007.
Yates et al., "Pharmacodynamic characterization of chemopreventive triterpenoids as exceptionally potent inducers of Nrf2-regulated genes," *Mol. Cancer Ther.*, 6:154-162, 2007.
Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," *Cancer Res.*, 66:2488-2494, 2006.
Yoh et al., "Nrf2-deficient female mice develop lupus-like autoimmune nephritis," *Kidney Int.*, 60(4): 1343-1353, 2001.
Yore et al., "The synthetic triterpenoid 1-[2-cyano-3,12-dioxooleana-1,9(11)-dien-28-oyl]imidazole blocks nuclear factor-kappaB activation through direct inhibition of IkappaB kinase beta," *Mol. Cancer Ther.*, 5 (12): 3232-3239, 2006.
You et al., "Synthesis and cytotoxic activity of a-ring modified betulinic acid derivatives ," *Bioorganic and Medicinal Chemistry Letters*, 13 (19): 3137-3140, 2003.
Yu et al., "Crosstalk between cancer and immune cells: role of STAT3 in the tumour microenvironment," *Nat. Rev. Immunol.*, 7:41-51, 2007.
Yue et al., "Depletion of intracellular glutathione contributes to JNK-mediated death receptor 5 upregulation and apoptosis induction by the novel synthetic triterpenoid methyl-2-cyano-3, 12-dioxooleana-1, 9-dien-28-oate (CDDO-Me).," *Cancer & Biology Therapy*, 5(5):492-497, 2006.

(56) References Cited

OTHER PUBLICATIONS

Zapata et al., "CDDO and CDDO-Im Reduce Tumor Burden in a Transgenic Mouse Model of CLL," *Blood*, 104:3477, 2004.

Zapata et al., "Triterpenoids show activity against leukemic cells in a transgenic mouse model of CLL," *Proc. Amer. Assoc. Cancer Res.*, 46: Abstract No. 5179, 2005.

Zhang et al., "Synthetic triterpenoid CDDO as effective therapy for HER2-expressing resistant breast cancer," *Proc. Amer. Assoc. Cancer Res.*, Abstract No. 3799, 2004.

Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," *J. Invest. Dermatol.*, 123:380-387, 2004.

Zhou et al., "Myeloid suppressor cell-associated immune dysfunction in CSA1M fibrosarcoma tumor-bearing mice," *Cancer Sci.*, 98:882-889, 2007.

Zingarelli et al., "Peroxisome proliferator activator receptor-gamma ligands, 15-deoxy-Delta(12,14)-prostaglandin J2 and ciglitazone, reduce systemic inflammation in polymicrobial sepsis by modulation of signal transduction pathways," *J. Immunol.*, 171(12): 6827-6837, 2003.

Zoretic et al., "Advanced tetracycles in a stereoselective approach to *d,l*-spongiatriol and related metabolites: the use of radicals in the synthesis of angular electrophores," *J. of Organic Chemistry*, 63 (4): 1162-1167, 1998.

Zou et al., "c-Jun NH2-terminal kinase-mediated up-regulation of death receptor 5 contributes to induction of apoptosis by the novel synthetic triterpenoid methyl-2-cyano-3,12-dioxooleana1, 9-dien-28-oate in human lung cancer cells," *Cancer Res.*, 64:7570-7578, 2004.

Zundel et al., "Backbone rearrangement of A-noreuphenone," *Bulletin de la Societe Chimique de France*, 11 Part 2: 3206-3208, 1973.

Alabran, et al., "Human neuroblastoma cells rapidly enter cell cycle arrest and apoptosis following exposure to C-28 derivatives of the synthetic triterpenoid CDDO", *Cancer Biology & Therapy*, 7(5):709-717, 2008.

Albini and Sporn, "Opinion: the tumour microenvironment as a target for chemoprevention", *Nature Reviews Cancer*, Abstract 501:149, 2002.

Ballesta-Acosta, et al., "A new 24-nor-oleanane triterpenoid from *Salvia carduacea*", *J. Nat. Prod.*, 65(10):1513-1515, 2002.

Campaigne and Forsch, "Rearrangement of 2-cyano-3-(1-methylcyclopentyl)indenone to 4a-methyl-9-oxo-10-cyano-1,2,3,4,4a,9-hexahydrophenanthrene", *J. Org. Chem.*, 43:1044-1050, 1978.

Chadalapaka, et al., "Structure-dependent inhibition of bladder and pancreatic cancer cell growth by 2-substituted glycyrrhetinic and ursolic acid derivatives", *Bioorganic & Medicinal Chemistry Letters*, 18:2633-2639, 2008.

Chintharlapalli, et al., "2-Cyano-lup-1-en-3-oxo-20-oic acid, a cyano derivative of betulinic acid, activates peroxisome proliferator-activated receptor γ in colon and pancreatic cancer cells", *Carcinogenesis*, 28(11):2337-2346, 2007.

Chintharlapalli, et al., "Structure-dependent activity of glycyrrhetinic acid derivatives as peroxisome proliferator-activated receptor γ agonists in colon cancer cells", *Molecular Cancer Therapeutics*, 6(5):1588-1598, 2007.

Chudek, et al., "Initial adduct formation by 1,4-benzoquinones in liquid ammonia to give 4-amino-4-hydroxycyclohexa-2,5-dienones and 3,6-diamino-3,6-dihydroxycyclohexa-1,4-dienes", *J. Chem. Soc., Perkin Trans. II*, 2:287-291, 1984.

Clinicaltrials.gov Study Record, NCT 00352040, "CDDO in treating patients with metastatic or unresectable solid tumors or lymphoma conditions: lymphoma; small intestine cancer; unspecified adult solid tumor, protocol specific", update of Jul. 6, 2009.

Clinicaltrials.gov Study Record, NCT 00508807, "RTA 402 in advanced solid tumors or lymphoid malignancies", update as of Sep. 7, 2008.

Clinicaltrials.gov Study Record, NCT 00508807, "RTA 402 in advanced solid tumors or lymphoid malignancies conditions: lymphoid malignancies; solid tumors", update of Aug. 27, 2008.

Clinicaltrials.gov Study Record, NCT 00508807, "RTA 402 in advanced solid tumors or lymphoid malignancies conditions: lymphoid malignancies; solid tumors", update of Oct. 5, 2010.

Clinicaltrials.gov Study Record, NCT 00529113, "Study with gemcitabine and RTA 402 for patients with unresectable pancreatic cancer", update of Dec. 1, 2010.

Clinicaltrials.gov Study Record, NCT 00529113, "Study with gemcitabine and RTA 402 for patients with unresectable pancreatic cancer", update of Jun. 12, 2008.

Clinicaltrials.gov Study Record, NCT 00529438, "RTA 402 in patients with advanced solid tumors or lymphoid malignancies conditions: advanced solid tumors; lymphoid malignancies", update of Dec. 21, 2008.

Clinicaltrials.gov Study Record, NCT 00550849, "Study to assess the safety, tolerability, and pharmacodynamics of RTA 402 in patients with hepatic dysfunction", update as of Nov. 29, 2007.

Clinicaltrials.gov Study Record, NCT 00550849, "Study to assess the safety, tolerability, and pharmacodynamics of RTA 402 in patients with hepatic dysfunction condition: liver disease", update of Nov. 6, 2007.

Clinicaltrials.gov Study Record, NCT 00664027, "Phase IIa trail to determine the effects of bardoxolone methyl on renal function in patients with diabetic nephropathy", update as of Dec. 21, 2008.

Clinicaltrials.gov Study Record, NCT 00664027, "Phase IIa trial to determine the effects of bardoxolone methyl on renal function in patients with diabetic nephropathy condition: diabetic nephropathy", update of Feb. 18, 2009.

Clinicaltrials.gov Study Record, NCT 00664027, "Phase IIa trial to determine the effects of bardoxolone methyl on renal function in patients with diabetic nephropathy condition: diabetic nephropathy", update of Jun. 25, 2011.

Clinicaltrials.gov Study Record, NCT 00811889, "Trial to determine the effects of bardoxolone methyl on eGFR in patients with type 2 diabetes and chronic kidney disease conditions: chronic kidney disease; type 2 diabetes; diabetic nephropathy", update as Jun. 4, 2009.

Clinicaltrials.gov Study Record, NCT 0352040, "CDDO in treating patients with metastatic or unresectable solid tumors or lymphoma", update as of Dec. 11, 2008.

Clinton, et al., "Steroidal[3,2-c]pyrazoles. II. Androstanes, 19-norandrostanes and their unsaturated analogs", *J. Am. Chem. Soc.*, 83:1478-1491, 1961.

Couch, et al., "2-cyano-3,12-dioxooleana-1,9(11)-diene-28-oic Acid Disrupts Microtubule Polymerization: A Possible Mechanism Contributing to Apoptosis", *Molecular Pharmacology*, 69:1158-1165, 2006.

Couch, et al., "Studies on the reactivity of CDDO, a promising new chemopreventive and chemotherapeutic agent: implications for a molecular mechanism of action", *Bioorganic and Medicinal Chemistry Letters*, 15(9):2215-2219, 2005.

De Ruggeri, et al., "Deidrogenazione e bromurazione di beta-chetonitrili steroidali", *Il Farmaco*, 20:358-388, 1964. (Italian, English Abstract).

Deeb, et al., "CDDO-Me Induces Apoptosis and Inhibits Akt, mTOR and NF-κB Signaling Proteins in Prostate Cancer Cells", *Anticancer Research*, 27:3035-3044, 2007.

Deeb, et al., "CDDO-Me inhibits proliferation, induces apoptosis, down-regulates Akt, mTOR, NF-κB and NF-κB-regulated antiapoptotic and proangiogenic proteins in TRAMP prostate cancer cells", *J. Experimental Therapeutics and Oncology*, 7:31-39, 2007.

Dragnev, et al., "Specific chemopreventive agents trigger proteasomal degradation of G1 cyclins: implications for combination therapy", *Clin. Cancer Research*, 10(7):2570-2577, 2004.

Ferguson, Heather E., "PPARγ ligands have potent anti-fibrotic activity: mechanism of action and implications for therapy of pulmonary fibrosis", Dissertation, University of Rochester, 2008.

Finlay, et al., "The Effect of A and C Ring Modification of Oleanolic and Ursolic Acid on the Inhibition of Nitric Oxide Formation in Mouse Macrophages", 213th American Chemical Society National Meeting, Abstract:084, 1997.

(56) References Cited

OTHER PUBLICATIONS

Gao, et al., "Synthetic triterpenoids inhibit growth and induce apoptosis in human glioblastoma and neuroblastoma cells through inhibition of prosurvival Akt, NF-κB and Notch1 signaling", *J. of Neurooncology*, 84(2): 147-157, 2007.
Gordon, et al., "The reactions of some substituted 2-hydroxybenzonitriles with nitrogen dioxide: x-ray structures of 2-cyano-t-6-hydroxy-3,4,5,6-tetramethyl-r-4,t-5-dinitro-cyclohex-2-enone, 2-cyano-3,4,5,6-tetramethyl-r-4,t-5,t-6-trinitrocyclohex-2-enone and 2-cyano-c-6-hydroxy-4,6-dimethyl-r-4,c-5-dinitrocyclohex-2-enone," *Aust. J. Chem.*, 43:579-91, 1990.
Greico and Speake, et al., "Synthetic Studies on Quassinoids: Total Synthesis and Biological Evaluation of (+)-Des-D-chaparrinone", *J. Org. Chem.*, 63:5929-5936, 1998.
Han, et al., "CDDO-Imidazolide inhibits growth and survival of c-Myc-induced mouse B cell and plasma cell neoplasms", *Molecular Cancer*, 5:22, 2006.
Heiss, et al., "Active NF-E2-related factor (Nrf2) contributes to keep endothelial NO synthase (eNOS) in the coupled state: role of reactive oxygen species (ROS), eNOS, and heme oxygenase (HO-1) levels", *J. Biol. Chem.*, 284:31579-31586, 2009.
Hill, et al., "Synthetical approaches to the pristimerin chromophore", *J. of the Chemical Society*, 361-375, 1965.
Hirota, et al., "Suppression of tumor promoter-induced inflammation of mouse ear by ursolic acid and 4,4-dimethycholestane derivatives", *Agric. Biol. Chem.*, 54:1073-1075, 1990.
Honda, et al., "New synthetic oleanane and ursane triterpenoids as inhibitors of nitric oxide production in mouse macrophages", The Fifth Chemical Congress of North America, Cancun, Mexico, Abstract 552 and slides for oral presentation, Nov. 1997.
Honda, et al., "Revision and confirmation of the regiochemistry of isoxazoles derived from methyl oleanonate and lanost-8-en-3-one. Synthesis of a new lanostane triterpenoid with a cyano-enone functionality in ring A", *J. Org. Chem.*, 68:4991-4993, 2003.
Hughes, et al., "The synthetic triterpenoid CDDO-Im inhibits fatty acid synthases expression and has antiproliferative and proapoptotic effects in human liposarcoma cells", *Cancer Investigation*, 26:118-127, 2008.
Hyer, et al., "Apoptotic activity and mechanism of 2-cyano-3,12-dioxoolean-1,9-dien-28-oic acid and related synthetic triterpenoids in prostate cancer", *Cancer Res.*, 68:2927-2933, 2008.
Ikeda, et al., "Triterpenoid CDDO-Im downregulates PML/RARα expression in acute promyelocytic leukemia cell", *Cell Death and Differentiation*, 12(5):523-531, 2005.
Inoue, et al., "CDDO induces apoptosis via the intrinsic pathway in lymphoid cells", *Leukemia*, 18(5):948-952, 2004.
Ji, et al., "The synthetic triterpenoid CDDO-imidazolide induces monocytic differentiation by activating the Smad and ERK signaling pathways in HL60 leukemia cells", *Molecular Cancer Therapeutics*, 5(6):1452-1458, 2006.
Kansanen, et al., "Regulation of Nrf2-dependent gene expression by 15-deoxy-412,14-prostaglandin Δ2", *Free Radic. Biol. Med.*, 47(9): 1310-1317, 2009.
Kim, et al., "An inducible Pathway for Degradation of FLIP protein Sensitizes Tumor Cells to Trail-induced Apoptosis", *J. Biological Chemistry*, 277(25):22320-22329, 2002.
Kobayashi, et al., "The antioxidant defense system Keap 1-Nrf2 comprises a multiple sensing mechanism for responding to a wide range of chemical compounds", *Mol. Cell Biol.*, 29(2):493-502, 2009.
Konopleva, et al., "PPARγ nuclear receptor as a novel therapeutic target in Aml", *Proc. of the AACR*, 42, Abstract #4458, 2001.
Korovin and Tkachev, "Synthesis of quinoxalines fused with triterpenes, ursolic acid and betulin derivatives", *Russian Chemical Bulletin* (Translation of Izvestiya Akademii Nauk, Seriya Khimicheskaya), 20(2):304-310, 2001.
Liby, et al., "The synthetic triterpenoids CDDO and CDDO-imidazole, are potent induces of heme oxygenase-1 and Nrf2/ARE signaling", *Cancer Research*, 65(11):4789-4798, 2005.

Liby, et al., "The synthetic triterpenoids CDDO-methyl ester and CDDO-ethyl amide prevent lung cancer induced by vinyl carbamate in A/J mice", *Cancer Research*, 67(6):1-7, 2007.
Liby, et al., "Triterpenoids and rexinoids as multifunctional agents for the prevention and treatment of cancer", *Nature Review Cancer*, 7(5):357-369, 2007.
Liu, et al., "Coordinate regulation of the enzyme markers for inflammation and for protection against oxidants and electrophiles", *Proc. Natl. Acad. Sci.*, 105(41):15926-15931, 2008.
Marty, et al., "RTA 402 (CDDO-Me) increases survival of mice administered high doses of cytotoxic chemotherapy", *European Organization for Research and Treatment of Cancer, American Association for Cancer Research and National Cancer Institute International Conference*, Nov. 2005, Poster presentation.
Morgan, et al., "Preparation and cycloaddition reactions of novel heterocyclic mesomeric betaines", *Tetrahedron*, 56:5523-5534, 2000.
Mori, et al., "Synthesis of 4,4-dimethyl-2-nitro-5α-cholest-l-en-3-one", *Chemical and Pharmaceutical Bulletin*, 30(12):4516-4517, 1982.
Morzycki and Wilczewska, "Reactions of 4-azacholest-5-en-3-one, 6-azacholest-4-en-7-one, and their N-methyl derivatives with electrophilic reagents", *Tetrahedron*, 52(44):14057-14068, 1996.
Niikura, et al., "The effects of synthetic triterpenoids on superficial zone protein synthesis in articular chondrocytes", Abstract, Orthopedic Research Society, San Diego, 2007.
Niikura, et al., "The effects of synthetic triterpenoids on szp synthesis in articular chondrocytes", Abstract P197, Osteoarthritis and Cartilage, 14(Suppl B):S112-S113, 2006.
Parra-Delgado, et al., "Synthesis and Comparative Molecular Field Analysis (CoMFA) of Argentatin B derivatives as Growth Inhibitors of Human Cancer Cell Lines", *Bioorganic & Medicinal Chemistry*, 14:1889-1901, 2006.
Place, Andrew E., "Pre-clincial evaluation of the novel synthetic triterpenoid CDDO-Imidazolide", Dissertation, Dartmouth College, May 4, 2005.
Ray, Denise M., et al., "The novel triterpenoid 2-cyano-3,12-dioxooleana-1,9-dien-28-oic acid (CDDO) Induces Apoptosis of Human Diffuse Large B-cell Lymphoma Cells through a Peroxisome Proliferator-activated Receptor γ-independent Pathway", *Experimental Hematology*, 34:1201-1210, 2006.
Riccioni, et al., "Resistance of acute myeloid leukemic cells to the triterpenoid CDDO-Imidazolide is associated with low caspase-8 and FADD levels", *Leukemia Research*, 32:1244-1258, 2008.
Samudio, et al., "Inhibition of mitochondrial metabolism by methyl-2-cyano-3,12-dioxoolean-1,9-diene-28-oate induces apoptotic or autophagic cell death in chronic myelogenous leukemia cells", *Mol. Cancer. Ther.*, 7(5):1130-1139, 2008.
Satoh, et al., "Activation of the Keap1/Nrf2 pathway for neuroprotection by electrophillic phase II inducers", *PNAS*, 103(3):768-773, 2006.
Shin, "Inhibitory roles of Nrf2 and an oleanolic triterpenoid on adipocyte differentiation and obesity", dissertation submitted to John Hopkins University in conformity with the requirements for the degree of Doctor of Philosophy, Mar. 2009.
Shin, et al., "Nrf2 modulates aryl hydrocarbon receptor signaling: influence on adipogenesis", *Molecular and Cellular Biology*, 27(20):7188-7197, 2007.
Shin, et al., "Role of Nrf2 in prevention of high-fat diet-induced obesity by synthetic triterpenoid CDDO-imidazolide", *Eur. J. Pharmacol.*, 620(1-3):138-144, 2009.
Slides/Handout by Reata Pharmaceuticals, "RTA 402, Therapeutic Properties III", podium presentation at BIO 2006 conference, Apr. 9-12, 2006, Chicago, Illinois.
Slides/Handout by Reata Pharmaceuticals, "RTA 402, Therapeutic Properties I", Private partnering meetings at BioSquare 2006 conference, Mar. 8-10, 2006, Geneva, Switzerland.
Slides/Handout by Reata Pharmaceuticals, "RTA 402, Therapeutic Properties II", Private partnering meetings at BIO 2006 conference, Apr. 9-12, 2006, Chicago, Illinois.
Slides/Handout by Reata Pharmaceuticals, "RTA 402, Therapeutic Properties IV", Private partnering meetings at BioPartnering Europe 2006 conference, Oct. 8-10, 2006, London, England.

(56) References Cited

OTHER PUBLICATIONS

Slides/Handout by Reata Pharmaceuticals, "RTA 402, Therapeutic Properties IX", Private partnering meeting at BIO Europe 2007 conference, Nov. 12-14, 2007, Hamburg, Germany.
Slides/Handout by Reata Pharmaceuticals, "RTA 402, Therapeutic Properties V", Private partnering meetings at BIO 2007 conference, May 6-9, 2007, Boston, Massachusetts.
Slides/Handout by Reata Pharmaceuticals, "RTA 402, Therapeutic Properties VI", Private partnering meetings at BIO 2007 conference, May 6-9, 2007, Boston, Massachusetts.
Slides/Handout by Reata Pharmaceuticals, "RTA 402, Therapeutic Properties VII", Podium presentation at BIO 2007 conference, May 6-9, 2007, Boston, Massachusetts.
Slides/Handout by Reata Pharmaceutical, "RTA 402, Therapeutic Properties VIII", Private partnering meetings at BIO Europe 2007 conference, Nov. 12-14, 2007, Hamburg, Germany.
Sporn, et al., "Prospects for prevention and treatment of cancer with selective PPARγ modulators (SPARMs)", *Trends in Molecular Medicine*, 7(9):395-400, 2001.
Sporn and Roberts, "Peptide growth factors and inflammation, tissue repair, and cancer", *J. Clin. Invest.*, 78:329-332, 1986.
Subba Rao, et al., "Chemical modifications of natural triterpenes-glycyrrhetinic and boswellic acids: evaluation of their biological activity", *Tetrahedron*, 64:11541-11548, 2008.
Sun, et al., "Therapeutic potential of synthetic triterpenoids in neuroblastoma", *Cancer Biology & Therapy*, 7(5):720-7, 2008.
Sussan, et al., "Targeting Nrf2 with the triterpenoid CDDO-imidazolide attenuate cigarette smoke-induced emphysema and cardiac dysfunction in mice", *Proc. Nat. Sci. Acad. USA*, 106:250-255, 2009.
Thimmulappa, et al., "Nrf2 is a critical regulator of the innate immune response and survival during experimental sepsis", *J. Clinical Investigations*, 116(4):984-995, 2006.

To, et al., "The synthetic triterpenoid 2-cyano-3,12-dioxooleana-1,9-dien-28-oic acid-imidazolide alters transforming growth factor B-dependent signaling and cell migration by affecting the cytoskeleton and the polarity complex", *J. Biol. Chem.*, 283:11700-11713, 2008.
Vannini, et al., "The synthetic oleanane triterpenoid, CDDO-methyl ester, is a potent antiangiogenic agent", *Molecular Cancer Therapeutics*, 6(12 Part 1):3139-3146, 2007.
Vazquez, et al., "Human immunodeficiency virus type 1-induced macrophage gene expression includes the p21 gene, a target for viral regulation", *J. Virol.*, 79:4479-4491, 2005.
Vene, et al., "Glycogen synthase kinase 3B regulates cell death by synthetic triterpenoids", *Cancer Research*, 68(17):6987-6996, 2008.
Vilayur and Harris, "Emerging therapies for chronic kidney disease: what is their role?", *Nature Reviews*, 5:375-383, 2009.
Vincenti, et al., "The synthetic triterpenoid TP-222 inhibits RANKL induction of differentiation and MMP-9 gene expression in osteoclasts", Abstract 1385, American College of Rheumatology Annual Scientific Meeting, 2006.
Wang, "Differentiating and anti-inflammatory activities of the triterpenoid, CDDO," Thesis, Dartmouth College, May 4, 2001.
Xu, et al., "Inhibition of the signal transducer and activator of transcription-3 (STAT3) signaling pathway by 4-oxo-l-phenyl-1,4-dihydroquinoline-3-carboxylic acid esters", *J. Med. Chem.*, 51:4115-4121, 2008.
Zou, et al., "c-FLIP downregulation contributes to apoptosis induction by the novel synthetic triterpenoid methyl-2-cyano-3,12-dioxooleana-1,9-dien-28-oate (CDDO-Me) in human lung cancer cells", *Cancer Biology & Therapy*, 6(10):1614-1620, 2007.
Zou, et al., "Coupling of Endoplasmic Reticulum Stress to CDDO-Me-Induced Up-Regulation of Death Receptor 5 via a CHOP-Dependent mechanism involving JNK activation", *Cancer Research*, 68(18):7484-7492, 2008.

\* cited by examiner

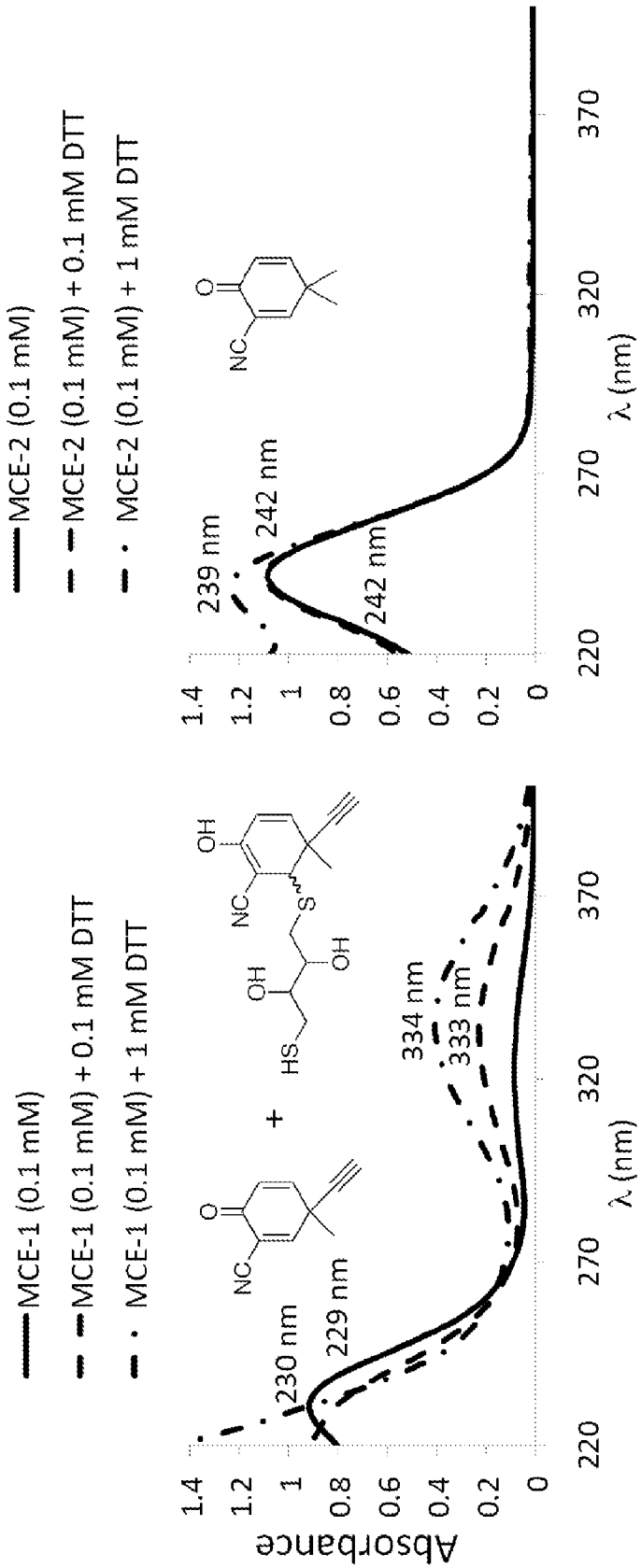

MONOCYCLIC CYANOENONES AND METHODS OF USE THEREOF

The present application is a continuation of U.S. patent application Ser. No. 13/055,418, filed Apr. 28, 2011, which is a national phase application under 35 U.S.C. §371 of International Patent Application No. PCT/US2009/051447 filed Jul. 22, 2009, which claims the benefit of priority to U.S. Provisional Application No. 61/082,550, filed Jul. 22, 2008, the entire contents of each of which are incorporated by reference in their entirety without disclaimer.

BACKGROUND OF THE INVENTION

I. Field of the Invention

The present invention relates generally to the fields of biology and medicine. More particularly, it concerns compounds and methods for the treatment and prevention of diseases such as those associated with oxidative stress and inflammation.

II. Description of Related Art

The IκB kinases, IKKα and IKKβ, are related kinases that play a major role in the activation and regulation of the transcription factor, NF-κB. They are induced by stimuli such as TNFα and IL-1 to phosphorylate residue $Ser^{32}$ and $Ser^{36}$ of IκBα, the regulatory subunit of NF-κB. The IκB kinase (IKK) complex comprises three proteins: the catalytic subunits, IKKα and IKKβ, and the regulatory subunit, IKKγ (NEMO). Without being bound by any particular mechanism or theory, the phosphorylation of IκBα results in ubiquitination and subsequent degradation in the proteasome. This releases NF-κB dimers from the cytoplastic NF-κB-IκB complex, allowing NF-κB to translocate to the nucleus where it regulates the transcription of numerous target genes. IKKβ appears to be the principal kinase, whereas IKKα is not required for activation of IKK and degradation of IκBα by proinflammatory stimuli. IKKβ triggers the activation of NF-κB in response to infectious agents and proinflammatory cytokines, making it an attractive drug target for the treatment of inflammatory diseases. In addition, NF-κB is over-expressed or constitutively activated in many cancer cells where it induces the expression of anti-apototic genes and/or suppression of pro-apototic genes. A number of anticancer agents can also induce the activation of NF-κB, which may culminate in the ability of the malignant cell to become drug resistant. Thus, the development of IKKβ inhibitors represents potential therapeutics for the treatment of both cancer and inflammation (Karin et al., 2004).

The anti-inflammatory and anti-proliferative activity of the naturally occurring triterpenoid, oleanolic acid, has been improved by chemical modifications. For example, 2-cyano-3,12-dioxooleana-1,9(11)-dien-28-oic acid (CDDO) and related compounds have been developed (Honda et al., 1997; Honda et al., 1998; Honda et al., 1999; Honda et al., 2000; Honda et al., 2000; Honda, et al., 2002; Suh et al. 1998; Suh et al., 1999; Place et al., 2003; Liby et al., 2005). The methyl ester, CDDO-Me, is currently being evaluated in phase II clinical trials for the treatment of melanoma, pancreatic cancer, diabetic nephropathy and chronic kidney disease.

Three-ringed compounds, whose rings A and C have enone functionalities similar to those of CDDO, have been shown to be a novel class of potent anti-inflammatory, cytoprotective, growth suppressive, and proapoptotic compounds (Favaloro et al., 2002; Honda et al., 2003; Honda et al., 2007). Among these compounds, TBE-31 was found to inhibit nitric oxide (NO) production at low nanomolecular concentrations in RAW cells stimulated by interferon-γ (iNOS assay). Notably, orally active TBE-31 is exceptionally potent against aflatoxin-induced liver cancer in rats (Liby et al., 2008). Furthermore, in vitro and in vivo potencies of TBE-31 are much higher than those of CDDO.

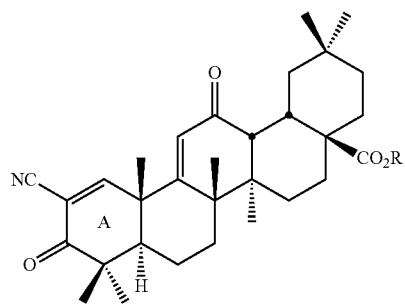

CDDO

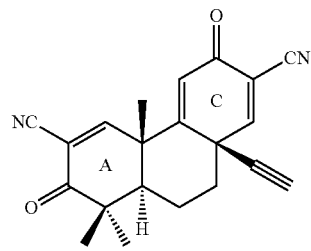

TBE-31

Both CDDO and TBE-31 are multifunctional agents, which regulate proteins involved in inflammation, oxidative stress, differentiation, apoptosis, and proliferation. Without being bound by any particular mechanism or theory, these proteins, including, e.g., IKKβ, Keap1, and JAK1, are regulated by CDDO and TBE-31 by reversible and selective Michael addition between their cyanoenone functionality and the SH groups of cysteine residues on these proteins (Scheme 1); Couch et al., 2005; Dinkova-Kostova et al., 2005). For example, $Cys^{179}$ on IKKβ was identified as one of targets of CDDO-Me (Ahmad et al., 2006). By binding to this site, CDDO-Me blocks the binding of NF-κB to DNA and thus inhibits transcriptional activation. It has also been reported that CDDO-Me inhibits the JAK1→STAT3 pathway by directly binding to JAK1 at $Cys^{1077}$ and STAT3 at $Cys^{259}$ (Ahmad et al., 2008). The small molecule inhibitors of the STAT3 pathway are effective as anticancer agents in vitro and in animal models.

Scheme 1:

Cysteine moiety

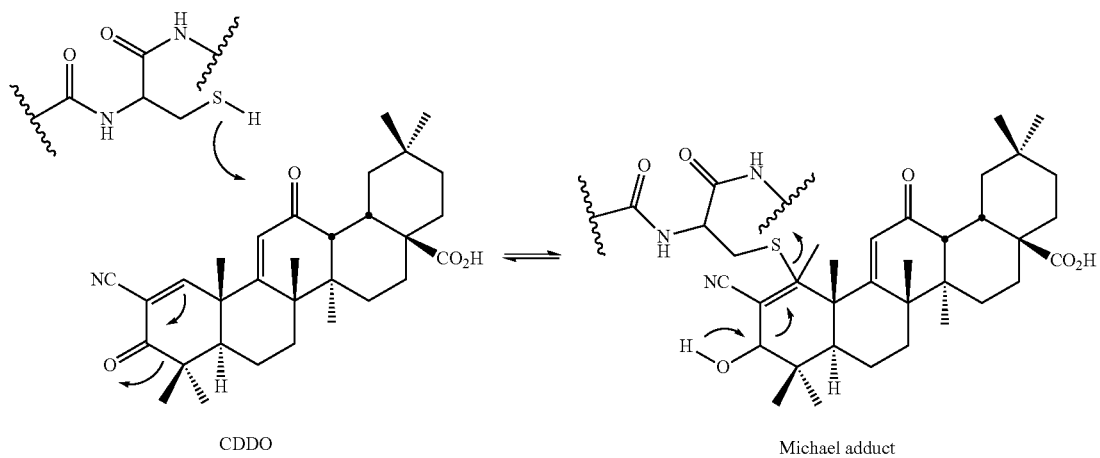

CDDO            Michael adduct

Synthetic triterpenoid analogs of oleanolic acid have also been shown to be inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference. For example, one of these, 2-cyano-3,12-dioxooleane-1,9(11)-dien-28-oic acid methyl ester (CDDO-Me), is currently in clinical trials for a variety of disorders related to inflammation, including cancer and diabetic nephropathy. Synthetic derivatives of another triterpenoid, betulinic acid, have also been shown to inhibit cellular inflammatory processes, although these compounds have been less extensively characterized (Honda et al., 2006). The pharmacology of these synthetic triterpenoid molecules is complex. Compounds derived from oleanolic acid have been shown to affect the function of multiple protein targets and thereby modulate the activity of several important cellular signaling pathways related to oxidative stress, cell cycle control, and inflammation (e.g., Dinkova-Kostova et al., 2005; Ahmad et al., 2006; Ahmad et al., 2008; Liby et al., 2007a). Derivatives of betulinic acid, though they have shown comparable anti-inflammatory properties, also appear to have significant differences in their pharmacology compared to OA-derived compounds (Liby et al., 2007b). Further, it is not certain that the triterpenoid starting materials employed to date have optimal properties compared to other possible starting materials. Given that the biological activity profiles of known triterpenoid derivatives vary, and in view of the wide variety of diseases that may be treated or prevented with compounds having potent antioxidant and anti-inflammatory effects, and the high degree of unmet medical need represented within this variety of diseases, it is desirable to synthesize new compounds with diverse structures that may have improved biological activity profiles for the treatment of one or more indications.

SUMMARY OF THE INVENTION

The present disclosure provides new monocyclic cyano enones (MCEs) antioxidant and anti-inflammatory properties, methods for their manufacture, and methods for their use.

In some aspects, the disclosure provides compounds of the formula:

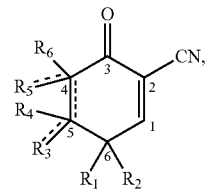

wherein:
$R_1$, $R_2$, $R_3$, $R_4$, $R_5$ and $R_6$ are each independently:
hydrogen, hydroxy, amino, cyano, or
alkyl$_{(C \leq 18)}$, alkenyl$_{(C \leq 18)}$, alkynyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, acyl$_{(C \leq 18)}$, alkoxy$_{(C \leq 18)}$, alkenyloxy$_{(C \leq 18)}$, alkynyloxy$_{(C \leq 18)}$, aryloxy$_{(C \leq 18)}$, aralkoxy$_{(C \leq 18)}$, heteroaryloxy$_{(C \leq 18)}$, heteroaralkoxy$_{(C \leq 18)}$, acyloxy$_{(C \leq 18)}$, alkylamino$_{(C \leq 18)}$, dialkylamino$_{(C \leq 18)}$, alkoxyamino$_{(C \leq 18)}$, alkenylamino$_{(C \leq 18)}$, alkynylamino$_{(C \leq 18)}$, arylamino$_{(C \leq 18)}$, aralkylamino$_{(C \leq 18)}$, heteroarylamino$_{(C \leq 18)}$, heteroaralkylamino$_{(C \leq 18)}$, alkylsulfonylamino$_{(C \leq 18)}$, amido$_{(C \leq 18)}$, alkylideneamino$_{(C \leq 18)}$, aralkylideneamino$_{(C \leq 18)}$;
$R_1$ and $R_3$ are taken together and are alkanediyl$_{(C \leq 18)}$, alkenediyl$_{(C \leq 18)}$, arenediyl$_{(C \leq 18)}$, alkoxydiyl$_{(C \leq 18)}$, alkenyloxydiyl$_{(C \leq 18)}$, alkylaminodiyl$_{(C \leq 18)}$, alkenylaminodiyl$_{(C \leq 18)}$, alkenylaminooxydiyl$_{(C \leq 18)}$, alkenylaminothiodiyl$_{(C \leq 18)}$, with $R_2$, $R_4$, $R_5$ and $R_6$ as defined above; or
$R_3$ and $R_5$ are taken together and are alkanediyl$_{(C \leq 18)}$, alkenediyl$_{(C \leq 18)}$, arenediyl$_{(C \leq 18)}$, alkoxydiyl$_{(C \leq 18)}$, alkenyloxydiyl$_{(C \leq 18)}$, alkylaminodiyl$_{(C \leq 18)}$, alkenylaminodiyl$_{(C \leq 18)}$, alkenylaminooxydiyl$_{(C \leq 18)}$, alkenylaminothiodiyl$_{(C \leq 18)}$, with $R_1$, $R_2$, $R_4$ and $R_6$ as defined above;
provided that: $R_4$ is absent when the atom to which it is bound forms part of a double bond; $R_6$ is absent when the atom to which it is bound forms part of a double bond; neither $R_1$ nor $R_2$ is hydrogen; and $R_1$ and $R_2$ are not both methyl;

or pharmaceutically acceptable salts, tautomers, prodrugs, or optical isomers thereof.

In some embodiments, the disclosure provides compounds of the formula:

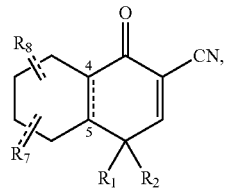

wherein:
R₁ and R₂ are each independently:
hydroxy, amino, cyano, or
alkyl$_{(C\leq 18)}$, alkenyl$_{(C\leq 18)}$, alkynyl$_{(C\leq 18)}$, aryl$_{(C\leq 18)}$, aralkyl$_{(C\leq 18)}$, heteroaryl$_{(C\leq 18)}$, heteroaralkyl$_{(C\leq 18)}$, acyl$_{(C\leq 18)}$, alkoxy$_{(C\leq 18)}$, alkenyloxy$_{(C\leq 18)}$, alkynyloxy$_{(C\leq 18)}$, aryloxy$_{(C\leq 18)}$, aralkoxy$_{(C\leq 18)}$, heteroaryloxy$_{(C\leq 18)}$, heteroaralkoxy$_{(C\leq 18)}$, acyloxy$_{(C\leq 18)}$, alkylamino$_{(C\leq 18)}$, dialkylamino$_{(C\leq 18)}$, alkoxyamino$_{(C\leq 18)}$, alkenylamino$_{(C\leq 18)}$, alkynylamino$_{(C\leq 18)}$, arylamino$_{(C\leq 18)}$, aralkylamino$_{(C\leq 18)}$, heteroarylamino$_{(C\leq 18)}$, heteroaralkylamino$_{(C\leq 18)}$, alkylsulfonylamino$_{(C\leq 18)}$, amido$_{(C\leq 18)}$, alkylideneamino$_{(C\leq 18)}$, aralkylideneamino$_{(C\leq 18)}$, provided that R₁ and R₂ are not both methyl; and
R₇ and R₈ are each independently:
hydrogen, hydroxy, halo, oxo, amino, hydroxyamino, nitro, imino, cyano, azido, mercapto, or thio; or
alkyl$_{(C\leq 6)}$, alkenyl$_{(C\leq 6)}$, alkynyl$_{(C\leq 6)}$, aryl$_{(C\leq 6)}$, aralkyl$_{(C\leq 6)}$, heteroaryl$_{(C\leq 6)}$, heteroaralkyl$_{(C\leq 6)}$, acyl$_{(C\leq 6)}$, alkylidene$_{(C\leq 6)}$, alkoxy$_{(C\leq 6)}$, alkenyloxy$_{(C\leq 6)}$, alkynyloxy$_{(C\leq 6)}$, aryloxy$_{(C\leq 6)}$, aralkoxy$_{(C\leq 6)}$, heteroaryloxy$_{(C\leq 6)}$, heteroaralkoxy$_{(C\leq 6)}$, acyloxy$_{(C\leq 6)}$, alkylamino$_{(C\leq 6)}$, dialkylamino$_{(C\leq 6)}$, alkoxyamino$_{(C\leq 6)}$, alkenylamino$_{(C\leq 6)}$, alkynylamino$_{(C\leq 6)}$, arylamino$_{(C\leq 6)}$, aralkylamino$_{(C\leq 6)}$, heteroarylamino$_{(C\leq 6)}$, heteroaralkylamino$_{(C\leq 6)}$, alkylsulfonylamino$_{(C\leq 6)}$, amido$_{(C\leq 6)}$, alkylimino$_{(C\leq 6)}$, alkenylimino$_{(C\leq 6)}$, alkynylimino$_{(C\leq 6)}$, arylimino$_{(C\leq 6)}$, aralkylimino$_{(C\leq 6)}$, heteroarylimino$_{(C\leq 6)}$, heteroaralkylimino$_{(C\leq 6)}$, acylimino$_{(C\leq 6)}$, alkylthio$_{(C\leq 6)}$, alkenylthio$_{(C\leq 6)}$, alkynylthio$_{(C\leq 6)}$, arylthio$_{(C\leq 6)}$, aralkylthio$_{(C\leq 6)}$, heteroarylthio$_{(C\leq 6)}$, heteroaralkylthio$_{(C\leq 6)}$, acylthio$_{(C\leq 6)}$, thioacyl$_{(C\leq 6)}$, alkylsulfonyl$_{(C\leq 6)}$, alkenylsulfonyl$_{(C\leq 6)}$, alkynylsulfonyl$_{(C\leq 6)}$, arylsulfonyl$_{(C\leq 6)}$, aralkylsulfonyl$_{(C\leq 6)}$, heteroarylsulfonyl$_{(C\leq 6)}$, heteroaralkylsulfonyl$_{(C\leq 6)}$, alkylammonium$_{(C\leq 6)}$, alkylsulfonium$_{(C\leq 6)}$, alkylsilyl$_{(C\leq 6)}$, alkylsilyloxy$_{(C\leq 6)}$, or a substituted version of any of these groups;
or pharmaceutically acceptable salts, tautomers, prodrugs, or optical isomers thereof.

In some embodiments, the disclosure provides compounds of the formula:

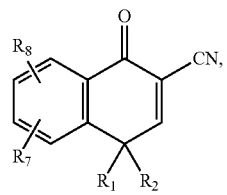

wherein:
R₁ and R₂ are each independently:
hydroxy, amino, cyano, or
alkyl$_{(C\leq 18)}$, alkenyl$_{(C\leq 18)}$, alkynyl$_{(C\leq 18)}$, aryl$_{(C\leq 18)}$, aralkyl$_{(C\leq 18)}$, heteroaryl$_{(C\leq 18)}$, heteroaralkyl$_{(C\leq 18)}$, acyl$_{(C\leq 18)}$, alkoxy$_{(C\leq 18)}$, alkenyloxy$_{(C\leq 18)}$, alkynyloxy$_{(C\leq 18)}$, aryloxy$_{(C\leq 18)}$, aralkoxy$_{(C\leq 18)}$, heteroaryloxy$_{(C\leq 18)}$, heteroaralkoxy$_{(C\leq 18)}$, acyloxy$_{(C\leq 18)}$, alkylamino$_{(C\leq 18)}$, dialkylamino$_{(C\leq 18)}$, alkoxyamino$_{(C\leq 18)}$, alkenylamino$_{(C\leq 18)}$, alkynylamino$_{(C\leq 18)}$, arylamino$_{(C\leq 18)}$, aralkylamino$_{(C\leq 18)}$, heteroarylamino$_{(C\leq 18)}$, heteroaralkylamino$_{(C\leq 18)}$, alkylsulfonylamino$_{(C\leq 18)}$, amido$_{(C\leq 18)}$, alkylideneamino$_{(C\leq 18)}$, aralkylideneamino$_{(C\leq 18)}$, provided that R₁ and R₂ are not both methyl; and
R₇ and R₈ are each independently:
hydrogen, hydroxy, halo, amino, hydroxyamino, nitro, cyano, azido, or mercapto; or
alkyl$_{(C\leq 6)}$, alkenyl$_{(C\leq 6)}$, alkynyl$_{(C\leq 6)}$, aryl$_{(C\leq 6)}$, aralkyl$_{(C\leq 6)}$, heteroaryl$_{(C\leq 6)}$, heteroaralkyl$_{(C\leq 6)}$, acyl$_{(C\leq 6)}$, alkoxy$_{(C\leq 6)}$, alkenyloxy$_{(C\leq 6)}$, alkynyloxy$_{(C\leq 6)}$, aryloxy$_{(C\leq 6)}$, aralkoxy$_{(C\leq 6)}$, heteroaryloxy$_{(C\leq 6)}$, heteroaralkoxy$_{(C\leq 6)}$, acyloxy$_{(C\leq 6)}$, alkylamino$_{(C\leq 6)}$, dialkylamino$_{(C\leq 6)}$, alkoxyamino$_{(C\leq 6)}$, alkenylamino$_{(C\leq 6)}$, alkynylamino$_{(C\leq 6)}$, arylamino$_{(C\leq 6)}$, aralkylamino$_{(C\leq 6)}$, heteroarylamino$_{(C\leq 6)}$, heteroaralkylamino$_{(C\leq 6)}$, amido$_{(C\leq 6)}$, alkylsilyl$_{(C\leq 6)}$, alkylsilyloxy$_{(C\leq 6)}$, or a substituted version of any of these groups;
or pharmaceutically acceptable salts, tautomers, prodrugs, or optical isomers thereof.

In some embodiments, the disclosure provides compounds of the formula:

amino$_{(C \leq 18)}$, aralkylideneamino$_{(C \leq 18)}$, provided that R$_1$ and R$_2$ are not both methyl; and R$_7$ and R$_8$ are each independently:

hydrogen, hydroxy, halo, amino, hydroxyamino, nitro, cyano, azido, or mercapto; or alkyl$_{(C \leq 6)}$, alkenyl$_{(C \leq 6)}$, alkynyl$_{(C \leq 6)}$, aryl$_{(C \leq 6)}$, aralkyl$_{(C \leq 6)}$, heteroaryl$_{(C \leq 6)}$, heteroaralkyl$_{(C \leq 6)}$, acyl$_{(C \leq 6)}$, alkoxy$_{(C \leq 6)}$, alkenyloxy$_{(C \leq 6)}$, alkynyloxy$_{(C \leq 6)}$, aryloxy$_{(C \leq 6)}$, aralkoxy$_{(C \leq 6)}$, heteroaryloxy$_{(C \leq 6)}$, heteroaralkoxy$_{(C \leq 6)}$, acyloxy$_{(C \leq 6)}$, alkylamino$_{(C \leq 6)}$, dialkylamino$_{(C \leq 6)}$, alkoxyamino$_{(C \leq 6)}$, alkenylamino$_{(C \leq 6)}$, alkynylamino$_{(C \leq 6)}$, arylamino$_{(C \leq 6)}$, aralkylamino$_{(C \leq 6)}$, heteroarylamino$_{(C \leq 6)}$, heteroaralkylamino$_{(C \leq 6)}$, amido$_{(C \leq 6)}$, alkylsilyl$_{(C \leq 6)}$, alkylsilyloxy$_{(C \leq 6)}$, or a substituted version of any of these groups;

or pharmaceutically acceptable salts, tautomers, prodrugs, or optical isomers thereof.

In some embodiments, the disclosure provides compounds of the formula:

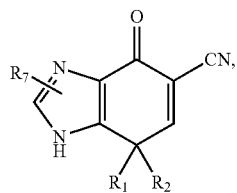

wherein:

R$_1$ and R$_2$ are each independently:

hydroxy, amino, cyano, or alkyl$_{(C \leq 18)}$, alkenyl$_{(C \leq 18)}$, alkynyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, acyl$_{(C \leq 18)}$, alkoxy$_{(C \leq 18)}$, alkenyloxy$_{(C \leq 18)}$, alkynyloxy$_{(C \leq 18)}$, aryloxy$_{(C \leq 18)}$, aralkoxy$_{(C \leq 18)}$, heteroaryloxy$_{(C \leq 18)}$, heteroaralkoxy$_{(C \leq 18)}$, acyloxy$_{(C \leq 18)}$, alkylamino$_{(C \leq 18)}$, dialkylamino$_{(C \leq 18)}$, alkoxyamino$_{(C \leq 18)}$, alkenylamino$_{(C \leq 18)}$, alkynylamino$_{(C \leq 18)}$, arylamino$_{(C \leq 18)}$, aralkylamino$_{(C \leq 18)}$, heteroarylamino$_{(C \leq 18)}$, heteroaralkylamino$_{(C \leq 18)}$, alkylsulfonylamino$_{(C \leq 18)}$, amido$_{(C \leq 18)}$, alkylideneamino$_{(C \leq 18)}$, aralkylideneamino$_{(C \leq 18)}$, provided that R$_1$ and R$_2$ are not both methyl; and R$_7$ is:

hydrogen, hydroxy, halo, amino, hydroxyamino, nitro, cyano, azido, or mercapto; or alkyl$_{(C \leq 6)}$, alkenyl$_{(C \leq 6)}$, alkynyl$_{(C \leq 6)}$, aryl$_{(C \leq 6)}$, aralkyl$_{(C \leq 6)}$, heteroaryl$_{(C \leq 6)}$, heteroaralkyl$_{(C \leq 6)}$, acyl$_{(C \leq 6)}$, alkoxy$_{(C \leq 6)}$, alkenyloxy$_{(C \leq 6)}$, alkynyloxy$_{(C \leq 6)}$, aryloxy$_{(C \leq 6)}$, aralkoxy$_{(C \leq 6)}$, heteroaryloxy$_{(C \leq 6)}$, heteroaralkoxy$_{(C \leq 6)}$, acyloxy$_{(C \leq 6)}$, alkylamino$_{(C \leq 6)}$, dialkylamino$_{(C \leq 6)}$, alkoxyamino$_{(C \leq 6)}$, alkenylamino$_{(C \leq 6)}$, alkynylamino$_{(C \leq 6)}$, arylamino$_{(C \leq 6)}$, aralkylamino$_{(C \leq 6)}$, heteroarylamino$_{(C \leq 6)}$, heteroaralkylamino$_{(C \leq 6)}$, amido$_{(C \leq 6)}$, alkylsilyl$_{(C \leq 6)}$, alkylsilyloxy$_{(C \leq 6)}$, or a substituted version of any of these groups;

or pharmaceutically acceptable salts, tautomers, prodrugs, or optical isomers thereof.

In some embodiments, the disclosure provides compounds of the formula:

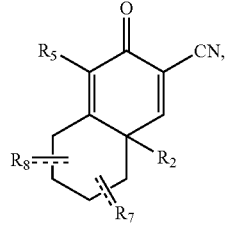

wherein:

R$_2$ and R$_5$ are each independently:

hydrogen, hydroxy, amino, cyano, or alkyl$_{(C \leq 18)}$, alkenyl$_{(C \leq 18)}$, alkynyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, acyl$_{(C \leq 18)}$, alkoxy$_{(C \leq 18)}$, alkenyloxy$_{(C \leq 18)}$, alkynyloxy$_{(C \leq 18)}$, aryloxy$_{(C \leq 18)}$, aralkoxy$_{(C \leq 18)}$, heteroaryloxy$_{(C \leq 18)}$, heteroaralkoxy$_{(C \leq 18)}$, acyloxy$_{(C \leq 18)}$, alkylamino$_{(C \leq 18)}$, dialkylamino$_{(C \leq 18)}$, alkoxyamino$_{(C \leq 18)}$, alkenylamino$_{(C \leq 18)}$, alkynylamino$_{(C \leq 18)}$, arylamino$_{(C \leq 18)}$, aralkylamino$_{(C \leq 18)}$, heteroarylamino$_{(C \leq 18)}$, heteroaralkylamino$_{(C \leq 18)}$, alkylsulfonylamino$_{(C \leq 18)}$, amido$_{(C \leq 18)}$, alkylideneamino$_{(C \leq 18)}$, aralkylideneamino$_{(C \leq 18)}$, provided that R$_2$ is not hydrogen; and R$_7$ and R$_8$ are each independently:

hydrogen, hydroxy, halo, oxo, amino, hydroxyamino, nitro, imino, cyano, azido, mercapto, or thio; or alkyl$_{(C \leq 6)}$, alkenyl$_{(C \leq 6)}$, alkynyl$_{(C \leq 6)}$, aryl$_{(C \leq 6)}$, aralkyl$_{(C \leq 6)}$, heteroaryl$_{(C \leq 6)}$, heteroaralkyl$_{(C \leq 6)}$, acyl$_{(C \leq 6)}$, alkylidene$_{(C \leq 6)}$, alkoxy$_{(C \leq 6)}$, alkenyloxy$_{(C \leq 6)}$, alkynyloxy$_{(C \leq 6)}$, aryloxy$_{(C \leq 6)}$, aralkoxy$_{(C \leq 6)}$, heteroaryloxy$_{(C \leq 6)}$, heteroaralkoxy$_{(C \leq 6)}$, acyloxy$_{(C \leq 6)}$, alkylamino$_{(C \leq 6)}$, dialkylamino$_{(C \leq 6)}$, alkoxyamino$_{(C \leq 6)}$, alkenylamino$_{(C \leq 6)}$, alkynylamino$_{(C \leq 6)}$, arylamino$_{(C \leq 6)}$, aralkylamino$_{(C \leq 6)}$, heteroarylamino$_{(C \leq 6)}$, heteroaralkylamino$_{(C \leq 6)}$, alkylsulfonylamino$_{(C \leq 6)}$, amido$_{(C \leq 6)}$, alkylimino$_{(C \leq 6)}$, alkenylimino$_{(C \leq 6)}$, alkynylimino$_{(C \leq 6)}$, arylimino$_{(C \leq 6)}$, aralkylimino$_{(C \leq 6)}$, heteroarylimino$_{(C \leq 6)}$, heteroaralkylimino$_{(C \leq 6)}$, acylimino$_{(C \leq 6)}$, alkylthio$_{(C \leq 6)}$, alkenylthio$_{(C \leq 6)}$, alkynylthio$_{(C \leq 6)}$, arylthio$_{(C \leq 6)}$, aralkylthio$_{(C \leq 6)}$, heteroarylthio$_{(C \leq 6)}$, heteroaralkylthio$_{(C \leq 6)}$, acylthio$_{(C \leq 6)}$, thioacyl$_{(C \leq 6)}$, alkylsulfonyl$_{(C \leq 6)}$, alkenylsulfonyl$_{(C \leq 6)}$, alkynylsulfonyl$_{(C \leq 6)}$, arylsulfonyl$_{(C \leq 6)}$, aralkylsulfonyl$_{(C \leq 6)}$, heteroarylsulfonyl$_{(C \leq 6)}$, heteroaralkylsulfonyl$_{(C \leq 6)}$, alkylammonium$_{(C \leq 6)}$, alkylsulfonium$_{(C \leq 6)}$, alkylsilyl$_{(C \leq 6)}$, alkylsilyloxy$_{(C \leq 6)}$, or a substituted version of any of these groups;

or pharmaceutically acceptable salts, tautomers, prodrugs, or optical isomers thereof.

In some embodiments, the disclosure provides compounds of the formula:

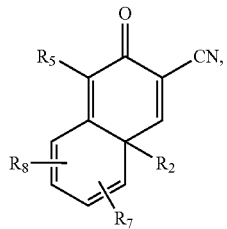

wherein:

$R_2$ and $R_5$ are each independently:

hydrogen, hydroxy, amino, cyano, or alkyl$_{(C\le18)}$, alkenyl$_{(C\le18)}$, alkynyl$_{(C\le18)}$, aryl$_{(C\le18)}$, aralkyl$_{(C\le18)}$, heteroaryl$_{(C\le18)}$, heteroaralkyl$_{(C\le18)}$, acyl$_{(C\le18)}$, alkoxy$_{(C\le18)}$, alkenyloxy$_{(C\le18)}$, alkynyloxy$_{(C\le18)}$, aryloxy$_{(C\le18)}$, aralkoxy$_{(C\le18)}$, heteroaryloxy$_{(C\le18)}$, heteroaralkoxy$_{(C\le18)}$, acyloxy$_{(C\le18)}$, alkylamino$_{(C\le18)}$, dialkylamino$_{(C\le18)}$, alkoxyamino$_{(C\le18)}$, alkenylamino$_{(C\le18)}$, alkynylamino$_{(C\le18)}$, arylamino$_{(C\le18)}$, aralkylamino$_{(C\le18)}$, heteroarylamino$_{(C\le18)}$, heteroaralkylamino$_{(C\le18)}$, alkylsulfonylamino$_{(C\le18)}$, amido$_{(C\le18)}$, alkylideneamino$_{(C\le18)}$, aralkylideneamino$_{(C\le18)}$, provided that $R_2$ is not hydrogen; and $R_7$ and $R_8$ are each independently:

hydrogen, hydroxy, halo, amino, hydroxyamino, nitro, cyano, azido, or mercapto; or alkyl$_{(C\le6)}$, alkenyl$_{(C\le6)}$, alkynyl$_{(C\le6)}$, aryl$_{(C\le6)}$, aralkyl$_{(C\le6)}$, heteroaryl$_{(C\le6)}$, heteroaralkyl$_{(C\le6)}$, acyl$_{(C\le6)}$, alkoxy$_{(C\le6)}$, alkenyloxy$_{(C\le6)}$, alkynyloxy$_{(C\le6)}$, aryloxy$_{(C\le6)}$, aralkoxy$_{(C\le6)}$, heteroaryloxy$_{(C\le6)}$, heteroaralkoxy$_{(C\le6)}$, acyloxy$_{(C\le6)}$, alkylamino$_{(C\le6)}$, dialkylamino$_{(C\le6)}$, alkoxyamino$_{(C\le6)}$, alkenylamino$_{(C\le6)}$, alkynylamino$_{(C\le6)}$, arylamino$_{(C\le6)}$, aralkylamino$_{(C\le6)}$, heteroarylamino$_{(C\le6)}$, heteroaralkylamino$_{(C\le6)}$, amido$_{(C\le6)}$, alkylsilyl$_{(C\le6)}$, alkylsilyloxy$_{(C\le6)}$, or a substituted version of any of these groups;

or pharmaceutically acceptable salts, tautomers, prodrugs, or optical isomers thereof.

In some embodiments, the disclosure provides compounds of the formula:

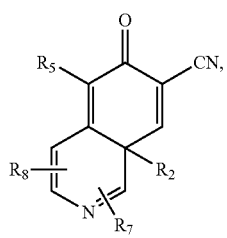

wherein:

$R_2$ and $R_5$ are each independently:

hydrogen, hydroxy, amino, cyano, or alkyl$_{(C\le18)}$, alkenyl$_{(C\le18)}$, alkynyl$_{(C\le18)}$, aryl$_{(C\le18)}$, aralkyl$_{(C\le18)}$, heteroaryl$_{(C\le18)}$, heteroaralkyl$_{(C\le18)}$, acyl$_{(C\le18)}$, alkoxy$_{(C\le18)}$, alkenyloxy$_{(C\le18)}$, alkynyloxy$_{(C\le18)}$, aryloxy$_{(C\le18)}$, aralkoxy$_{(C\le18)}$, heteroaryloxy$_{(C\le18)}$, heteroaralkoxy$_{(C\le18)}$, acyloxy$_{(C\le18)}$, alkylamino$_{(C\le18)}$, dialkylamino$_{(C\le18)}$, alkoxyamino$_{(C\le18)}$, alkenylamino$_{(C\le18)}$, alkynylamino$_{(C\le18)}$, arylamino$_{(C\le18)}$, aralkylamino$_{(C\le18)}$, heteroarylamino$_{(C\le18)}$, heteroaralkylamino$_{(C\le18)}$, alkylsulfonylamino$_{(C\le18)}$, amido$_{(C\le18)}$, alkylideneamino$_{(C\le18)}$, aralkylideneamino$_{(C\le18)}$, provided that $R_2$ is not hydrogen; and $R_7$ and $R_8$ are each independently:

hydrogen, hydroxy, halo, amino, hydroxyamino, nitro, cyano, azido, or mercapto; or alkyl$_{(C\le6)}$, alkenyl$_{(C\le6)}$, alkynyl$_{(C\le6)}$, aryl$_{(C\le6)}$, aralkyl$_{(C\le6)}$, heteroaryl$_{(C\le6)}$, heteroaralkyl$_{(C\le6)}$, acyl$_{(C\le6)}$, alkoxy$_{(C\le6)}$, alkenyloxy$_{(C\le6)}$, alkynyloxy$_{(C\le6)}$, aryloxy$_{(C\le6)}$, aralkoxy$_{(C\le6)}$, heteroaryloxy$_{(C\le6)}$, heteroaralkoxy$_{(C\le6)}$, acyloxy$_{(C\le6)}$, alkylamino$_{(C\le6)}$, dialkylamino$_{(C\le6)}$, alkoxyamino$_{(C\le6)}$, alkenylamino$_{(C\le6)}$, alkynylamino$_{(C\le6)}$, arylamino$_{(C\le6)}$, aralkylamino$_{(C\le6)}$, heteroarylamino$_{(C\le6)}$, heteroaralkylamino$_{(C\le6)}$, amido$_{(C\le6)}$, alkylsilyl$_{(C\le6)}$, alkylsilyloxy$_{(C\le6)}$, or a substituted version of any of these groups;

or pharmaceutically acceptable salts, tautomers, prodrugs, or optical isomers thereof.

In some embodiments, the disclosure provides compounds of the formula:

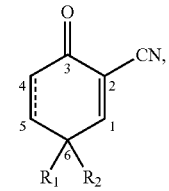

wherein:

$R_1$ and $R_2$ are independently:

hydroxy, amino, cyano, or alkyl$_{(C\le18)}$, alkenyl$_{(C\le18)}$, alkynyl$_{(C\le18)}$, aryl$_{(C\le18)}$, aralkyl$_{(C\le18)}$, heteroaryl$_{(C\le18)}$, heteroaralkyl$_{(C\le18)}$, acyl$_{(C\le18)}$, alkoxy$_{(C\le18)}$, alkenyloxy$_{(C\le18)}$, alkynyloxy$_{(C\le18)}$, aryloxy$_{(C\le18)}$, aralkoxy$_{(C\le18)}$, heteroaryloxy$_{(C\le18)}$, heteroaralkoxy$_{(C\le18)}$, acyloxy$_{(C\le18)}$, alkylamino$_{(C\le18)}$, dialkylamino$_{(C\le18)}$, alkoxyamino$_{(C\le18)}$, alkenylamino$_{(C\le18)}$, alkynylamino$_{(C\le18)}$, arylamino$_{(C\le18)}$, aralkylamino$_{(C\le18)}$, heteroarylamino$_{(C\le18)}$, heteroaralkylamino$_{(C\le18)}$, alkylsulfonylamino$_{(C\le18)}$, amido$_{(C\le18)}$, alkylideneamino$_{(C\le18)}$, aralkylideneamino$_{(C\le18)}$, or a substituted version of any of these groups, provided that $R_1$ and $R_2$ are not both methyl;

or pharmaceutically acceptable salts, tautomers, prodrugs, or optical isomers thereof.

In some variants of the above embodiments, the bond between atoms 4 and 5 is a single bond. In other embodiments, the bond between atoms 4 and 5 is a double bond.

In some variants of the above embodiments, $R_2$ is alkenyl$_{(C\le12)}$, substituted alkenyl$_{(C\le12)}$, alkynyl$_{(C\le12)}$ or substituted alkynyl$_{(C\le12)}$. In other variants, $R_2$ is alkynyl$_{(C\le8)}$ or substituted alkynyl$_{(C\le8)}$. For example, $R_2$ can be —C≡C—$R_9$, wherein $R_9$ is:

hydrogen or cyano; or alkyl$_{(C\le6)}$, aryl$_{(C\le6)}$, acyl$_{(C\le6)}$, alkylsilyl$_{(C\le6)}$ or a substituted version of any of these groups.

In variants of the above embodiments, $R_9$ is hydrogen. In other variants, $R_9$ is —Si(CH$_3$)$_2$C(CH$_3$)$_3$. In other variants, $R_9$ is cyano. In other variants, $R_9$ is —CO$_2$H or —CO$_2$CH$_3$. $R_9$ is phenyl.

In some variants of the above embodiments, $R_2$ is alkenyl$_{(C \leq 8)}$ or substituted alkenyl$_{(C \leq 8)}$. For example, $R_2$ can be ethenyl (vinyl). In other variants, $R_2$ is cyano. In other variants, $R_2$ is aralkyl$_{(C \leq 18)}$, substituted aralkyl$_{(C \leq 18)}$, heteroaralkyl$_{(C \leq 18)}$ or substituted heteroaralkyl$_{(C \leq 18)}$. In other variants, $R_2$ is phenylmethyl. In other variants, $R_2$ is alkyl$_{(C \leq 8)}$ or substituted alkyl$_{(C \leq 8)}$. For example, $R_2$ can be aminomethyl or hydroxymethyl. In other variants, $R_2$ is aralkyl$_{(C \leq 8)}$ or substituted acyl$_{(C \leq 8)}$. For example, $R_2$ can be —$CO_2H$, —$C(O)NH_2$ or —$C(O)CH_3$.

In some variants of the above embodiments, $R_1$ is alkyl$_{(C \leq 8)}$ or substituted alkyl$_{(C \leq 8)}$. For example, $R_1$ can be methyl, ethyl or —$(CH_2)_2C(CH_3)_3$. In other variants, $R_1$ is alkenyl$_{(C \leq 8)}$ or substituted alkenyl$_{(C \leq 8)}$. For example, $R_1$ can be allyl. In other variants, $R_1$ is alkynyl$_{(C \leq 8)}$ or substituted alkynyl$_{(C \leq 8)}$. For example, $R_1$ can be —$CH_2C \equiv CH$. In other variants, $R_1$ is aralkyl$_{(C \leq 18)}$, substituted aralkyl$_{(C \leq 18)}$, heteroaralkyl$_{(C \leq 18)}$ or substituted heteroaralkyl$_{(C \leq 18)}$. For example, $R_1$ can be aralkyl$_{(C \leq 12)}$ or substituted aralkyl$_{(C \leq 12)}$. For example, $R_1$ can be phenylmethyl or phenylethyl.

In some variants of the above embodiments, $R_1$ is -L-$R_{10}$, wherein:

$R_{10}$ is:

hydrogen, hydroxy, halo, amino, hydroxyamino, cyano or mercapto; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkoxy$_{(C \leq 12)}$, alkenyloxy$_{(C \leq 12)}$, alkynyloxy$_{(C \leq 12)}$, aryloxy$_{(C \leq 12)}$, aralkoxy$_{(C \leq 12)}$, heteroaryloxy$_{(C \leq 12)}$, heteroaralkoxy$_{(C \leq 12)}$, acyloxy$_{(C \leq 12)}$, alkylamino$_{(C \leq 12)}$, dialkylamino$_{(C \leq 12)}$, alkoxyamino$_{(C \leq 12)}$, alkenylamino$_{(C \leq 12)}$, alkynylamino$_{(C \leq 12)}$, arylamino$_{(C \leq 12)}$, aralkylamino$_{(C \leq 12)}$, heteroarylamino$_{(C \leq 12)}$, heteroaralkylamino$_{(C \leq 12)}$, alkylsulfonylamino$_{(C \leq 12)}$, amido$_{(C \leq 12)}$, alkylthio$_{(C \leq 12)}$, alkenylthio$_{(C \leq 12)}$, alkynylthio$_{(C \leq 12)}$, arylthio$_{(C \leq 12)}$, aralkylthio$_{(C \leq 12)}$, heteroarylthio$_{(C \leq 12)}$, heteroaralkylthio$_{(C \leq 12)}$, acylthio$_{(C \leq 12)}$, thioacyl$_{(C \leq 12)}$, alkylsulfonyl$_{(C \leq 12)}$, alkenylsulfonyl$_{(C \leq 12)}$, alkynylsulfonyl$_{(C \leq 12)}$, arylsulfonyl$_{(C \leq 12)}$, aralkylsulfonyl$_{(C \leq 12)}$, hetero-arylsulfonyl$_{(C \leq 12)}$, heteroaralkylsulfonyl$_{(C \leq 12)}$, alkylammonium$_{(C \leq 12)}$, alkylsulfonium$_{(C \leq 12)}$, alkylsilyl$_{(C \leq 12)}$, alkylsilyloxy$_{(C \leq 12)}$, or a substituted version of any of these groups; and L is alkanediyl$_{(C \leq 6)}$ or substituted alkanediyl$_{(C \leq 6)}$.

In some variants of the above embodiments, L is alkanediyl$_{(C1-3)}$. For example, L can be methanediyl, ethanediyl or propanediyl.

In some variants of the above embodiments, $R_{10}$ is alkyl$_{(C \leq 8)}$ or a substituted version thereof. For example, $R_{10}$ can be tert-butyl. In other variants, $R_{10}$ is aryl$_{(C \leq 12)}$, aralkyl$_{(C \leq 12)}$, heteroaryl$_{(C \leq 12)}$, heteroaralkyl$_{(C \leq 12)}$, or a substituted version of any of these groups. For example, $R_{10}$ can be aryl$_{(C \leq 8)}$ or a substituted version thereof. For example, $R_{10}$ can be phenyl. In other variants, $R_{10}$ is amino, alkylamino$_{(C \leq 8)}$, substituted alkylamino$_{(C \leq 8)}$, dialkylamino$_{(C \leq 8)}$ or substituted dialkylamino$_{(C \leq 8)}$. For example, $R_{10}$ can be amino. In other variants, $R_{10}$ is hydroxy, alkoxy$_{(C \leq 8)}$ or substituted alkoxy$_{(C \leq 8)}$. For example, $R_{10}$ can be hydroxy. In other variants, $R_{10}$ is acyl$_{(C \leq 8)}$ or substituted acyl$_{(C \leq 8)}$. For example, $R_{10}$ can be —$CO_2H$. In other variants, $R_{10}$ is alkynyl$_{(C \leq 8)}$ or substituted alkynyl$_{(C \leq 8)}$. For example, $R_{10}$ can be —$C \equiv C$—$R_{11}$, wherein $R_{11}$ is:

hydrogen, hydroxy, halo, amino, hydroxyamino, cyano, mercapto, or thio; or alkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, heteroaryl$_{(C \leq 8)}$, heteroaralkyl$_{(C \leq 8)}$, acyl$_{(C \leq 8)}$, alkoxy$_{(C \leq 8)}$, alkenyloxy$_{(C \leq 8)}$, alkynyloxy$_{(C \leq 8)}$, aryloxy$_{(C \leq 8)}$, aralkoxy$_{(C \leq 8)}$, heteroaryloxy$_{(C \leq 8)}$, heteroaralkoxy$_{(C \leq 8)}$, acyloxy$_{(C \leq 8)}$, alkylamino$_{(C \leq 8)}$, dialkylamino$_{(C \leq 8)}$, alkoxyamino$_{(C \leq 8)}$, alkenylamino$_{(C \leq 8)}$, alkynylamino$_{(C \leq 8)}$, arylamino$_{(C \leq 8)}$, aralkylamino$_{(C \leq 8)}$, heteroarylamino$_{(C \leq 8)}$, heteroaralkylamino$_{(C \leq 8)}$, alkylsulfonylamino$_{(C \leq 8)}$, amido$_{(C \leq 8)}$, alkylammonium$_{(C \leq 8)}$, alkylsulfonium$_{(C \leq 8)}$, alkylsilyl$_{(C \leq 8)}$, alkylsilyloxy$_{(C \leq 8)}$, or a substituted version of any of these groups.

In some variants of the above embodiments, $R_{11}$ is heteroaryl$_{(C \leq 8)}$, heteroaralkyl$_{(C \leq 8)}$, or substituted versions of either of these groups. For example, $R_{11}$ can be imidazoyl.

In some variants of the above embodiments, $R_1$ is aralkylideneamino$_{(C \leq 12)}$ or substituted aralkylideneamino$_{(C \leq 8)}$. For example, $R_1$ can be —$N=CHCH_2Ph$. In other variants, $R_1$ is cyano.

In some embodiments, the compound is further defined as:

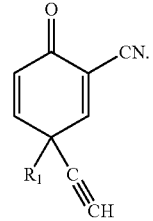

wherein $R_1$ is:

cyano, or alkyl$_{(C \leq 18)}$, alkenyl$_{(C \leq 18)}$, alkynyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, acyl$_{(C \leq 18)}$, alkoxy$_{(C \leq 18)}$, alkenyloxy$_{(C \leq 18)}$, alkynyloxy$_{(C \leq 18)}$, aryloxy$_{(C \leq 18)}$, aralkoxy$_{(C \leq 18)}$, heteroaryloxy$_{(C \leq 18)}$, heteroaralkoxy$_{(C \leq 18)}$, acyloxy$_{(C \leq 18)}$, alkylamino$_{(C \leq 18)}$, dialkylamino$_{(C \leq 18)}$, alkoxyamino$_{(C \leq 18)}$, alkenylamino$_{(C \leq 18)}$, alkynylamino$_{(C \leq 18)}$, arylamino$_{(C \leq 18)}$, aralkylamino$_{(C \leq 18)}$, heteroarylamino$_{(C \leq 18)}$, heteroaralkylamino$_{(C \leq 18)}$, alkylsulfonylamino$_{(C \leq 18)}$, amido$_{(C \leq 18)}$, alkylideneamino$_{(C \leq 18)}$, aralkylideneamino$_{(C \leq 18)}$, or a substituted version of any of these groups;

or pharmaceutically acceptable salts, tautomers, prodrugs, or optical isomers thereof.

In some variants of the above embodiments, $R_3$ is hydrogen. In some variants of the above embodiments, $R_4$ is hydrogen. In some variants of the above embodiments, $R_5$ is hydrogen. In some variants of the above embodiments, $R_6$ is hydrogen. In some variants of the above embodiments, $R_7$ is hydrogen. In some variants of the above embodiments, $R_8$ is hydrogen.

Examples of compounds disclosed herein include:

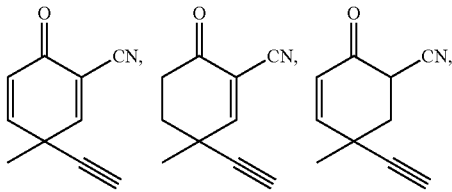

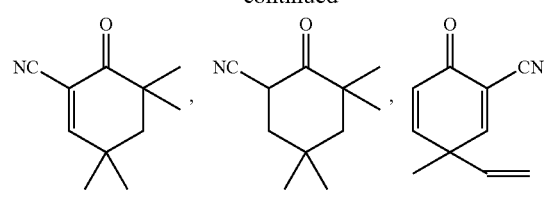
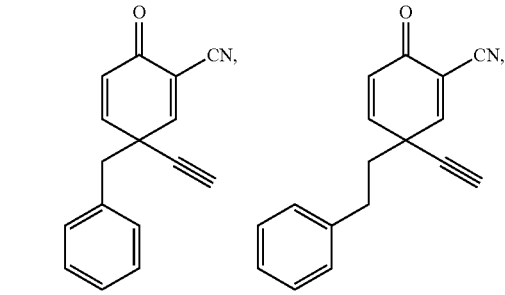
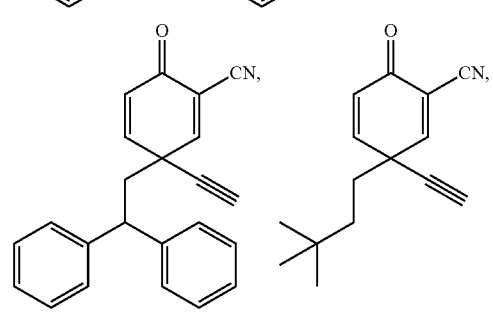
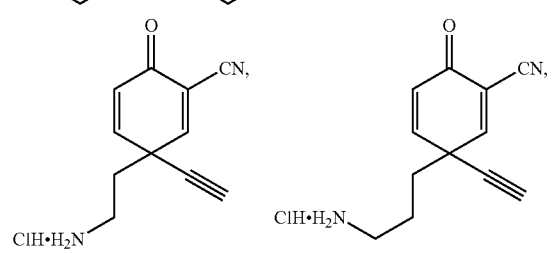
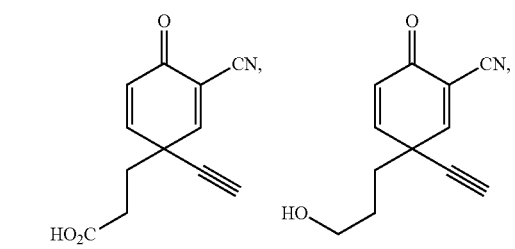
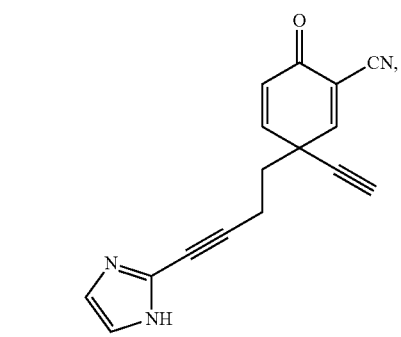
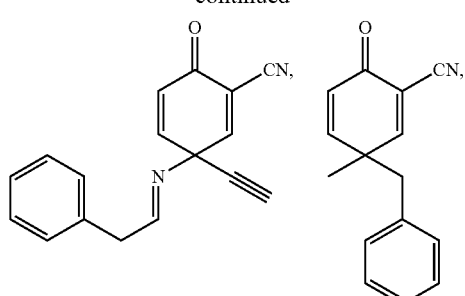
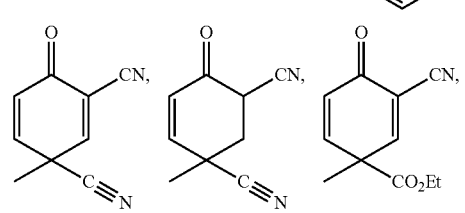
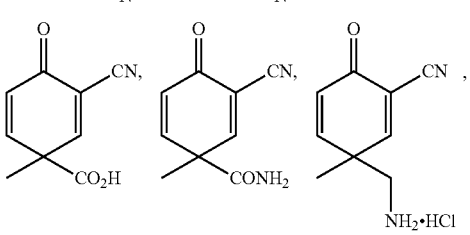
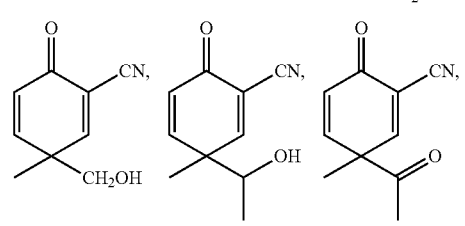
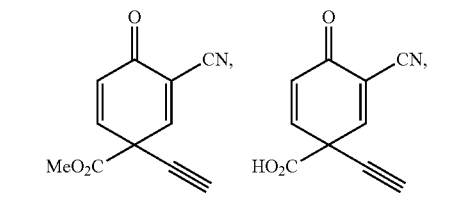
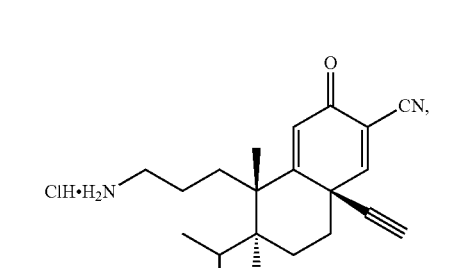
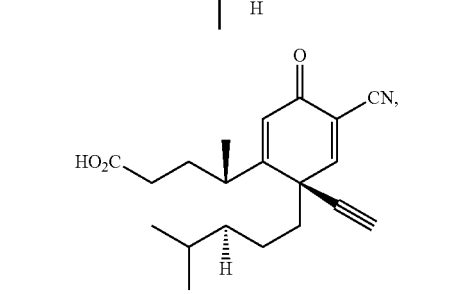

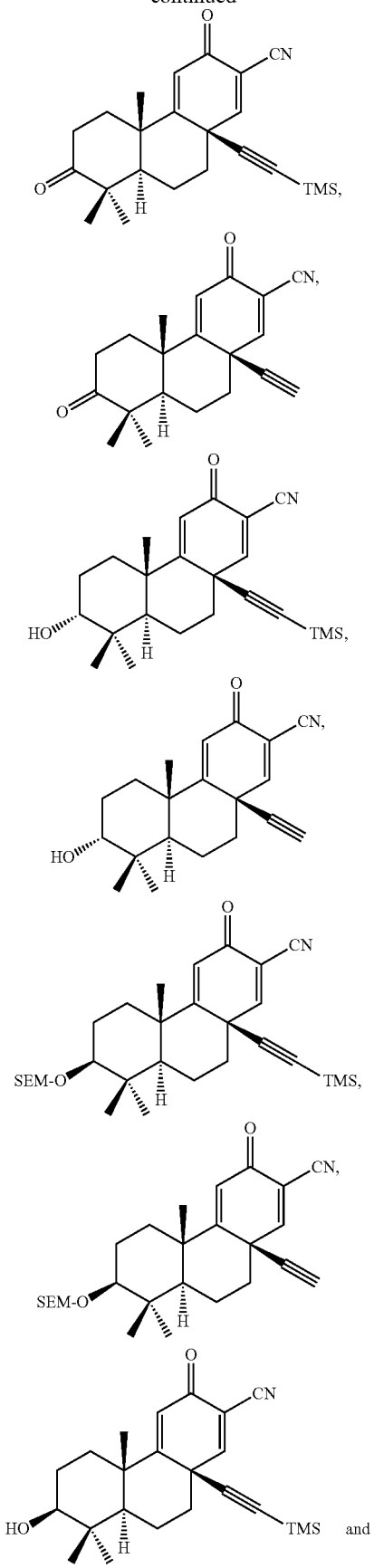

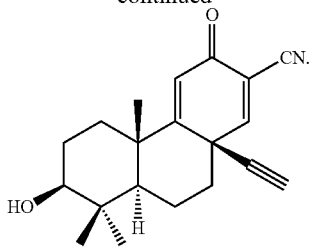

In some embodiments, compounds of the present disclosure are in the form of pharmaceutically acceptable salts. In other embodiments, compounds of the present disclosure are not be in the form of a pharmaceutically acceptable salts.

In some embodiments, the compounds of the present disclosure are present as mixtures of stereoisomers. In other embodiments, the compounds of the present disclosure are present as single stereoisomers.

In some embodiments, compounds of the present disclosure may be used as inhibitors of IFN-γ-induced nitrous oxide (NO) production in macrophages, for example, having an $IC_{50}$ value of less than 0.2 µM.

Other general aspects of the present disclosure contemplate a pharmaceutical composition comprising as an active ingredient a compound of the present disclosure and a pharmaceutically acceptable carrier. The composition may, for example, be adapted for administration by a route selected from the group consisting of orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, via localized perfusion, bathing target cells directly, or any combination thereof. In particular embodiments, the composition may be formulated for oral delivery. In particular embodiments, the composition is formulated as a hard or soft capsule, a tablet, a syrup, a suspension, a wafer, or an elixir. In certain embodiments, the soft capsule is a gelatin capsule. Certain compositions may comprise a protective coating, such as those compositions formulated for oral delivery. Certain compositions further comprise an agent that delays absorption, such as those compositions formulated for oral delivery. Certain compositions may further comprise an agent that enhances solubility or dispersibility, such as those compositions formulated for oral delivery. Certain compositions may comprise a compound of the present disclosure, wherein the compound is dispersed in a liposome, an oil and water emulsion or a water and oil emulsion.

Yet another general aspect of the present disclosure contemplates a therapeutic method comprising administering a pharmaceutically effective compound of the present disclosure to a subject. The subject may, for example, be a human. These or any other methods of the present disclosure may further comprise identifying a subject in need of treatment.

Another method of the present disclosure contemplates a method of treating cancer in a subject, comprising administering to the subject a pharmaceutically effective amount of a compound of the present disclosure. The cancer may be any type of cancer, such as a carcinoma, sarcoma, lymphoma, leukemia, melanoma, mesothelioma, multiple myeloma, or seminoma. Other types of cancers include cancer of the bladder, blood, bone, brain, breast, central nervous system, colon, endometrium, esophagus, genitourinary tract, head, larynx, liver, lung, neck, ovary, pancreas, prostate, spleen, small intestine, large intestine, stomach, or testicle. In these or any other methods, the subject may be a primate. This or any other method may further comprise identifying a subject in need of treatment. The subject may have a family or patient history of cancer. In certain embodiments, the subject has symptoms of cancer. The compounds disclosed herein may be administered via any method described herein, such as locally. In certain embodiments, the compound is administered by direct intratumoral injection or by injection into tumor vasculature. In certain embodiments, the compounds may be administered systemically. The compounds may be administered intravenously, intra-arterially, intramuscularly, intraperitoneally, subcutaneously or orally, in certain embodiments.

In certain embodiments regarding methods of treating cancer in a subject, comprising administering to the subject a pharmaceutically effective amount of a compound of the present disclosure, the pharmaceutically effective amount is 0.1-1000 mg/kg. In certain embodiments, the pharmaceutically effective amount is administered in a single dose per day. In certain embodiments, the pharmaceutically effective amount is administered in two or more doses per day. The compound may be administered by contacting a tumor cell during ex vivo purging, for example. The method of treatment may comprise any one or more of the following: a) inducing cytotoxicity in a tumor cell; b) killing a tumor cell; c) inducing apoptosis in a tumor cell; d) inducing differentiation in a tumor cell; or e) inhibiting growth in a tumor cell. The tumor cell may be any type of tumor cell, such as a leukemia cell. Other types of cells include, for example, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

Combination treatment therapy is also contemplated by the present disclosure. For example, regarding methods of treating cancer in a subject, comprising administering to the subject a pharmaceutically effective amount of a compound of the present disclosure, the method may further comprise a treatment selected from the group consisting of administering a pharmaceutically effective amount of a second drug, radiotherapy, gene therapy, and surgery. Such methods may further comprise (1) contacting a tumor cell with the compound prior to contacting the tumor cell with the second drug, (2) contacting a tumor cell with the second drug prior to contacting the tumor cell with the compound, or (3) contacting a tumor cell with the compound and the second drug at the same time. The second drug may, in certain embodiments, be an antibiotic, anti-inflammatory, anti-neoplastic, anti-proliferative, anti-viral, immunomodulatory, or immunosuppressive. The second drug may be an alkylating agent, androgen receptor modulator, cytoskeletal disruptor, estrogen receptor modulator, histone-deacetylase inhibitor, HMG-CoA reductase inhibitor, prenyl-protein transferase inhibitor, retinoid receptor modulator, topoisomerase inhibitor, or tyrosine kinase inhibitor. In certain embodiments, the second drug is 5-azacitidine, 5-fluorouracil, 9-cis-retinoic acid, actinomycin D, alitretinoin, all-trans-retinoic acid, annamycin, axitinib, belinostat, bevacizumab, bexarotene, bosutinib, busulfan, capecitabine, carboplatin, carmustine, CD437, cediranib, cetuximab, chlorambucil, cisplatin, cyclophosphamide, cytarabine, dacarbazine, dasatinib, daunorubicin, decitabine, docetaxel, dolastatin-10, doxifluridine, doxorubicin, doxorubicin, epirubicin, erlotinib, etoposide, etoposide, gefitinib, gemcitabine, gemtuzumab ozogamicin, hexamethylmelamine, idarubicin, ifosfamide, imatinib, irinotecan, isotretinoin, ixabepilone, lapatinib, LBH589, lomustine, mechlorethamine, melphalan, mercaptopurine, methotrexate, mitomycin, mitoxantrone, MS-275, neratinib, nilotinib, nitrosourea, oxaliplatin, paclitaxel, plicamycin, procarbazine, semaxanib, semustine, sodium butyrate, sodium phenylacetate, streptozotocin, suberoylanilide hydroxamic acid, sunitinib, tamoxifen, teniposide, thiopeta, tioguanine, topotecan, TRAIL, trastuzumab, tretinoin, trichostatin A, valproic acid, valrubicin, vandetanib, vinblastine, vincristine, vindesine, or vinorelbine.

Methods of treating or preventing a disease with an inflammatory component in a subject, comprising administering to the subject a pharmaceutically effective amount of a compound of the present disclosure are also contemplated. The disease may be, for example, lupus or rheumatoid arthritis. The disease may be an inflammatory bowel disease, such as Crohn's disease or ulcerative colitis. The disease with an inflammatory component may be a cardiovascular disease. The disease with an inflammatory component may be diabetes, such as type 1 or type 2 diabetes. Compounds of the present disclosure may also be used to treat complications associated with diabetes. Such complications are well-known in the art and include, for example, obesity, hypertension, atherosclerosis, coronary heart disease, stroke, peripheral vascular disease, hypertension, nephropathy, neuropathy, myonecrosis, retinopathy and metabolic syndrome (syndrome X). The disease with an inflammatory component may be a skin disease, such as psoriasis, acne, or atopic dermatitis. Administration of a compound of the present disclosure in treatment methods of such skin diseases may be, for example, topical or oral.

The disease with an inflammatory component may be metabolic syndrome (syndrome X). A patient having this syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670, incorporated herein by reference. Patients with metabolic syndrome, whether or not they have or develop overt diabetes mellitus, have an increased risk of developing the macrovascular and microvascular complications that are listed above that occur with type 2 diabetes, such as atherosclerosis and coronary heart disease.

Another general method of the present disclosure entails a method of treating or preventing a cardiovascular disease in a subject, comprising administering to the subject a pharmaceutically effective amount of a compound of the present disclosure. The cardiovascular disease may be, for example, atherosclerosis, cardiomyopathy, congenital heart disease, congestive heart failure, myocarditis, rheumatic heart disease, valve disease, coronary artery disease, endocarditis, or myocardial infarction. Combination therapy is also contemplated for such methods. For example, such methods may further comprise administering a pharmaceutically effective amount of a second drug. The second drug may be, for example, a cholesterol lowering drug, an anti-hyperlipidemic, a calcium channel blocker, an anti-hypertensive, or an HMG-CoA reductase inhibitor. Non-limiting examples of second drugs include amlodipine, aspirin, ezetimibe, felodipine, lacidipine, lercanidipine, nicardipine, nifedipine, nimodipine, nisoldipine or nitrendipine. Other non-limiting examples of second drugs include atenolol, bucindolol, carvedilol, clonidine, doxazosin, indoramin, labetalol, methyldopa, metoprolol, nadolol, oxprenolol, phenoxybenzamine, phentolamine, pindolol, prazosin, propranolol, terazosin, timolol or tolazoline. The second drug may be, for example, a statin, such as atorvastatin, cerivastatin, fluvastatin, lovastatin, mevastatin, pitavastatin, pravastatin, rosuvastatin or simvastatin.

Methods of treating or preventing a neurodegenerative disease in a subject, comprising administering to the subject a pharmaceutically effective amount of a compound of the present disclosure are also contemplated. The neurodegenerative disease may, for example, be selected from the group consisting of Parkinson's disease, Alzheimer's disease, multiple sclerosis (MS), Huntington's disease and amyotrophic lateral sclerosis. In particular embodiments, the neurodegenerative disease is Alzheimer's disease. In particular embodiments, the neurodegenerative disease is MS, such as primary progressive, relapsing-remitting secondary progressive or progressive relapsing MS. The subject may be, for example, a primate. The subject may be a human.

In particular embodiments of methods of treating or preventing a neurodegenerative disease in a subject, comprising administering to the subject a pharmaceutically effective amount of a compound of the present disclosure, the treatment suppresses the demyelination of neurons in the subject's brain or spinal cord. In certain embodiments, the treatment suppresses inflammatory demyelination. In certain embodiments, the treatment suppresses the transection of neuron axons in the subject's brain or spinal cord. In certain embodiments, the treatment suppresses the transection of neurites in the subject's brain or spinal cord. In certain embodiments, the treatment suppresses neuronal apoptosis in the subject's brain or spinal cord. In certain embodiments, the treatment stimulates the remyelination of neuron axons in the subject's brain or spinal cord. In certain embodiments, the treatment restores lost function after an MS attack. In certain embodiments, the treatment prevents a new MS attack. In certain embodiments, the treatment prevents a disability resulting from an MS attack.

One general aspect of the present disclosure contemplates a method of treating or preventing a disorder characterized by overexpression of iNOS genes in a subject, comprising administering to the subject a pharmaceutically effective amount of a compound of the present disclosure.

Another general aspect of the present disclosure contemplates a method of inhibiting IFN-γ-induced nitric oxide production in cells of a subject, comprising administering to said subject a pharmaceutically effective amount of a compound of the present disclosure.

Yet another general method of the present disclosure contemplates a method of treating or preventing a disorder characterized by overexpression of COX-2 genes in a subject, comprising administering to the subject a pharmaceutically effective amount of compound of the present disclosure.

Methods of treating renal/kidney disease (RKD) in a subject, comprising administering to the subject a pharmaceutically effective amount of a compound of the present disclosure are also contemplated. See U.S. patent application Ser. No. 12/352,473, which is incorporated by reference herein in its entirety. The RKD may result from, for example, a toxic insult. The toxic insult may result from, for example, an imaging agent or a drug. The drug may be a chemotherapeutic, for example. The RKD may result from ischemia/reperfusion injury, in certain embodiments. In certain embodiments, the RKD results from diabetes or hypertension. The RKD may result from an autoimmune disease. The RKD may be further defined as chronic RKD, or acute RKD.

In certain methods of treating renal/kidney disease (RKD) in a subject, comprising administering to the subject a pharmaceutically effective amount of a compound of the present disclosure, the subject has undergone or is undergoing dialysis. In certain embodiments, the subject has undergone or is a candidate to undergo kidney transplant. The subject may be a primate. The primate may be a human. The subject in this or any other method may be, for example, a cow, horse, dog, cat, pig, mouse, rat or guinea pig.

Also contemplated by the present disclosure is a method for improving glomerular filtration rate or creatinine clearance in a subject, comprising administering to the subject a pharmaceutically effective amount of a compound of the present disclosure.

Kits are also contemplated by the present disclosure, such as a kit comprising: a compound of the present disclosure; and instructions which comprise one or more forms of information selected from the group consisting of indicating a disease state for which the compound is to be administered, storage information for the compound, dosing information and instructions regarding how to administer the compound. The kit may comprise a compound of the present disclosure in a multiple dose form.

In certain embodiments, compounds of the present disclosure may be used in preventing and treating diseases and disorders whose pathology involves oxidative stress, inflammation, and dysregulation of inflammatory signaling pathways. In particular embodiments, compounds disclosed herein may be used in treating diseases and disorders characterized by overexpression of inducible nitric oxide synthase (iNOS), inducible cyclooxygenase (COX-2), or both, in affected tissues; high levels of production of reactive oxygen species (ROS) or reactive nitrogen species (RNS) such as superoxide, hydrogen peroxide, nitric oxide or peroxynitrite; or excessive production of inflammatory cytokines or other inflammation-related proteins such as TNFα, IL-6, IL-1, IL-8, ICAM-1, VCAM-1, and VEGF. Such diseases or disorders may, in some embodiments, involve undesirable proliferation of certain cells, as in the case of cancer (e.g., solid tumors, leukemias, myelomas, lymphomas, and other cancers), fibrosis associated with organ failure, or excessive scarring. Other such disorders include (but are not limited to) autoimmune diseases such as lupus, rheumatoid arthritis, juvenile-onset diabetes, multiple sclerosis, psoriasis, and Crohn's disease; cardiovascular diseases such as atherosclerosis, heart failure, myocardial infarction, acute coronary syndrome, restenosis following vascular surgery, hypertension, and vasculitis; neurodegenerative or neuromuscular diseases such as Alzheimer's disease, Parkinson's disease, Huntington's disease, ALS, and muscular dystrophy; neurological disorders such as epilepsy and dystonia; neuropsychiatric conditions such as major depression, bipolar disorder, post-traumatic stress disorder, schizophrenia, anorexia nervosa, ADHD, and autism-spectrum disorders; retinal diseases such as macular degeneration, diabetic retinopathy, glaucoma, and retinitis; chronic and acute pain syndromes, including inflammatory and neuropathic pain; hearing loss and tinnitus; diabetes and complications of diabetes, including metabolic syndrome, diabetic nephropathy, diabetic neuropathy, and diabetic ulcers; respiratory diseases such as asthma, chronic obstructive pulmonary disease, acute respiratory distress syndrome, and cystic fibrosis; inflammatory bowel diseases; osteoporosis, osteoarthritis, and other degenerative conditions of bone and cartilage; acute or chronic organ failure, including renal failure, liver failure (including cirrhosis and hepatitis), and pancreatitis; ischemia-reperfusion injury associated with thrombotic or hemorrhagic stroke, subarachnoid hemorrhage, cerebral vasospasm, myocardial infarction, shock, or trauma; complications of organ or tissue transplantation including acute or chronic transplant failure or rejection and graft-versus-host disease; skin diseases including atopic dermatitis and acne; sepsis and septic shock; excessive inflammation associated with infection, including respiratory inflammation associated with influenza and upper respiratory infections; mucositis associated with cancer therapy, including radiation therapy or chemotherapy; and severe burns.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

FIGS. 1A-D show how the UV spectra of four MCEs change in the presence of dithiothreitol (DTT) (MCE-1, FIG. 1A; MCE-2, FIG. 1B; MCE-3, FIG. 1C) or NaOH (MCE-4 (dhMCE-1), FIG. 1D).

DESCRIPTION OF ILLUSTRATIVE EMBODIMENTS

I. Definitions

Figures 1C, 1D:
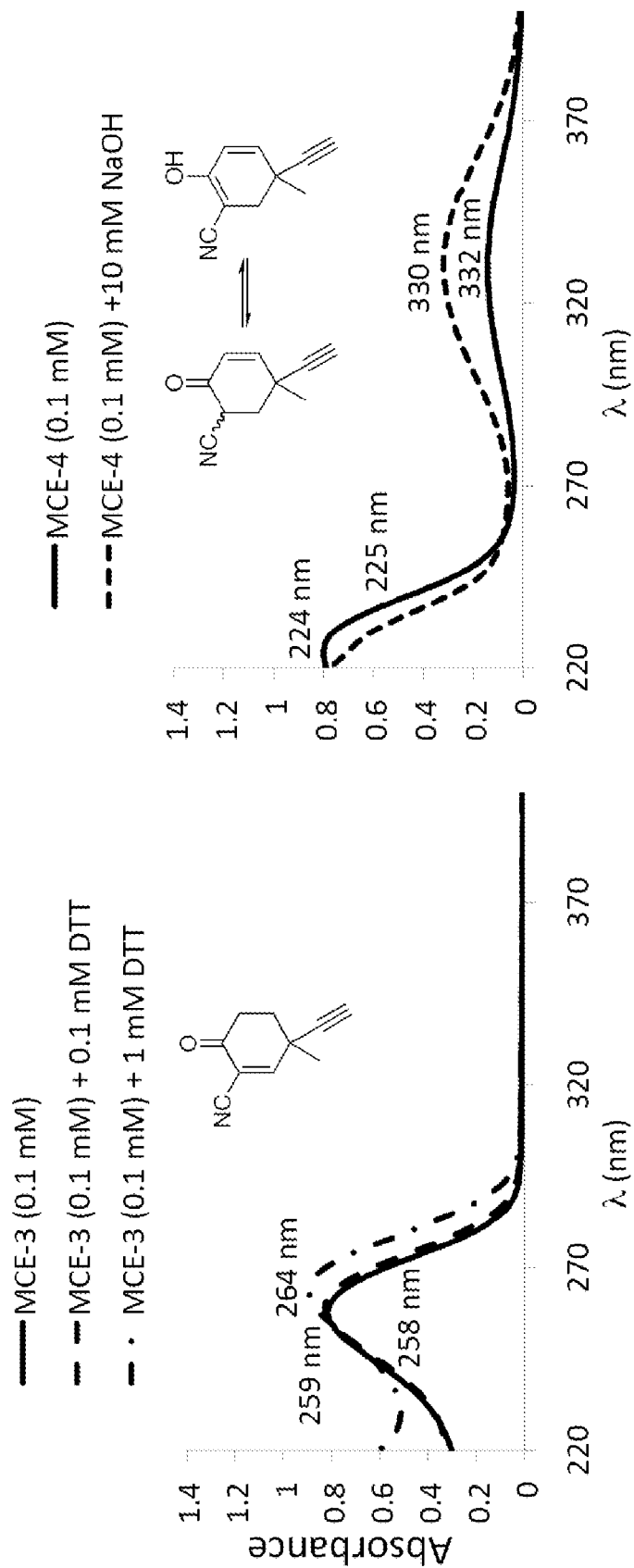

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "thioether" means —S—; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); "sulfinyl" means —S(O)— (see below for definitions of groups containing the term sulfinyl, e.g., alkylsulfinyl); and "silyl" means —SiH$_3$ (see below for definitions of group(s) containing the term silyl, e.g., alkylsilyl).

The symbol "—" means a single bond, "=" means a double bond, and "≡" means triple bond. The symbol "⁃⁃⁃⁃" represents a single bond or a double bond. The symbol "⁓", when drawn perpendicularly across a bond indicates a point of attachment of the group. It is noted that the point of attachment is typically only identified in this manner for larger groups in order to assist the reader in rapidly and unambiguously identifying a point of attachment. The symbol "◀" means a single bond where the group attached to the thick end of the wedge is "out of the page." The symbol "⁞⁞⁞⁞" means a single bond where the group attached to the thick end of the wedge is "into the page". The symbol "⁓" means a single bond where the conformation is unknown (e.g., either R or S), the geometry is unknown (e.g., either E or Z) or the compound is present as mixture of conformation or geometries (e.g., a 50%/50% mixture).

When a group "R" is depicted as a "floating group" on a ring system, for example, in the formula:

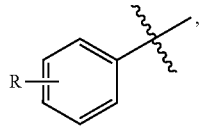

then R may replace any hydrogen atom attached to any of the ring atoms, including a depicted, implied, or expressly defined hydrogen, so long as a stable structure is formed.

When a group "R" is depicted as a "floating group" on a fused ring system, as for example in the formula:

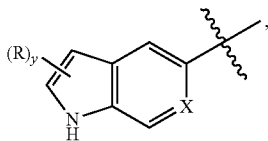

then R may replace any hydrogen attached to any of the ring atoms of either of the fuzed rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

When y is 2 and "(R)$_y$," is depicted as a floating group on a ring system having one or more ring atoms having two replaceable hydrogens, e.g., a saturated ring carbon, as for example in the formula:

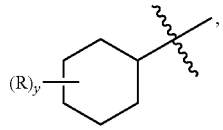

then each of the two R groups can reside on the same or a different ring atom. For example, when R is methyl and both R groups are attached to the same ring atom, a geminal dimethyl group results. Where specifically provided for, two R groups may be taken together to form a divalent group, such as one of the divalent groups further defined below. When such a divalent group is attached to the same ring atom, a spirocyclic ring structure will result.

In the case of a double-bonded R group (e.g., oxo, imino, thio, alkylidene, etc.), any pair of implicit or explicit hydrogen atoms attached to one ring atom can be replaced by the R group. This concept is exemplified below:

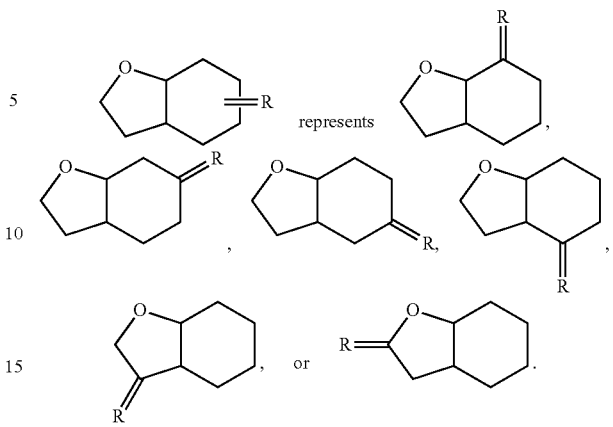

For the groups below, the following parenthetical subscripts further define the groups as follows: "(Cn)" defines the exact number (n) of carbon atoms in the group. "(C≤n)" defines the maximum number (n) of carbon atoms that can be in the group, with the minimum number of carbon atoms in such at least one, but otherwise as small as possible for the group in question. E.g., it is understood that the minimum number of carbon atoms in the group "alkenyl$_{(C\leq 8)}$" is two. For example, "alkoxy$_{(C\leq 10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O) OH, —CH$_2$C(O)OCH$_3$, —CH$_2$C(O)NH$_2$, —CH$_2$C(O) NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N (CH$_3$)$_2$, —CH$_2$CH$_2$Cl, —CH$_2$CH$_2$OH, —CH$_2$CF$_3$, —CH$_2$CH$_2$C(O)CH$_3$, —CH$_2$CH$_2$NHCO$_2$C(CH$_3$)$_3$, and —CH$_2$Si(CH$_3$)$_3$.

The term "alkanediyl" when used without the "substituted" modifier refers to a non-aromatic divalent group, wherein the alkanediyl group is attached with two σ-bonds, The groups, —CH$_2$— (methylene), —CH$_2$CH$_2$—, —CH$_2$C(CH$_3$)$_2$ CH$_2$—, —CH$_2$CH$_2$CH$_2$—, and

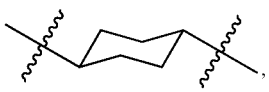 [SMILES: *C1CCC(*)CC1]

are non-limiting examples of alkanediyl groups. The term "substituted alkanediyl" refers to a non-aromatic monovalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "alkenediyl" when used without the "substituted" modifier refers to a divalent group that is nonaromatic prior to attachment, wherein the alkenediyl group is attached with two σ-bonds, which may become aromatic upon attachment, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, —CH=CH—CH=CH—, and

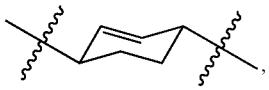 [SMILES: *C1C=CC(*)CC1]

are non-limiting examples of alkenediyl groups. The term "substituted alkenediyl" refers to a divalent group that is nonaromatic prior to attachment, wherein the alkenediyl group is attached with two σ-bonds, which may become aromatic upon attachment, with two carbon atoms as points of attachment, a linear or branched, cyclo, cyclic or acyclic structure, at least one nonaromatic carbon-carbon double bond, no carbon-carbon triple bonds, and at least one atom independently selected from the group consisting of N, O, F, Cl, Br, I, Si, P, and S. The following groups are non-limiting examples of substituted alkenediyl groups: —CF=CH—, —C(OH)=CH—, and —CH$_2$CH=C(Cl)—.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "alkynediyl" when used without the "substituted" modifier refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH$_2$—, and —C≡CCH(CH$_3$)— are non-limiting examples of alkynediyl groups. The term "substituted alkynediyl" refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and at least one atom independently selected from the group consisting of N, O, F, Cl, Br, I, Si, P, and S. The groups —C≡CCFH— and —C≡CHCH(Cl)— are non-limiting examples of substituted alkynediyl groups.

The term "aryl" when used without the "substituted" modifier refers to a monovalent group with an aromatic carbon atom as the point of attachment, said carbon atom forming part of one or more six-membered aromatic ring structure(s) wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH=CH$_2$ (vinylphenyl), —C$_6$H$_4$CH=CHCH$_3$, —C$_6$H$_4$C≡CH, —C$_6$H$_4$C≡CCH$_3$, naphthyl, and the monovalent group derived from biphenyl. The term "substituted aryl" refers to a monovalent group with an aromatic carbon atom as the point of attachment, said carbon atom forming part of one or more six-membered aromatic ring structure(s) wherein the ring atoms are all carbon, and wherein the monovalent group further has at least one atom independently selected from the group consisting of N, O, F, Cl, Br, I, Si, P, and S. Non-limiting examples of substituted aryl groups include the groups: —C$_6$H$_4$F, —C$_6$H$_4$Cl, C$_6$H$_4$Br, C$_6$H$_4$I, C$_6$H$_4$OH, C$_6$H$_4$OCH$_3$, —C$_6$H$_4$OCH$_2$CH$_3$, —C$_6$H$_4$C(O)CH$_3$, C$_6$H$_4$NH$_2$, C$_6$H$_4$NHCH$_3$, —C$_6$H$_4$N(CH$_3$)$_2$, —C$_6$H$_4$CH$_2$OH, C$_6$H$_4$CH$_2$C(O)CH$_3$, C$_6$H$_4$CH$_2$NH$_2$, C$_6$H$_4$CF$_3$, C$_6$H$_4$CN, C$_6$H$_4$CHO, C$_6$H$_4$CHO, C$_6$H$_4$C(O)CH$_3$, C$_6$H$_4$C(O)C$_6$H$_5$, C$_6$H$_4$CO$_2$H, C$_6$H$_4$CO$_2$CH$_3$, C$_6$H$_4$CONH$_2$, —C$_6$H$_4$CONHCH$_3$, and —C$_6$H$_4$CON(CH$_3$)$_2$.

The term "arenediyl" when used without the "substituted" modifier refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of arenediyl groups include:

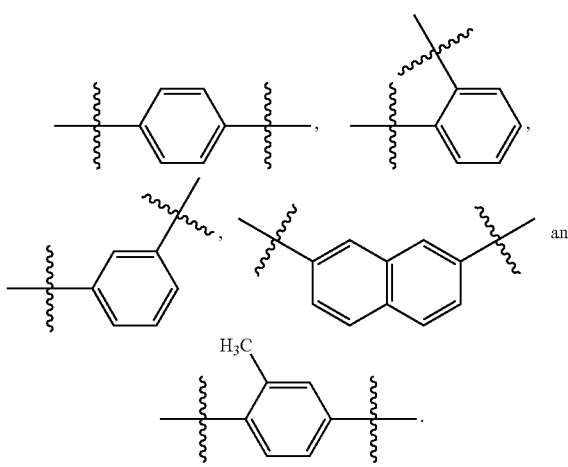

The term "substituted arenediyl" refers to a divalent group, wherein the arenediyl group is attached with two σ-bonds, with two aromatic carbon atoms as points of attachment, said carbon atoms forming part of one or more six-membered aromatic rings structure(s), wherein the ring atoms are carbon, and wherein the divalent group further has at least one atom independently selected from the group consisting of N, O, F, Cl, Br, I, Si, P, and S.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroarenediyl" when used without the "substituted" modifier refers to a divalent group, wherein the heteroarenediyl group is attached with two σ-bonds, with an aromatic carbon atom or nitrogen atom as the point of attachment, said carbon atom or nitrogen atom forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. Non-limiting examples of heteroarenediyl groups include:

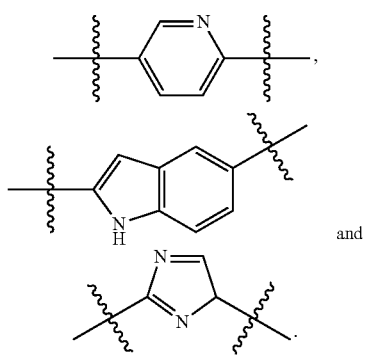

The term "substituted heteroarenediyl" refers to a divalent group, wherein the heteroarenediyl group is attached with two σ-bonds, with an aromatic carbon atom or nitrogen atom as points of attachment, said carbon atom or nitrogen atom forming part of one or more six-membered aromatic ring structure(s), wherein at least one of the ring atoms is nitrogen, oxygen or sulfur, and wherein the divalent group further has at least one atom independently selected from the group consisting of non-aromatic nitrogen, non-aromatic oxygen, non aromatic sulfur F, Cl, Br, I, Si, and P.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, C(O)C$_6$H$_5$, C(O)C$_6$H$_4$CH$_3$, C(O)C$_6$H$_4$CH$_2$CH$_3$, COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H (carboxyl), —CO$_2$CH$_3$ (methylcarboxyl), —CO$_2$CH$_2$CH$_3$, CO$_2$CH$_2$CH$_2$CH$_3$, —CO$_2$C$_6$H$_5$, CO$_2$CH(CH$_3$)$_2$, CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CON-HCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups.

The term "alkylidene" when used without the "substituted" modifier refers to the divalent group =CRR', wherein the alkylidene group is attached with one σ-bond and one π-bond, in which R and R' are independently hydrogen, alkyl, alkenyl, or R and R' are taken together to represent alkanediyl or alkenediyl. Non-limiting examples of alkylidene groups include: =CH$_2$, =CH(CH$_2$CH$_3$), and =C(CH$_3$)$_2$. The term "substituted alkylidene" refers to the group =CRR', wherein the alkylidene group is attached with one σ-bond and one π-bond, in which R and R' are independently hydrogen, alkyl, substituted alkyl, alkenyl, substituted alkenyl, provided that either one of R and R' is a substituted alkyl or substituted alkenyl, or R and R' are taken together to represent a substituted alkanediyl or a substituted alkenediyl.

The term "aralkylidene" when used without the "substituted" modifier refers to the divalent group =CRR', wherein the aralkylidene group is attached with one σ-bond and one π-bond, in which R and R' are independently hydrogen, alkyl, aryl or aralkyl, provided that at least one of R and R' is aryl or aralkyl. The term "substituted aralkylidene" refers to the group =CRR', wherein the aralkylidene group is attached with one σ-bond and one π-bond, in which R and R' are independently hydrogen, alkyl, substituted alkyl, aryl, substituted aryl, aralkyl or substituted aralkyl, provided that at least one of R and R' is aryl, substituted aryl, aralkyl or substituted aralkyl.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

The term "alkoxydiyl" when used without the "substituted" modifier refers to a non-aromatic divalent group, wherein the alkoxydiylgroup is attached with two σ-bonds, with (a) two saturated carbon atoms as points of attachment, (b) one saturated carbon atom and one oxygen atom as points of attachment, or (c) two oxygen atoms as points of attachment, further having a linear or branched, cyclo, cyclic or acyclic structure, no carbon-carbon double or triple bonds in the group's backbone, further having no backbone atoms other than carbon or oxygen and having at least one of each of these atoms in the group's backbone, and no side chains comprising groups other than hydrogen or alkyl. The groups, —O—CH$_2$CF$_{12}$—, —CH$_2$—O—CH$_2$CH$_2$—, —O—CH$_2$CH$_2$—O— and —O—CH$_2$—O— are non-limiting examples of alkoxydiyl groups. The term "substituted alkanyloxydiyl" refers to a divalent group that is attached with two σ-bonds, with (a) two saturated carbon atoms as points of attachment, (b) one saturated carbon atom and one oxygen atom as points of attachment, or (c) two oxygen atoms as points of attachment, further having a linear or branched, cyclo, cyclic or acyclic structure, no carbon-carbon double or triple bonds, and at least one atom independently selected from the group consisting of N, F, Cl, Br, I, Si, P, and S, or having additional oxygen atoms beyond those in the group's backbone. The following groups are non-limiting example of a substituted alkoxydiylgroups: —O—CH$_2$C(OH)H—O— and —O—CH$_2$C(Cl)H—O—.

Similarly, the terms "alkenyloxy", "alkynyloxy", "aryloxy", "aralkoxy", "heteroaryloxy", "heteroaralkoxy" and "acyloxy", when used without the "substituted" modifier, refers to groups, defined as —OR, in which R is alkenyl, alkynyl, aryl, aralkyl, heteroaryl, heteroaralkyl and acyl, respectively, as those terms are defined above. When any of the terms alkenyloxy, alkynyloxy, aryloxy, aralkyloxy and acyloxy is modified by "substituted," it refers to the group —OR, in which R is substituted alkenyl, alkynyl, aryl, aralkyl, heteroaryl, heteroaralkyl and acyl, respectively.

The term "alkenyloxydiyl" when used without the "substituted" modifier refers to a divalent group that is nonaromatic prior to attachment, wherein the alkenyloxydiyl group is attached with two σ-bonds, which may become aromatic upon attachment, with (a) two carbon atoms as points of attachment, (b) one carbon atom and one oxygen atom as points of attachment, or (c) two oxygen atoms as points of attachment, further having a linear or branched, cyclo, cyclic or acyclic structure, at least one carbon-carbon double bond that is non-aromatic at least prior to attachment, further having no backbone atoms other than carbon or oxygen and having at least one of each of these atoms in the group's backbone, and no side chains comprising groups other than hydrogen or alkyl. The groups, —O—CH=CH—, —O—CH=CHO— and —O—CH=CHCH$_2$— are non-limiting examples of alkenyloxydiyl groups. The term "substituted alkenyloxydiyl" refers to a divalent group that is nonaromatic prior to attachment, wherein the substituted alkenyloxydiyl group is attached with two σ-bonds, which may become aromatic upon attachment, with (a) two carbon atoms as points of attachment, (b) one carbon atom and one oxygen atom as points of attachment, or (c) two oxygen atoms as points of attachment, further having a linear or branched, cyclo, cyclic or acyclic structure, at least one carbon-carbon double bond that is non-aromatic at least prior to attachment and at least one atom independently selected from the group consisting of N, F, Cl, Br, I, Si, P, and S, or having additional oxygen atoms beyond those in the group's backbone. The following groups are non-limiting example of a substituted alkenyloxydiyl groups: —O—CH=C(OH)—O— and —O—CH=C(Cl)—O—.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH— cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

The terms "alkoxyamino", "alkenylamino", "alkynylamino", "arylamino", "aralkylamino", "heteroarylamino", "heteroaralkylamino", and "alkylsulfonylamino" when used without the "substituted" modifier, refers to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$. When any of the terms alkoxyamino, alkenylamino, alkynylamino, arylamino, aralkylamino, heteroarylamino, heteroaralkylamino and alkylsulfonylamino is modified by "substituted," it refers to the group —NHR, in which R is substituted alkoxy, alkenyl, alkynyl, aryl, aralkyl, heteroaryl, heteroaralkyl and alkylsulfonyl, respectively.

The term "amido" (acylamino), when used without the "substituted" modifier, refers to the group —NHR, in which R is acyl, as that term is defined above. A non-limiting example of an acylamino group is —NHC(O)CH$_3$. When the term amido is used with the "substituted" modifier, it refers to groups, defined as —NHR, in which R is substituted acyl, as that term is defined above. The groups —NHC(O)OCH$_3$ and —NHC(O)NHCH$_3$ are non-limiting examples of substituted amido groups.

The term "alkylideneamino" when used without the "substituted" modifier refers to the group —N=R$_a$, in which R$_a$ is an alkylidene, as that term is defined above. The term "substituted alkylideneamino" refers to the group N=R$_a$, in which R$_a$ is a substituted alkylidene, as that term is defined above.

The term "aralkylideneamino" when used without the "substituted" modifier refers to the group —N=R$_a$, in which R$_a$ is an aralkylidene, as that term is defined above. The term "substituted aralkylideneamino" refers to the group N=R$_a$, in which R$_a$ is a substituted aralkylidene, as that term is defined above.

The term "alkylaminodiyl" when used without the "substituted" modifier refers to a non-aromatic divalent group, wherein the alkylaminodiyl group is attached with two σ-bonds, with (a) two saturated carbon atoms as points of attachment, (b) one saturated carbon atom and one nitrogen atom as points of attachment, or (c) two nitrogen atoms as points of attachment, further having a linear or branched, cyclo, cyclic or acyclic structure, no double or triple bonds in the group's backbone, further having no backbone atoms other than carbon or nitrogen and having at least one of each of these atoms in the group's backbone, and no side chains comprising groups other than hydrogen or alkyl. The groups, —NH—CH$_2$CH$_2$—, —CH$_2$—NH—CH$_2$CH$_2$—, —NH—CH$_2$CH$_2$—NH— and —NH—CH$_2$—NH— are non-limiting examples of alkylaminodiyl groups. The term "substituted alkylaminodiyl" refers to a divalent group, wherein the substituted alkylaminodiyl group is attached with two σ-bonds, with (a) two saturated carbon atoms as points of attachment, (b) one saturated carbon atom and one nitrogen atom as points of attachment, or (c) two nitrogen atoms as points of attachment, further having a linear or branched, cyclo, cyclic or acyclic structure, no carbon-carbon double or triple bonds in the group's backbone, and at least one atom independently selected from the group consisting of O, F, Cl, Br, I, Si, P, and S, or having additional nitrogen atom beyond those in the group's backbone. The following groups are non-limiting example of a substituted alkylaminodiyl groups: —NH—CH$_2$C(OH)H—NH— and —NH—CH$_2$C(Cl)H—CH$_2$—.

The term "alkenylaminodiyl" when used without the "substituted" modifier refers to a divalent group that is nonaromatic prior to attachment, wherein the alkenylaminodiyl group is attached with two σ-bonds, which may become aromatic upon attachment, with (a) two carbon atoms as points of attachment, (b) one carbon atom and one nitrogen atom as points of attachment, or (c) two nitrogen atoms as points of attachment, further having a linear or branched, cyclo, cyclic or acyclic structure, at least one carbon-carbon double bond or carbon-nitrogen double that is non-aromatic at least prior to attachment, further having no backbone atoms other than carbon or nitrogen, and no side chains comprising groups other than hydrogen or alkyl. The groups, —NH—CH=CH—, —NH—CH=N— and —NH—CH=CH—NH— are non-limiting examples of alkenylaminodiyl groups. The term "substituted alkenylaminodiyl" refers to a divalent group that is nonaromatic prior to attachment, wherein the substituted alkenylaminodiyl group is attached with two σ-bonds, which may become aromatic upon attachment, with (a) two carbon atoms as points of attachment, (b) one carbon atom and one nitrogen atom as points of attachment, or (c) two nitrogen atoms as points of attachment, further having a linear or branched, cyclo, cyclic or acyclic structure, at least one carbon-carbon double bond or carbon nitrogen double bond that is non-aromatic at least prior to attachment and at least one atom independently selected from the group consisting of O, F, Cl, Br, I, Si, P, and S, or having additional nitrogen atoms beyond those in the group's backbone. The following groups are non-limiting example of a substituted alkenylaminodiyl groups: —NH—CH=C(OH)—CH$_2$— and —N=CHC(Cl)H—.

The term "alkenylaminooxydiyl" when used without the "substituted" modifier refers to a divalent group, wherein the alkenylaminooxydiyl group is attached with two σ-bonds, which may become aromatic upon attachment, with two atoms selected from the group consisting of carbon, oxygen and nitrogen as points of attachment, further having a linear or branched, cyclo, cyclic or acyclic structure, at least one carbon-carbon double bond, carbon-nitrogen double, or nitrogen-nitrogen double bond that is non-aromatic at least prior to attachment, further having no backbone atoms other than carbon nitrogen or oxygen and having at least one of each of these three atoms in the backbone, and no side chains comprising groups other than hydrogen or alkyl. The group —O—CH=N—, is a non-limiting example of an alkenylaminooxydiyl group. The term "substituted alkenylaminooxydiyl" refers to a divalent group that is attached with two σ-bonds, which may become aromatic upon attachment with two atoms selected from the group consisting of carbon, oxygen and nitrogen as points of attachment, further having a linear or branched, cyclo, cyclic or acyclic structure, at least one carbon-carbon double bond or carbon nitrogen double bond that is non-aromatic at least prior to attachment and at least one atom independently selected from the group consisting of F, Cl, Br, I, Si, P, and S, or having one or more additional nitrogen and/or oxygen atoms beyond those in the group's backbone. The following groups are non-limiting example of a substituted alkenylaminooxydiyl groups: —NH—CH=C(OH)—O— and —N=CHC(Cl)H—O—.

The term "alkenylaminothiodiyl" when used without the "substituted" modifier refers to a divalent group that is non-aromatic prior to attachment, wherein the alkenylaminothiodiyl group is attached with two σ-bonds, which may become aromatic upon attachment, with two atoms selected from the group consisting of carbon, nitrogen and sulfur as points of attachment, further having a linear or branched, cyclo, cyclic or acyclic structure, at least one carbon-carbon double bond, carbon-nitrogen double, or nitrogen-nitrogen double bond that is non-aromatic at least prior to attachment, further having no backbone atoms other than carbon, nitrogen or sulfur and having at least one of each of these three atoms in the backbone, and no side chains comprising groups other than hydrogen or alkyl. The group —S—CH═N—, is a non-limiting example of an alkenylaminothiodiyl group. The term "substituted alkenylaminothiodiyl" refers to a divalent group that is attached with two σ-bonds, which may become aromatic upon attachment with two atoms selected from the group consisting of carbon, nitrogen and sulfur as points of attachment, further having a linear or branched, cyclo, cyclic or acyclic structure, at least one carbon-carbon double bond or carbon nitrogen double bond that is non-aromatic at least prior to attachment and at least one atom independently selected from the group consisting of O, F, Cl, Br, I, Si, and P, or having one or more additional nitrogen and/or sulfur atoms beyond those in the group's backbone. The following groups are non-limiting example of a substituted alkenylaminothiodiyl groups: —NH—CH═C(OH)—S— and —N═CHC(Cl)H—S—.

The term "alkylimino" when used without the "substituted" modifier refers to the group ═NR, wherein the alkylimino group is attached with one σ-bond and one π-bond, in which R is an alkyl, as that term is defined above. Non-limiting examples of alkylimino groups include: ═NCH$_3$, ═NCH$_2$CH$_3$ and ═N-cyclohexyl. The term "substituted alkylimino" refers to the group ═NR, wherein the alkylimino group is attached with one σ-bond and one π-bond, in which R is a substituted alkyl, as that term is defined above. For example, ═NCH$_2$CF$_3$ is a substituted alkylimino group.

Similarly, the terms "alkenylimino", "alkynylimino", "arylimino", "aralkylimino", "heteroarylimino", "heteroaralkylimino" and "acylimino", when used without the "substituted" modifier, refers to groups, defined as ═NR, wherein the alkylimino group is attached with one σ-bond and one π-bond, in which R is alkenyl, alkynyl, aryl, aralkyl, heteroaryl, heteroaralkyl and acyl, respectively, as those terms are defined above. When any of the terms alkenylimino, alkynylimino, arylimino, aralkylimino and acylimino is modified by "substituted," it refers to the group ═NR, wherein the alkylimino group is attached with one σ-bond and one π-bond, in which R is substituted alkenyl, alkynyl, aryl, aralkyl, heteroaryl, heteroaralkyl and acyl, respectively.

The term "fluoroalkyl" when used without the "substituted" modifier refers to an alkyl, as that term is defined above, in which one or more fluorines have been substituted for hydrogens. The groups, —CH$_2$F, —CF$_2$H, —CF$_3$, and —CH$_2$CF$_3$ are non-limiting examples of fluoroalkyl groups. The term "substituted fluoroalkyl" refers to a non-aromatic monovalent group with a saturated carbon atom as the point of attachment, a linear or branched, cyclo, cyclic or acyclic structure, at least one fluorine atom, no carbon-carbon double or triple bonds, and at least one atom independently selected from the group consisting of N, O, Cl, Br, I, Si, P, and S. The following group is a non-limiting example of a substituted fluoroalkyl: —CFHOH.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "substituted alkylphosphate" refers to the group —OP(O)(OH)(OR), in which R is a substituted alkyl, as that term is defined above.

The term "dialkylphosphate" when used without the "substituted" modifier refers to the group —OP(O)(OR)(OR), in which R and R' can be the same or different alkyl groups, or R and R' can be taken together to represent an alkanediyl having two or more saturated carbon atoms, at least two of which are attached via the oxygen atoms to the phosphorus atom. Non-limiting examples of dialkylphosphate groups include: —OP(O)(OMe)$_2$, —OP(O)(OEt)(OMe) and —OP(O)(OEt)$_2$. The term "substituted dialkylphosphate" refers to the group —OP(O)(OR)(OR'), in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached via the oxygen atoms to the phosphorous.

The term "alkylthio" when used without the "substituted" modifier refers to the group —SR, in which R is an alkyl, as that term is defined above. Non-limiting examples of alkylthio groups include: —SCH$_3$, —SCH$_2$CH$_3$, —SCH$_2$CH$_2$CH$_3$, —SCH(CH$_3$)$_2$, —SCH(CH$_2$)$_2$, —S-cyclopentyl, and —S-cyclohexyl. The term "substituted alkylthio" refers to the group —SR, in which R is a substituted alkyl, as that term is defined above. For example, —SCH$_2$CF$_3$ is a substituted alkylthio group.

Similarly, the terms "alkenylthio", "alkynylthio", "arylthio", "aralkylthio", "heteroarylthio", "heteroaralkylthio", and "acylthio", when used without the "substituted" modifier, refers to groups, defined as —SR, in which R is alkenyl, alkynyl, aryl, aralkyl, heteroaryl, heteroaralkyl and acyl, respectively, as those terms are defined above. When any of the terms alkenylthio, alkynylthio, arylthio, aralkylthio, heteroarylthio, heteroaralkylthio, and acylthio is modified by "substituted," it refers to the group —SR, in which R is substituted alkenyl, alkynyl, aryl, aralkyl, heteroaryl, heteroaralkyl and acyl, respectively.

The term "thioacyl" when used without the "substituted" modifier refers to a monovalent group with a carbon atom of a thiocarbonyl group as the point of attachment, further having a linear or branched, cyclo, cyclic or acyclic structure, further having no additional atoms that are not carbon or hydrogen, beyond the sulfur atom of the carbonyl group. The groups, —CHS, —C(S)CH$_3$, —C(S)CH$_2$CH$_3$, —C(S)CH$_2$CH$_2$CH$_3$, —C(S)CH(CH$_3$)$_2$, —C(S)CH(CH$_2$)$_2$, —C(S)C$_6$H$_5$, —C(S)C$_6$H$_4$CH$_3$, —C(S)C$_6$H$_4$CH$_2$CH$_3$, —C(S)C$_6$H$_3$(CH$_3$)$_2$, and —C(S)CH$_2$C$_6$H$_5$, are non-limiting examples of thioacyl groups. The term "thioacyl" therefore encompasses, but is not limited to, groups sometimes referred to as "alkyl thiocarbonyl" and "aryl thiocarbonyl" groups. The term "substituted thioacyl" refers to a radical with a carbon atom as the point of attachment, the carbon atom being part of a thiocarbonyl group, further having a linear or branched, cyclo, cyclic or acyclic structure, further having at least one atom, in addition to the sulfur atom of the carbonyl group, independently selected from the group consisting of N, O, F, Cl, Br, I, Si, P, and S. The groups, —C(S)CH$_2$CF$_3$, —C(S)O$_2$H, —C(S)OCH$_3$, —C(S)OCH$_2$CH$_3$, —C(S)OCH$_2$CH$_2$CH$_3$, —C(S)OC$_6$H$_5$, —C(S)OCH(CH$_3$)$_2$, —C(S)OCH(CH$_2$)$_2$, —C(S)NH$_2$, and —C(S)NHCH$_3$, are non-limiting examples of substituted thioacyl groups. The term "substituted thioacyl" encompasses, but is not limited to, "heteroaryl thiocarbonyl" groups.

The term "alkylsulfonyl" when used without the "substituted" modifier refers to the group —S(O)$_2$R, in which R is an alkyl, as that term is defined above. Non-limiting examples of alkylsulfonyl groups include: —S(O)$_2$CH$_3$, —S(O)$_2$CH$_2$CH$_3$, —S(O)$_2$CH$_2$CH$_2$CH$_3$, —S(O)$_2$CH(CH$_3$)$_2$, —S(O)$_2$CH(CH$_2$)$_2$, —S(O)$_2$-cyclopentyl, and —S(O)$_2$-cyclohexyl. The term "substituted alkylsulfonyl" refers to the group —S(O)₂R, in which R is a substituted alkyl, as that term is defined above. For example, —S(O)₂CH₂CF₃ is a substituted alkylsulfonyl group.

Similarly, the terms "alkenylsulfonyl", "alkynylsulfonyl", "arylsulfonyl", "aralkylsulfonyl", "heteroarylsulfonyl", and "heteroaralkylsulfonyl" when used without the "substituted" modifier, refers to groups, defined as —S(O)₂R, in which R is alkenyl, alkynyl, aryl, aralkyl, heteroaryl, and heteroaralkyl, respectively, as those terms are defined above. When any of the terms alkenylsulfonyl, alkynylsulfonyl, arylsulfonyl, aralkylsulfonyl, heteroarylsulfonyl, and heteroaralkylsulfonyl is modified by "substituted," it refers to the group —S(O)₂R, in which R is substituted alkenyl, alkynyl, aryl, aralkyl, heteroaryl and heteroaralkyl, respectively.

The term "alkylsulfinyl" when used without the "substituted" modifier refers to the group —S(O)R, in which R is an alkyl, as that term is defined above. Non-limiting examples of alkylsulfinyl groups include: —S(O)CH₃, —S(O)CH₂CH₃, —S(O)CH₂CH₂CH₃, —S(O)CH(CH₃)₂, —S(O)CH(CH₂)₂, —S(O)-cyclopentyl, and —S(O)-cyclohexyl. The term "substituted alkylsulfinyl" refers to the group —S(O)R, in which R is a substituted alkyl, as that term is defined above. For example, —S(O)CH₂CF₃ is a substituted alkylsulfinyl group.

Similarly, the terms "alkenylsulfinyl", "alkynylsulfinyl", "arylsulfinyl", "aralkylsulfinyl", "heteroarylsulfinyl", and "heteroaralkylsulfinyl" when used without the "substituted" modifier, refers to groups, defined as —S(O)R, in which R is alkenyl, alkynyl, aryl, aralkyl, heteroaryl, and heteroaralkyl, respectively, as those terms are defined above. When any of the terms alkenylsulfinyl, alkynylsulfinyl, arylsulfinyl, aralkylsulfinyl, heteroarylsulfinyl, and heteroaralkylsulfinyl is modified by "substituted," it refers to the group —S(O)R, in which R is substituted alkenyl, alkynyl, aryl, aralkyl, heteroaryl and heteroaralkyl, respectively.

The term "alkylammonium" when used without the "substituted" modifier refers to a group, defined as —NH₂R⁺, —NHRR'⁺, or —NRR'R"⁺, in which R, R' and R" are the same or different alkyl groups, or any combination of two of R, R' and R" can be taken together to represent an alkanediyl. Non-limiting examples of alkylammonium cation groups include: —NH₂(CH₃)⁺, —NH₂(CH₂CH₃)⁺, —NH₂(CH₂CH₂CH₃)⁺, —NH(CH₃)₂⁺, —NH(CH₂CH₃)₂⁺, —NH(CH₂CH₂CH₃)₂⁺, —N(CH₃)₃⁺, —N(CH₃)(CH₂CH₃)₂⁺, —N(CH₃)₂(CH₂CH₃)⁺, —NH₂C(CH₃)₃⁺, —NH(cyclopentyl)₂⁺, and —NH₂(cyclohexyl)⁺. The term "substituted alkylammonium" refers —NH₂R⁺, —NHRR'⁺, or —NRR'R"⁺, in which at least one of R, R' and R" is a substituted alkyl or two of R, R' and R" can be taken together to represent a substituted alkanediyl. When more than one of R, R' and R" is a substituted alkyl, they can be the same of different. Any of R, R' and R" that are not either substituted alkyl or substituted alkanediyl, can be either alkyl, either the same or different, or can be taken together to represent a alkanediyl with two or more carbon atoms, at least two of which are attached to the nitrogen atom shown in the formula.

The term "alkylsulfonium" when used without the "substituted" modifier refers to the group —SRR'⁺, in which R and R' can be the same or different alkyl groups, or R and R' can be taken together to represent an alkanediyl. Non-limiting examples of alkylsulfonium groups include: —SH(CH₃)⁺, —SH(CH₂CH₃)⁺, —SH(CH₂CH₂CH₃)⁺, —S(CH₃)₂⁺, —S(CH₂CH₃)₂⁺, —S(CH₂CH₂CH₃)₂⁺, —SH(cyclopentyl)⁺, and —SH(cyclohexyl)⁺. The term "substituted alkylsulfonium" refers to the group —SRR'⁺, in which R and R' can be the same or different substituted alkyl groups, one of R or R' is an alkyl and the other is a substituted alkyl, or R and R' can be taken together to represent a substituted alkanediyl. For example, —SH(CH₂CF₃)⁺ is a substituted alkylsulfonium group.

The term "alkylsilyl" when used without the "substituted" modifier refers to a monovalent group, defined as —SiH₂R, —SiHRR', or —SiRR'R", in which R, R' and R" can be the same or different alkyl groups, or any combination of two of R, R' and R" can be taken together to represent an alkanediyl. The groups, —SiH₂CH₃, —SiH(CH₃)₂, —Si(CH₃)₃ and —Si(CH₃)₂C(CH₃)₃, are non-limiting examples of unsubstituted alkylsilyl groups. The term "substituted alkylsilyl" refers to —SiH₂R, —SiHRR', or —SiRR'R", in which at least one of R, R' and R" is a substituted alkyl or two of R, R' and R" can be taken together to represent a substituted alkanediyl. When more than one of R, R' and R" is a substituted alkyl, they can be the same of different. Any of R, R' and R" that are not either substituted alkyl or substituted alkanediyl, can be either alkyl, either the same or different, or can be taken together to represent a alkanediyl with two or more saturated carbon atoms, at least two of which are attached to the silicon atom.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include ¹³C and ¹⁴C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

A compound having a formula that is represented with a dashed bond is intended to include the formulae optionally having zero, one or more double bonds. Thus, for example, the structure

includes the structures

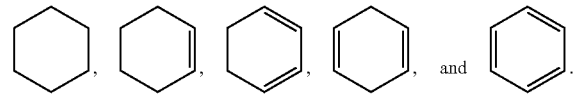

As will be understood by a person of skill in the art, no one such ring atom forms part of more than one double bond.

Any undefined valency on an atom of a structure shown in this application implicitly represents a hydrogen atom bonded to the atom.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties, and Use* (2002).

As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

The invention contemplates that for any stereocenter or axis of chirality for which stereochemistry has not been defined, that stereocenter or axis of chirality can be present in its R form, S form, or as a mixture of the R and S forms, including racemic and non-racemic mixtures.

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five, and optionally amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxybenzyloxycarbonyl); and haloethoxycarbonyl groups (such as β,β,β-trichloroethoxycarbonyl and β-iodoethoxycarbonyl).

"Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the term "water soluble" means that the compound dissolves in water at least to the extent of 0.010 mole/liter or is classified as soluble according to literature precedence.

Other abbreviations used herein are as follows: DMSO, dimethyl sulfoxide; NO, nitric oxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFNγ or IFN-γ, interferon-γ; LPS, bacterial endotoxic lipopolysaccharide; TNFα or TNF-α, tumor necrosis factor-α; IL-1β, interleukin-1α; GAPDH, glyceraldehyde-3-phosphate dehydrogenase; MTT, 3-[4,5-dimethylthiazol-2-yl]-2, 5-diphenyltetrazolium bromide; TCA, trichloroacetic acid; HO-1, inducible heme oxygenase.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Monocyclic Cyano Enones

Novel monocyclic cyano enones (MCEs) were synthesized and their Michael reactivity and biological activity were tested in order to identify useful fragments for drug discovery. As part of these investigations, MCE-1 was found to be a highly reactive Michael acceptor. MCE-1 gives reversible and selective Michael adducts with thiol nucleophiles. MCE-1 is also highly potent for inhibition of NO production in RAW cells stimulated by interferon-γ (iNOS assay) and induction of the phase 2 response, specifically, on elevation of NAD(P)H-quinone oxidoreductase in Hepa1c1c7 cells (NQO1 assay).

The potency of MCE-1 was found to be higher than CDDO in the iNOS assay. A homology model of the IKKβ based on the X-ray structure of the checkpoint-2 kinase has been generated and employing it binding models of MCE-1 with Cys$^{179}$ of IKKβ examined Without being bound by theory or mechanism, these studies are consistent with our belief that ligands comprising the MCE-1 pharmacore, the A-ring of CDDO and TBE-31, will reversibly and selectively act on Cys$^{179}$ in the kinase domain on IKKβ. This series of new ligands provide unique IKKβ inhibitors which are ATP-noncompetitive. The compounds disclosed herein may also be used to interact with a number of different protein targets including JAK1 and Keap1.

A. Synthesis

MCE-1, 3, and 4 were synthesized by the sequence shown in Scheme 2 (Example 2). Compound 2 was prepared in 99% yield by ketalization of commercially available 4-oxocyclohexanonecarboxylic acid ethyl ester (1) (Phansavath et al., 1998). Nucleophilic addition of the enolate of 2 to iodomethane gave 3 in 85% yield. Reduction of 3 with LiAlH$_4$, followed by oxidation with CrO$_3$ afforded 5 (94% yield). Wittig reaction of 5 with (chloro-methyl)triphenylphosphonium chloride (Mella et al., 1988), followed by dehydrochlorination with MeLi and subsequent treatment with chlorotrimethylsilane (TMSCl) (Corey et al., 1973) produced 6 in 71% yield. The ketal of 6 was removed under acidic conditions to yield 7 in 98% yield. Enone 8 was prepared by addition of phenylselenyl group to lithium enolate of 7 and subsequent oxidation/elimination with 30% aqueous hydrogen peroxide (36% yield). Formylation of 8 with ethyl formate, followed by the condensation with hydroxylamine, gave isoxazole 9 in 94% yield. The cleavage of the isoxazole ring of 9 under basic conditions produced MCE-4 (5,6-dihydro-MCE-1, dhMCE-1) in quantitative yield. MCE-1 was obtained from MCE-4 (dhMCE-1) by DDQ oxidation (47% yield). Compound 10 was prepared in 78% yield from 7 by cyanation with p-toluenesulfonyl cyanide (p-TsCN, Kahne et al., 1981), followed by DDQ oxidation. Removal of TMS group from 10 afforded MCE-3 in 50% yield. MCE-1 itself would be synthesized in four steps from a known compound, 4-ethynyl-4-methylcyclohex-2-en-1-one (Semmelhack et al., 1993) by the same sequence as for MCE-1 from 8.

Known compound MCE-2 was prepared from 4,4-dimethylcyclohex-2-enone according to the methods in the literature (Liu et al., 2000, which is incorporated herein by reference), as summarized here:

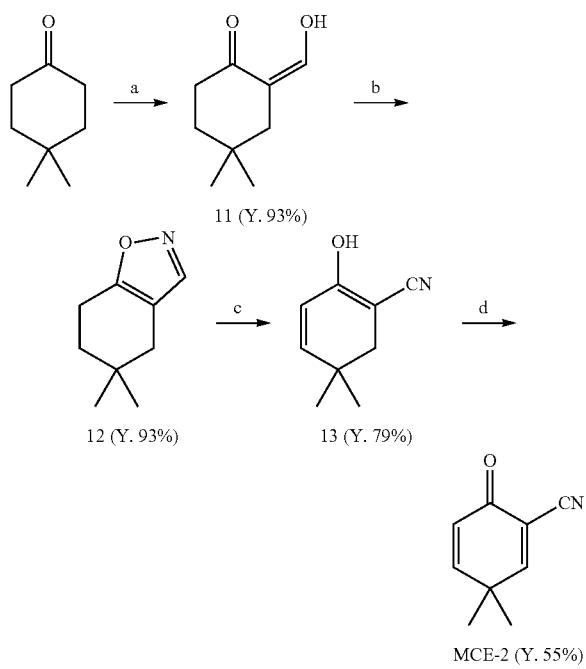

(a) HCO$_2$Et, NaOMe, PhH; (b) NH$_2$OH•HCl, aqueous EtOH;
(c) NaOMe, MeOH, Et$_2$O; (d) DDQ, PhH.

New compound, MCE-5 was synthesized in 5 steps from 14 (Scheme 3, Example 3), which was prepared by Robinson annulation with isobutyraldehyde and ethyl vinyl ketone (Paquette et al. 1989, which is incorporated herein by reference). Known compound 15 was prepared in 50% yield by reductive methylation of 14 (Smith et al., 1967, which is incorporated herein by reference). Formylation of 15, followed by the treatment with hydroxylamine, gave 17 in 77% yield. The cleavage of the isoxazole of 17 with sodium methoxide afforded dhMCE-5 in 90% yield. MCE-5 was obtained by DDQ oxidation of dhMCE-5 in 23% yield.

New compound, MCE-15 was synthesized from 5 by the sequence shown in Scheme 4 (Example 4). Wittig reaction of 5 with methyltriphenylphosphonium iodide, followed by deketalization, gave 19 in 86% yield. Enone 20 was obtained as an inseparable mixture of 20 and 19 (mole ratio 1.4:1) by addition of phenylselenyl group to lithium enolate of 19 and subsequent oxidation/elimination with 30% aqueous hydrogen peroxide. Formylation of the mixture with ethyl formate afforded a mixture of 21 and 22. Compound 21 was isolated from the mixture by flash chromatography. MCE-15 was prepared from 21 by the same sequence as for MCE-2 (see above).

MCE-1 analogue, MCE-13 having a benzyl group was synthesized by the sequence shown in Scheme 5 (Example 5). Nucleophilic addition of the enolate of 2 to benzyl bromide gave 25 in 81% yield. Reduction of 25, followed by oxidation produced 27 in 59% yield. The aldehyde 27 was converted to 28 using the Bestmann-Ohira reagent (dimethyl-1-diazo-2-oxopropylphosphonate) and potassium carbonate (85% yield, Müller, et al., 1996). The ethynyl group of 28 was protected by TMS group to give 29 in 89% yield. MCE-13 was obtained in 3.4% yield from 29 by the same sequence as for MCE-1 from 6 (see Scheme 2 below).

MCE-7, tricycle containing MCE-1 as a fragment, was synthesized from known compound 33 (Honda et al., 2007) by the sequence shown in Scheme 6. The ethynyl group of 33 was protected by TMS group to give 34 in 89% yield. A chromium-mediated allylic oxidation (Muzart, 1987) afforded 35 in 47% yield. Compound 36 was synthesized in 57% yield by cyanation of 35 with LDA and p-TsCN, followed by DDQ oxidation. Deketalization of 36 under acidic conditions gave 37 in 86% yield. The TMS group was removed by tetra-(n-butyl)ammonium fluoride (TBAF) to give MCE-7 in 81% yield.

The compounds of the present disclosure were made using the methods outlined above and in the Examples section below. These methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein.

B. UV Studies Using DTT and Keap1

MCE-1 gives the second UV absorption at a high wavelength (around 334 nm) according to the addition of dithiothreitol (DTT) under the dilute (0.1 mM of MCE-1) and neutral aqueous conditions (pH 7.4 phosphate buffered saline 1% ethanol), which are similar to the physiological conditions (see FIG. 1A). The absorption of MCE-1 at high wavelength, which increases according to the addition of DTT, is identical with the absorption of MCE-4 (dhMCE-1) (see FIG. 1D) at high wavelength (around 330 nm), which increases by the addition of NaOH (presumably due to enhanced H-bonding to the enol hydroxyl). This observation is consistent with the second absorption of MCE-1 being derived from the Michael adduct of DTT with MCE-1, because the chromophore of the Michael adduct should be the same as the enol form of MCE-4 (dhMCE-1), which shows the absorption at higher wavelength than the keto form of MCE-4 (dhMCE-1).

Figure 2:
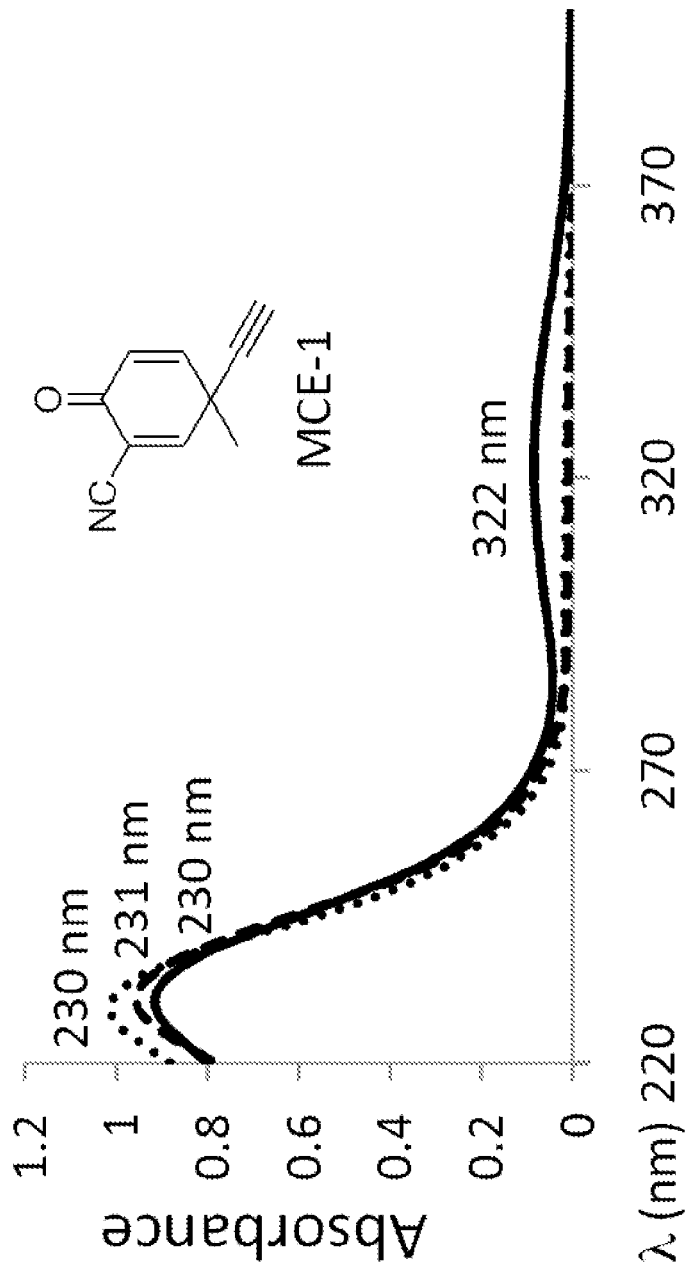
FIG. 2 shows the UV spectra of MCE-1 in different solvents.
Figure 3:
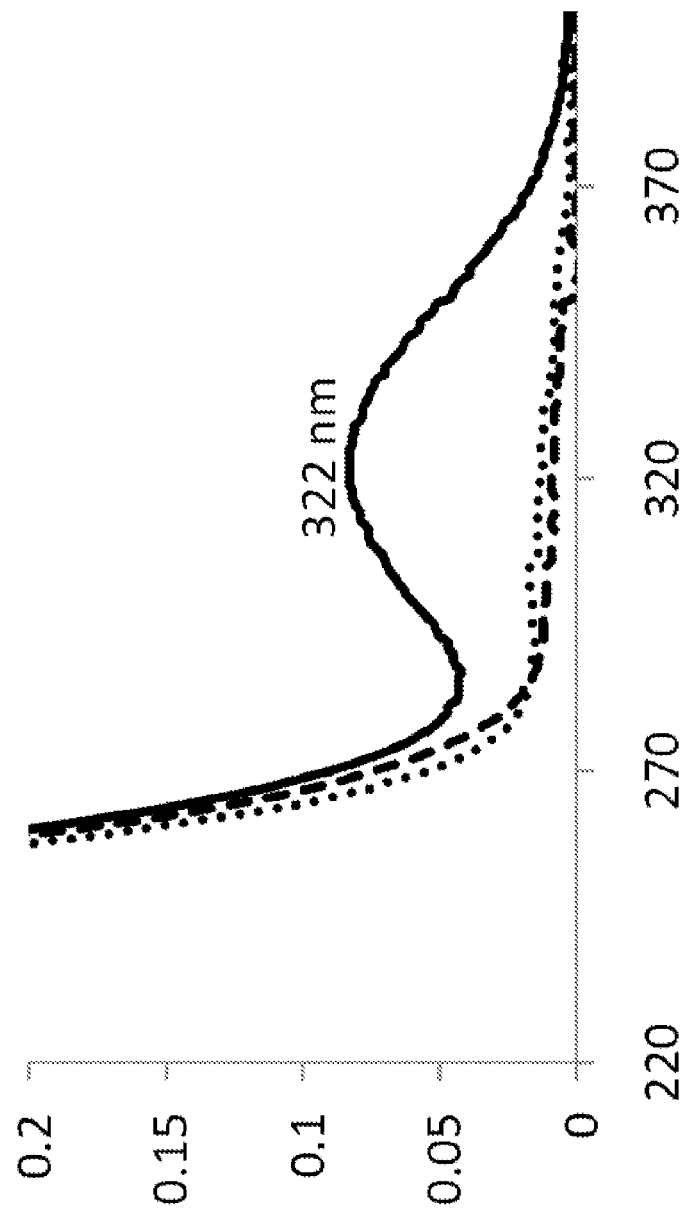
FIG. 3 shows the UV spectra of MCE-1 in different solvents. In contrast to FIG. 2, the lower absorbance range is expanded.

Applicants note that the UV spectrum of MCE-1 (c=0.1 mM) in pH 7.4 phosphate buffer solution shows two absorptions at 230 nm (log ϵ=3.96) and 322 nm (log ϵ=2.92). However, in ethanol and deionized water, the long wavelength band is not observed (FIGS. 2 and 3). The phosphate buffer (pH 7.4) includes 1 mM KH$_2$PO$_4$, 5.6 mM Na$_2$HPO$_4$, and 154 mM NaCl. Although the phosphate and chloride anions are much weaker nucleophiles than the SH group, because the concentration of NaCl is 1540 times more than the concentration of DTT (0.1 mM), these results suggest that that MCE-1 reacts with chloride anion to give a Michael adduct.

Once DTT (0.1 mM) is added to the buffer solution of MCE-1, the adduct with chloride disappears (322 nm) and the adduct with DTT appears (333 nm) (see FIG. 1A), thereby providing evidence that MCE-1 gives selective Michael adduction with thiol nucleophiles. Applicants note that this result is obtained despite that the concentration of DTT is 1,540 times lower than that of NaCl.

Figure 4:
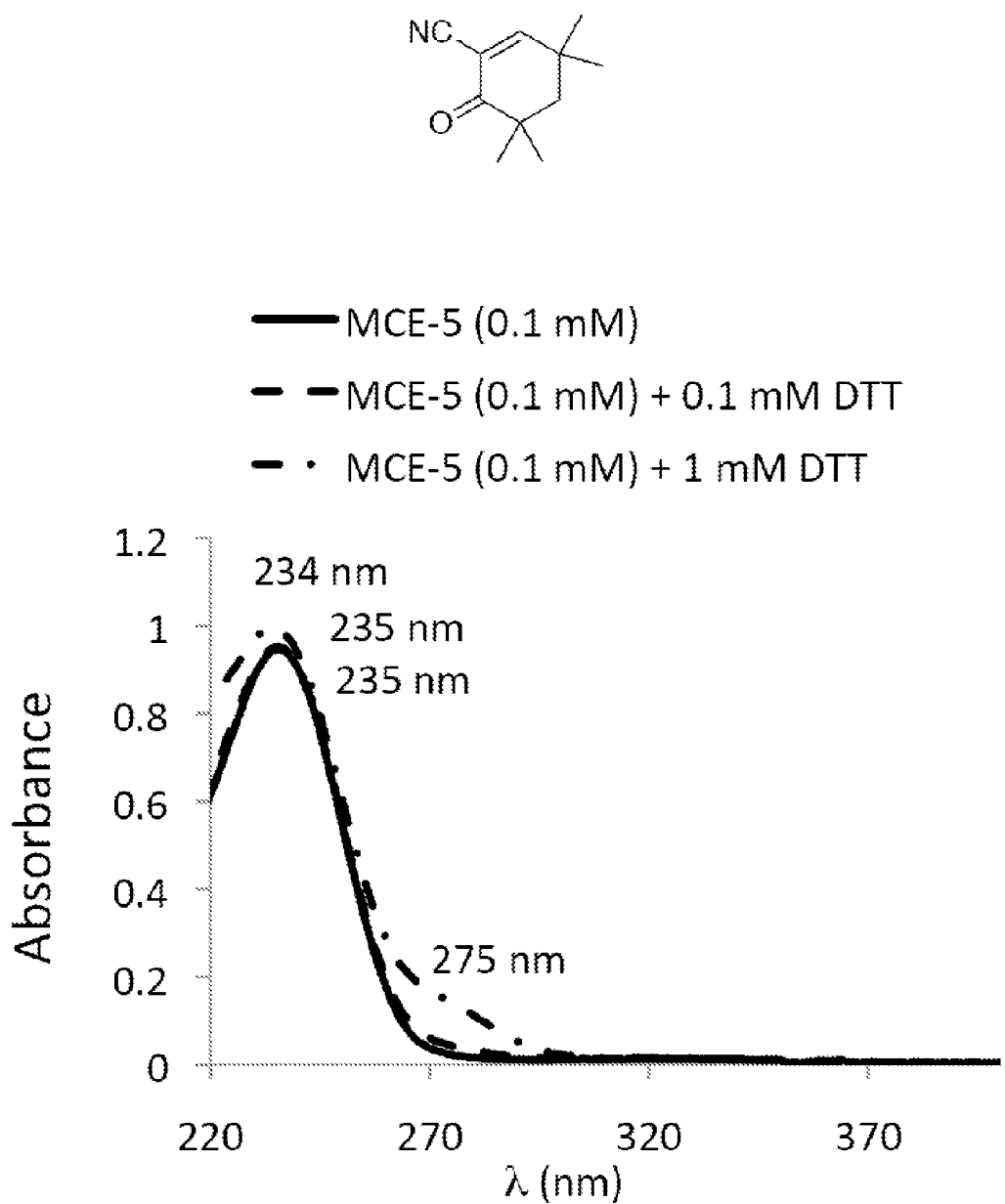
FIG. 4 shows how the UV spectrum of MCE-5 changes in the presence of dithiothreitol (DTT).
Figure 5:
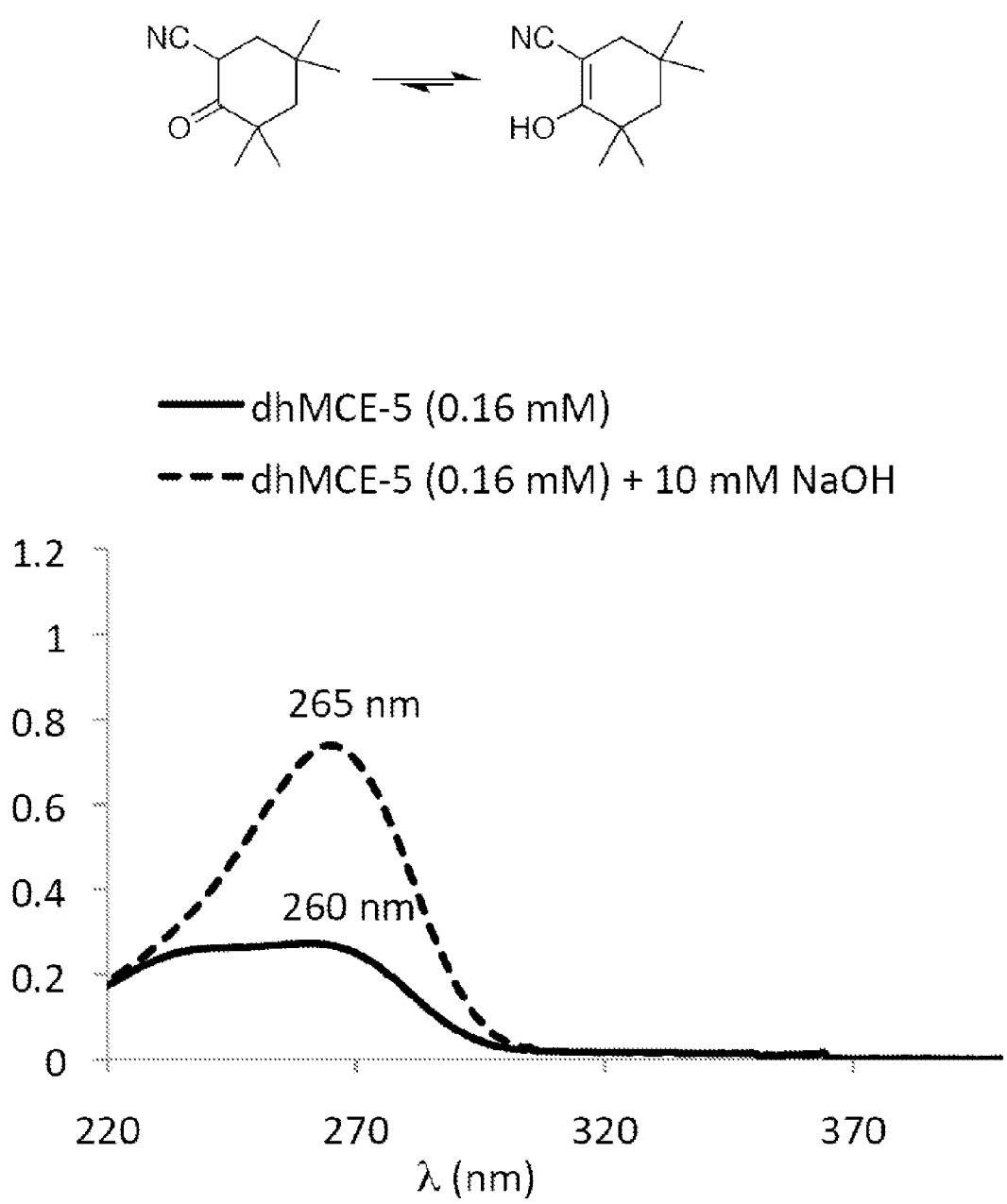
FIG. 5 shows how the presence of base effects the UV spectra of the dhMCE-5 tautomers.
Figure 6:
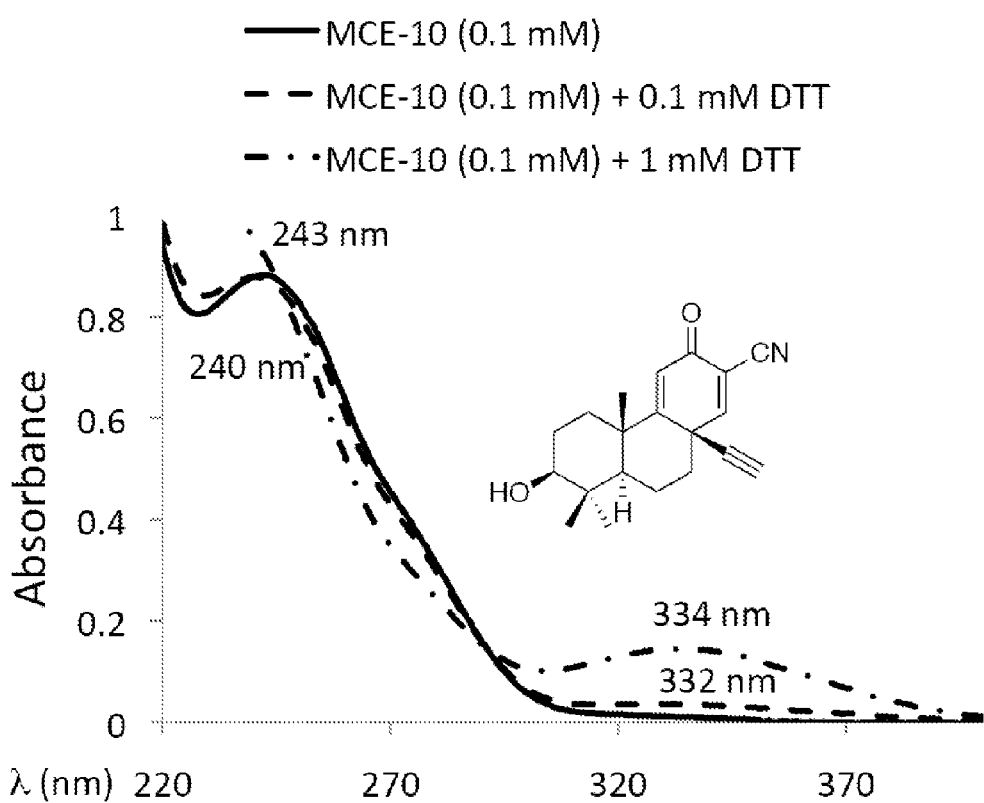
FIG. 6 shows how the UV spectrum of MCE-10 changes in the presence of dithiothreitol (DTT).
Figure 7:
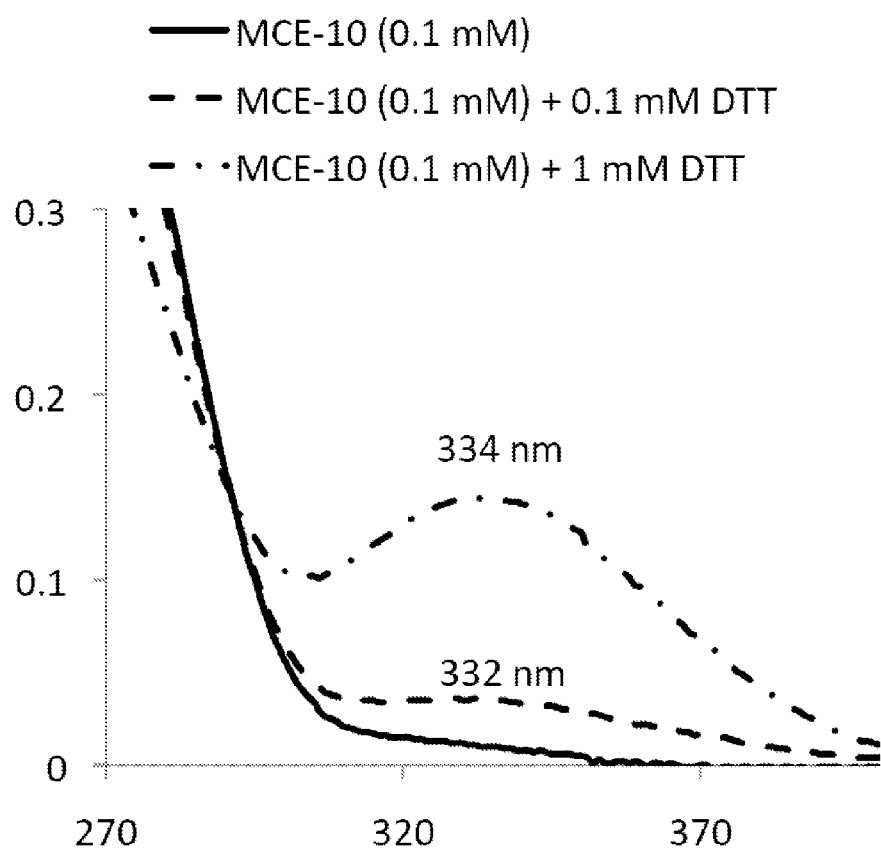
FIG. 7 shows how the UV spectrum of MCE-10 changes in the presence of dithiothreitol (DTT). In contrast to FIG. 6, the lower absorbance range is expanded.
Figure 8:
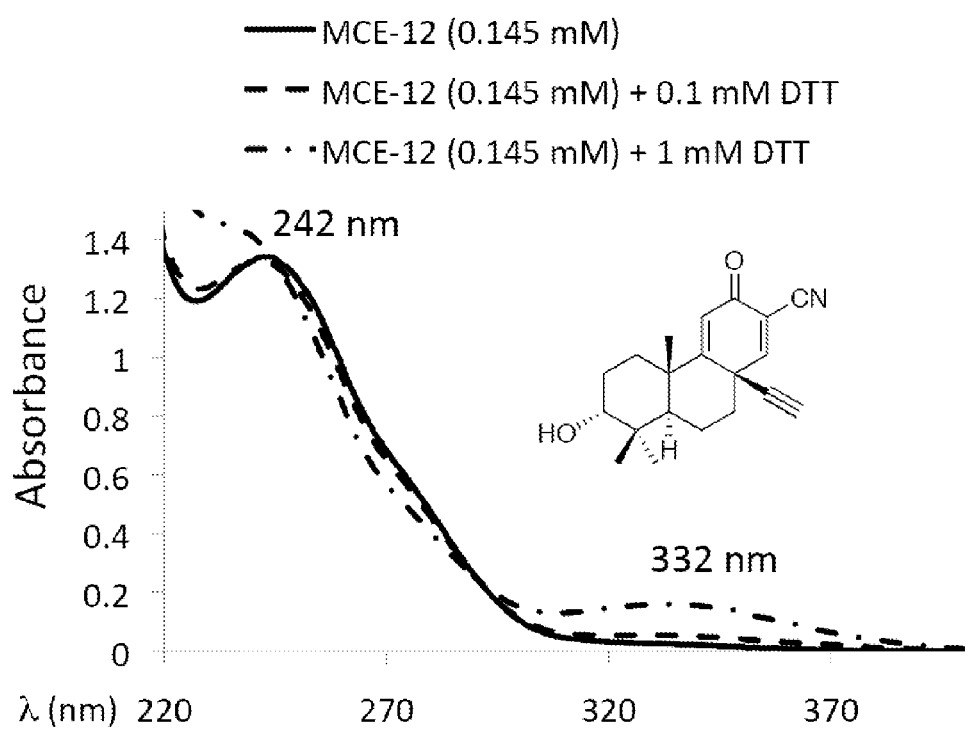
FIG. 8 shows how the UV spectrum of MCE-12 changes in the presence of dithiothreitol (DTT).
Figure 9:
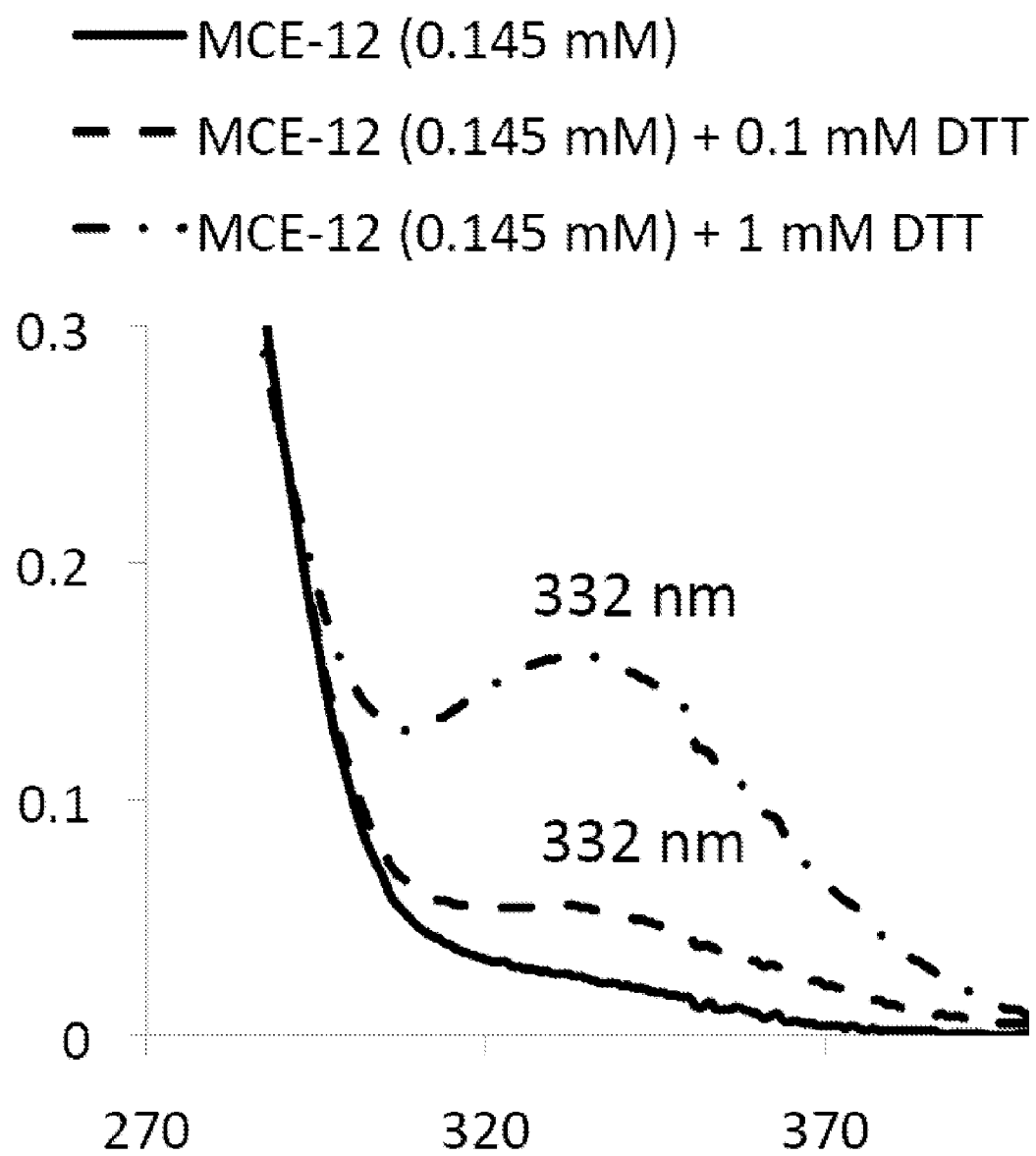
FIG. 9 shows how the UV spectrum of MCE-12 changes in the presence of dithiothreitol (DTT). In contrast to FIG. 8, the lower absorbance range is expanded.

UV spectrum of MCE-5 shows a weak absorption at 275 nm upon the addition of 1.0 mM DTT, while no apparent change occurs upon addition of 0.1 mM DTT (FIG. 4). Applicants note that this absorption is consistent with the absorption of dhMCE-5 at 265 nm which increases by the addition of NaOH (FIG. 5), suggesting that the weak absorption detected for MCE-5 with 1.0 nM DTT is derived from the Michael adduct of DTT with MCE-5.

Figure 10:
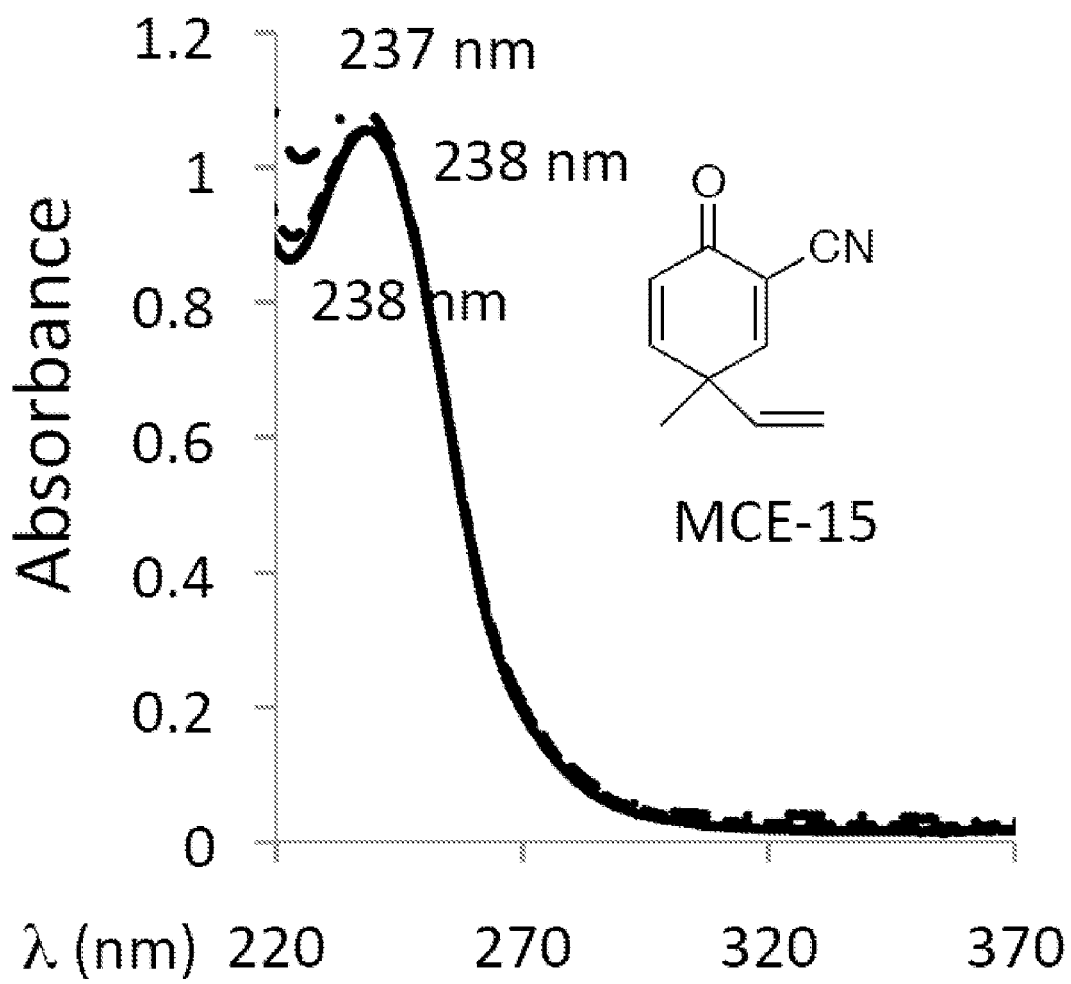
FIG. 10 shows how the UV spectrum of MCE-15 changes in the presence of dithiothreitol (DTT). The solid line corresponds to the UV spectrum in the absence of DTT, the dashed line corresponds to the UV spectrum in the presence of 0.1 mM DTT, and the dashed-and-dotted line corresponds to the UV spectrum in the presence of 1 mM DTT.

MCE-2 and MCE-15 do not give the second absorption by the addition of DTT under the same conditions as for MCE-1. See FIGS. 1B and 10, which provide the results for MCE-2 and 15. MCE-3 (acetylenic enolizable cyano enone) does not change when 0.1 mM of DTT is added while they show small red shift when 1 mM of DTT is added (FIG. 1C).

Figure 11:
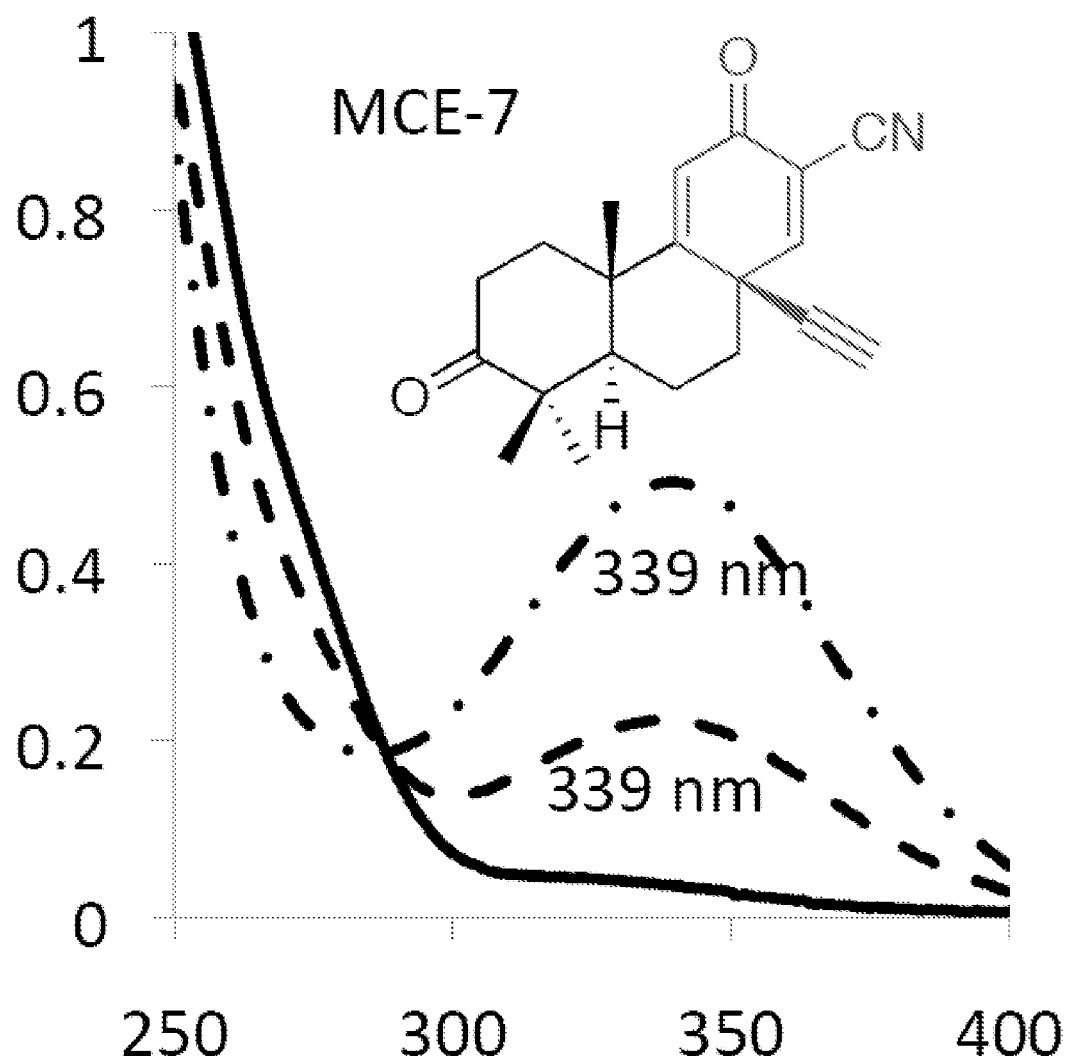
FIG. 11 shows how the UV spectrum of MCE-7 changes in the presence of dithiothreitol (DTT). The solid line corresponds to the UV spectrum in the absence of DTT, the dashed line corresponds to the UV spectrum in the presence of 0.1 mM DTT, and the dashed-and-dotted line corresponds to the UV spectrum in the presence of 1 mM DTT.
Figure 12:
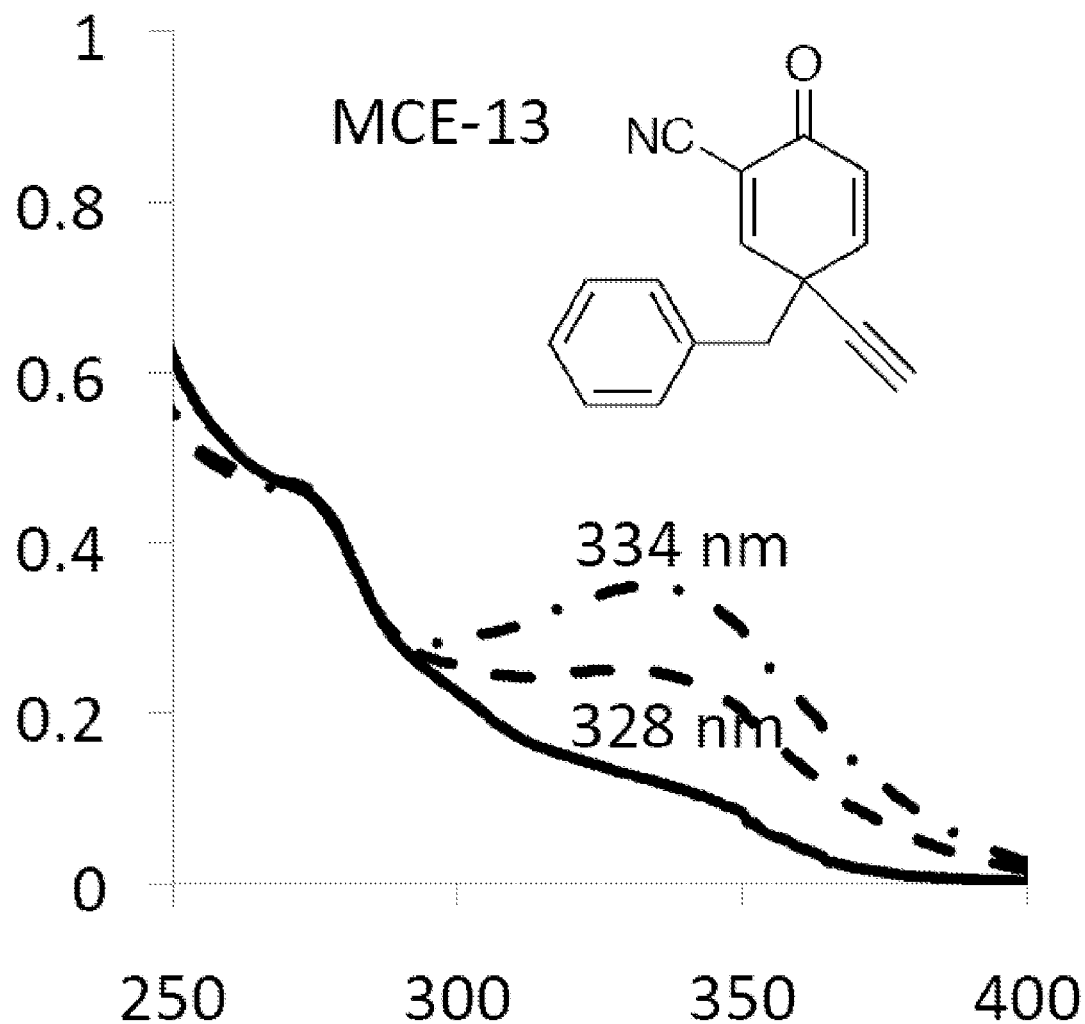
FIG. 12 shows how the UV spectrum of MCE-13 changes in the presence of dithiothreitol (DTT). The solid line corresponds to the UV spectrum in the absence of DTT, the dashed line corresponds to the UV spectrum in the presence of 0.1 mM DTT, and the dashed-and-dotted line corresponds to the UV spectrum in the presence of 1 mM DTT.

MCE-7 and 13 like MCE-1 show second absorptions at around 330 nm, which are derived from Michael adducts with DTT. The absorbance of MCE-7 (FIG. 11) is similarly intense as the corresponding absorption of MCE-1. The absorbance of MCE-13 is a bit weaker than the corresponding absorption of MCE-1 (FIG. 12)

Keap1 is an electrophile sensor in the cellular Keap1-Nrf2-antioxidant response elements (ARE) phase II response pathway that regulates the transcription of genes for cytoprotective enzymes such as HO-1 and NQO1. Keap1 is a thiol-rich protein possessing 25 cysteine residues, some of which are highly reactive (Dinkova-Kostova et al., 2002, which is incorporated herein by reference). UV studies on MCEs with Keap1 are consistent with those with DTT, with MCE-1 showing the highest reactivity of the group. That is MCE-1 showed the highest reactivity both on a thiol-rich protein as well as on a small thiol nucleophiles, further confirming the hypothesis that MCE-1 selectively reacts with thiol nucleophiles.

C. $^1$H-NMR Studies

Figure 13:
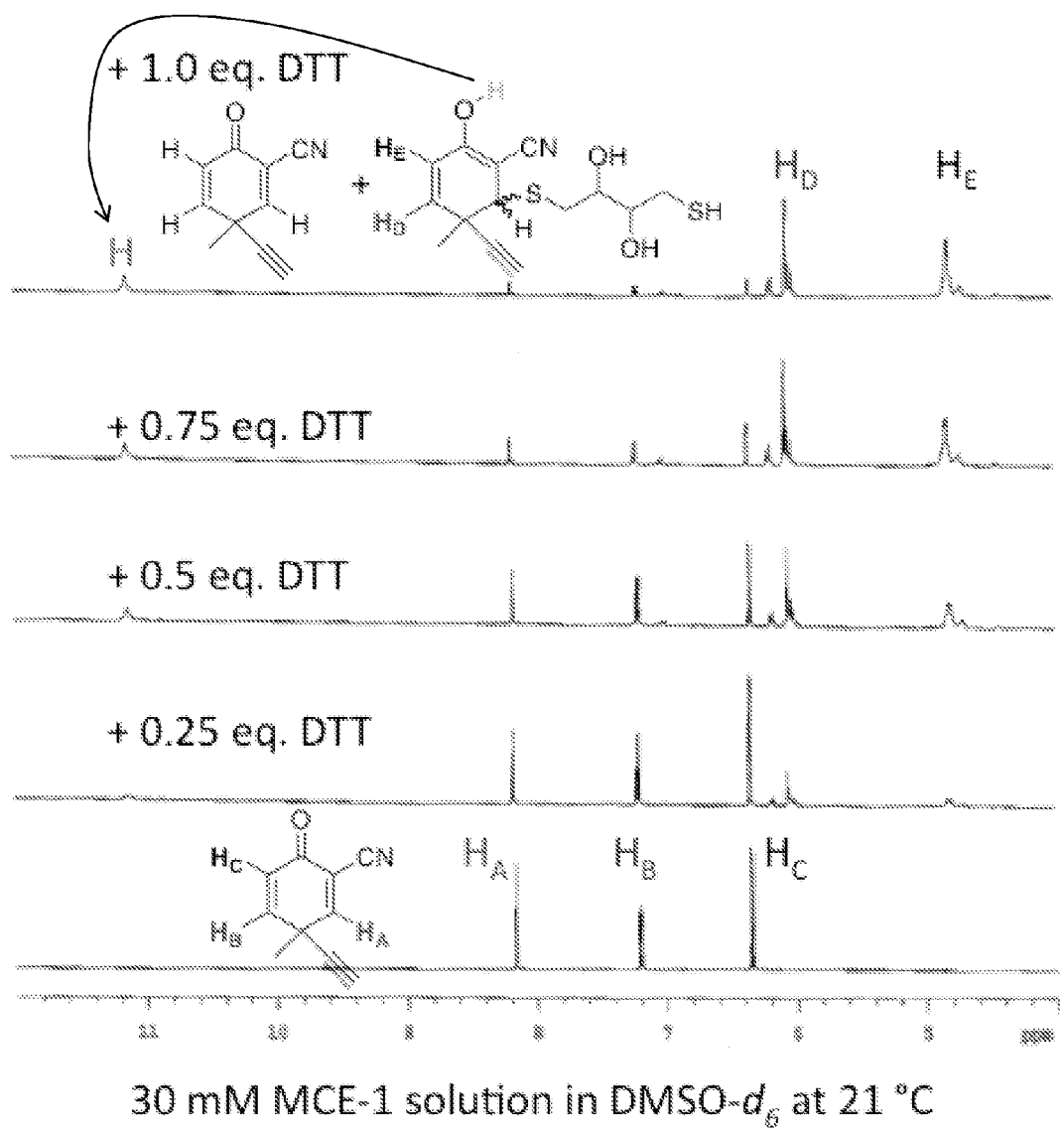
FIG. 13 shows that MCE-1 gives a reversible Michael adduct by $^1$H-NMR. In the $^1$H NMR (500 MHz, DMSO-$d_6$ at 21° C.) of MCE-1, the olefinic protons $H_A$, $H_B$, and $H_C$ are observed at δ 8.17 ppm (d, J=3 Hz), 7.21 ppm (dd, J=3 and 10 Hz), and 6.35 ppm (d, J=10 Hz), respectively, while olefinic protons $H_A$, $H_B$, and $H_C$ of MCE-1 decrease, an enol proton [at δ 11.12 ppm (brs)] and new olefinic protons $H_D$ and $H_E$ appear and increase according to increasing amounts of DTT.

Also disclosed herein are $^1$H-NMR results providing further evidence that MCE-1 gives a reversible Michael adduct with DTT. In the $^1$H NMR (500 MHz, DMSO-$d_6$ at 21° C.) of MCE-1, the olefinic protons $H_A$, $H_B$, and $H_C$ are observed at δ 8.17 ppm (d, J=3 Hz), 7.21 ppm (dd, J=3 and 10 Hz), and 6.35 ppm (d, J=10 Hz), respectively, while olefinic protons $H_A$, $H_B$, and $H_C$ of MCE-1 decrease, an enol proton [at δ 11.12 ppm (brs)] and new olefinic protons $H_D$ and $H_E$ appear and increase according to increasing amounts of DTT. See FIG. 13. These new protons are consistent with adduct formation via Michael addition of DTT to MCE-1. The development of additional small signals suggests that a second stereoisomeric adduct forms as well.

Figure 14:
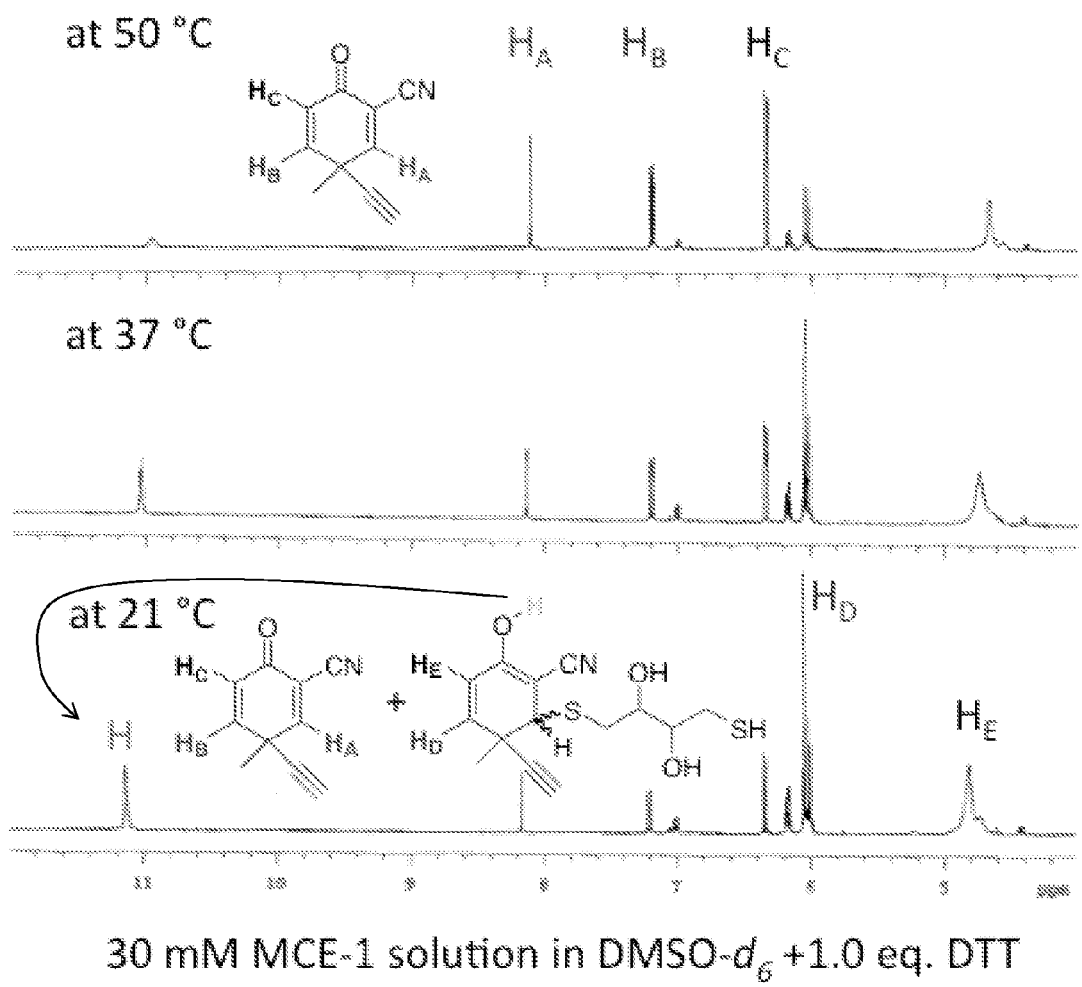
FIG. 14 shows how the $^1$H-NMR spectrum of MCE-1+1 eq. of DTT (500 MHz, DMSO-$d_6$ at 21° C.) changes as the temperature is increased.

In further experiments, at elevated temperatures, although the enol proton and olefinic protons $H_D$ and $H_E$ of Michael adduct decrease, the olefinic protons $H_A$, $H_B$, and $H_C$ of MCE-1 increase. See FIG. 14. These observations are consistent with reversible Michael addition. Although Michael adducts of CDDO and MCE-1 with DTT are observed by NMR and UV, isolation has not been possible and may not be possible. These results suggest that the conversion of the Michael adducts to CDDO and MCE-1 is fast (Couch et al., 2005, which is incorporated herein by reference).

D. Biological Activity

Compounds of the present disclosure have been tested for inhibition of nitric oxide (NO) production in RAW cells stimulated by interferon-γ (iNOS assay) and induction of NAD(P)H-quinone oxidoreductase in Hepa1c1c7 cells (NQO1 assay), both assay systems we have previously employed. At the same time, CDDO and TBE-31 were tested as a positive controls in the same assays. The results of the iNOS assay are shown in Table 1. Notably, MCE-1 shows the highest potency amongst MCEs in both assays. The potency in the iNOS assay is more than CDDO (pentacycle), whose methyl ester is currently evaluated in Phase II clinical trials as an anti-inflammatory drug. Also the potency correlates to their reactivity as Michael acceptors based on the above-summarized UV studies. However, although the reactivity of MCE-7 is similar to MCE-1 (compare FIG. 1A with FIG. 11), it is inactive at a concentration of 300 nM in the iNOS assay and less potent than MCE-1 in the NQO1 assay.

TABLE 1

Suppression of IFNγ-induced NO production.

| Compound | Structure | RAW (10 ng/ml IFNγ) $IC_{50}$ |
|---|---|---|
| MCE-1 | 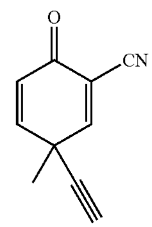 | 8 nM |
| MCE-2 | 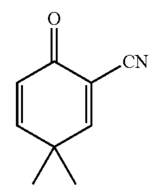 | 380 nM |
| MCE-7 | 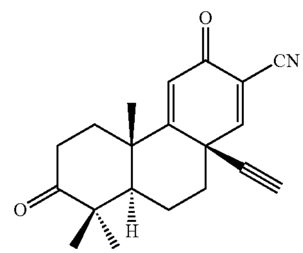 | >300 nM |
| MCE-15 | 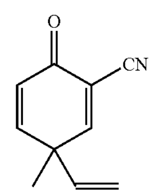 | 300 nM |
| CDDO | 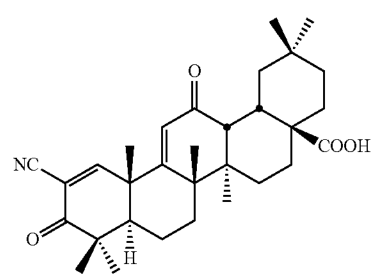 | 20 nM |
| TBE-31 | 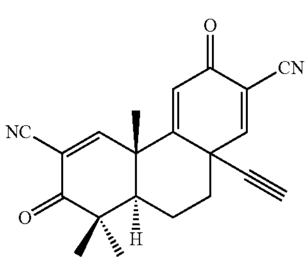 | 1 nM |

III. Homology Model of IKKβ and Identification of Further MCE Candidates

A homology model of the IKKβ based on the X-ray structure of the checkpoint-2 kinase (2CN5.ent) was generated, and the two pockets, one hydrophobic and one hydrophilic, surrounding Cys$^{179}$ were targeted to identify further lead compounds. The proposed syntheses of these compounds (as well as others) are provided in the examples section below.

The homology model of IKKβ was built using SWISS-MODEL and the X-ray structures of other related kinases (checkpoint-2 kinase, 2cn5.pdb) within the Protein Data Bank. The sequence comparison of the two proteins has a sufficient sequence similarity (36% sequence identity) to provide a good working model. The homology-based IKKβ dimer was subjected to several cycles of energy minimization to remove initial strain, using the AMBER force field within the InsightII (Molecular Simulations, Inc.) program. The complex was then placed centrally in a cube of 12 nm and soaked with water (37,700 water molecules) and then energy minimized using a steepest descent algorithm. Extensive molecular dynamics (MD) simulations (at 300 K, with an integration time step of 2 fs, and constant pressure of 1 bar) were carried out with the complex using the GROMACS program (Berendsen et al., 1995, which is incorporated herein by reference) Pentium III processors running Linux. Starting with this initial homology model, an initial set of ligands for which biological activity (MCE-1, CDDO, TBE-31) was examined (see Table 1).

For example, the binding of MCE-1 to Cys$^{179}$ based on molecular dynamics simulations and energy minimization suggests that two Gln (Q176/Q197) make up the binding pocket to the cyano/hydroxyl function, while L178, F182, and L194 make up the hydrophobic pocket.

Based on this approach, additional ligands may be rationally designed to further enhance binding, targeting the two pockets proximal to the Cys$^{179}$. Examples of such ligands and their synthesis and/or proposed synthesis is provided in the Examples section below. Additionally, two "non-rational" approaches can be utilized to further expand the pool of possible ligands (autodock, fragment tethering). All three of these methods can be used in an iterative procedure, along with the results from the biological assays, in order to optimize binding affinity.

Rational Structure Based Screening

Ligand designs and/or modifications can be examined by molecular modeling and computer simulations. which allows refinement and optimization of the physicochemical properties before undertaking the synthesis. INSIGHT II and Chimera (UCSF) are utilized for the viewing and interactive manipulation and building of the protein structures. For extensive homology modeling one can utilize WHATIF (Vriend, 1990, which is incorporated herein by reference) or Modeler. Procheck (Laskowski et al., 1996), which is incorporated herein by reference will be used to examine the "health" of all of the protein structures. The protein structures are then refined using extensive molecular dynamics simulations using the GROMACs or NAMD simulation programs, within a fully solvated simulation cell.

Virtual Screening Through a Fragment Tethering Strategy

Complementary to the rational design "educated" screening approach, a de novo design of analogs via a fragment tethering strategy can also be undertaken. This method involves growing substituents onto a pharmacophore core of the lead compound to generate a compound library for virtual screening, analyzing the binding pocket, and determining where a specific functional group might bind tightly to the useful sites in the pocket.

Subsequently, these chemical groups are virtually tethered to produce a molecular skeleton which is converted into a plausible bioorganic molecule to be synthesized. The computer program, Discovery Studio, allows such a "fragment-tethering" strategy to grow substituents onto a pharmacophore core of the lead compound to generate a compound library for virtual screening. It offers the possibility of discovering novel inhibitory molecules without a potentially biased effort toward a specific class of compounds in the existing libraries/databases.

For example, using the structure of MCE-1 docked to IKKβ as the core structure, two sites of substitution can be examined with fragments of different bulkiness and stereoelectronic properties from an in-house "fragment library" selected for synthetic availability and pharmacological properties. The resulting "virtual" compounds can then be docked into the IKKβ pockets to prioritize the binding affinity.

AutoDock

Different ligand targets may also be identified by utilizing docking to obtain starting structures/topological orientations that can then be further refined with MD simulations. The docking may be carried out with autodock4.0 (Scripps) using the homology model of the IKKβ generated as described above. This rigid docking procedure will provide multiple starting structures for further refinement via MD simulations, which is important to account for conformational changes that may take place during binding, an aspect that is being increasingly appreciated in computational drug design. In addition to the autodock, we have recently begun using GOLD (version 2.0) and the associated libraries of small molecules. The inventors will carry out GOLD docking to generate novel molecular fragments that fit well into the binding pockets surrounding Cys 179, that can then be incorporated into the synthetic efforts detailed in Aim #2. The complexes obtained from both of the docking procedures will be soaked with TIP4 water molecules and then undergo extensive MD simulations using the GROMACS program. During the MD simulations both the protein and ligand will be allowed to undergo conformational changes, allowing for the generation of optimal fit. We have developed shell scripts to automatic conversion of the output files from the docking procedures to these MD simulations.

A homology model of the IKKβ based on the X-ray structure of the checkpoint-2 kinase (2CN5.ent) was generated, and the two pockets, one hydrophobic and one hydrophilic, surrounding Cys$^{179}$ were targeted to generate identify further lead compounds. Based on the identified hydrophobic and hydrophilic pockets surrounding Cys179 of IKKβ and that the distance between Cys$^{179}$ and either the hydrophobic or hydrophilic pocket is both 7-8 Å, a preliminary set of compounds has been designed. The proposed synthesis of some of the compounds is provided in the Examples section below.

In certain embodiments, there is provided a hydrophobic series, for example, with structures as defined by formulas I and II, with compounds 38 and 39 as respective examples of each.

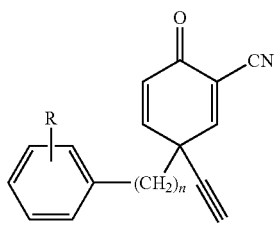

I

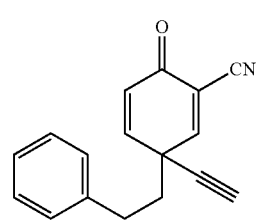

I (n = 2, R = H)

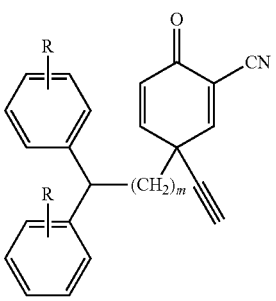

II

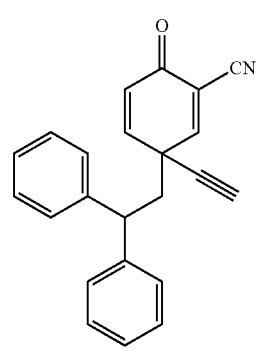

I (m = 1, R = H)

Without being bound by theory or mechanism, based on the information gleaned from the IKKβ homology model, n=1-3 and m=1-2 would give a reasonable length in some embodiments because the distance between the reactive site of the Michael acceptor and the phenyl group of these molecules is similar to the distance between Cys[179] and hydrophobic pocket (about 7-8 Å).

In certain embodiments, there is provided a hydrophilic series, for example, with structures as defined by formulas III, with compounds 48 as an example thereof

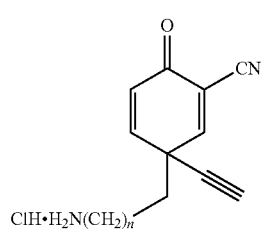

III

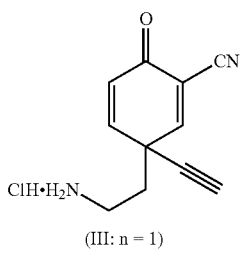

48

(III: n = 1)

Without being bound by theory or mechanism, based on the information gleaned from the IKKβ homology model, n=1-2 would provide a reasonable length in some embodiments. A proposed synthesis for 48 and other compounds of the hydrophilic series is provided in the Examples section below. Other examples hydrophilic groups includes compounds having hydroxyl or carboxyl groups. See, e.g., Example 13.

Various compounds appropriately sized for either hydrophilic or hydrophobic pockets may be synthesized using Sonogashira coupling (Sonogashira et al., 1975), for example, between known compound 65 (Phansavath et al., 1998, which is incorporated herein by reference) and an aromatic halide.

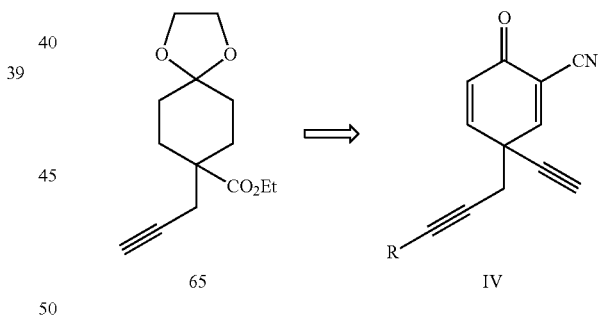

If one inserts, for example, a phenyl, a thiophenyl, or a furyl groups, the resulting compound of generalized formula IV would have a hydrophobic moiety attached. If once were instead to insert pyridinyl and imidazolyl groups, the resulting compound of formula IV would have hydrophilic moiety attached. As thiazolyl and oxazolyl groups are neutral, they are hydrophobic. However, quaternary salts of both groups are hydrophilic. Therefore, compounds IV having a thiazolyl or oxazolyl group might show either hydrophobic or hydrophilic properties and may vary depending on the conditions, for example, the environment within in living cells or proximate to a living cell. Scheme A provides examples of moieties with these different properties.

In addition to monocyclic cyanoenones, the invention also provides bicyclic and tricyclic cyanoenones. For example:

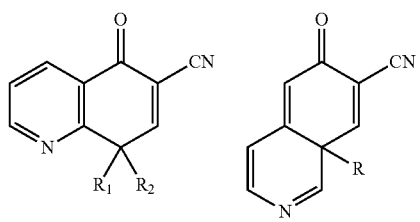
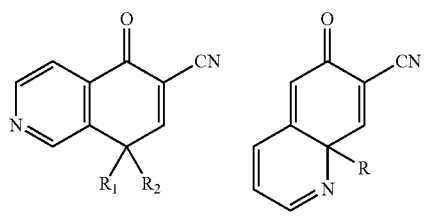
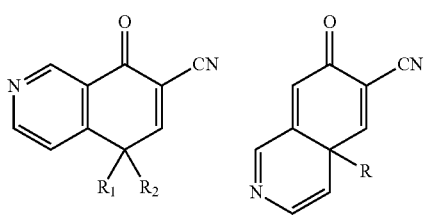
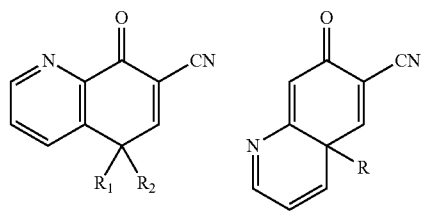

In some embodiments, such compounds made have both hydrophilic and hydrophobic groups, for example, compounds according to formula VII:

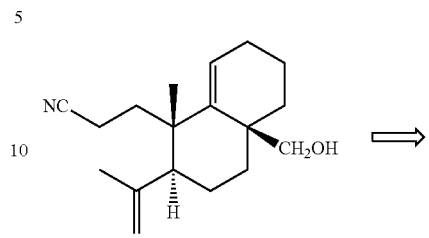

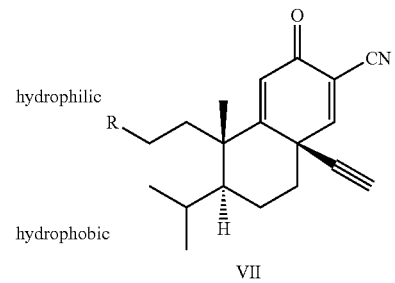

VII

R = —CO$_2$H, —CH$_2$NH$_2$, —CH$_2$OH$_2$, etc,

The syntheses of certain bicyclic cyanoenones of formula VII are proposed in Example 17 below. Examples of tricyclic cyanoenones are provided in Examples 6-8, below.

Scheme A

Hydrophobic groups:

R = 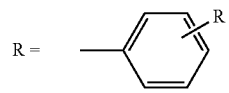 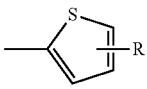 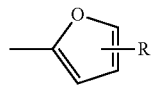

Hydrophilic group:

R = 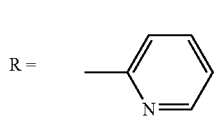 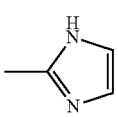

Once synthesized these compounds can be further evaluated for the biological activity, for example, through an in vitro IKKβ kinase assay using a commercially available HTScan® IKKβ Kinase Assay Kit. A suitable protocol for such an assay is described in Example 1 below.

IV. Diseases Associated with Inflammation and/or Oxidative Stress

Inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines such as TNF-α and IL-1, and production of reactive oxygen or nitrogen species such as hydrogen peroxide, superoxide and peroxynitrite. In later stages of inflammation, tissue remodeling, angiogenesis, and scar formation (fibrosis) may occur as part of the wound healing process. Under normal circumstances, the inflammatory response is regulated and temporary and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications.

Many serious and intractable human diseases involve dysregulation of inflammatory processes, including diseases such as cancer, atherosclerosis, and diabetes, which were not traditionally viewed as inflammatory conditions. In the case of cancer, the inflammatory processes are associated with tumor formation, progression, metastasis, and resistance to therapy. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia. Excessive production of reactive oxygen species and reactive nitrogen species such as superoxide, hydrogen peroxide, nitric oxide, and peroxynitrite is a hallmark of inflammatory conditions. Evidence of dysregulated peroxynitrite production has been reported in a wide variety of diseases (Szabo et al., 2007; Schulz et al., 2008; Forstermann, 2006; Pall, 2007).

Autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins such as inducible nitric oxide synthase (iNOS). Chronic organ failure such as renal failure, heart failure, and chronic obstructive pulmonary disease is closely associated with the presence of chronic oxidative stress and inflammation, leading to the development of fibrosis and eventual loss of organ function.

Many other disorders involve oxidative stress and inflammation in affected tissues, including inflammatory bowel disease; inflammatory skin diseases; mucositis related to radiation therapy and chemotherapy; eye diseases such as uveitis, glaucoma, macular degeneration, and various forms of retinopathy; transplant failure and rejection; ischemia-reperfusion injury; chronic pain; degenerative conditions of the bones and joints including osteoarthritis and osteoporosis; asthma and cystic fibrosis; seizure disorders; and neuropsychiatric conditions including schizophrenia, depression, bipolar disorder, post-traumatic stress disorder, attention deficit disorders, autism-spectrum disorders, and eating disorders such as anorexia nervosa. Dysregulation of inflammatory signaling pathways is believed to be a major factor in the pathology of muscle wasting diseases including muscular dystrophy and various forms of cachexia.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines such as TNF-α and IL-1. This is believed to be a factor in mortality arising from severe influenza, severe acute respiratory syndrome, and sepsis.

The aberrant or excessive expression of either iNOS or cyclooxygenase-2 (COX-2) has been implicated in the pathogenesis of many disease processes. For example, it is clear that NO is a potent mutagen (Tamir and Tannebaum, 1996), and that nitric oxide can also activate COX-2 (Salvemini et al., 1994). Furthermore, there is a marked increase in iNOS in rat colon tumors induced by the carcinogen, azoxymethane (Takahashi et al., 1997). A series of synthetic triterpenoid analogs of oleanolic acid have been shown to be powerful inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference.

In one aspect, compounds disclosed herein are characterized by their ability to inhibit the production of nitric oxide in macrophage-derived RAW 264.7 cells induced by exposure to γ-interferon. They are further characterized by their ability to induce the expression of antioxidant proteins such as NQO1 and reduce the expression of pro-inflammatory proteins such as COX-2 and inducible nitric oxide synthase (iNOS). These properties are relevant to the treatment of a wide array of diseases involving oxidative stress and dysregulation of inflammatory processes including cancer, mucositis resulting from radiation therapy or chemotherapy, autoimmune diseases, cardiovascular diseases including atherosclerosis, ischemia-reperfusion injury, acute and chronic organ failure including renal failure and heart failure, respiratory diseases, diabetes and complications of diabetes, severe allergies, transplant rejection, graft-versus-host disease, neurodegenerative diseases, diseases of the eye and retina, acute and chronic pain, degenerative bone diseases including osteoarthritis and osteoporosis, inflammatory bowel diseases, dermatitis and other skin diseases, sepsis, burns, seizure disorders, and neuropsychiatric disorders.

Without being bound by theory, the activation of the anti-oxidant/anti-inflammatory Keap1/Nrf2/ARE pathway is believed to be implicated in both the anti-inflammatory and anti-carcinogenic properties of the compounds disclosed herein.

In another aspect, compounds disclosed herein may be used for treating a subject having a condition caused by elevated levels of oxidative stress in one or more tissues. Oxidative stress results from abnormally high or prolonged levels of reactive oxygen species such as superoxide, hydrogen peroxide, nitric oxide, and peroxynitrite (formed by the reaction of nitric oxide and superoxide). The oxidative stress may be accompanied by either acute or chronic inflammation. The oxidative stress may be caused by mitochondrial dysfunction, by activation of immune cells such as macrophages and neutrophils, by acute exposure to an external agent such as ionizing radiation or a cytotoxic chemotherapy agent (e.g., doxorubicin), by trauma or other acute tissue injury, by ischemia/reperfusion, by poor circulation or anemia, by localized or systemic hypoxia or hyperoxia, by elevated levels of inflammatory cytokines and other inflammation-related proteins, and/or by other abnormal physiological states such as hyperglycemia or hypoglycemia.

In animal models of many such conditions, stimulating expression of inducible heme oxygenase (HO-1), a target gene of the Nrf2 pathway, has been shown to have a significant therapeutic effect including models of myocardial infarction, renal failure, transplant failure and rejection, stroke, cardiovascular disease, and autoimmune disease (e.g., Sacerdoti et al., 2005; Abraham & Kappas, 2005; Bach, 2006; Araujo et al., 2003; Liu et al., 2006; Ishikawa et al., 2001; Kruger et al., 2006; Satoh et al., 2006; Zhou et al., 2005; Morse and Choi, 2005; Morse and Choi, 2002). This enzyme breaks free heme down into iron, carbon monoxide (CO), and biliverdin (which is subsequently converted to the potent antioxidant molecule, bilirubin).

In another aspect, compounds of this invention may be used in preventing or treating tissue damage or organ failure, acute and chronic, resulting from oxidative stress exacerbated by inflammation. Examples of diseases that fall in this category include: heart failure, liver failure, transplant failure and rejection, renal failure, pancreatitis, fibrotic lung diseases (cystic fibrosis and COPD, among others), diabetes (including complications), atherosclerosis, ischemia-reperfusion injury, glaucoma, stroke, autoimmune disease, autism, macular degeneration, and muscular dystrophy. For example, in the case of autism, studies suggest that increased oxidative stress in the central nervous system may contribute to the development of the disease (Chauhan and Chauhan, 2006).

Evidence also links oxidative stress and inflammation to the development and pathology of many other disorders of the central nervous system, including psychiatric disorders such as psychosis, major depression, and bipolar disorder; seizure disorders such as epilepsy; pain and sensory syndromes such as migraine, neuropathic pain or tinnitus; and behavioral syndromes such as the attention deficit disorders. See, e.g., Dickerson et al., 2007; Hanson et al., 2005; Kendall-Tackett, 2007; Lencz et al., 2007; Dudhgaonkar et al., 2006; Lee et al., 2007; Morris et al., 2002; Ruster et al., 2005; McIver et al., 2005; Sarchielli et al., 2006; Kawakami et al., 2006; Ross et al., 2003, which are all incorporated by reference herein. For example, elevated levels of inflammatory cytokines, including TNF, interferon-γ, and IL-6, are associated with major mental illness (Dickerson et al., 2007). Microglial activation has also been linked to major mental illness. Therefore, down-regulating inflammatory cytokines and inhibiting excessive activation of microglia could be beneficial in patients with schizophrenia, major depression, bipolar disorder, autism-spectrum disorders, and other neuropsychiatric disorders.

Accordingly, in pathologies involving oxidative stress alone or oxidative stress exacerbated by inflammation, treatment may comprise administering to a subject a therapeutically effective amount of a compound of this invention, such as those described above or throughout this specification. Treatment may be administered preventively, in advance of a predictable state of oxidative stress (e.g., organ transplantation or the administration of radiation therapy to a cancer patient), or it may be administered therapeutically in settings involving established oxidative stress and inflammation.

The compounds disclosed herein may be generally applied to the treatment of inflammatory conditions, such as sepsis, dermatitis, autoimmune disease and osteoarthritis. In one aspect, the compounds of this invention may be used to treat inflammatory pain and/or neuropathic pain, for example, by inducing Nrf2 and/or inhibiting NF-κB.

In one aspect, the compounds disclosed herein may be used to function as antioxidant inflammation modulators (AIMs) having potent anti-inflammatory properties that mimic the biological activity of cyclopentenone prostaglandins (cyPGs). In one embodiment, the compounds disclosed herein may be used to control the production of pro-inflammatory cytokines by selectively targeting regulatory cysteine residues (RCRs) on proteins that regulate the transcriptional activity of redox-sensitive transcription factors. Activation of RCRs by cyPGs or AIMs has been shown to initiate a pro-resolution program in which the activity of the antioxidant and cytoprotective transcription factor Nrf2 is potently induced, and the activities of the pro-oxidant and pro-inflammatory transcription factors NF-κB and the STATs are suppressed. This increases the production of antioxidant and reductive molecules (e.g., NQO1, HO-1, SOD1, and/or γ-GCS) and/or decreases oxidative stress and the production of pro-oxidant and pro-inflammatory molecules (e.g., iNOS, COX-2, and/or TNF-α).

In some embodiments, the compounds disclosed herein may be used in the treatment and prevention of diseases such as cancer, inflammation, Alzheimer's disease, Parkinson's disease, multiple sclerosis, autism, amyotrophic lateral sclerosis, autoimmune diseases such as rheumatoid arthritis, lupus, and MS, inflammatory bowel disease, all other diseases whose pathogenesis is believed to involve excessive production of either nitric oxide or prostaglandins, and pathologies involving oxidative stress alone or oxidative stress exacerbated by inflammation.

Another aspect of inflammation is the production of inflammatory prostaglandins such as prostaglandin E. These molecules promote vasodilation, plasma extravasation, localized pain, elevated temperature, and other symptoms of inflammation. The inducible form of the enzyme COX-2 is associated with their production, and high levels of COX-2 are found in inflamed tissues. Consequently, inhibition of COX-2 may relieve many symptoms of inflammation and a number of important anti-inflammatory drugs (e.g., ibuprofen and celecoxib) act by inhibiting COX-2 activity. Recent research, however, has demonstrated that a class of cyclopentenone prostaglandins (cyPGs) (e.g., 15-deoxy prostaglandin J2, a.k.a. PGD2) plays a role in stimulating the orchestrated resolution of inflammation (e.g., Rajakariar et al., 2007). COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time.

In one aspect, the compounds disclosed herein may be used to control the production of pro-inflammatory cytokines within the cell by selectively activating regulatory cysteine residues (RCRs) on proteins that regulate the activity of redox-sensitive transcription factors. Activation of RCRs by cyPGs has been shown to initiate a pro-resolution program in which the activity of the antioxidant and cytoprotective transcription factor Nrf2 is potently induced and the activities of the pro-oxidant and pro-inflammatory transcription factors NF-κB and the STATs are suppressed. In some embodiments, this increases the production of antioxidant and reductive molecules (NQO1, HO-1, SOD1, γ-GCS) and decreases oxidative stress and the production of pro-oxidant and pro-inflammatory molecules (iNOS, COX-2, TNF-α). In some embodiments, the compounds of this invention may cause the cells that host the inflammatory event to revert to a non-inflammatory state by promoting the resolution of inflammation and limiting excessive tissue damage to the host.

E. Cancer

Further, the compounds of the present disclosure may be used to induce apoptosis in tumor cells, to induce cell differentiation, to inhibit cancer cell proliferation, to inhibit an inflammatory response, and/or to function in a chemopreventative capacity. For example, the invention provides new compounds that have one or more of the following properties: (1) an ability to induce apoptosis and differentiate both malignant and non-malignant cells, (2) an activity at sub-micromolar or nanomolar levels as an inhibitor of proliferation of many malignant or premalignant cells, (3) an ability to suppress the de novo synthesis of the inflammatory enzyme inducible nitric oxide synthase (iNOS), (4) an ability to inhibit NF-κB activation, and (5) an ability to induce the expression of heme oxygenase-1 (HO-1).

The levels of iNOS and COX-2 are elevated in certain cancers and have been implicated in carcinogenesis and COX-2 inhibitors have been shown to reduce the incidence of primary colonic adenomas in humans (Rostom et al., 2007; Brown and DuBois, 2005; Crowel et al., 2003). iNOS is expressed in myeloid-derived suppressor cells (MDSCs) (Angulo et al., 2000) and COX-2 activity in cancer cells has been shown to result in the production of prostaglandin $E_2$ ($PGE_2$), which has been shown to induce the expression of arginase in MDSCs (Sinha et al., 2007). Arginase and iNOS are enzymes that utilize L-arginine as a substrate and produce L-ornithine and urea, and L-citrulline and NO, respectively. The depletion of arginine from the tumor microenvironment by MDSCs, combined with the production of NO and peroxynitrite has been shown to inhibit proliferation and induce apoptosis of T cells (Bronte et al., 2003) Inhibition of COX-2 and iNOS has been shown to reduce the accumulation of MDSCs, restore cytotoxic activity of tumor-associated T cells, and delay tumor growth (Sinha et al., 2007; Mazzoni et al., 2002; Zhou et al., 2007).

Inhibition of the NF-κB and JAK/STAT signaling pathways has been implicated as a strategy to inhibit proliferation of cancer epithelial cells and induce their apoptosis. Activation of STAT3 and NF-κB has been shown to result in suppression of apoptosis in cancer cells, and promotion of proliferation, invasion, and metastasis. Many of the target genes involved in these processes have been shown to be transcriptionally regulated by both NF-κB and STAT3 (Yu et al., 2007).

In addition to their direct roles in cancer epithelial cells, NF-κB and STAT3 also have important roles in other cells found within the tumor microenvironment. Experiments in animal models have demonstrated that NF-κB is required in both cancer cells and hematopoeitic cells to propagate the effects of inflammation on cancer initiation and progression (Greten et al., 2004). NF-κB inhibition in cancer and myeloid cells reduces the number and size, respectively, of the resultant tumors. Activation of STAT3 in cancer cells results in the production of several cytokines (IL-6, IL-10) which suppress the maturation of tumor-associated dendritic cells (DC). Furthermore, STAT3 is activated by these cytokines in the dendritic cells themselves. Inhibition of STAT3 in mouse models of cancer restores DC maturation, promotes antitumor immunity, and inhibits tumor growth (Kortylewski et al., 2005).

F. Treatment of Multiple Sclerosis

The compounds and methods of this invention may be used for treating patients for multiple sclerosis (MS). MS is known to be an inflammatory condition of the central nervous system (Williams et al., 1994; Merrill and Benvenist, 1996; Genain and Nauser, 1997). Based on several investigations, there is evidence suggesting that inflammatory, oxidative, and/or immune mechanisms are involved in the pathogenesis of Alzheimer's disease (AD), Parkinson's disease (PD), amyotrophic lateral sclerosis (ALS), and MS (Bagasra et al., 1995; McGeer and McGeer, 1995; Simonian and Coyle, 1996; Kaltschmidt et al., 1997). Both reactive astrocytes and activated microglia have been implicated in causation of neurodegenerative disease (NDD) and neuroinflammatory disease (NID); there has been a particular emphasis on microglia as cells that synthesize both NO and prostaglandins as products of the respective enzymes, iNOS and COX-2. De novo formation of these enzymes may be driven by inflammatory cytokines such as interferon-γ or interleukin-1. In turn, excessive production of NO may lead to inflammatory cascades and/or oxidative damage in cells and tissues of many organs, including neurons and oligodendrocytes of the nervous system, with consequent manifestations in AD and MS, and possible PD and ALS (Coyle and Puttfarcken, 1993; Beal, 1996; Merrill and Benvenist, 1996; Simonian and Coyle, 1996; Vodovotz et al., 1996). Epidemiologic data indicate that chronic use of NSAID's which block synthesis of prostaglandins from arachidonate, markedly lower the risk for development of AD (McGeer et al., 1996; Stewart et al., 1997). Thus, agents that block formation of NO and prostaglandins, may be used in approaches to prevention and treatment of NDD. Successful therapeutic candidates for treating such a disease typically require an ability to penetrate the blood-brain barrier. See, for example, U.S. Patent Publication 2009/0060873, which is incorporated by reference herein in its entirety.

G. Neuroinflammation

Neuroinflammation encapsulates the idea that microglial and astrocytic responses and actions in the central nervous system have a fundamentally inflammation-like character, and that these responses are central to the pathogenesis and progression of a wide variety of neurological disorders. This idea originated in the field of Alzheimer's disease (Griffin et al., 1989; Rogers et al., 1988), where it has revolutionized our understanding of this disease (Akiyama et al., 2000). These ideas have been extended to other neurodegenerative diseases (Eikelenboom et al., 2002; Ishizawa and Dickson, 2001), to ischemic/toxic diseases (Gehrmann et al., 1995; Touzani et al., 1999), to tumor biology (Graeber et al., 2002) and even to normal brain development.

Neuroinflammation incorporates a wide spectrum of complex cellular responses that include activation of microglia and astrocytes and induction of cytokines, chemokines, complement proteins, acute phase proteins, oxidative injury, and related molecular processes. These events may have detrimental effects on neuronal function, leading to neuronal injury, further glial activation, and ultimately neurodegeneration.

Based on experimental results obtained, including those presented in this application, the compounds and methods of this invention may be used for treating patients with neuroinflammation.

H. Treatment of Renal Failure

Another aspect of the present disclosure concerns new methods and compounds for the treatment and prevention of renal disease. See U.S. patent application Ser. No. 12/352,473, which is incorporated by reference herein in its entirety. Renal failure, resulting in inadequate clearance of metabolic waste products from the blood and abnormal concentrations of electrolytes in the blood, is a significant medical problem throughout the world, especially in developed countries. Diabetes and hypertension are among the most important causes of chronic renal failure (CKD), but it is also associated with other conditions such as lupus. Acute renal failure may arise from exposure to certain drugs (e.g., acetaminophen) or toxic chemicals, or from ischemia-reperfusion injury associated with shock or surgical procedures such as transplantation, and may result in chronic renal failure. In many patients, renal failure advances to a stage in which the patient requires regular dialysis or kidney transplantation to continue living. Both of these procedures are highly invasive and associated with significant side effects and quality of life issues. Although there are effective treatments for some complications of renal failure, such as hyperparathyroidism and hyperphosphatemia, no available treatment has been shown to halt or reverse the underlying progression of renal failure. Thus, agents that can improve compromised renal function would represent a significant advance in the treatment of renal failure.

Inflammation contributes significantly to the pathology of CKD. There is also a strong mechanistic link between oxidative stress and renal dysfunction. The NF-κB signaling pathway plays an important role in the progression of CKD as NF-κB regulates the transcription of MCP-1, a chemokine that is responsible for the recruitment of monocytes/macrophages resulting in an inflammatory response that ultimately injures the kidney (Wardle, 2001). The Keap1/Nrf2/ARE pathway controls the transcription of several genes encoding antioxidant enzymes, including heme oxygenase-1 (HO-1). Ablation of the Nrf2 gene in female mice results in the development of lupus-like glomerular nephritis (Yoh et al., 2001). Furthermore, several studies have demonstrated that HO-1 expression is induced in response to renal damage and inflammation and that this enzyme and its products—bilirubin and carbon monoxide—play a protective role in the kidney (Nath et al., 2006).

The glomerulus and the surrounding Bowman's capsule constitute the basic functional unit of the kidney. Glomerular filtration rate (GFR) is the standard measure of renal function. Creatinine clearance is commonly used to measure GFR. However, the level of serum creatinine is commonly used as a surrogate measure of creatinine clearance. For instance, excessive levels of serum creatinine are generally accepted to indicate inadequate renal function and reductions in serum creatinine over time are accepted as an indication of improved renal function. Normal levels of creatinine in the blood are approximately 0.6 to 1.2 milligrams (mg) per deciliter (dl) in adult males and 0.5 to 1.1 milligrams per deciliter in adult females.

Acute kidney injury (AKI) can occur following ischemia-reperfusion, treatment with certain pharmacological agents such as cisplatin and rapamycin, and intravenous injection of radiocontrast media used in medical imaging. As in CKD, inflammation and oxidative stress contribute to the pathology of AKI. The molecular mechanisms underlying radiocontrast-induced nephropathy (RCN) are not well understood; however, it is likely that a combination of events including prolonged vasoconstriction, impaired kidney autoregulation, and direct toxicity of the contrast media all contribute to renal failure (Tumlin et al., 2006). Vasoconstriction results in decreased renal blood flow and causes ischemia-reperfusion and the production of reactive oxygen species. HO-1 is strongly induced under these conditions and has been demonstrated to prevent ischemia-reperfusion injury in several different organs, including the kidney (Nath et al., 2006). Specifically, induction of HO-1 has been shown to be protective in a rat model of RCN (Goodman et al., 2007). Reperfusion also induces an inflammatory response, in part though activation of NF-κB signaling (Nichols, 2004). Targeting NF-κB has been proposed as a therapeutic strategy to prevent organ damage (Zingarelli et al., 2003).

Based on experimental results obtained, including those presented in this application, the compounds and methods of this invention may be used for treating patients with renal failure.

I. Cardiovascular Disease

The compounds and methods of this invention may be used for treating patients with cardiovascular disease. See U.S. patent application Ser. No. 12/352,473, which is incorporated by reference herein in its entirety. Cardiovascular (CV) disease is among the most important causes of mortality worldwide, and is the leading cause of death in many developed nations. The etiology of CV disease is complex, but the majority of causes are related to inadequate or completely disrupted supply of blood to a critical organ or tissue. Frequently such a condition arises from the rupture of one or more atherosclerotic plaques, which leads to the formation of a thrombus that blocks blood flow in a critical vessel. Such thrombosis is the principal cause of heart attacks, in which one or more of the coronary arteries is blocked and blood flow to the heart itself is disrupted. The resulting ischemia is highly damaging to cardiac tissue, both from lack of oxygen during the ischemic event and from excessive formation of free radicals after blood flow is restored (a phenomenon known as ischemia-reperfusion injury). Similar damage occurs in the brain during a thrombotic stroke, when a cerebral artery or other major vessel is blocked by thrombosis. Hemorrhagic strokes, in contrast, involve rupture of a blood vessel and bleeding into the surrounding brain tissue. This creates oxidative stress in the immediate area of the hemorrhage, due to the presence of large amounts of free heme and other reactive species, and ischemia in other parts of the brain due to compromised blood flow. Subarachnoid hemorrhage, which is frequently accompanied by cerebral vasospasm, also causes ischemia/reperfusion injury in the brain.

Alternatively, atherosclerosis may be so extensive in critical blood vessels that stenosis (narrowing of the arteries) develops and blood flow to critical organs (including the heart) is chronically insufficient. Such chronic ischemia can lead to end-organ damage of many kinds, including the cardiac hypertrophy associated with congestive heart failure.

Atherosclerosis, the underlying defect leading to many forms of cardiovascular disease, occurs when a physical defect or injury to the lining (endothelium) of an artery triggers an inflammatory response involving the proliferation of vascular smooth muscle cells and the infiltration of leukocytes into the affected area. Ultimately, a complicated lesion known as an atherosclerotic plaque may form, composed of the above-mentioned cells combined with deposits of cholesterol-bearing lipoproteins and other materials (e.g., Hansson et al., 2006).

Pharmaceutical treatments for cardiovascular disease include preventive treatments, such as the use of drugs intended to lower blood pressure or circulating levels of cholesterol and lipoproteins, as well as treatments designed to reduce the adherent tendencies of platelets and other blood cells (thereby reducing the rate of plaque progression and the risk of thrombus formation). More recently, drugs such as streptokinase and tissue plasminogen activator have been introduced and are used to dissolve the thrombus and restore blood flow. Surgical treatments include coronary artery bypass grafting to create an alternative blood supply, balloon angioplasty to compress plaque tissue and increase the diameter of the arterial lumen, and carotid endarterectomy to remove plaque tissue in the carotid artery. Such treatments, especially balloon angioplasty, may be accompanied by the use of stents, expandable mesh tubes designed to support the artery walls in the affected area and keep the vessel open. Recently, the use of drug-eluting stents has become common in order to prevent post-surgical restenosis (renarrowing of the artery) in the affected area. These devices are wire stents coated with a biocompatible polymer matrix containing a drug that inhibits cell proliferation (e.g., paclitaxel or rapamycin). The polymer allows a slow, localized release of the drug in the affected area with minimal exposure of non-target tissues. Despite the significant benefits offered by such treatments, mortality from cardiovascular disease remains high and significant unmet needs in the treatment of cardiovascular disease remain.

As noted above, induction of HO-1 has been shown to be beneficial in a variety of models of cardiovascular disease, and low levels of HO-1 expression have been clinically correlated with elevated risk of CV disease. Compounds disclosed herein, therefore, may be used in treating or preventing a variety of cardiovascular disorders including but not limited to atherosclerosis, hypertension, myocardial infarction, chronic heart failure, stroke, subarachnoid hemorrhage, and restenosis.

J. Diabetes

Diabetes is a complex disease characterized by the body's failure to regulate circulating levels of glucose. See U.S. patent application Ser. No. 12/352,473, which is incorporated by reference herein in its entirety. This failure may result from a lack of insulin, a peptide hormone that regulates the both the production and absorption of glucose in various tissues. Deficient insulin compromises the ability of muscle, fat, and other tissues to absorb glucose properly, leading to hyperglycemia (abnormally high levels of glucose in the blood). Most commonly, such insulin deficiency results from inadequate production in the islet cells of the pancreas. In the majority of cases this arises from autoimmune destruction of these cells, a condition known as type 1 or juvenile-onset diabetes, but may also be due to physical trauma or some other cause.

Diabetes may also arise when muscle and fat cells become less responsive to insulin and do not absorb glucose properly, resulting in hyperglycemia. This phenomenon is known as insulin resistance, and the resulting condition is known as Type 2 diabetes. Type 2 diabetes, the most common type, is highly associated with obesity and hypertension. Obesity is associated with an inflammatory state of adipose tissue that is thought to play a major role in the development of insulin resistance (e.g., Hotamisligil, 2006; Guilherme et al., 2008).

Diabetes is associated with damage to many tissues, largely because hyperglycemia (and hypoglycemia, which can result from excessive or poorly timed doses of insulin) is a significant source of oxidative stress. Chronic kidney failure, retinopathy, peripheral neuropathy, peripheral vasculitis, and the development of dermal ulcers that heal slowly or not at all are among the common complications of diabetes. Because of their ability to protect against oxidative stress, particularly by the induction of HO-1 expression, compounds disclosed herein may be used in treatments for many complications of diabetes. As noted above (Cai et al., 2005), chronic inflammation and oxidative stress in the liver are suspected to be primary contributing factors in the development of Type 2 diabetes. Furthermore, PPARγ agonists such as thiazolidinediones are capable of reducing insulin resistance and are known to be effective treatments for Type 2 diabetes.

Based on experimental results obtained, including those presented in this application, the compounds and methods of this invention may be used for treating patients with neuroinflammation.

The effect of treatment of diabetes may be evaluated as follows. Both the biological efficacy of the treatment modality as well as the clinical efficacy are evaluated, if possible. For example, disease manifests itself by increased blood sugar, the biological efficacy of the treatment therefore can be evaluated, for example, by observation of return of the evaluated blood glucose towards normal. Measuring a clinical endpoint which can give an indication of b-cell regeneration after, for example, a six-month period of time, can give an indication of the clinical efficacy of the treatment regimen.

Based on experimental results obtained, including those presented in this application, the compounds and methods of this invention may be used for treating patients with diabetes.

K. Rheumatoid Arthritis

The compounds and methods of this invention may be used for treating patients with RA. Typically the first signs of rheumatoid arthritis (RA) appear in the synovial lining layer, with proliferation of synovial fibroblasts and their attachment to the articular surface at the joint margin (Lipsky, 1998). Subsequently, macrophages, T cells and other inflammatory cells are recruited into the joint, where they produce a number of mediators, including the cytokines interleukin-1 (IL-1), which contributes to the chronic sequelae leading to bone and cartilage destruction, and tumour necrosis factor (TNF-α), which plays a role in inflammation (Dinarello, 1998; Arend and Dayer, 1995; van den Berg, 2001). The concentration of IL-1 in plasma is significantly higher in patients with RA than in healthy individuals and, notably, plasma IL-1 levels correlate with RA disease activity (Eastgate et al., 1988). Moreover, synovial fluid levels of IL-1 are correlated with various radiographic and histologic features of RA (Kahle et al., 1992; Rooney et al., 1990).

In normal joints, the effects of these and other proinflammatory cytokines are balanced by a variety of anti-inflammatory cytokines and regulatory factors (Burger and Dayer, 1995). The significance of this cytokine balance is illustrated in juvenile RA patients, who have cyclical increases in fever throughout the day (Prieur et al., 1987). After each peak in fever, a factor that blocks the effects of IL-1 is found in serum and urine. This factor has been isolated, cloned and identified as IL-1 receptor antagonist (IL-1ra), a member of the IL-1 gene family (Hannum et al., 1990). IL-1ra, as its name indicates, is a natural receptor antagonist that competes with IL-1 for binding to type I IL-1 receptors and, as a result, blocks the effects of IL-1 (Arend et al., 1998). A 10- to 100-fold excess of IL-1ra may be needed to block IL-1 effectively; however, synovial cells isolated from patients with RA do not appear to produce enough IL-1ra to counteract the effects of IL-1 (Firestein et al., 1994; Fujikawa et al., 1995).

L. Psoriatic Arthritis

Psoriasis is an inflammatory and proliferative skin disorder with a prevalence of 1.5-3%. Approximately 20% of patients with psoriasis develop a characteristic form of arthritis that has several patterns (Gladman, 1992; Jones et al., 1994; Gladman et al., 1995). Some individuals present with joint symptoms first but in the majority, skin psoriasis presents first. About one-third of patients have simultaneous exacerbations of their skin and joint disease (Gladman et al., 1987) and there is a topographic relationship between nail and distal interphalangeal joint disease (Jones et al., 1994; Wright, 1956). Although the inflammatory processes which link skin, nail and joint disease remain elusive, an immune-mediated pathology is implicated.

Psoriatic arthritis (PsA) is a chronic inflammatory arthropathy characterized by the association of arthritis and psoriasis and was recognized as a clinical entity distinct from rheumatoid arthritis (RA) in 1964 (Blumberg et al., 1964). Subsequent studies have revealed that PsA shares a number of genetic, pathogenic and clinical features with other spondyloarthropathies (SpAs), a group of diseases that comprise ankylosing spondylitis, reactive arthritis and enteropathic arthritis (Wright, 1979). The notion that PsA belongs to the SpA group has recently gained further support from imaging studies demonstrating widespread enthesitis in the, including PsA but not RA (McGonagle et al., 1999; McGonagle et al., 1998). More specifically, enthesitis has been postulated to be one of the earliest events occurring in the SpAs, leading to bone remodeling and ankylosis in the spine, as well as to articular synovitis when the inflamed entheses are close to peripheral joints. However, the link between enthesitis and the clinical manifestations in PsA remains largely unclear, as PsA can present with fairly heterogeneous patterns of joint involvement with variable degrees of severity (Marsal et al., 1999; Salvarani et al., 1998). Thus, other factors must be posited to account for the multifarious features of PsA, only a few of which (such as the expression of the HLA-B27 molecule, which is strongly associated with axial disease) have been identified. As a consequence, it remains difficult to map the disease manifestations to specific pathogenic mechanisms, which means that the treatment of this condition remains largely empirical.

Family studies have suggested a genetic contribution to the development of PsA (Moll and Wright, 1973). Other chronic inflammatory forms of arthritis, such as ankylosing spondylitis and rheumatoid arthritis, are thought to have a complex genetic basis. However, the genetic component of PsA has been difficult to assess for several reasons. There is strong evidence for a genetic predisposition to psoriasis alone that may mask the genetic factors that are important for the development of PsA. Although most would accept PsA as a distinct disease entity, at times there is a phenotypic overlap with rheumatoid arthritis and ankylosing spondylitis. Also, PsA itself is not a homogeneous condition and various subgroups have been proposed.

Increased amounts of TNF-$\alpha$ have been reported in both psoriatic skin (Ettehadi et al., 1994) and synovial fluid (Partsch et al., 1997). Recent trials have shown a positive benefit of anti-TNF treatment in both PsA (Mease et al., 2000) and ankylosing spondylitis (Brandt et al., 2000).

Based on experimental results obtained, including those presented in this application, the compounds and methods of this invention may be used for treating patients with psoriatic arthritis.

M. Reactive Arthritis

In reactive arthritis (ReA) the mechanism of joint damage is unclear, but it is likely that cytokines play critical roles. A more prevalent Th1 profile high levels of interferon gamma (IFN-$\gamma$) and low levels of interleukin 4 (IL-4) has been reported (Lahesmaa et al., 1992; Schlaak et al., 1992; Simon et al., 1993; Schlaak et al., 1996; Kotake et al., 1999; Ribbens et al., 2000), but several studies have shown relative predominance of IL-4 and IL-10 and relative lack of IFN-$\gamma$ and tumour necrosis factor alpha (TNF-$\alpha$) in the synovial membrane (Simon et al., 1994; Yin et al., 1999) and fluid (SF) (Yin et al., 1999; Yin et al., 1997) of reactive arthritis patients compared with rheumatoid arthritis (RA) patients. A lower level of TNF-$\alpha$ secretion in reactive arthritis than in RA patients has also been reported after ex vivo stimulation of peripheral blood mononuclear cells (PBMC) (Braun et al., 1999).

It has been argued that clearance of reactive arthritis-associated bacteria requires the production of appropriate levels of IFN-$\gamma$ and TNF-$\alpha$, while IL-10 acts by suppressing these responses (Autenrieth et al., 1994; Sieper and Braun, 1995). IL-10 is a regulatory cytokine that inhibits the synthesis of IL-12 and TNF-$\gamma$ by activated macrophages (de Waal et al., 1991; Hart et al., 1995; Chomarat et al., 1995) and of IFN-$\gamma$ by T cells (Macatonia et al., 1993).

Based on experimental results obtained, including those presented in this application, the compounds and methods of this invention may be used for treating patients with reactive arthritis.

N. Enteropathic Arthritis

Typically enteropathic arthritis (EA) occurs in combination with inflammatory bowel diseases (IBD) such as Crohn's disease or ulcerative colitis. It also can affect the spine and sacroiliac joints. Enteropathic arthritis involves the peripheral joints, usually in the lower extremities such as the knees or ankles. It commonly involves only a few or a limited number of joints and may closely follow the bowel condition. This occurs in approximately 11% of patients with ulcerative colitis and 21% of those with Crohn's disease. The synovitis is generally self-limited and non-deforming.

Enteropathic arthropathies comprise a collection of rheumatologic conditions that share a link to GI pathology. These conditions include reactive (i.e., infection-related) arthritis due to bacteria (e.g., *Shigella, Salmonella, Campylobacter, Yersinia* species, *Clostridium difficile*), parasites (e.g., *Strongyloides stercoralis, Taenia saginata, Giardia lamblia, Ascaris lumbricoides, Cryptosporidium* species), and spondyloarthropathies associated with inflammatory bowel disease (IBD). Other conditions and disorders include intestinal bypass (jejunoileal), arthritis, celiac disease, Whipple disease, and collagenous colitis.

Based on experimental results obtained, including those presented in this application, the compounds and methods of this invention may be used for treating patients with enteropathic arthritis.

O. Juvenile Rheumatoid Arthritis

Juvenile rheumatoid arthritis (JRA), a term for the most prevalent form of arthritis in children, is applied to a family of illnesses characterized by chronic inflammation and hypertrophy of the synovial membranes. The term overlaps, but is not completely synonymous, with the family of illnesses referred to as juvenile chronic arthritis and/or juvenile idiopathic arthritis in Europe.

Both innate and adaptive immune systems use multiple cell types, a vast array of cell surface and secreted proteins, and interconnected networks of positive and negative feedback (Lo et al., 1999). Furthermore, while separable in thought, the innate and adaptive wings of the immune system are functionally intersected (Fearon and Locksley, 1996), and pathologic events occurring at these intersecting points are likely to be highly relevant to our understanding of pathogenesis of adult and childhood forms of chronic arthritis (Warrington, et al., 2001).

Polyarticular JRA is a distinct clinical subtype characterized by inflammation and synovial proliferation in multiple joints (four or more), including the small joints of the hands (Jarvis, 2002). This subtype of JRA may be severe, because of both its multiple joint involvement and its capacity to progress rapidly over time. Although clinically distinct, polyarticular JRA is not homogeneous, and patients vary in disease manifestations, age of onset, prognosis, and therapeutic response. These differences very likely reflect a spectrum of variation in the nature of the immune and inflammatory attack that can occur in this disease (Jarvis, 1998).

Based on experimental results obtained, including those presented in this application, the compounds and methods of this invention may be used for treating patients with JRA.

P. Early Inflammatory Arthritis

The compounds and methods of this invention may be used for treating patients with early inflammatory arthritis. The clinical presentation of different inflammatory arthropathies is similar early in the course of disease. As a result, it is often difficult to distinguish patients who are at risk of developing the severe and persistent synovitis that leads to erosive joint damage from those whose arthritis is more self-limited. Such distinction is critical in order to target therapy appropriately, treating aggressively those with erosive disease and avoiding unnecessary toxicity in patients with more self-limited disease. Current clinical criteria for diagnosing erosive arthropathies such as rheumatoid arthritis (RA) are less effective in early disease and traditional markers of disease activity such as joint counts and acute phase response do not adequately identify patients likely to have poor outcomes (Harrison et al., 1998). Parameters reflective of the pathologic events occurring in the synovium are most likely to be of significant prognostic value.

Recent efforts to identify predictors of poor outcome in early inflammatory arthritis have identified the presence of RA specific autoantibodies, in particular antibodies towards citrullinated peptides, to be associated with erosive and persistent disease in early inflammatory arthritis cohorts. On the basis of this, a cyclical citrullinated peptide (CCP) has been developed to assist in the identification of anti-CCP antibodies in patient sera. Using this approach, the presence of anti-CCP antibodies has been shown to be specific and sensitive for RA, can distinguish RA from other arthropathies, and can potentially predict persistent, erosive synovitis before these outcomes become clinically manifest. Importantly, anti-CCP antibodies are often detectable in sera many years prior to clinical symptoms suggesting that they may be reflective of subclinical immune events (Nielen et al., 2004; Rantapaa-Dahlqvist et al., 2003).

Q. Ankylosing Spondylitis

AS is a disease subset within a broader disease classification of spondyloarthropathy. Patients affected with the various subsets of spondyloarthropathy have disease etiologies that are often very different, ranging from bacterial infections to inheritance. Yet, in all subgroups, the end result of the disease process is axial arthritis. Despite the early clinically differences seen in the various patient populations, many of them end up nearly identical after a disease course of ten-to-twenty years. Recent studies suggest the mean time to clinical diagnosis of ankylosing spondylitis from disease onset of disease is 7.5 years (Khan, 1998). These same studies suggest that the spondyloarthropathies may have prevalence close to that of rheumatoid arthritis (Feldtkeller et al., 2003; Doran et al., 2003).

AS is a chronic systemic inflammatory rheumatic disorder of the axial skeleton with or without extraskeletal manifestations. Sacroiliac joints and the spine are primarily affected, but hip and shoulder joints, and less commonly peripheral joints or certain extra-articular structures such as the eye, vasculature, nervous system, and gastrointestinal system may also be involved. Its etiology is not yet fully understood (Wordsworth, 1995; Calin and Taurog, 1998). It is strongly associated with the major histocompatibility class I (MHC I) HLA-B27 allele (Calin and Taurog, 1998). AS affects individuals in the prime of their life and is feared because of its potential to cause chronic pain and irreversible damage of tendons, ligaments, joints, and bones (Brewerton et al., 1973a; Brewerton et al., 1973b; Schlosstein et al., 1973). AS may occur alone or in association with another form of spondyloarthropathy such as reactive arthritis, psoriasis, psoriatic arthritis, enthesitis, ulcerative colitis, irritable bowel disease, or Crohn's disease, in which case it is classified as secondary AS.

Typically, the affected sites include the discovertebral, apophyseal, costovertebral, and costotransverse joints of the spine, and the paravertebral ligamentous structures. Inflammation of the entheses, which are sites of musculotendinous and ligamentous attachment to bones, is also prominent in this disease (Calin and Taurog, 1998). The site of enthesitis is known to be infiltrated by plasma cells, lymphocytes, and polymorphonuclear cells. The inflammatory process frequently results in gradual fibrous and bony ankylosis, (Ball, 1971; Khan, 1990).

Delayed diagnosis is common because symptoms are often attributed to more common back problems. A dramatic loss of flexibility in the lumbar spine is an early sign of AS. Other common symptoms include chronic pain and stiffness in the lower back which usually starts where the lower spine is joined to the pelvis, or hip. Although most symptoms begin in the lumbar and sacroiliac areas, they may involve the neck and upper back as well. Arthritis may also occur in the shoulder, hips and feet. Some patients have eye inflammation, and more severe cases must be observed for heart valve involvement.

The most frequent presentation is back pain, but disease can begin atypically in peripheral joints, especially in children and women, and rarely with acute iritis (anterior uveitis). Additional early symptoms and signs are diminished chest expansion from diffuse costovertebral involvement, low-grade fever, fatigue, anorexia, weight loss, and anemia. Recurrent back pain—often nocturnal and of varying intensity—is an eventual complaint, as is morning stiffness typically relieved by activity. A flexed or bent-over posture eases back pain and paraspinal muscle spasm; thus, some degree of kyphosis is common in untreated patients.

Systemic manifestations occur in ⅓ of patients. Recurrent, usually self-limited, acute iritis (anterior uveitis) rarely is protracted and severe enough to impair vision. Neurologic signs can occasionally result from compression radiculitis or sciatica, vertebral fracture or subluxation, and cauda equina syndrome (which consists of impotence, nocturnal urinary incontinence, diminished bladder and rectal sensation, and absence of ankle jerks). Cardiovascular manifestations can include aortic insufficiency, angina, pericarditis, and ECG conduction abnormalities. A rare pulmonary finding is upper lobe fibrosis, occasionally with cavitation that may be mistaken for TB and can be complicated by infection with *Aspergillus*.

AS is characterized by mild or moderate flares of active spondylitis alternating with periods of almost or totally inactive inflammation. Proper treatment in most patients results in minimal or no disability and in full, productive lives despite back stiffness. Occasionally, the course is severe and progressive, resulting in pronounced incapacitating deformities. The prognosis is bleak for patients with refractory iritis and for the rare patient with secondary amyloidosis.

Based on experimental results obtained, including those presented in this application, the compounds and methods of this invention may be used for treating patients with ankylosing spondylitis.

R. Ulcerative Colitis

Ulcerative colitis is a disease that causes inflammation and sores, called ulcers, in the lining of the large intestine. The inflammation usually occurs in the rectum and lower part of the colon, but it may affect the entire colon. Ulcerative colitis rarely affects the small intestine except for the end section, called the terminal ileum. Ulcerative colitis may also be called colitis or proctitis. The inflammation makes the colon empty frequently, causing diarrhea. Ulcers form in places where the inflammation has killed the cells lining the colon; the ulcers bleed and produce pus.

Ulcerative colitis is an inflammatory bowel disease (IBD), the general name for diseases that cause inflammation in the small intestine and colon. Ulcerative colitis can be difficult to diagnose because its symptoms are similar to other intestinal disorders and to another type of IBD, Crohn's disease. Crohn's disease differs from ulcerative colitis because it causes inflammation deeper within the intestinal wall. Also, Crohn's disease usually occurs in the small intestine, although it can also occur in the mouth, esophagus, stomach, duodenum, large intestine, appendix, and anus.

Ulcerative colitis may occur in people of any age, but most often it starts between ages 15 and 30, or less frequently between ages 50 and 70. Children and adolescents sometimes develop the disease. Ulcerative colitis affects men and women equally and appears to run in some families. Theories about what causes ulcerative colitis abound, but none have been proven. The most popular theory is that the body's immune system reacts to a virus or a bacterium by causing ongoing inflammation in the intestinal wall. People with ulcerative colitis have abnormalities of the immune system, but doctors do not know whether these abnormalities are a cause or a result of the disease. Ulcerative colitis is not caused by emotional distress or sensitivity to certain foods or food products, but these factors may trigger symptoms in some people.

The most common symptoms of ulcerative colitis are abdominal pain and bloody diarrhea. Patients also may experience fatigue, weight loss, loss of appetite, rectal bleeding, and loss of body fluids and nutrients. About half of patients have mild symptoms. Others suffer frequent fever, bloody diarrhea, nausea, and severe abdominal cramps. Ulcerative colitis may also cause problems such as arthritis, inflammation of the eye, liver disease (hepatitis, cirrhosis, and primary sclerosing cholangitis), osteoporosis, skin rashes, and anemia. No one knows for sure why problems occur outside the colon. Scientists think these complications may occur when the immune system triggers inflammation in other parts of the body. Some of these problems go away when the colitis is treated.

A thorough physical exam and a series of tests may be required to diagnose ulcerative colitis. Blood tests may be done to check for anemia, which could indicate bleeding in the colon or rectum. Blood tests may also uncover a high white blood cell count, which is a sign of inflammation somewhere in the body. By testing a stool sample, the doctor can detect bleeding or infection in the colon or rectum. The doctor may do a colonoscopy or sigmoidoscopy. For either test, the doctor inserts an endoscope—a long, flexible, lighted tube connected to a computer and TV monitor—into the anus to see the inside of the colon and rectum. The doctor will be able to see any inflammation, bleeding, or ulcers on the colon wall. During the exam, the doctor may do a biopsy, which involves taking a sample of tissue from the lining of the colon to view with a microscope. A barium enema x ray of the colon may also be required. This procedure involves filling the colon with barium, a chalky white solution. The barium shows up white on x-ray film, allowing the doctor a clear view of the colon, including any ulcers or other abnormalities that might be there.

Treatment for ulcerative colitis depends on the seriousness of the disease. Most people are treated with medication. In severe cases, a patient may need surgery to remove the diseased colon. Surgery is the only cure for ulcerative colitis. Some people whose symptoms are triggered by certain foods are able to control the symptoms by avoiding foods that upset their intestines, like highly seasoned foods, raw fruits and vegetables, or milk sugar (lactose). Each person may experience ulcerative colitis differently, so treatment is adjusted for each individual. Emotional and psychological support is important. Some people have remissions—periods when the symptoms go away—that last for months or even years. However, most patients' symptoms eventually return. This changing pattern of the disease means one cannot always tell when a treatment has helped. Some people with ulcerative colitis may need medical care for some time, with regular doctor visits to monitor the condition.

Based on experimental results obtained, including those presented in this application, the compounds and methods of this invention may be used for treating patients with ulcerative colitis.

S. Crohn's Disease

Another disorder for which immunosuppression has been tried is Crohn's disease. Crohn's disease symptoms include intestinal inflammation and the development of intestinal stenosis and fistulas; neuropathy often accompanies these symptoms. Anti-inflammatory drugs, such as 5-aminosalicylates (e.g., mesalamine) or corticosteroids, are typically prescribed, but are not always effective (reviewed in Botoman et al., 1998). Immunosuppression with cyclosporine is sometimes beneficial for patients resistant to or intolerant of corticosteroids (Brynskov et al., 1989).

Efforts to develop diagnostic and treatment tools against Crohn's disease have focused on the central role of cytokines (Schreiber, 1998; van Hogezand and Verspaget, 1998). Cytokines are small secreted proteins or factors (5 to 20 kD) that have specific effects on cell-to-cell interactions, intercellular communication, or the behavior of other cells. Cytokines are produced by lymphocytes, especially $T_H1$ and $T_H2$ lymphocytes, monocytes, intestinal macrophages, granulocytes, epithelial cells, and fibroblasts (reviewed in Rogler and. Andus, 1998; Galley and Webster, 1996). Some cytokines are pro-inflammatory (e.g., TNF-$\alpha$, IL-1($\alpha$ and $\beta$), IL-6, IL-8, IL-12, or leukemia inhibitory factor [LIF]); others are anti-inflammatory (e.g., IL-1 receptor antagonist, IL-4, IL-10, IL-11, and TGF-13). However, there may be overlap and functional redundancy in their effects under certain inflammatory conditions.

In active cases of Crohn's disease, elevated concentrations of TNF-$\alpha$ and IL-6 are secreted into the blood circulation, and TNF-$\alpha$, IL-1, IL-6, and IL-8 are produced in excess locally by mucosal cells (id.; Funakoshi et al., 1998). These cytokines can have far-ranging effects on physiological systems including bone development, hematopoiesis, and liver, thyroid, and neuropsychiatric function. Also, an imbalance of the IL-1$\beta$/IL-1ra ratio, in favor of pro-inflammatory IL-1$\beta$, has been observed in patients with Crohn's disease (Rogler and Andus, 1998; Saiki et al., 1998; Dionne et al., 1998; but see Kuboyama, 1998). One study suggested that cytokine profiles in stool samples could be a useful diagnostic tool for Crohn's disease (Saiki et al., 1998).

Treatments that have been proposed for Crohn's disease include the use of various cytokine antagonists (e.g., IL-1ra), inhibitors (e.g., of IL-1$\beta$ converting enzyme and antioxidants) and anti-cytokine antibodies (Rogler and Andus, 1998; van Hogezand and Verspaget, 1998; Reimund et al., 1998; Lugering et al., 1998; McAlindon et al., 1998). In particular, monoclonal antibodies against TNF-α have been tried with some success in the treatment of Crohn's disease (Targan et al., 1997; Stack et al., 1997; van Dullemen et al., 1995). These compounds may be used in combination therapy with compounds of the present disclosure.

Another approach to the treatment of Crohn's disease has focused on at least partially eradicating the bacterial community that may be triggering the inflammatory response and replacing it with a non-pathogenic community. For example, U.S. Pat. No. 5,599,795 discloses a method for the prevention and treatment of Crohn's disease in human patients. Their method was directed to sterilizing the intestinal tract with at least one antibiotic and at least one anti-fungal agent to kill off the existing flora and replacing them with different, select, well-characterized bacteria taken from normal humans. Borody taught a method of treating Crohn's disease by at least partial removal of the existing intestinal microflora by lavage and replacement with a new bacterial community introduced by fecal inoculum from a disease-screened human donor or by a composition comprising *Bacteroides* and *Escherichia coli* species. (U.S. Pat. No. 5,443,826).

Based on experimental results obtained, including those presented in this application, the compounds and methods of this invention may be used for treating patients with Crohn's disease.

T. Systemic Lupus Erythematosus

There has also been no known cause for autoimmune diseases such as systemic lupus erythematosus. Systemic lupus erythematosus (SLE) is an autoimmune rheumatic disease characterized by deposition in tissues of autoantibodies and immune complexes leading to tissue injury (Kotzin, 1996). In contrast to autoimmune diseases such as MS and type 1 diabetes mellitus, SLE potentially involves multiple organ systems directly, and its clinical manifestations are diverse and variable (reviewed by Kotzin and O'Dell, 1995). For example, some patients may demonstrate primarily skin rash and joint pain, show spontaneous remissions, and require little medication. At the other end of the spectrum are patients who demonstrate severe and progressive kidney involvement that requires therapy with high doses of steroids and cytotoxic drugs such as cyclophosphamide (Kotzin, 1996).

The serological hallmark of SLE, and the primary diagnostic test available, is elevated serum levels of IgG antibodies to constituents of the cell nucleus, such as double-stranded DNA (dsDNA), single-stranded DNA (ss-DNA), and chromatin. Among these autoantibodies, IgG anti-dsDNA antibodies play a major role in the development of lupus glomerulonephritis (G N) (Hahn and Tsao, 1993; Ohnishi et al., 1994). Glomerulonephritis is a serious condition in which the capillary walls of the kidney's blood purifying glomeruli become thickened by accretions on the epithelial side of glomerular basement membranes. The disease is often chronic and progressive and may lead to eventual renal failure.

Based on experimental results obtained, including those presented in this application, the compounds and methods of this invention may be used for treating patients with SLE.

U. Irritable Bowel Syndrome

The compounds and methods of this invention may be used for treating patients with Irritable bowel syndrome (IBS). IBS is a functional disorder characterized by abdominal pain and altered bowel habits. This syndrome may begin in young adulthood and can be associated with significant disability. This syndrome is not a homogeneous disorder. Rather, subtypes of IBS have been described on the basis of the predominant symptom—diarrhea, constipation, or pain. In the absence of "alarm" symptoms, such as fever, weight loss, and gastrointestinal bleeding, a limited workup is needed. Once a diagnosis of IBS is made, an integrated treatment approach can effectively reduce the severity of symptoms. IBS is a common disorder, although its prevalence rates have varied. In general, IBS affects about 15% of US adults and occurs about three times more often in women than in men (Jailwala et al., 2000).

IBS accounts for between 2.4 million and 3.5 million visits to physicians each year. It not only is the most common condition seen by gastroenterologists but also is one of the most common gastrointestinal conditions seen by primary care physicians (Everhart et al., 1991; Sandler, 1990).

IBS is also a costly disorder. Compared with persons who do not have bowel symptoms, persons with IBS miss three times as many workdays and are more likely to report being too sick to work (Drossman et al., 1993; Drossman et al., 1997). Moreover, those with IBS incur hundreds of dollars more in medical charges than persons without bowel disorders (Talley et al., 1995).

No specific abnormality accounts for the exacerbations and remissions of abdominal pain and altered bowel habits experienced by patients with IBS. The evolving theory of IBS suggests dysregulation at multiple levels of the brain-gut axis. Dysmotility, visceral hypersensitivity, abnormal modulation of the central nervous system (CNS), and infection have all been implicated. In addition, psychosocial factors play an important modifying role. Abnormal intestinal motility has long been considered a factor in the pathogenesis of IBS. Transit time through the small intestine after a meal has been shown to be shorter in patients with diarrhea-predominant IBS than in patients who have the constipation-predominant or pain-predominant subtype (Cann et al., 1983).

In studies of the small intestine during fasting, the presence of both discrete, clustered contractions and prolonged, propagated contractions has been reported in patients with IBS (Kellow and Phillips, 1987). They also experience pain with irregular contractions more often than healthy persons (Kellow and Phillips, 1987; Horwitz and Fisher, 2001)

These motility findings do not account for the entire symptom complex in patients with IBS; in fact, most of these patients do not have demonstrable abnormalities (Rothstein, 2000). Patients with IBS have increased sensitivity to visceral pain. Studies involving balloon distention of the rectosigmoid colon have shown that patients with IBS experience pain and bloating at pressures and volumes much lower than control subjects (Whitehead et al., 1990). These patients maintain normal perception of somatic stimuli.

Multiple theories have been proposed to explain this phenomenon. For example, receptors in the viscera may have increased sensitivity in response to distention or intraluminal contents. Neurons in the dorsal horn of the spinal cord may have increased excitability. In addition, alteration in CNS processing of sensations may be involved (Drossman et al., 1997). Functional magnetic resonance imaging studies have recently shown that compared with control subjects, patients with IBS have increased activation of the anterior cingulate cortex, an important pain center, in response to a painful rectal stimulus (Mertz et al., 2000).

Increasingly, evidence suggests a relationship between infectious enteritis and subsequent development of IBS. Inflammatory cytokines may play a role. In a survey of patients with a history of confirmed bacterial gastroenteritis (Neal et al., 1997), 25% reported persistent alteration of bowel habits. Persistence of symptoms may be due to psychological stress at the time of acute infection (Gwee et al., 1999).

Recent data suggest that bacterial overgrowth in the small intestine may have a role in IBS symptoms. In one study (Pimentel et al., 2000), 157 (78%) of 202 IBS patients referred for hydrogen breath testing had test findings that were positive for bacterial overgrowth. Of the 47 subjects who had follow-up testing, 25 (53%) reported improvement in symptoms (i.e., abdominal pain and diarrhea) with antibiotic treatment.

IBS may present with a range of symptoms. However, abdominal pain and altered bowel habits remain the primary features. Abdominal discomfort is often described as crampy in nature and located in the left lower quadrant, although the severity and location can differ greatly. Patients may report diarrhea, constipation, or alternating episodes of diarrhea and constipation. Diarrheal symptoms are typically described as small-volume, loose stools, and stool is sometimes accompanied by mucus discharge. Patients also may report bloating, fecal urgency, incomplete evacuation, and abdominal distention. Upper gastrointestinal symptoms, such as gastroesophageal reflux, dyspepsia, or nausea, may also be present (Lynn and Friedman, 1993).

Persistence of symptoms is not an indication for further testing; it is a characteristic of IBS and is itself an expected symptom of the syndrome. More extensive diagnostic evaluation is indicated in patients whose symptoms are worsening or changing. Indications for further testing also include presence of alarm symptoms, onset of symptoms after age 50, and a family history of colon cancer. Tests may include colonoscopy, computed tomography of the abdomen and pelvis, and barium studies of the small or large intestine.

V. Sjögren's Syndrome

The compounds and methods of this invention may be used for treating patients with SS. Primary Sjögren's syndrome (SS) is a chronic, slowly progressive, systemic autoimmune disease, which affects predominantly middle-aged women (female-to-male ratio 9:1), although it can be seen in all ages including childhood (Jonsson et al., 2002). It is characterized by lymphocytic infiltration and destruction of the exocrine glands, which are infiltrated by mononuclear cells including CD4+, CD8+ lymphocytes and B-cells (Jonsson et al., 2002). In addition, extraglandular (systemic) manifestations are seen in one-third of patients (Jonsson et al., 2001).

The glandular lymphocytic infiltration is a progressive feature (Jonsson et al., 1993), which, when extensive, may replace large portions of the organs. Interestingly, the glandular infiltrates in some patients closely resemble ectopic lymphoid microstructures in the salivary glands (denoted as ectopic germinal centers) (Salomonsson et al., 2002; Xanthou et al., 2001). In SS, ectopic GCs are defined as T and B cell aggregates of proliferating cells with a network of follicular dendritic cells and activated endothelial cells. These GC-like structures formed within the target tissue also portray functional properties with production of autoantibodies (anti-Ro/SSA and anti-La/SSB) (Salomonsson and Jonsson, 2003).

In other systemic autoimmune diseases, such as RA, factors critical for ectopic GCs have been identified. Rheumatoid synovial tissues with GCs were shown to produce chemokines CXCL13, CCL21 and lymphotoxin (LT)-β (detected on follicular center and mantle zone B cells). Multivariate regression analysis of these analytes identified CXCL13 and LT-β as the solitary cytokines predicting GCs in rheumatoid synovitis (Weyand and Goronzy, 2003). Recently CXCL13 and CXCR5 in salivary glands has been shown to play an essential role in the inflammatory process by recruiting B and T cells, therefore contributing to lymphoid neogenesis and ectopic GC formation in SS (Salomonsson et al., 2002).

W. Psoriasis

The compounds and methods of this invention may be used for treating patients with psoriasis. Psoriasis is a chronic skin disease of scaling and inflammation that affects 2 to 2.6 percent of the United States population, or between 5.8 and 7.5 million people. Although the disease occurs in all age groups, it primarily affects adults. It appears about equally in males and females. Psoriasis occurs when skin cells quickly rise from their origin below the surface of the skin and pile up on the surface before they have a chance to mature. Usually this movement (also called turnover) takes about a month, but in psoriasis it may occur in only a few days. In its typical form, psoriasis results in patches of thick, red (inflamed) skin covered with silvery scales. These patches, which are sometimes referred to as plaques, usually itch or feel sore. They most often occur on the elbows, knees, other parts of the legs, scalp, lower back, face, palms, and soles of the feet, but they can occur on skin anywhere on the body. The disease may also affect the fingernails, the toenails, and the soft tissues of the genitals and inside the mouth. While it is not unusual for the skin around affected joints to crack, approximately 1 million people with psoriasis experience joint inflammation that produces symptoms of arthritis. This condition is called psoriatic arthritis.

Psoriasis is a skin disorder driven by the immune system, especially involving a type of white blood cell called a T cell. Normally, T cells help protect the body against infection and disease. In the case of psoriasis, T cells are put into action by mistake and become so active that they trigger other immune responses, which lead to inflammation and to rapid turnover of skin cells. In about one-third of the cases, there is a family history of psoriasis. Researchers have studied a large number of families affected by psoriasis and identified genes linked to the disease. People with psoriasis may notice that there are times when their skin worsens, then improves. Conditions that may cause flareups include infections, stress, and changes in climate that dry the skin. Also, certain medicines, including lithium and beta blockers, which are prescribed for high blood pressure, may trigger an outbreak or worsen the disease.

X. Infectious Diseases

Compounds of the present disclosure may be useful in the treatment of infectious diseases, including viral and bacterial infections. As noted above, such infections may be associated with severe localized or systemic inflammatory responses. For example, influenza may cause severe inflammation of the lung and bacterial infection can cause the systemic hyperinflammatory response, including the excessive production of multiple inflammatory cytokines, that is the hallmark of sepsis. In addition, compounds disclosed herein may be useful in directly inhibiting the replication of viral pathogens. Previous studies have demonstrated that related compounds such as CDDO can inhibit the replication of HIV in macrophages (Vazquez et al., 2005). Other studies have indicated that inhibition of NF-kappa B signaling may inhibit influenza virus replication, and that cyclopentenone prostaglandins may inhibit viral replication (e.g., Mazur et al., 2007; Pica et al., 2000).

V. Pharmaceutical Formulations and Routes of Administration

The compounds of the present disclosure may be administered by a variety of methods, e.g., orally or by injection (e.g. subcutaneous, intravenous, intraperitoneal, etc.).

Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. A "therapeutically effective amount" preferably reduces the amount of symptoms of the condition in the infected patient by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

VI. Combination Therapy

In addition to being used as a monotherapy, the compounds of the present disclosure may also find use in combination therapies. Effective combination therapy may be achieved with a single composition or pharmacological formulation that includes both agents, or with two distinct compositions or formulations, at the same time, wherein one composition includes a compound of the present disclosure, and the other includes the second agent(s). Alternatively, the therapy may precede or follow the other agent treatment by intervals ranging from minutes to months.

Various combinations may be employed, such as when a compound of the present disclosure is "A" and "B" represents a secondary agent, non-limiting examples of which are described below:

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | A/A/B/B | A/B/A/B | A/B/B/A | B/B/A/A | |
| B/A/B/A | B/A/A/B | A/A/A/B | B/A/A/A | A/B/A/A | A/A/B/A | |

Administration of the compounds of the present disclosure to a patient will follow general protocols for the administration of pharmaceuticals, taking into account the toxicity, if any, of the drug. It is expected that the treatment cycles would be repeated as necessary.

Beta interferons may be suitable secondary agents. These are medications derived from human cytokines which help regulate the immune system. They include interferon β-1b and interferon β-1a. Betaseron has been approved by the FDA for relapsing forms of secondary progressive MS. Furthermore, the FDA has approved the use of several β-interferons as treatments for people who have experienced a single attack that suggests multiple sclerosis, and who may be at risk of future attacks and developing definite MS. For example, risk of MS may be suggested when an MRI scan of the brain shows lesions that predict a high risk of conversion to definite MS.

Glatiramer acetate is a further example of a secondary agent that may be used in a combination treatment. Glatiramer is presently used to treat relapsing remitting MS. It is made of four amino acids that are found in myelin. This drug is reported to stimulate T cells in the body's immune system to change from harmful, pro-inflammatory agents to beneficial, anti-inflammatory agents that work to reduce inflammation at lesion sites.

Another potential secondary agent is mitoxantrone, a chemotherapy drug used for many cancers. This drug is also FDA-approved for treatment of aggressive forms of relapsing remitting MS, as well as certain forms of progressive MS. It is given intravenously, typically every three months. This medication is effective, but is limited by cardiac toxicity. Novantrone has been approved by the FDA for secondary progressive, progressive-relapsing, and worsening relapsing-remitting MS.

Another potential secondary agent is natalizumab. In general, natalizumab works by blocking the attachment of immune cells to brain blood vessels, which is a necessary step for immune cells to cross into the brain, thus reducing the immune cells' inflammatory action on brain neurons. Natalizumab has been shown to significantly reduce the frequency of attacks in people with relapsing MS.

In the case of relapsing remitting MS, patients may be given intravenous corticosteroids, such as methylprednisolone, as a secondary agent, to end the attack sooner and leave fewer lasting deficits.

Other common drugs for MS that may be used in combination with compounds of the present disclosure include immunosuppressive drugs such as azathioprine, cladribine, and cyclophosphamide.

It is contemplated that other anti-inflammatory agents may be used in conjunction with the treatments of the current invention. Other COX inhibitors may be used, including arylcarboxylic acids (salicylic acid, acetylsalicylic acid, diflunisal, choline magnesium trisalicylate, salicylate, benorylate, flufenamic acid, mefenamic acid, meclofenamic acid and triflumic acid), arylalkanoic acids (diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin and sulindac) and enolic acids (phenylbutazone, oxyphenbutazone, azapropazone, feprazone, piroxicam, and isoxicam. See, e.g., U.S. Pat. No. 6,025,395.

Histamine H2 receptor blocking agents may also be used in conjunction with the compounds of the current invention, including cimetidine, ranitidine, famotidine and nizatidine.

Treatment with acetylcholinesterase inhibitors such as tacrine, donepizil, metrifonate and rivastigmine for the treatment of Alzheimer's and other disease in conjunction with the compounds of the present disclosure is contemplated. Other acetylcholinesterase inhibitors may be developed which may be used once approved include rivastigmine and metrifonate. Acetylcholinesterase inhibitors increase the amount of neurotransmitter acetylcholine at the nerve terminal by decreasing its breakdown by the enzyme cholinesterase.

MAO-B inhibitors such as selegilene may be used in conjunction with the compounds of the current invention. Selegilene is used for Parkinson's disease and irreversibly inhibits monoamine oxidase type B (MAO-B). Monoamine oxidase is an enzyme that inactivates the monoamine neurotransmitters norepinephrine, serotonin and dopamine.

Dietary and nutritional supplements with reported benefits for treatment or prevention of Parkinson's, Alzheimer's, multiple sclerosis, amyotrophic lateral sclerosis, rheumatoid arthritis, inflammatory bowel disease, and all other diseases whose pathogenesis is believed to involve excessive production of either nitric oxide (NO) or prostaglandins, such as acetyl-L-carnitine, octacosanol, evening primrose oil, vitamin B6, tyrosine, phenylalanine, vitamin C, L-dopa, or a combination of several antioxidants may be used in conjunction with the compounds of the current invention.

For the treatment or prevention of cancer, compounds disclosed herein may be combined with one or more of the following: radiation, chemotherapy agents (e.g., cytotoxic agents such as anthracyclines, vincristine, vinblastin, microtubule-targeting agents such as paclitaxel and docetaxel, 5-FU and related agents, cisplatin and other platinum-containing compounds, irinotecan and topotecan, gemcitabine, temozolomide, etc.), targeted therapies (e.g., imatinib, bortezomib, bevacizumab, rituximab), or vaccine therapies designed to promote an enhanced immune response targeting cancer cells.

For the treatment or prevention of autoimmune disease, compounds disclosed herein may be combined with one or more of the following: corticosteroids, methotrexate, anti-TNF antibodies, other TNF-targeting protein therapies, and NSAIDs. For the treatment of prevention of cardiovascular diseases, compounds disclosed herein may be combined with antithrombotic therapies, anticholesterol therapies such as statins (e.g., atorvastatin), and surgical interventions such as stenting or coronary artery bypass grafting. For the treatment of osteoporosis, compounds disclosed herein may be combined with antiresorptive agents such as bisphosphonates or anabolic therapies such as teriparatide or parathyroid hormone. For the treatment of neuropsychiatric conditions, compounds disclosed herein may be combined with antidepressants (e.g., imipramine or SSRIs such as fluoxetine), antipsychotic agents (e.g., olanzapine, sertindole, risperidone), mood stabilizers (e.g., lithium, valproate semisodium), or other standard agents such as anxiolytic agents. For the treatment of neurological disorders, compounds disclosed herein may be combined with anticonvulsant agents (e.g., valproate semisodium, gabapentin, phenyloin, carbamazepine, and topiramate), antithrombotic agents (e.g., tissue plasminogen activator), or analgesics (e.g., opioids, sodium channel blockers, and other antinociceptive agents).

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods and Materials

UV spectra were measured on Shimadzu UV1201 UV-VIS spectrophotometer. All NMR spectra were recorded on a Fourier transform spectrometer. The two instruments used were either 500 MHz for $^1$H and 125 MHz for $^{13}$C or 300 MHz for $^1$H and 75 MHz for $^{13}$C. The chemical shifts are reported in δ (ppm) using the δ 7.27 signal of CHCl$_3$ ($^1$H NMR) and the δ 77.23 signal of CDCl$_3$ ($^{13}$C NMR) as internal standards for deuterated chlorform, the δ 2.05 signal of CD$_3$COCHD$_2$ ($^1$H NMR) and the δ 29.92 signal of CD$_3$COCD$_3$ ($^{13}$C NMR) as internal standards for acetone-d$_6$. Coupling constants are reported in hertz (Hz) and the apparent multiplicity is described as s=singlet, m=multiplet, d=doublet, and t=triplet.

Low resolution and high resolution mass spectroscopy data were obtained by the ESI+ and EI.

Precoated TLC plates with silica gel 60 F254 were used for TLC and preparative TLC.

Flash column chromatography was performed with silica gel (230-400 mesh). All experiments were performed under a nitrogen atmosphere unless stated differently.

Anhydrous tetraydrofuran and dichloromethane were prepared by a solvent purification system. All solvents (analytical grade) including anhydrous solvents and reagents were used as received. All references to "water" correspond to reverse osmosis deionized (RODI) water. All references to "brine" refer to a saturated aqueous sodium chloride solution.

The term "in vacuo" refers to solvent removal by rotary evaporation followed by a lower pressure environment (≤0.2 Torr).

For the iNOS assay, RAW cells were treated with various concentrations of compounds and interferon-γ (10 ng/mL) for 24 h. Supernatants were analyzed for nitric oxide (NO) by the Griess reaction. IC$_{50}$ values are an average of two separate experiments.

In Vitro IKKβ Kinase Assay Using Commercially Available HTScan® IKKβ Kinase Assay Kit.

The protocol is shown as follows: 1. One hundred μL of 10 mM ATP is added to 1.25 mL of 6 μM IκB-α (Ser32) biotinylated peptide (substrate peptide). The mixture was diluted with deionized H$_2$O to 2.5 mL to make ATP/substrate cocktail ([ATP]=400 μM, [substrate]=3 μM). 2. IKKβ Kinase (recombinant, human) (enzyme, 5 μg) is transferred from −80° C. to ice. The enzyme is allowed to thaw on ice. 3. The enzyme is microcentrifuged briefly at 4° C. to bring liquid to the bottom of the vial. The enzyme is returned immediately to ice. 4. One mL of kinase buffer [1 mL of Kinase Buffer: 250 mM Tris-HCl pH 7.5, 100 mM MgCl$_2$, 1 mM Na$_3$VO$_4$, 50 mM β-glycerophosphate] is added to 1.5 mL of deionized H$_2$O to make 2.5 mL of reaction buffer. 5. One and quarter mL of the reaction buffer is transferred to the enzyme tube to make reaction cocktail ([enzyme])=4 ng/μL in the reaction cocktail). 6. Twelve and a half μL of the reaction cocktail is added to 12.5 μL/well of solution of new ligands at each concentration and the mixture is incubated for 5 minutes at room temperature. 7. Twentyfive μL of the ATP/substrate cocktail is added to 25 μL/well preincubated reaction cocktail/compound. [At this stage, Final Assay Conditions for a 50 μL Reaction are 25 mM Tris-HCl (pH 7.5), 10 mM MgCl$_2$, 5 mM β-glycerophosphate, 0.1 mM Na$_3$VO$_4$, 200 μM ATP, 1.5 μM peptide, 50 ng IKKβ Kinase] 8. The reaction plate is incubated at room temperature for 30 minutes. 9. Fifty μL/well Stop Buffer (50 mM EDTA, pH 8) is added to stop the reaction. 10. Twenty-five μL of each reaction is transferred to a 96-well streptavidin-coated plate containing 75 μL of deionized H$_2$O/well and is incubated at room temperature for 60 minutes. 11. The reaction mixture is washed three times with 200 μL/well PBS/T. 12. Dilution of primary antibody, phospho-IκB-α (Ser32/36) (5A5) Mouse mAb, 1:1000 in PBS/T with 1% BSA is prepared. A hundred μL/well primary antibody is added to the reaction mixture. 13. The mixture is incubated at room temperature for 120 minutes. 14. The reaction mixture is washed three times with 200 μL/well PBS/T. The reaction mixture is evaluated by colorimetric ELISA assay as follows: 1. Appropriate dilution of horseradish peroxidase (HRP) labeled secondary antibody in PBS/T with 1% BSA (1:500 dilution for anti-mouse IgG or 1:1000 for anti-rabbit IgG) is prepared. 2. A hundred μL/well secondary antibody solution is added to the reaction mixture which is obtained at 14. 3. The mixture is incubated at room temperature for 30 minutes. 4. The mixture is washed five times with 200 Owen PBS/T. 5. A hundred μL/well TMB (3,3',5,5"-tetramethylbenzidine) substrate is added to the resulting mixture. 6. The mixture is incubate at room temperature for 15 minutes. 7. A hundred μL/well of stop solution is added, and then is mixed well. 8. The absorbance at 450 nm is measured with a microtiter plate reader.

Example 2

Synthesis and Characterization of MCE-1 and MCE-3

MCE-1 and MCE-3 were synthesized as described below and summarized in Scheme 2.

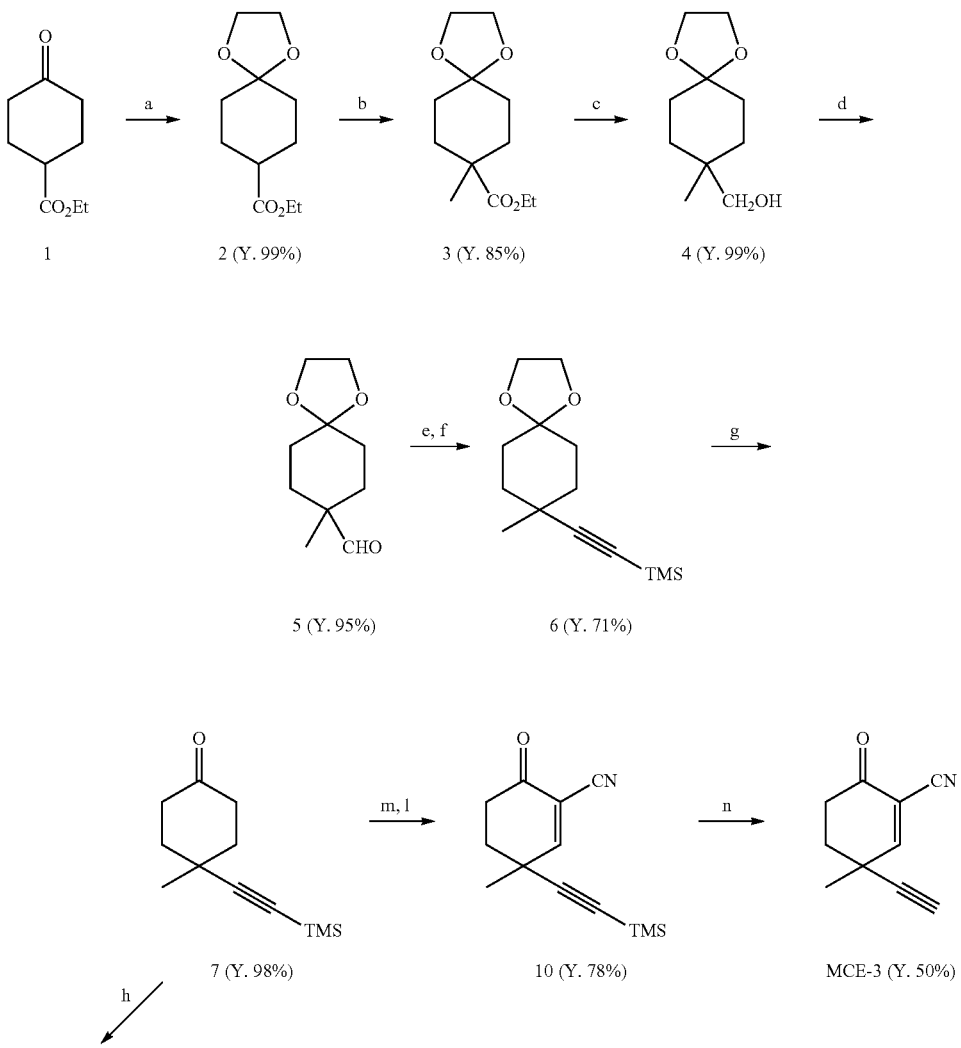

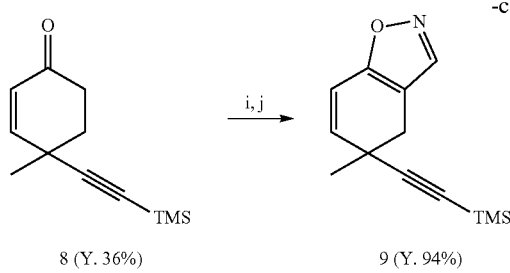
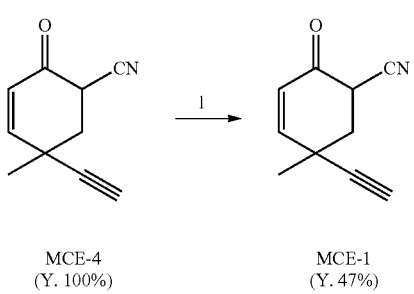

8 (Y. 36%)     9 (Y. 94%)     MCE-4 (Y. 100%)     MCE-1 (Y. 47%)

(a) ethylene glycol, (+)-CSA, PhH;
(b) LDA, CH₃I;
(c) LiAlH₄, Et₂O; (d) CrO₃, pyr. CH₂Cl₂;
(e) Ph₃PCH₂Cl(Cl), n-BuLi, THF;
(f) MeLi, THF; TMSCl;
(g) aq. HCl, acetone;
(h) LDA, PhSeCl; 30% H₂O₂, CH₂Cl₂;
(i) HCO₂Et, NaOMe, PhH;
(j) NH₂OH•HCl, aqueous EtOH;
(k) NaOMe, MeOH, Et₂O; (l) DDQ, PhH;
(m) p-TsCN, LDA, THF;
(n) TBAF, THF.

Ethyl 1,4-dioxaspiro[4,5]decane-8-carboxilate (2)

A mixture of ethyl 4-oxocyclohexanecarboxylate (25 g), 10-campharsulfonic acid, ethylene glycol (40 mL), and toluene (400 mL) was heated under reflux with a Dean-Stark apparatus for 2.5 h (bath temp. 135° C.). The mixture was cooled down, and then was diluted with ether (200 mL). After the ethylene glycol layer was separated, the organic layer was washed with saturated aqueous sodium bicarbonate solution (2×) and brine (1×), dried over MgSO4, and filtered. The filtrate was evaporated in vacuo to give 2 as an oil (31.29 g, 99%): $^{1}$H NMR (CDCl$_{3}$) δ 4.13 (2H, q, J=7.1 Hz), 3.95 (4H, s), 2.33 (1H, m), 1.93 (2H, m), 1.79 (4H, m), 1.56 (2H, m) 1.25 (3H, t, J=7.1 Hz); $^{13}$C NMR (CDCl$_{3}$) δ 175.4, 108.3, 64.5, 60.5, 41.8, 33.9, 26.5, 14.4.

Ethyl 8-methyl-1,4-dioxa-spiro[4,5]decane-8-carboxylate (3)

Ethyl 1,4-dioxaspiro[4,5]decane-8-carboxilate (2) (5.8 g) was dissolved under a nitrogen atmosphere in dry THF (60 mL) and cooled in a dry ice/isopropanol bath to −78° C. LDA (2M solution in THF/n-heptane/ethylbenzene, 20 mL, 40 mmol) was added dropwise to the stirred solution and the mixture was allowed to warm to room temperature for 30 minutes. The reaction mixture was again cooled to −78° C. and to it was added a solution of iodomethane (5.5 g, 39 mmol) in dry THF (15 mL) using a syringe pump over 20 minutes. This mixture was stirred at −78° C. for 1 h. The reaction mixture was allowed to reach room temperature. The reaction mixture was then diluted with ethyl ether (100 mL) and the organic layer was washed with saturated aqueous ammonium chloride solution (2×50 mL) and brine (1×50 mL), then dried over magnesium chloride, filtered, and concentrated in vacuo to give a yellow-brown oil (8 g). The oil was purified by flash column chromatography [petroleum ether-ethyl ether (2:1)] to give 3 (5.22 g, 85%) as a colorless oil: $^{1}$H NMR (CDCl$_{3}$) δ 4.14 (2H, q, J=7.1 Hz), 3.93 (4H, s), 2.13 (2H, m), 1.64 (6H, m), 1.25 (3H, t, J=7.1 Hz), 1.18 (3H, s); $^{13}$C NMR (CDCl$_{3}$) δ 177.2, 108.7, 64.4, 60.6, 42.5, 33.1, 32.3, 26.2, 14.4.

(8-Methyl-1,4-dioxa-spiro[4,5]dec-8-yl)-methanol (4)

Under a nitrogen atmosphere, lithium aluminum hydride (31.2 mmol, 1.25 g, 2.43 eq.) was added to a stirred solution of 3 (12.84 mmol, 2.93 g) in anhydrous ethyl ether (275 mL) cooled to 0° C. in an ice bath. The resulting mixture was stirred at room temperature for 1.5 hours. In order to quench remaining lithium aluminum hydride, water (2.48 mL) followed by 40% aqueous sodium hydroxide solution (1.68 mL) and additional water (3.47 mL) were successively added with stirring to the reaction mixture. The insoluble precipitate was then removed by decanting and filtration. The filtrate was dried over magnesium sulfate, filtered, and concentrated in vacuo to give 4 (12.75 mmol, 2.28 g, 99%) as a yellow oil that was used in the next reaction without further purification: $^{1}$H NMR (CDCl$_{3}$) δ 3.94 (4H, s), 3.39 (2H, s), 1.68-1.35 (8H, m), 0.96 (3H, s); $^{13}$C NMR (CDCl$_{3}$) δ 109.3, 71.8, 64.4, 34.5, 31.5, 30.7, 21.3.

8-Methyl-1,4-dioxa-spiro[4,5]decane-8-carbaldehyde (5)

Under a nitrogen atmosphere, solid chromium (IV) oxide (84.7 mmol, 8.47 g, 6.6 eq.) was added to a stirred solution of extra dry pyridine (171 mmol, 14.53 mL, 13.3 eq.) in dry methylene chloride (123 mL) cooled to 0° C. in an ice bath. The resulting solution was stirred at room temperature for 15 minutes. To this mixture was then added a solution of 4 (12.83 mmol, 2.28 g) in dry methylene chloride (19 mL) and the resulting mixture was stirred at room temperature for 30 minutes. The reaction mixture was then decanted into a seperatory funnel and the residue was washed with ethyl ether (40 mL and 50 mL). The washings were combined and the organic layer was washed with 5% aqueous sodium hydroxide solution (2×40 mL), 5% aqueous hydrochloric acid solution (3×40 mL), saturated aqueous sodium bicarbonate solution (3×40 mL) and brine (3×40 mL), then dried over magnesium sulfate, filtered, and concentrated in vacuo to give 5 (12.24 mmol, 2.35 g, 95%) as an amorphous solid. The product was used in the next reaction without further purification: $^{1}$H NMR (CDCl$_{3}$) δ 9.47 (1H, s), 3.95 (4H, s), 2.00-

1.96 (2H, m), 1.71-1.67 (2H, m), 1.61-1.53 (4H, m), 1.05 (s, 3H); $^{13}$C NMR (CDCl$_3$) δ 205.9, 108.4, 64.4, 64.4, 45.7, 31.4, 29.9, 21.2.

Trimethyl(8-methyl-1,4-dioxaspiro[4.5]decan-8-yl) ethynyl)silane (6)

To a suspension of chloromethylene triphenylphosphonyl chloride (95%, 24.2 g, 66 mmol) in THF (72 mL) was added n-BuLi (1.6 M in hexane, 41.5 mL, 66 mmol) dropwise in an ice-water bath. To the mixture was added HMPA (11.8 mL). The mixture was stirred at room temperature for 20 min. To the mixture was added a solution of 5 (3.06 g, 16.6 mmol) in THF (72 mL). The mixture was stirred at room temperature for 1 h. To the mixture was added saturated aqueous ammonium chloride solution (600 mL) The aqueous mixture was extracted with methylene chloride/ether (1:2, 300 mL ×3). The extract was washed with brine (×2), dried over MgSO$_4$, and filtered. The filtrate was evaporated in vacuo to give a brown crystalline solid (21.31 g). The solid was washed with ether several times. The ether solution was evaporated in vacuo to give a crystalline solid (9.78 g). The solid was purified by flash chromatography [petroleum ether-ether (5:1)] to give 8-(2-chlorovinyl)-8-methyl-1,4-dioxaspiro [4.5]decane (2.74 g, 76%). To a solution of the solid in THF (340 mL) was added MeLi (1.6 M in ether, 100 mL, 160 mmol) dropwise in an ice-water bath. The mixture was stirred at room temperature over night. To the reaction mixture was added water (500 mL). The aqueous mixture was extracted with methylene chloride/ether (1:2, 300 mL ×3). The extract was washed with saturated aqueous sodium bicarbonate solution (300 mL ×1) and brine (300 mL ×2), dried over MgSO$_4$, and filtered. The filtrate was evaporated in vacuo to give an oil (3.2 g). The oil was purified by flash chromatography to give 6 as a crystalline solid (2.86 g, 90%): $^1$H NMR (CDCl$_3$) δ 3.94 (4H, m), 1.95, 1.73, 1.61, 1.50 (each 2H, m), 1.22 (3H, s), 0.14 (9H,$); $^{13}$C NMR (CDCl$_3$) δ 112.8, 108.9, 85.1, 64.4, 36.9, 32.7, 32.2, 29.4, 0.5.

4-Methyl-4-((trimethylsilyl)ethynyl)cyclohexanone (7)

To a solution of 6 (2.1 g, 8.3 mmol) in acetone (25 mL) was added 10% aqueous HCl solution (15 mL). The solution was cloudy. Thus, to the cloudy solution, was acetone dropwise (total 12 mL) until the solution was clear. The clear solution was stirred at room temperature for 5 h. The mixture was diluted with brine (250 mL). The aqueous mixture was extracted with methylene chloride/ether (1:2, 200 mL ×3). The extract was washed with saturated aqueous bicarbonate solution (2×100 mL) and brine (100 mL ×1), dried over MgSO$_4$, and filtered. The filtrate was evaporated in vacuo to give 7 as a crystalline solid (1.7 g, 98%): $^1$H NMR (CDCl$_3$) δ 2.75, 2.29, 2.04, 1.65 (each 2H, m), 1.32 (3H, s), 0.17 (9H, s); $^{13}$C NMR (CDCl$_3$) δ 211.8, 110.8, 86.9, 39.2, 38.8, 32.9, 28.8, 0.4.

4-Methyl-4-((trimethylsilyl)ethynyl)cyclohex-2-enone (8)

To a solution of 7 (260 mg, 1.25 mmol) in THF (10 mL) was added LDA (2 M in THF/n-heptane/ethylbenzene, 935 µL, 1.87 mmol) at −78° C. (in an isopropanol-dry ice bath). The mixture was allowed to reach room temperature over 20 min. To the mixture was added a solution of phenylselenyl chloride (472 mg, 2.5 mmol) in THF (3 mL) at −78° C. The mixture was stirred at room temperature for 2 h. The reaction mixture was quenched with brine (10 mL). The aqueous mixture was extracted with methylene chloride/ether (1:2, 50 mL ×3). The extract was washed with brine (50 mL ×1), dried over MgSO$_4$, and filtered. The filtrate was evaporated in vacuo to give a brown residue (758 mg). To a solution of the residue in methylene chloride (20 mL) was added 30% aqueous hydrogen peroxide (0.3 mL). Five minutes after the addition, 30% aqueous hydrogen peroxide (0.3 mL) was added again. The brown color became to a pale yellow. Five minutes later, the reaction mixture was washed with water (5 mL ×1), saturated aqueous sodium bicarbonate solution (5 mL ×2), and brine (5 mL ×1), dried over MgSO$_4$, and filtered. The filtrate was evaporated in vacuo to give a residue (290 mg). The residue was purified by flash chromatography [petroleum ether-ether (5:1)] to give 8 as a crystalline solid (91.5 mg, 36%): $^1$H NMR (CDCl$_3$) δ 6.69 (1H, dd, J=1.5 and 10 Hz), 5.88 (1H, d, J=10 Hz), 2.73 (1H, m), 2.44 (1H, m), 2.22 (1H, m), 1.95 (1H, m), 1.43 (3H, s), 0.14 (9H, s); $^{13}$C NMR (CDCl$_3$) δ 199.2, 153.7, 127.6, 107.8, 99.4, 36.7, 35.2, 28.2, 0.2.

5-Methyl-5-((trimethylsilyl)ethynyl)-4,5-dihydrobenzo[d]isoxazole (9)

To a solution of 8 (139 mg, 0.67 mmol) in dry benzene (7.8 mL) were added ethyl formate (97%, 244 mg, 3.2 mmol) and sodium methoxide (176 mg, 3.3 mmol), successively. The mixture was stirred at room temperature for 1 h. The mixture was diluted with methylene chloride/ether (1:2, 40 mL). The mixture was washed with 5% aqueous HCl solution (15 mL ×2). The acidic washings were extracted with methylene chloride/ether (1:2, 20 mL ×1). The original organic solution and the extract were combined. The combined solution was washed with water (15 mL ×2) and brine (15 mL ×1), dried over MgSO$_4$, and filtered. The filtrate was evaporate in vacuo to give 6-(hydroxymethylene)-4-methyl-4-((trimethylsilyl)-ethynyl)cyclohex-2-enone (148 mg, 94%): $^1$H NMR (CDCl$_3$) δ 13.69 (1H, brs), 7.53 (1H, s), 6.64 (1H, d, J=9.9 Hz), 6.00 (1H, d, J=9.9 Hz), 2.78 (1H, d, J=14.6 Hz), 2.47 (1H, d, J=14.6 Hz), 1.38 (3H, s), 0.14 (9H, s); $^{13}$C NMR (CDCl$_3$) δ 187.7, 168.0, 152.3, 126.8, 110.2, 109.5, 106.1, 37.2, 37.1, 26.9, 0.2. This material was used without further purification for the next step.

To a solution of 6-(hydroxymethylene)-4-methyl-4-((trimethylsilyl)ethynyl)-cyclohex-2-enone (147 mg, 0.63 mmol) in ethanol (15 mL) was added a solution of hydroxylamine hydrochloride (452 mg) in water (0.65 mL). The mixture was heated under reflux for 1 h. To the mixture was added water (50 mL). The aqueous mixture was extracted with methylene chloride/ether (1:2, 50 mL ×3). The extract was washed with saturated aqueous sodium bicarbonate solution (50 mL ×1) and brine (50 mL ×1), dried over MgSO$_4$, and filtered. The filtrate was evaporated in vacuo to give 9 as a crystalline solid (145 mg, quantitative yield): $^1$H NMR (CDCl$_3$) δ 8.06 (1H, s), 6.47 (1H, d, J=9.9 Hz), 6.03 (1H, d, J=9.9 Hz), 3.07 (1H, d, J=16.1 Hz), 2.77 (1H, d, J=16.1 Hz), 1.37 (3H, s), 0.14 (9H, s). This material was used without further purification for the next step.

5-Ethynyl-5-methyl-2-oxocyclohex-3-enecarbonitrile (MCE-4, dhMCE-1)

To a solution of 9 (75 mg, 0.32 mmol) in dry ether (7.4 mL) was added a solution of sodium methoxide (565 mg) in dry methanol (6 mL). The mixture was stirred at room temperature for 1 h. The mixture was diluted with methylene chloride/ether (1:2, 40 mL). The mixture was washed with 5% aqueous HCl solution (10 mL ×2). The acidic washings were extracted with methylene chloride/ether (1:2, 10 mL ×1). The original organic solution and the extract were combined. The combined solution was washed with water (15 mL ×2) and brine (15 mL ×1), dried over MgSO$_4$, and filtered. The filtrate was evaporated in vacuo to give MCE-4 as a crystalline solid (51 mg, quantitative yield). This material was used without further purification for the next step.

3-Ethynyl-3-methyl-6-oxocyclohexa-1,4-dienecarbonitrile (MCE-1)

A solution of MCE-4 (47.7 mg, 0.3 mmol) and DDQ (102 mg, 0.45 mmol,) in dry benzene (3 mL) was heated under reflux for 15 min. After removal of insoluble matter, the filtrate was concentrated in vacuo to give a residue (149 mg). The residue was purified by flash chromatography [hexanes-ethyl acetate (2:1)] and subsequent preparative TLC [hexanes-ethyl acetate (2:1)] to give MCE-1 as a crystalline solid (22.3 mg, 47%): $^1$H NMR (CDCl$_3$) δ 7.54 (1H, d, J=2.9 Hz), 6.96 (1H, dd, J=2.9 and 9.9 Hz), 6.34 (1H, d, J=9.9 Hz), 2.44 (1H, s), 1.65 (3H, s); $^{13}$C NMR (CDCl$_3$) δ 177.9, 160.0, 150.6, 126.6, 116.5, 113.5, 79.2, 73.5, 36.0, 27.2.

3-Methyl-6-oxo-3-((trimethylsilyl)ethynyl)cyclohex-1-enecarbonitrile (10)

To a solution of 7 (163 mg, 0.78 mmol) in THF (8.8 mL) was added LDA (2M solution in THF/n-heptane/ethylbenzene, 1.08 mL, 2.16 mmol) at −78° C. (in an isopropanol-dry ice bath). The mixture was allowed to reach room temperature over 20 min. To the mixture was added a cloudy solution of p-toluenesulfonyl cyanide (95%, 591 mg, 3.1 mmol) in THF (6.8 mL) at −78° C. The mixture was stirred at −78° C. for 30 min. To the reaction mixture was added saturated aqueous ammonia solution (4.5 mL) at −78° C. The mixture was allowed to reach room temperature. The mixture was acidified with 10% aqueous HCl solution. The mixture was extracted with ethyl acetate (30 mL ×3). The extract was washed with saturated aqueous sodium bicarbonate solution (40 mL ×2) and brine (40 mL), dried over MgSO$_4$, and filtered. The filtrate was evaporated in vacuo to give 5-methyl-2-oxo-5-((trimethylsilyl)ethynyl)cyclohexanecarbonitrile (270 mg).

A solution of 5-methyl-2-oxo-5-((trimethylsilyl)ethynyl) cyclohexane-carbonitrile (270 mg) and DDQ (350 mg) in benzene (20 mL) was heated under reflux for 10 min. After removal of insoluble matter, the filtrate was concentrated in vacuo to give a residue (407 mg). The residue was purified by flash chromatography [hexanes-ethyl acetate (4:1)] to give 10 as a crystalline solid (142 mg, 78%): $^1$H NMR (acetone-d$_6$) δ 7.71 (1H, d, J=1.5 Hz), 2.72 (1H, m), 2.62 (1H, m), 2.21 (2H, m), 1.55 (3H, s), 0.15 (9H, s); $^{13}$C NMR (acetone-d$_6$) δ 192.0, 164.8, 116.4, 114.8, 106.5, 88.7, 35.9, 35.0, 0.0.

3-Ethynyl-3-methyl-6-oxocyclohex-1-enecarbonitrile (MCE-3)

A solution of 10 (20 mg, 0.086 mmol) in THF (0.6 mL) was degassed by gentle argon stream for 5 min. To the solution was added tetra-(n-butyl)ammonium fluoride (TBAF, 70 mg). The mixture was stirred at room temperature for 20 min. The mixture was diluted with methylene chloride/ether (1:2, 20 mL). The mixture was extracted with saturated aqueous sodium bicarbonate solution (10 mL ×3). The basic extract was acidified with 5% aqueous HCl solution. The acidic mixture was extracted with methylene chloride/ether (1:2, 10 mL ×4). The extract was washed with water (10 mL ×2), dried over MgSO$_4$, and filtered. The filtrate was evaporated in vacuo to give a crystalline solid. The solid was purified by preparative TLC [hexanes-ethyl acetate (2.5:1)] to give MCE-3 as a crystalline solid (6.9 mg, 50%): $^1$H NMR (CDCl$_3$) δ 7.39 (1H, d, J=1.8 Hz), 2.84 (1H, m), 2.62 (1H, m), 2.38 (1H, s), 2.32 (1H, m), 2.05 (1H, m), 1.55 (3H, s).

Example 3

Synthesis and Characterization of MCE-5

MCE-5 was synthesized as described below and summarized in Scheme 3.

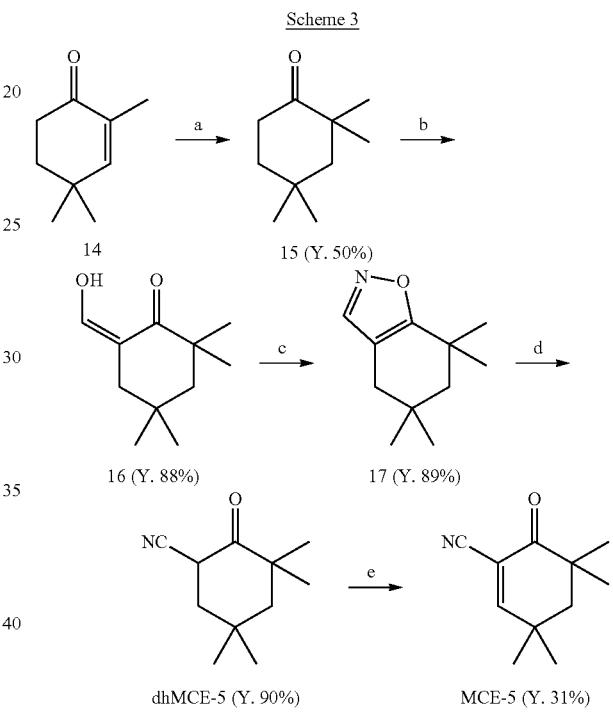

(a) NH$_3$, Li, t-BuOH, MeI; (b) HCO$_2$Et, NaOMe, PhH;
(c) NH$_2$OH•HCl, EtOH; (d) NaOMe, Et$_2$O, MeOH; (e) DDQ, PhH.

2,2,4,4-Tetramethylcyclohexanone (2)

A three-necked flask fitted with an additional funnel and dry ice condenser was dried in vacuo with heating. Under a nitrogen atmosphere, liquid ammonia (45 mL) was collected in the flask from condensation of ammonia gas. The flask was cooled to −78° C. in an isopropanol/dry ice bath and to it was added freshly cut lithium wire (108 mg, 15.5 mmol, 2.6 eq) until a blue color persisted. The mixture was stirred at −78° C. for 15 minutes. A solution of 14 (829.3 mg, 6 mmol) and tert-butanol (445 mg, 6 mmol, 1 eq) in anhydrous ethyl ether (24 mL) was then added dropwise over fifteen minutes. When the solution was completely added, the isopropanol bath was removed and the reaction mixture was allowed to warm to room temperature and begin to reflux. The solution was then cooled to −33° C. in a carbon tetrachloride (CCl$_4$)/dry ice bath and the reaction was stirred at reflux for 45 minutes, after which the CCl$_4$ bath was removed. At this time, the blue color still persisted, indicating an excess of lithium. Therefore, isoprene (0.2 mL) was added to the reaction mixture until the blue color disappeared. The reaction mixture was then cooled to −78° C. and a solution of methyl iodide (2.24 mL, 36 mmol, 6 eq) in anhydrous ethyl ether (15 mL) was added dropwise over 15 minutes. The isopropanol bath was again removed and when the reaction mixture began to reflux, it was placed in a CCl$_4$ bath and stirred at reflux for 1 hour. The CCl$_4$ bath was then removed. Finally, the liquid ammonia was removed with the aid of a nitrogen stream and remaining ammonia was neutralized by addition of 10% aqueous hydrochloric acid solution (25 mL). The resulting solution was extracted with methylene chloride/ethyl ether (1:2, 5×30 mL), and the organic phases were combined and washed with saturated aqueous sodium bicarbonate solution (1×40 mL) and brine (1×40 mL), dried over magnesium sulfate, filtered, and concentrated in vacuo to give crude 15 (724.1 mg) as an orange-brown liquid. The crude product was purified by flash column chromatography [hexanes-ethyl acetate (9:1)] to give 15 (461 mg, 2.98 mmol, 50%) as a yellow-brown oil: $^1$H NMR (CDCl$_3$) δ 2.44 (2H, t, J=6.8 Hz), 1.70 (2H, t, J=6.8 Hz), 1.59 (2H, s), 1.12 (6H, s), 1.08 (6H, s); $^{13}$C NMR (CDCl$_3$) δ 217.7, 53.5, 38.8, 35.4, 30.8, 30.3, 28.0.

6-Hydroxymethylene-2,2,4,4-tetramethylcyclohexanone (16)

Under an argon atmosphere, ethyl formate (1.18 mL, 14.3 mmol, 11 eq) then sodium methoxide (772.5 mg, 14.3 mmol, 11 eq) were successively added to a solution of 15 (200 mg, 1.30 mmol) in dry benzene (5.83 mL). This mixture was stirred at room temperature for 1 hour, during which time a color change to a cloudy, pale yellow solution occurred. The mixture was then diluted with a mixture of methylene chloride/ethyl ether (1:2, 20 mL) and washed with saturated aqueous ammonium chloride solution (2×8 mL). The aqueous washings were combined and extracted with methylene chloride/ethyl ether (1:2, 3×8 mL). The organic layers were then combined and washed with brine (1×8 mL), dried over magnesium sulfate, filtered, and concentrated in vacuo to give 16 as a yellow liquid (207.6 mg, 1.14 mmol, 88%). The product was used in the next reaction without further purification: $^1$H NMR (CDCl$_3$) δ 14.82 (1H, d, J=4 Hz), 8.42 (1H, d, J=5 Hz), 2.12 (2H, s), 1.45 (2H, s), 1.22 (6H, s), 0.99 (6H, s); $^{13}$C NMR (CDCl$_3$) δ 193.6, 185.1, 106.8, 50.8, 38.4, 38.0, 30.6, 29.3, 29.2. MS: No molecular ion peak is observed by ESI+ and EI methods.

5,5,7,7-Tetramethyl-4,5,6,7-tetrahydrobenzo[r]isoxazole (17)

Under a nitrogen atmosphere and with stirring, a solution of 16 (140 mg, 0.77 mmol) in ethanol (19.1 mL) was added to a solution of hydroxylamine hydrochloride (7.98 mmol, 555 mg, 10.4 eq) in water (980 µL) at room temperature. The mixture was heated to 110° C. and stirred at reflux for 1 hour. After heating, the reaction mixture was diluted with water (10 mL) and the aqueous layer was extracted with methylene chloride/ethyl ether (1:2, 3×10 mL). The organic layers were then combined and washed with saturated aqueous sodium bicarbonate solution (1×12 mL) and brine (2×12 mL), dried over magnesium sulfate, filtered, and concentrated in vacuo to give 17 as a yellow oil (122 mg, 0.68 mmol, 89%). The material was used in the next reaction without further purification: $^1$H NMR (CDCl$_3$) δ 8.00 (1H, s), 2.24 (2H, s), 1.60 (2H, s), 1.34 (6H, s), 1.03 (6H, s); $^{13}$C NMR (CDCl$_3$) δ 173.2, 150.0, 110.4, 52.4, 34.4, 32.6, 32.4, 29.7, 29.3. MS: No molecular ion peak is observed by ESI+ and EI methods.

3,3,5,5-Tetramethyl-2-oxocyclohex-1-enecarbonitrile (MCE-5)

Under an argon atmosphere and with stirring, a solution of 17 (152 mg, 0.848 mmol) in anhydrous ethyl ether (19.5 mL) was added to a solution of sodium methoxide (687 mg, 12.7 mmol, 15 eq) in dry methanol (15.8 mL). The mixture was stirred at room temperature for 2 hours, giving a light yellow solution. The reaction mixture was then diluted with methylene chloride/ethyl ether (1:2, 30 mL) and washed with 5% aqueous hydrochloric acid solution (2×7 mL). The aqueous layers were combined and extracted with methylene chloride/ethyl ether (1:2, 3×15 mL). The organic layers were then combined and washed with water (2×10 mL) and brine (1×10 mL), dried over magnesium sulfate, filtered, and concentrated in vacuo to give dhMCE-5 as a yellow oil (136.1 mg, 90%).

The calculations for the next step of the reaction were performed assuming the previous step gave a quantitative yield. 2,3-dichloro-5,6-dicyanobenzoquinone (DDQ) (148.6 mg, 0.642 mmol, 1 eq) was introduced into a flask containing dhMCE-5 (115 mg, 0.642 mmol), and the contents of the flask were dissolved under a nitrogen atmosphere in dry benzene (18.6 mL). The mixture was heated under reflux for 20 minutes. The reaction mixture was then allowed to cool to room temperature and was filtered through a Pasteur pipette with cotton and rinsed with benzene. The resulting solution was concentrated in vacuo to give a dark red solid as the crude product. The crude was purified by flash column chromatography [hexanes:ethyl acetate (4:1)] to give MCE-5 (35.0 mg, 0.197 mmol, 31%) as a white solid: $^1$H NMR (CDCl$_3$) δ 7.32 (1H, s), 1.83 (2H, d, J=1 Hz), 1.27 (6H, s), 1.20 (6H, s); $^{13}$C NMR (CDCl$_3$) δ 197.5, 169.0, 114.8, 113.7, 48.2, 41.5, 34.4, 29.9, 26.9. MS (ESI+) m/z 178.1 [M+H]$^+$, HRMS (ESI+) calcd for C$_{11}$H$_{15}$NO+H 178.1232. found 178.1227.

Example 4

Synthesis and Characterization of MCE-15

MCE-15 was synthesized as described below and summarized in Scheme 4.

Scheme 4

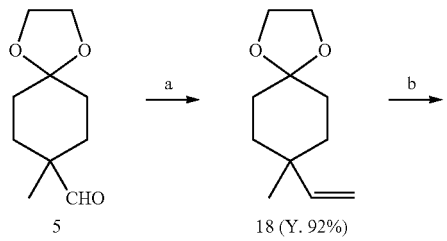

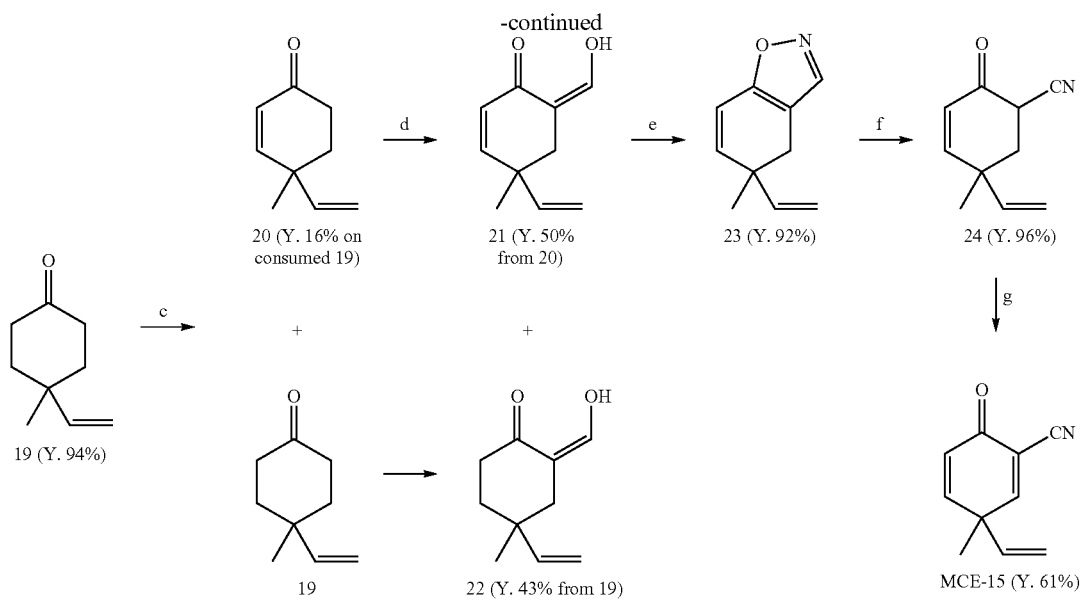

(a) Ph₃PMeI, t-BuOK, THF; (b) aq. HCl, acetone; (c) LDA, PhSeCl; 30% H₂O₂, CH₂Cl₂; (d) HCO₂Et, NaOMe, PhH;
(e) NH₂Cl·HCl, aqueous EtOH; (f) NaOMe, MeOH, Et₂O; (g) DDQ, PhH 8-Methyl-8-vinyl-1,4-dioxaspiro[4,5]decane (18)

In a three-necked flask under a nitrogen atmosphere, potassium tert-butoxide (73.2 mmol, 8.21 g, 7.93 eq.) was added to a stirred solution of methyltriphenylphosphonium iodide (87.3 mmol, 35.7 g, 9.73 eq.) in dry THF (130 mL), and the resulting mixture was stirred at room temperature for 5 minutes. To the mixture was added a solution of 5 (9.23 mmol, 1.7 g) in dry THF (130 mL) and the resulting mixture was stirred at room temperature for 1 hour. The mixture was then diluted with water (255 mL) and extracted with methylene chloride/ethyl ether (1:2, 3×300 mL). The organic layers were combined and washed with brine (2×350 mL), then dried with magnesium sulfate, filtered, and concentrated in vacuo to give a yellow solid (13.4 g). The crude product was purified by washing with petroleum ether-ethyl ether (2:1, 5×75 mL washes) and separating the soluble compound from the insoluble reaction residue. The washes were then combined, filtered, and concentrated in vacuo, revealing residual insoluble material in the form of white crystals. The soluble material was therefore decanted, and the crystals were washed with petroleum ether-ethyl ether (2:1, 2×50 mL washes). The washes were again combined, filtered, and concentrated in vacuo to give 18 (8.5 mmol, 1.55 g, 92%) as a yellow residue: ¹H NMR (CDCl₃) δ 5.79 (1H, dd, J=13.5, 18 Hz), 5.03 (1H, dd, J=1.2, 4.5 Hz), 4.98 (1H, dd, J=1.2, 2.7 Hz), 3.94 (4H, s), 1.70-1.61 (6H, m), 1.55-1.46 (2H, m), 1.01 (3H, s); ¹³C NMR (CDCl₃) δ 147.2, 111.6, 109.3, 64.4, 64.3, 35.9, 34.8, 31.4. MS: No molecular ion peak is observed by ESI+ and EI methods.

4-Methyl-4-vinylcyclohexanone (19)

To a stirred solution of 2 (1.98 mmol, 360 mg) in acetone (7.76 mL) was added 10% aqueous hydrochloric acid solution (3.02 mL), and the resulting mixture was stirred at room temperature for 2.5 hours. The reaction mixture was then diluted with brine (40 mL) and extracted with methylene chloride/ethyl ether (1:2, 3×30 mL). The organic layers were combined and washed with saturated aqueous sodium bicarbonate solution (2×30 mL) and brine (1×30 mL), then dried over magnesium sulfate, filtered, and concentrated in vacuo to give 19 (251.6 mg, 1.92 mmol, 94%) as a yellow oil that was used in the next reaction without further purification: ¹H NMR (CDCl₃) δ 5.89 (1H, dd, J=0.5, 17.3 Hz), 5.15 (1H, dd, J=1, 3.5 Hz), 5.12 (1H, dd, J=0.5, 10 Hz), 2.42-2.28 (4H, m), 1.97-1.91 (2H, m), 1.74-1.68 (2H, m), 1.12 (3H, s); ¹³C NMR (CDCl₃) δ 212.4, 145.5, 112.9, 38.2, 37.1, 27.4; MS (EI) m/z 138.1 [M⁺], 123.1, 110.1, 105.1, 97.1, 86.0 (100%), 68.1, 63.0, 54.9; HRMS (EI) calcd for C₉H₁₄O 138.1045 found 138.1048.

4-Methyl-4-vinylcyclohex-2-enone (20)

Under a nitrogen atmosphere, a stirred solution of 19 (123.8 mg, 0.899 mmol) in dry THF (7.12 mL) was cooled to −78° C. in a dry ice/isopropanol bath and to it was added LDA (2M in THF/n-heptane/ethylbenzene, 672 µL, 1.34 mmol, 1.5 eq.). The dry ice bath was then removed and the mixture was allowed to warm to room temperature for 20 minutes. To the mixture was added a solution of phenylselenenyl chloride (350 mg, 1.79 mmol, 2 eq.) in dry THF (2.2 mL) and the resulting mixture was stirred at room temperature for 2 hours. The reaction was quenched with brine (10 mL) and then extracted with methylene chloride/ethyl ether (1:2, 3×15 mL). The organic layers were combined and washed with brine (1×25 mL), then dried over magnesium sulfate, filtered, and concentrated in vacuo to give a yellow oil. This residue was then dissolved in methylene chloride (13.5 mL) and to it was added 3 successive portions of hydrogen peroxide (3×210 µL), allowing the mixture to stir 5 minutes at room temperature between each addition. After the third portion, the solution became light yellow and optically clear. The mixture was then diluted with ethyl ether (20 mL) and the organic layer was washed with water (1×10 mL), saturated aqueous sodium bicarbonate solution (2×10 mL) and brine (1×10 mL), then dried over magnesium sulfate, filtered, and concentrated in vacuo to give a yellow oil (153.8 mg). The crude product was combined with the crude from a previous identical reaction (131.7 mg) and purified by flash column chromatography [hexanes-ethyl acetate (7:1)] to give a yellow oil (62.1 mg). When the oil was analyzed by $^1$H NMR, starting material 19 was found to exist with the desired product 20 in a 1:1.4 ratio. Therefore, the purified product included 0.204 mmol of 20, giving 16% yield overall. $^1$H NMR (CDCl$_3$) δ 6.63 (1H, d, J=10 Hz), 5.99 (1H, d, J=10.2 Hz), 5.83 (1H, dd, J=6.5, 30 Hz), 5.12 (1H, ddd, J=1, 13, 18 Hz), 5.02 (1H, dd, J=1, 30 Hz), 2.5-2.26 (4H, m), 1.25 (3H, s); $^{13}$C NMR (CDCl$_3$) δ 156.1, 142.7, 128.7, 114.5, 38.3, 34.9, 34.4, 27.2.

6-Hydroxymethylene-4-methyl-4-vinyl-cyclohex-2-enone (21) and 6-hydroxymethylene-4-methyl-4-vinyl-cyclohexanone (22)

The product of the previous reaction (62.1 mg) was combined with the purified product of a subsequent identical reaction and purification sequence (455 mg) that was also found to contain 19 (starting material) in a 1:1.4 ratio with 20. To a solution of this starting material (517 mg, 1.56 mmol 3, 2.18 mmol 20) under an argon atmosphere in dry benzene (39 mL) was added ethyl formate (1.9 g, 26 mmol, 10 eq. per mol 20, 5 eq. per mol 19 (double)) followed by sodium methoxide (1.3 g, 24 mmol, 10 eq. per mol 20, 5 eq. per mol 19), and the resulting solution was stirred at room temperature for 1 hour. The reaction mixture was then transferred to a seperatory funnel, and to it was added 5% aqueous hydrochloric acid solution and methylene chloride/ethyl ether (1:2) until a separation of layers was observed. The organic layer was then washed with 5% aqueous hydrochloric acid solution, and the combined aqueous washings were extracted with methylene chloride/ethyl ether (1:2, 3×). The organic layers were then combined and washed with brine (3×), dried over magnesium sulfate, filtered, and concentrated in vacuo to give an oil (500 mg). The crude product was purified by flash column chromatography [petroleum ether-ethyl ether (5:1) followed by petroleum ether-ethyl ether (3:1) to elute remaining product] to obtain 22 (114 mg, 0.686 mmol, 43% yield from 19) and 5 (183.6 mg, 1.118 mmol, 50% yield from 20) as separate fractions.

21: $^1$H NMR (CDCl$_3$) δ 13.72 (1H, bs), 7.45 (1H, bs), 6.48 (1H, d, J=10 Hz), 6.06 (1H, d, J=10 Hz), 5.80 (1H, dd, J=10.6, 17.2 Hz), 5.06 (1H, dd, J=1, 4.4 Hz), 5.01 (J=1, 11 Hz), 2.42 (2H, s), 1.22 (3H, s); $^{13}$C NMR (CDCl$_3$) δ 188.8, 167.2, 164.6, 154.4, 143.0, 127.6, 113.7, 39.7, 36.2, 25.7; MS (ESI+) m/z 165.1 [M+H]$^+$, HRMS (ESI+) calcd for C$_{10}$H$_{12}$O$_2$+H 165.0916. found 165.0908.

22: $^1$H NMR (CDCl$_3$) δ 14.41 (1H, bs), 8.60 (1H, s), 5.78 (1H, dd, J=10.6 Hz, 17.2 Hz), 5.03 (1H, dd, J=1, 4 Hz), 4.98 (1H, dd, J=1.1, 10.6 Hz), 2.39-2.16 (4H, m), 1.70-1.50 (2H, m), 1.07 (3H, s); $^{13}$C NMR (CDCl$_3$) δ 187.3, 184.8, 145.4, 112.4, 107.6, 35.6, 34.5, 32.2, 28.9, 26.2. MS: No molecular ion peak is observed by ESI+ and EI methods.

5-methyl-5-vinyl-4,5-dihydro-benzo[d]isoxazole (23)

To a stirred solution of 21 (177 mg, 1.078 mmol) in ethanol (15 mL) under a nitrogen atmosphere was added a solution of hydroxylamine hydrochloride (741 mg, 10.66 mmol, 10 eq.) in water (1 mL). The reaction mixture was heated to reflux at 115° C. for 1 hour. Water was then added to the mixture until it became cloudy and the aqueous mixture was extracted with methylene chloride/ethyl ether (1:2, 4×). The organic layers were then combined and washed with saturated sodium bicarbonate solution (1×) and brine (1×), dried over magnesium sulfate, filtered and concentrated in vacuo to give 23 (159.7 mg, 0.99 mmol, 92%) as an oil. The product was used in the next reaction without further purification: $^1$H NMR (CDCl$_3$) δ 8.03 (1H, s), 6.52 (1H, dd, J=0.6, 10 Hz), 5.87 (1H, d, J=10 Hz), 5.81 (1H, d, J=10.6 Hz), 5.04 (1H, dd, J=0.6, 18.3 Hz), 5.00 (1H, dd, J=1.2, 11.4 Hz), 2.69 (2H, dd, J=16.2, 34.8 Hz) 1.23 (3H, s); $^{13}$C NMR (CDCl$_3$) δ 165.0, 148.8, 143.6, 141.6, 114.4, 112.7, 109.5, 40.4, 31.4, 26.0; MS (ESI+) m/z 162.1 [M+H]$^+$, HRMS (ESI+) calcd for C$_{10}$H$_{11}$NO+H 162.0919. found 169.0913.

3-methyl-6-oxo-3-vinyl-cyclohexa-1,4-dienecarbonitrile (MCE-15)

Under an argon atmosphere, a solution of 23 (155 mg, 0.962 mmol) in anhydrous ethyl ether (17 mL) was added to a stirred solution of sodium methoxide (1.6 g, 29.61 mmol, 30 eq.) in dry methanol and the resulting mixture was stirred at room temperature for 1 hour. The reaction mixture was then diluted with methylene chloride/ethyl ether (1:2, 120 mL) and the solution was washed with 5% aqueous hydrochloric acid solution (2×). The acidic washings were combined and extracted with methylene chloride/ethyl ether (1:2, 30 mL). All of the organic layers were then combined and washed with water (2×) and brine (1×), dried over magnesium sulfate, filtered, and concentrated in vacuo to give 24 as a yellow oil (148.8 mg, 96%).

Calculations for the next step of the reaction were done assuming that the previous step gave a quantitative yield. Under a nitrogen atmosphere, the yellow oil (80 mg, 0.5 mmol) was dissolved in dry benzene (4 mL) and to it was added DDQ (150 mg, 0.661 mmol, 1.33 eq). The reaction mixture was heated to reflux for 10 minutes. When checked by thin layer chromatography, some starting material still remained. Therefore, additional DDQ (40 mg, 0.176 mmol) was added and the reaction mixture was again stirred at reflux for 10 minutes. The reaction was allowed to cool to room temperature, and insoluble material was removed by filtration through a Pasteur pipette with cotton and washing with benzene. The filtrate was concentrated in vacuo to give an orange residue (400 mg). The crude residue was then purified by flash column chromatography [petroleum ether-ethyl ether (1:1)] to give MCE-15 (48 mg, 0.301 mmol, 61%) as a crystalline solid: $^1$H NMR (CDCl$_3$) δ 7.51 (1H, d, J=3 Hz), 6.90 (1H, dd, J=3, 10.2 Hz), 6.34 (1H, d, J=10.2 Hz), 5.73 (1H, dd, J=10.2, 17.7 Hz), 5.27 (1H, d, J=10.5 Hz), 5.21 (1H, d, J=17.4 Hz), 1.46 (3H, s); $^{13}$C NMR (CDCl$_3$) δ 179.0, 163.8, 153.8, 136.7, 126.8, 110.1, 116.1, 114.0, 45.0, 24.1; MS (ESI+) m/z 160.1 [M+H]$^+$, HRMS (ESI+) calcd for C$_{10}$H$_9$NO+H 160.0762. found 160.0755.

Example 5

Synthesis and Characterization of MCE-13

MCE-13 was synthesized as described below and summarized in Scheme 5.

Scheme 5

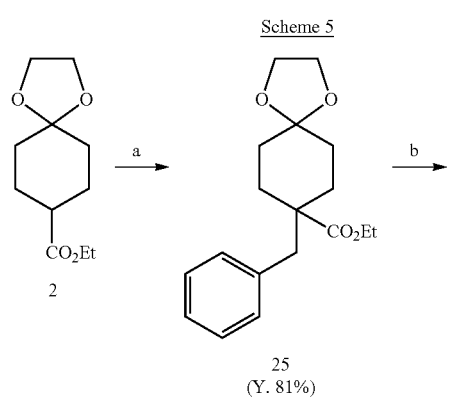

25
(Y. 81%)

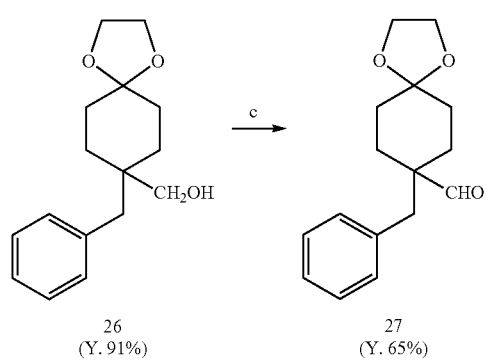

26     27
(Y. 91%)   (Y. 65%)

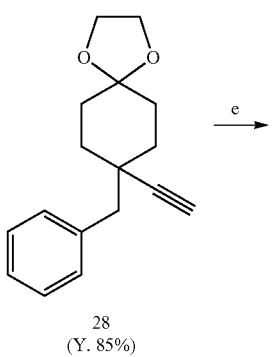

28
(Y. 85%)

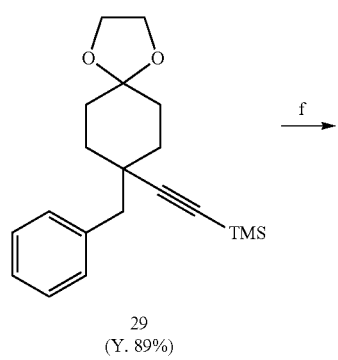

29
(Y. 89%)

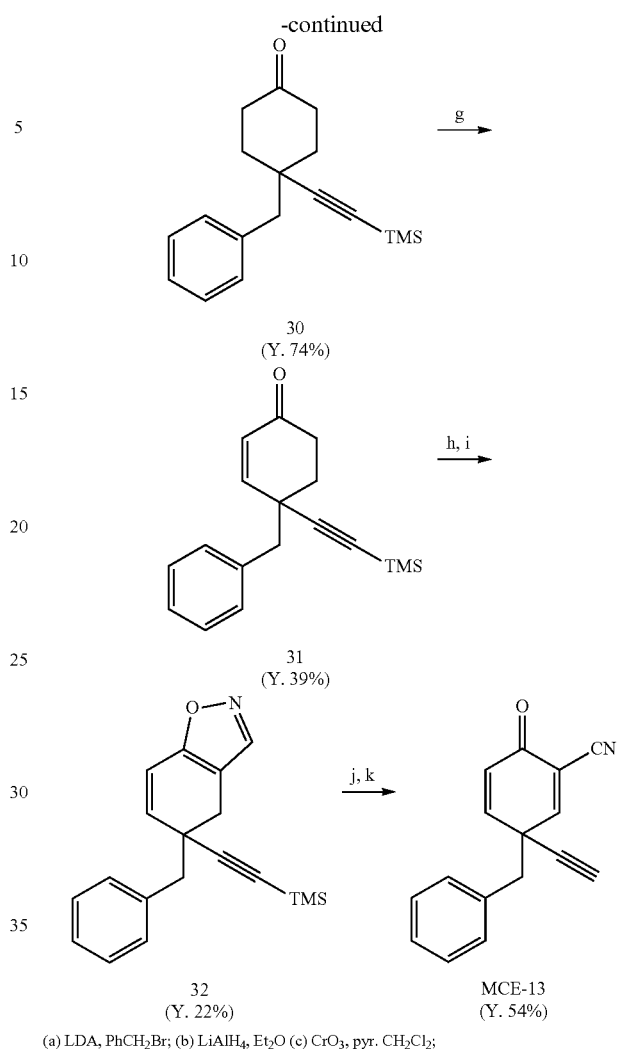

30
(Y. 74%)

31
(Y. 39%)

32     MCE-13
(Y. 22%)   (Y. 54%)

(a) LDA, PhCH$_2$Br; (b) LiAlH$_4$, Et$_2$O (c) CrO$_3$, pyr. CH$_2$Cl$_2$;
(d) (MeO)$_2$POCN$_2$COCH$_3$, K$_2$CO$_3$; (e) MeLi, THF; TMSCl; (f) aq. HCl, acetone;
(g) LDA, PhSeCl; 30% H$_2$O$_2$, CH$_2$Cl$_2$; (h) HCO2Et, NaOMe, PhH;
(i) NH$_2$OH·HCl, EtOH; (j) NaOMe, MeOH, Et$_2$O; (k) DDQ, PhH.

Ethyl 8-benzyl-1,4-dioxa-spiro[4,5]decane-8-carboxylate (25)

Under a nitrogen atmosphere, LDA (2M in THF/n-heptane/ethylbenzene, 20 mL, 40 mmol, 1.5 eq.) was added dropwise with stirring to a solution of 2 (5.8 g, 27 mmol) in dry tetrahydrofuran (THF, 60 mL) cooled to −78° C. in a dry ice/isopropanol bath. The mixture was allowed to slowly warm to room temperature over 20 minutes. The reaction mixture was again cooled to −78° C. and to it was added a solution of benzyl bromide (5.42 g, 32 mmol, 1.17 eq.) in dry THF (15 mL) using a syringe pump over 20 minutes. The reaction mixture was then stirred at −78° C. in the dry ice/isopropanol bath for 1 hour. After warming to room temperature, the mixture was diluted with ethyl ether (100 mL) and the organic layer was washed with saturated aqueous ammonium chloride solution (2×50 mL) and brine (1×50 mL) then dried over magnesium sulfate, filtered, and concentrated in vacuo to give a brown residue (14.9 g) as a crude. The crude product was purified by flash column chromatography [hexanes-ethyl acetate (4:1)] to give 25 (6.67 g, 81%) as an oil. $^1$H NMR (CDCl$_3$) δ 7.28-7.18 (3H, m), 7.07-7.04 (2H, m), 4.08 (4H, q, J=7.1 Hz), 3.94 (4H, s), 2.83 (2H, s), 2.17-2.14 (2H, m), 1.72-1.53 (6H, m); $^{13}$C NMR (CDCl$_3$) δ 175.5, 137.3, 130.0, 128.2, 126.8, 108.8, 64.5, 64.4, 60.5, 47.9, 46.7, 33.9, 32.3, 31.7, 26.5, 14.3; MS (ESI+) m/z 305.2 [M+H]$^+$, HRMS (ESI+) calcd for C$_{18}$H$_{24}$O$_4$+H 305.1753. found 305.1753.

(8-Benzyl-1,4-dioxa-spiro[4,5]dec-8-yl)-methanol (26)

A sample of 25 (687.6 mg, 2.26 mmol) was dissolved in anhydrous ethyl ether (48.8 mL) at 0° C. under a nitrogen atmosphere and with stirring. To this was added lithium aluminum hydride (214.4 mg, 5.64 mmol, 2.5 eq.), and the resulting mixture was stirred at room temperature for 2 hours. After verifying the completion of the reaction by thin layer chromatography, water (3.6 mL), 40% aqueous sodium hydroxide solution (2.56 mL), and additional water (5.2 mL) were added successively to the mixture while stirring to quench excess lithium aluminum hydride. The resulting solution was filtered, then dried over magnesium sulfate, filtered again, and concentrated in vacuo to give a colorless oil (1.50 g). The crude product was combined with the crude from a previous identical reaction (84.8 mg) and purified by flash column chromatography [hexanes-ethyl acetate (5:1)] to give 26 (609.6 mg, 2.32 mmol, 91%) as an oil: $^1$H NMR (CDCl$_3$) δ 7.31-7.19 (5H, m), 3.96 (4H, t, J=2.3 Hz), 3.37 (2H, d, J=4.8 Hz), 2.71 (2H, s), 1.81-1.51 (8H, m), 1.34 (1H, bs); $^{13}$C NMR (CDCl$_3$) δ138.6, 130.6, 128.3, 126.3, 109.2, 66.3, 64.5, 40.7, 30.7, 30.0; MS (ESI+) m/z 263.1 [M+H]$^+$, HRMS (ESI+) calcd for C$_{16}$H$_{22}$O$_3$+H 263.1647. found 263.1640.

8-benzyl-1,4-dioxa-spiro[4,5]decane-8-carbaldehyde (27)

Under a nitrogen atmosphere and with stirring solid chromium (IV) oxide (140 mg, 1.40 mmol, 7 eq.) was added to a solution of extra dry pyridine (220 µL, 2.72 mmol, 13.6 eq.) in dry methylene chloride (2.44 mL) cooled to 0° C. in an ice bath. The resulting mixture was stirred at room temperature for 15 minutes, and to it was added a solution of 3 (52.0 mg, 0.2 mmol) in dry methylene chloride (0.4 mL+(3×5 mL) rinse). After stirring at room temperature for 30 minutes, the reaction mixture was decanted into a seperatory funnel and the residue was washed with ethyl ether (1.67 mL+1.3 mL+1.3 mL). The organic layer was then washed with 5% aqueous sodium hydroxide solution (3×1.67 mL), saturated aqueous sodium bicarbonate solution (3×1.67 mL) and brine (3×1.67 mL). The resulting solution was dried over magnesium sulfate, filtered and concentrated in vacuo to give a while solid (29.7 mg). The solid was dissolved in a minimum of hexanes-ethyl acetate (3:1) and combined with the crude product from a subsequent identical reaction (364.7 mg), then purified by flash column chromatography [hexanes-ethyl acetate (3:1)] to give 27 (332.8 mg, 1.27 mmol, 61%) as colorless oil above a white amorphous solid. Note, additional impure material (33.9 mg) was recovered and saved for purification at a later date, giving 65% yield overall. $^1$H NMR (CDCl$_3$) δ 9.55 (1H, s), 7.32-0.04 (5H, m), 3.93 (4H, s), 2.78 (2H, s), 1.68-1.47 (8H, m).

8-Benzyl-8-ethynyl-1,4-dioxaspiro[4,5]decane (28)

Under a nitrogen atmosphere, potassium carbonate (343 mg, 2.48 mmol, 2 eq.) followed by a solution of 27 (324 mg, 1.24 mmol) in dry methanol (10 mL) were added to a stirred solution of freshly prepared dimethyl-1-diazo-2-oxopropylphosphonate (397 mg, 2.06 mmol, 1.5 eq.) (Müller, et. al) in dry methanol (10 mL) cooled in an ice bath. The reaction mixture was stirred in the ice bath for 30 minutes, and then stirred at room temperature overnight. The reaction was quenched with saturated aqueous ammonium chloride solution (28.6 mL) and extracted with methylene chloride (4×57 mL). The organic layers were combined and dried over magnesium sulfate, filtered, and dried in vacuo to give a beige solid (351.3 mg). The crude product was combined with the product from a previous identical reaction (36.3 mg) and dissolved in hexanes-ethyl acetate (5:1). The material was found to be only slightly soluble, with thin layer chromatography showing the insoluble crystals (86.9 mg) to be almost pure product. The crystals were therefore separated by decanting, and the soluble material was purified by flash column chromatography [hexanes-ethyl acetate (5:1)] to give a white crystalline solid (212.6 mg). The two crystalline samples were combined to give pure product 28 (299.5 mg, 1.17 mmol, 85%): $^1$H NMR (CDCl$_3$) δ 7.32-7.21 (5H, m), 3.94 (4H, dd, J=2.5, 3 Hz), 2.76 (2H, s), 2.20 (1H, s), 2.01-1.91, 1.76-1.56 (8H, m); $^{13}$C NMR (CDCl$_3$) δ 137.6, 130.8, 127.9, 126.7, 110.0, 108.9, 87.9, 72.3, 64.5, 64.4, 48.1, 37.0, 35.1, 31.8. MS (ES+) m/z 257.1 [M+H]$^+$, HRMS (ESI+) calcd for C$_{17}$H$_{20}$O$_2$+H 257.1542. found 257.1541.

((8-Benzyl-1,4-dioxaspiro[4,5]decan-8-yl)ethynyl) trimethylsilane (29)

Under nitrogen atmosphere and with stirring at 0° C., methyllithium (1.6 M in hexanes, 4.78 mL, 7.65 mmol, 9.2 eq) was added dropwise to a solution of 28 (212.6 mg, 0.829 mmol) in dry THF (9.56 mL). The ice bath was then removed and the mixture was stirred at room temperature for 25 minutes. To the mixture was added dropwise a solution of trimethylsilyl chloride (3.24 mL, 24.87 mmol, 30 eq) in dry THF (3.9 mL) and the resulting mixture was stirred at room temperature for 45 minutes. During this time the solution became opaque and pale yellow. The reaction was then quenched with water (15 mL) and the aqueous layer was extracted with methylene chloride/ethyl ether (1:2, 3×15 mL). The organic layers were combined and washed with saturated aqueous sodium bicarbonate solution (1×15 mL) and brine (1×15 mL), dried over magnesium sulfate, filtered, and concentrated in vacuo to give 29 (243.1 mg, 0.74 mmol, 89%) as pale yellow crystals. The product was used in the next reaction without further purification: $^1$H NMR (CDCl$_3$) δ 7.32-7.30 (5H, m), 3.95 (4H, dd, J=2.5, 3.5 Hz), 2.72 (2H, s), 2.00-1.90, 1.71-1.50 (8H, m), 0.14 (9H, s); $^{13}$C NMR (CDCl$_3$) δ 137.8, 130.9, 127.7, 126.5, 110.6, 109.1, 88.2, 64.5, 64.4, 48.2, 38.0, 35.2, 31.9, 0.36. MS (EI) m/z 328.1 [M$^+$], 284.2, 237.2, 193.1, 99.1 (100%), 73.1, 59.0; HRMS (EI) calcd for C$_{20}$H$_{28}$O$_2$Si 328.1859. found 328.1856.

4-Benzyl-4-((trimethylsilyl)ethynyl)cyclohexanone (30)

A sample of 29 (243.1 mg, 0.74 mmol) was dissolved in acetone (2.89 mL) to give a translucent, yellow solution. To the solution was added a solution of 10% aqueous hydrochloric acid solution (1.15 mL) and the reaction mixture was stirred at room temperature for 5 hours. The mixture was then diluted with brine (25 mL) and the aqueous layer was extracted with methylene chloride/ethyl ether (1:2, 3×20 mL). The organic layers were combined and washed with saturated aqueous sodium bicarbonate solution (2×20 mL) and brine (1×20 mL), then dried over magnesium sulfate, filtered, and concentrated in vacuo to give the crude 30 as pale yellow crystals (195 mg). The crystals were combined with the crude product of a previous reaction (62.5 mg) and were purified by flash column chromatography [hexanes-ethyl acetate (5:1)] to give 30 as white crystals (197.1 mg, 0.69 mmol, 74%). Note, an impure fraction was collected and saved for future purification: $^1$H NMR (CDCl$_3$) δ 7.31-7.24 (5H, m), 2.81 (2H, s), 2.74 (1H, td, J=6, 14.5 Hz), 2.30 (2H, dt, J=2, 15 Hz), 2.00 (2H, dt, J=3, 14 Hz), 1.68 (2H, dt, J=4, 13.5 Hz), 0.17 (9H, s); $^{13}$C NMR (CDCl$_3$) δ 211.7, 137.1, 130.8, 128.0, 126.9, 109.0, 47.6, 38.6, 38.0, 37.2, 0.29. MS (ESI+) m/z 285.1 [M+H]$^+$, HRMS (ESI+) calcd for C$_{18}$H$_{24}$OSi+H 285.1675. found 285.1661.

4-Benzyl-4-((trimethylsilanyl)ethynyl)cyclohex-2-enone (31)

Under a nitrogen atmosphere and with stirring, a sample of 30 (50 mg, 0.176 mmol) was suspended in dry THF (1.4 mL) and the solution was cooled to −78° C. in a dry ice/isopropanol bath. To the stirred mixture was added lithium diisopropylamide (LDA, 2 M in THF/n-heptane/ethylbenzene, 132 µL, 0.26 mmol) dropwise. The isopropanol bath was then removed and the mixture was allowed to reach room temperature over 20 minutes. The mixture was again cooled to −78° C. and to it was added dropwise a solution of phenylselenenyl chloride (66.5 mg, 0.347 mmol, 2 eq) in dry THF (0.42 mL). The isopropanol bath was removed and the reaction was stirred at room temperature for 2 hours. During this time a yellow precipitate appeared, indicating the formation of solid lithium chloride. The reaction was then quenched with brine (5 mL) and the aqueous layer was extracted with dichloromethane/ethyl ether (1:2, 3×4 mL). The organic layers were combined, washed with brine (1×4 mL), dried over magnesium sulfate, filtered, and concentrated in vacuo to give a dark yellow-brown residue. This residue was dissolved in ethyl ether (2.82 mL) and hydrogen peroxide (30% aqueous, 3×42.3 µL) was added in 3 successive portions, allowing the mixture to stir 5 minutes between each addition. After the third portion was added, the color of the mixture changed from brown to pale yellow and translucent. The reaction mixture was then washed with water (1×4 mL), saturated aqueous sodium bicarbonate solution (2×4 mL), and brine (1×4 mL). The organic layers were combined and dried over magnesium sulfate, filtered, and concentrated in vacuo to give the crude product as a yellow oil (43.1 mg). The crude was purified by flash column chromatography [hexanes-ethyl acetate (5:1)] to give 31 (19.2 mg, 0.068 mmol, 39%) as a clear oil: $^1$H NMR (CDCl$_3$) δ 7.34-7.24 (5H, m), 6.74 (1H, dd, J=1.5, 10 Hz), 5.94 (1H, dd, J=0.6, 10 Hz), 2.98 (1H, d, J=13 Hz), 2.89 (1H, d, J=13 Hz), 2.46 (2H, dt, J=5, 17 Hz), 2.08 (2H, td, J=1.5, 6 Hz), 0.16 (9H, s); $^{13}$C NMR (CDCl$_3$) δ 209.1, 199.1, 152.1, 135.9, 130.9, 128.2, 128.1, 127.3, 109.0, 106.1, 89.4, 46.4, 38.5, 35.0, 34.5, 0.11; MS (ESI+) m/z 283.1 [M+H]$^+$, HRMS (ESI+) calcd for C$_{18}$H$_{22}$OSi+H 283.1518. found 283.1508.

5-Benzyl-5-((trimethylsilyl)ethynyl)-4,5-dihydrobenzo[r]isoxazole (32)

Under an argon atmosphere, ethyl formate (110.6 µL, 1.33 mmol, 5 eq) then sodium methoxide (71.7 mg, 1.33 mmol, 3 eq) were successively added to a solution of 31 (75 mg, 0.265 mmol) in dry benzene (3.07 mL). This mixture was stirred at room temperature for 1 hour, during which time a color change from orange to red-brown occurred. The mixture was then diluted with a mixture of methylene chloride/ethyl ether (1:2, 20 mL) and washed with saturated aqueous ammonium chloride solution (2×8 mL). The aqueous washings were combined and extracted with methylene chloride/ethyl ether (1:2, 3×10 mL). The organic layers were then combined and washed with brine (1×10 mL), dried over magnesium sulfate, filtered, and concentrated in vacuo to give 4-benzyl-6-hydroxymethylene-4-((trimethyl-silyl)ethynyl)cyclohex-2-enone (83 mg, 100%) as a yellow-brown oil. The product was used in the next reaction without further purification: $^1$H NMR (CDCl$_3$) δ 13.67 (1H, bs), 7.45 (1H, bs), 7.23-7.16 (5H, m), 6.51 (1H, dd, J=1, 10.5 Hz), 5.98 (1H, d, J=10 Hz), 2.84 (1H, d, J=13 Hz), 2.68 (1H, d, J=13 Hz), 2.57 (1H, dd, J=1, 14.5 Hz), 2.40 (1H, d, J=15 Hz); $^{13}$C NMR (CDCl$_3$) δ 187.5, 168.7, 151.4, 136.0, 130.8, 128.5, 128.1, 127.2, 127.1, 109.9, 108.0, 44.4, 38.9, 34.6, 0.10.

Under a nitrogen atmosphere a solution of 4-benzyl-6-hydroxymethylene-4-((trimethylsilyl)ethynyl)cyclohex-2-enone (76 mg, 0.245 mmol) in ethanol (6.13 mL) was added to a stirred solution of hydroxylamine hydrochloride (177.6 mg, 2.53 mmol, 10.3 eq) in water (256 µL) at room temperature. The mixture was heated to 120° C. and stirred at reflux for 1 hour. After heating, the reaction mixture was diluted with water (10 mL) and the aqueous layer was extracted with dichloromethane/ethyl ether (1:2, 3×10 mL). The organic layers were then combined and washed with saturated aqueous sodium bicarbonate solution (1×10 mL) and brine (2×10 mL), dried over magnesium sulfate, filtered, and concentrated in vacuo to give the crude product as a yellow-brown oil (76.4 mg). The crude was purified first by dissolving the product in petroleum ether/ethyl ether (5:1) and decanting the soluble portion from the insoluble solid. The insoluble material was washed with petroleum ether/ethyl ether (5:1) several times and the resulting mother liquor was found by thin layer chromatography (TLC) to contain the desired compound. The mother liquor was purified by flash column chromatography [petroleum ether-ethyl ether (5:1)] to give 32 (17.1 mg, 0.055 mmol, 22%) as a colorless oil: $^1$H NMR (CDCl$_3$) δ 8.09 (1H, s), 7.32-7.22 (5H, m), 6.56 (1H, dd, J=1, 10 Hz), 6.0 (1H, d, J=10 Hz), 2.96 (1H, d? J=16 Hz), 2.94 (1H, d, J=13 Hz), 2.83 (1H, d, J=16 Hz), 2.73 (1H, d, J=13 Hz), 0.16 (9H, s); $^{13}$C NMR (CDCl$_3$) δ 164.4, 148.7, 139.3, 135.0, 131.0, 128.0, 127.1, 114.4, 109.1, 88.4, 44.2, 39.2, 30.3, 0.13. MS (ESI+) m/z 308.1 [M+H]$^+$, HRMS (ESI+) calcd for C$_{19}$H$_{21}$NOSi+H 308.1471. found 308.1467.

3-Benzyl-3-ethynyl-6-oxocyclohexa-1,4-dienecarbonitrile (MCE-13)

Under an argon atmosphere and with stirring, a solution of 32 (17.1 mg, 0.055 mmol) in anhydrous ethyl ether (1.27 mL) was added to a solution of sodium methoxide (44.7 mg, 0.829 mmol, 15 eq) in dry methanol (1.03 mL). The mixture was stirred at room temperature for 2 hours. The reaction mixture was then diluted with methylene chloride/ethyl ether (1:2, 10 mL) and washed with 5% aqueous hydrochloric acid solution (2×5 mL). The aqueous layers were combined and extracted with methylene chloride/ethyl ether (1:2, 3×8 mL). The organic layers were then combined and washed with water (2×8 mL) and brine (1×8 mL), dried over magnesium sulfate, filtered, and concentrated in vacuo to give a yellow oil (12.2 mg).

The following reaction step was calculated assuming the last reaction gave a quantitative yield. DDQ (11.76 mg, 0.0518 mmol, 1 eq) was introduced into a flask containing dhMCE-13 (12.2 mg, 0.0518 mmol, 1 eq), and the contents of the flask were dissolved under a nitrogen atmosphere in dry benzene (1.5 mL). The mixture was heated under reflux and stirred for 20 minutes. The reaction mixture was then allowed to cool to room temperature and was filtered through a Pasteur pipette with cotton and rinsed with benzene. The resulting solution was concentrated in vacuo to give a crude product dark orange solid. The crude was purified by flash column chromatography [hexanes-ethyl acetate (2:1)] to give MCE-13 (6.5 mg, 0.0277 mmol, 54%) as a white solid: $^1$H NMR (CDCl$_3$) δ 7.50 (1H, d, J=3 Hz), 7.34-7.33 (3H, m), 7.20-7.18 (2H, m), 6.92 (1H, dd, J=3, 10 Hz), 6.34 (1H, d, J=10 Hz), 3.32 (1H, d, J=13 Hz), 3.20 (1H, d, J=13 Hz), 2.53 (1H, s).

Example 6

Synthesis and Characterization of MCE-6 and MCE-7

MCE-6 and MCE-7 were synthesized as described below and summarized in Scheme 6.

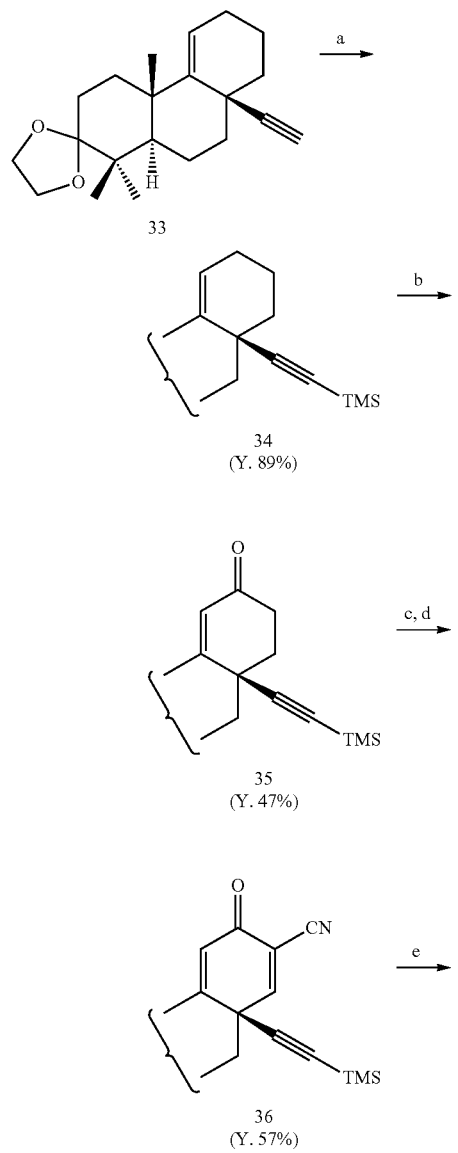

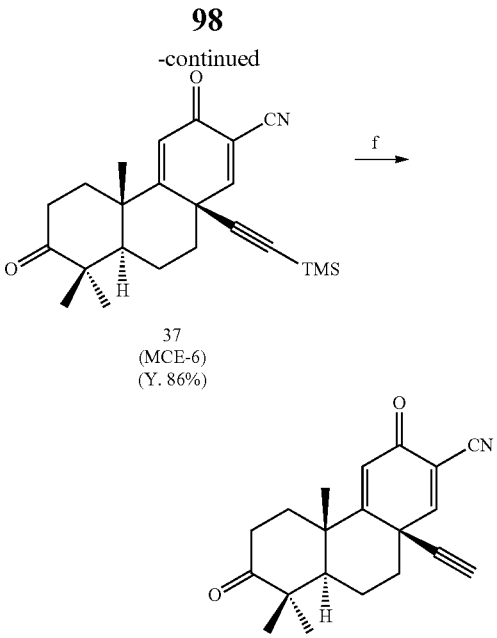

(a) TMSCl, MeLi, THF; (b) CrO$_3$, t-BuOOH; CH$_2$Cl$_2$; (c) p-TsCN, LDA, THF; (d) DDQ, PhH; (e) aqueous HCl, MeOH; (f) TBAF, THF.

Protocol for the Synthesis of 34:

To a stirred solution of 33 (1.5 mmol, 472 mg) in dry THF (14 mL) was added dropwise at 0° C. under N$_2$ MeLi (1.6M in hexanes, 4 eq, 6 mmol, 3.75 mL). The yellow solution was stirred at room temperature for 30 min. Then TMSCl (98%, 4 eq, 6 mmol, 785 µL) was added dropwise and the mixture was stirred at room temperature for 1 hour. After addition of 25 mL of H$_2$O, the two layers were separated and the aqueous layer was extracted with Et$_2$O/CH$_2$Cl$_2$: 2/1 (3×20 mL). The combined organic layers were washed with a saturated NaHCO$_3$ aqueous solution (1×25 mL) and with brine (1×25 mL), dried over MgSO$_4$ and filtered. The filtrate was concentrated under reduced pressure to afford 630 mg of crude as a yellow oil. The crude was purified by flash column chromatography (Hexanes/EtOAc:10/1) to afford 34 (518 mg, 89%) as a white solid. $^1$H NMR (CDCl$_3$) δ 5.43-5.46 (m, 1H), 3.84-4.01 (m, 4H), 1.34 (s, 3H), 1.01 (s, 3H), 0.86 (s, 3H), 0.13 (s, 9H); $^{13}$C NMR (CDCl$_3$) δ 148.3, 118.8, 115.8, 113.4, 84.7, 65.1, 65.0, 52.1, 43.1, 42.6, 40.9, 40.4, 36.3, 35.5, 27.3, 26.3, 23.3, 23.2, 20.3, 19.7, 19.3, 0.3.

Protocol for the Synthesis of 35:

To a stirred solution of 34 (0.914 mmol, 353 mg) in dry CH$_2$Cl$_2$ (4.6 mL) were successively added under N$_2$ K$_2$CO$_3$ (0.5 eq, 0.457 mmol, 63 mg) and Rh$_2$(cap)$_4$ (0.5%, 0.00455 mmol, 3 mg). To the blue suspension was added t-BuOOH in once (5M in decane, 5 eq, 4.57 mmol, 910 µL) so that the mixture turned immediately in red purple. After 1 h 15 m of stirring at room temperature, Rh$_2$(cap)$_4$ (0.5%, 0.00455 mmol, 3 mg) then t-BuOOH in once (5M in decane, 5 eq, 4.57 mmol, 910 µL) were still added. The mixture was stirring at room temperature for an additional hour. The mixture was filtered through a pad of silica with CH$_2$Cl$_2$/MeOH: 95/5 to get rid of the catalyst. The filtrate was concentrated under reduced pressure to give 682 mg of crude as a purple residue. The crude was purified by flash chromatography (Hexanes/EtOAc:5/1) to afford 35 (175 mg, 47%) as a white solid. $^1$H NMR (CDCl$_3$) δ 5.86 (s, 1H), 3.87-4.38 (m, 4H), 2.77-2.85 (ddd, 1H, J=4.5, 15.0, 17 Hz), 2.35-2.40 (dt, 1H, J=2.7, 17 Hz), 2.17-2.21 (dt, 1H, J=3.0, 12.8 Hz), 2.05-2.10 (ddd, 1H, J=2.6, 4.4, 12.8 Hz), 1.80-1.96 (m, 3H), 1.61-1.75 (m, 4H), 1.43-1.50 (m, 2H), 1.40 (s, 3H), 1.04 (s, 3H), 0.89 (s, 3H), 0.13 (s, 9H); $^{13}$C NMR (CDCl$_3$) δ 201.1, 172.7, 122.4, 112.6, 109.1, 87.2, 65.2, 65.1, 50.7, 42.9, 42.5, 41.7, 39.3, 36.9, 34.9, 34.6, 27.0, 23.3, 23.1, 20.5, 19.3, 0.1.

Protocol for the Synthesis of 36:

A stirred solution of 35 (0.307 mmol, 123 mg) in dry THF (1.5 mL) was cooled to −78° C. and LDA (2M in THF/heptane, 1.4 eq, 0.43 mmol, 215 µL) was added. The brown mixture was stirred at room temperature for 20 min and then cooled back to −78° C. A cloudy solution of p-TsCN (95%, 1.7 eq, 0.522 mmol, 100 mg) in dry THF (1 mL) was added and the mixture was stirred at −78° C. for 45 min. A saturated NH$_4$OH aqueous solution (1.5 mL) was then added and the mixture was let to reach room temperature. It was extracted with EtOAc (3×10 mL). The combined organic layers were washed with a saturated NaHCO$_3$ aqueous solution (1×10 mL) and with brine (1×10 mL), dried over MgSO$_4$ and filtered. The filtrate was concentrated under reduced pressure to give 158 mg of a crude product as a brown oil. This reaction was considered to be complete and the crude was directly dissolved under N$_2$ in dry benzene (9 mL). DDQ (98%, 1.5 eq, 0.460 mmol, 106 mg) was added and the brown suspension was refluxed at 100° C. for 10 min. After cooling to room temperature, the suspension was filtered and the filtrate was concentrated under reduced pressure to give 230 mg of crude as a brown oil. The crude was purified by flash column chromatography (CH$_2$Cl$_2$/Acetone: 100/1) to afford 36 (75 mg, 57%) as a pale pink solid. $^1$H NMR (CDCl$_3$) δ 7.34 (s, 1H), 6.24 (s, 1H), 3.86-4.01 (m, 4H), 2.78-2.31 (dt, 1H, J=3.0, 12.5 Hz), 2.01-2.09 (m, 1H), 1.93-1.99 (m, 1H), 1.80-1.85 (m, 2H), 1.65-1.71 (m, 2H), 1.48-1.53 (m, 1H), 1.48 (s, 3H), 1.38-1.41 (dd, 1H, J=2.0, 12.5 Hz), 1.06 (s, 3H), 0.88 (s, 3H), 0.16 (s, 9H); $^{13}$C NMR (CDCl$_3$) δ 180.4, 168.9, 160.7, 121.5, 113.9, 112.2, 109.9, 101.2, 92.4, 65.2, 65.1, 51.6, 43.2, 42.3, 40.7, 40.1, 34.6, 27.0, 23.3, 21.5, 20.2, 18.9, −0.3.

Protocol for the Synthesis of 37 (MCE-6):

A suspension of 36 0.177 mmol, 75 mg) in methanol (3.5 mL) was refluxed to get a total dissolution. Then, a 10% HCl aqueous solution (2 mL) was added to the hot solution and the mixture was stirred at room temperature for 15 min. After neutralization at neutral pH with Et$_3$N to get neutral pH, the mixture was concentrated in vacuo. The white residue was dissolved in H$_2$O (5 mL) and extracted with EtOAc (3×10 mL). The combined organic layers were washed with a saturated NaHCO$_3$ aqueous solution (1×10 mL) and with brine (1×10 mL), dried over MgSO$_4$ and filtered. The filtrate was concentrated under reduced pressure to give 78 mg of crude as a pale brown solid. The crude was purified by flash column chromatography (CH$_2$Cl$_2$/Acetone: 100/1) to afford 37 (58 mg, 86%) as a white solid. $^1$H NMR (CDCl$_3$) δ 7.37 (s, 1H), 6.24 (s, 1H), 2.75-2.82 (ddd, 1H, J=6.7, 12.7, 16.5 Hz), 2.51-2.56 (ddd, 1H, J=2.7, 5.7, 16.5 Hz), 2.33-2.37 (dt, 1H, J=3.1, 12.8 Hz), 2.18-2.27 (m, 1H), 2.08-2.13 (ddd, 1H, J=2.7, 6.7, 12.8 Hz), 1.81-1.91 (m, 2H), 1.65 (s, 3H), 1.50-1.55 (m, 1H), 1.43-1.46 (dd, 1H, J=2.7, 12.2 Hz), 1.18 (s, 3H), 1.13 (s, 3H), 0.10 (s, 9H); $^{13}$C NMR (CDCl$_3$) δ 214.2, 180.0, 167.1, 160.4, 122.3, 114.2, 113.7, 100.7, 93.1, 53.8, 48.1, 41.9, 40.7, 39.4, 36.3, 34.2, 26.2, 22.1, 20.7, 20.0, −0.3.

Protocol for the Synthesis of MCE-7:

A solution of TBAF (98%, 3 eq, 0.336 mmol, 90 mg) in THF (850 µL) was added to 37. The yellow solution was stirred at room temperature for 15 min. After dilution in EtOAc (8 mL), the organic layer was washed with a saturated NaHCO$_3$ aqueous solution (2×4 mL). The basic aqueous layers were extracted with EtOAc (2×4 mL). The combined organic layers were washed with brine (1×7 mL), dried over MgSO$_4$ and filtered. The filtrate was concentrated under reduced pressure to get 48 mg of crude as a pale yellow solid. The crude was purified by flash column chromatography (CH$_2$Cl$_2$/Acetone: 99/1) to afford MCE-7 (28 mg, 81%) as a white solid. $^1$H NMR (CDCl$_3$) δ 7.40 (s, 1H), 6.27 (s, 1H), 2.77-2.84 (ddd, 1H, J 6.7, 12.7, 16.5 Hz), 2.53 (s, 1H), 2.51-2.57 (ddd, 1H, J=2.7, 6.0, 19.2 Hz), 2.38-2.42 (dt, 1H, J=3.1, 12.8 Hz), 2.23-2.29 (m, 1H), 2.10-2.14 (ddd, 1H, J=2.7, 6.7, 12.8 Hz), 1.84-1.92 (m, 1H), 1.66 (s, 3H), 1.53-1.59 (m, 1H), 1.44-1.47 (dd, 1H, J=2.5, 7.5 Hz), 1.18 (s, 3H), 1.14 (s, 3H); $^{13}$C NMR (CDCl$_3$) δ 214.1, 179.8, 166.7, 160.2, 122.5, 114.6, 113.4, 80.4, 75.6, 53.8, 48.1, 41.9, 39.5, 39.4, 36.2, 34.2, 26.2, 22.2, 20.7, 20.0.

Overall yield of MCE-7 (from 33): 16%.

Example 7

Synthesis and Characterization of MCE-12

MCE-12 was synthesized as described below and summarized in Scheme 7.

Scheme 7

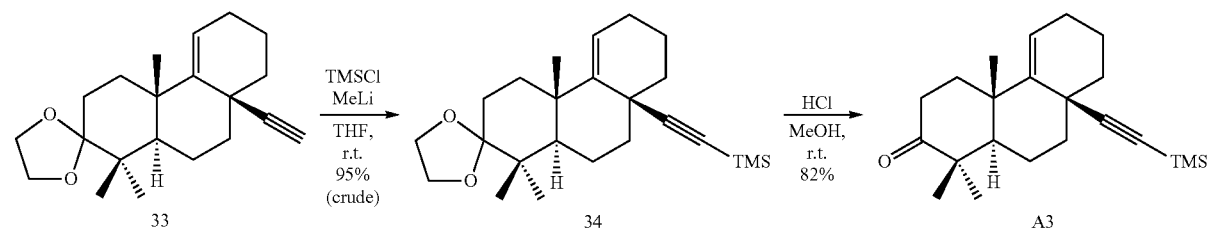

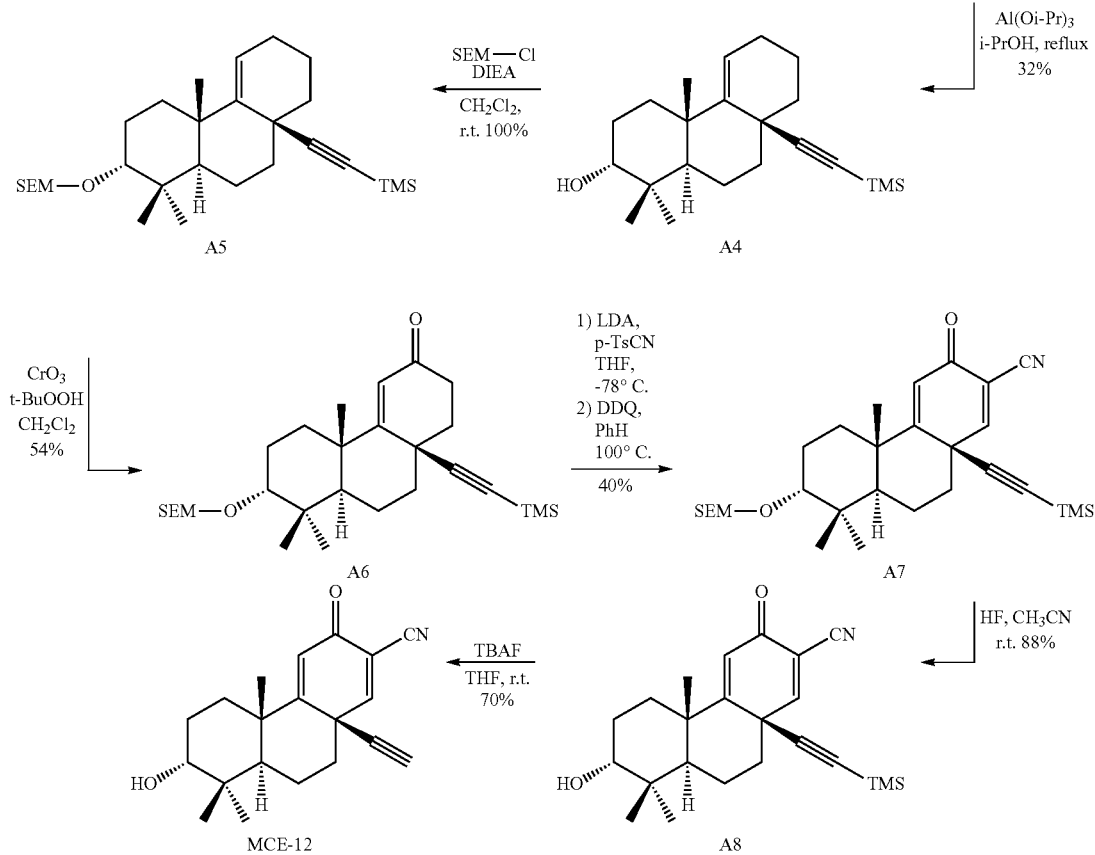

Protocol for the Synthesis of 34:

To a stirred solution of 33 (2 mmol, 629 mg) in dry THF (18 mL) was added dropwise at 0° C. under N₂ MeLi (1.6M in hexanes, 3 eq, 6 mmol, 3.75 mL). The yellow solution was stirred at room temperature for 30 min. Then TMSCl (98%, 3 eq, 6 mmol, 780 μL) was added dropwise and the mixture was stirred at room temperature for 1 hour. After addition of 20 mL of H₂O, the two layers were separated and the aqueous layer was extracted with Et₂O/CH₂Cl₂: 2/1 (3×25 mL). The combined organic layers were washed with a saturated NaHCO₃ aqueous solution (1×25 mL) and with brine (1×25 mL), dried over MgSO₄ and filtered. The filtrate was concentrated under reduced pressure to afford 34 (738 mg, 95% crude) of crude as a yellow solid. The crude was used for the next deketalization step without further purification.

Protocol for the Synthesis of A3:

A suspension of 34 (1.91 mmol, 738 mg) in methanol (40 mL) was heated at 60° C. to get a total dissolution. Then, a 10% HCl aqueous solution (8 mL) was added to the hot solution and the mixture was stirred at room temperature for 30 min. After neutralization at neutral pH with Et₃N to get neutral pH, the mixture was concentrated in vacuo. The white residue was dissolved in H₂O (20 mL) and extracted with EtOAc (3×25 mL). The combined organic layers were washed with a saturated NaHCO₃ aqueous solution (1×25 mL) and with brine (1×25 mL), dried over MgSO₄ and filtered. The filtrate was concentrated under reduced pressure to give 683 mg of crude as a pale yellow solid. The crude was purified by flash column chromatography (Hexanes/EtOAc: 10/1) to afford A3 (537 mg, 82%) as a white solid. $^1$H NMR (CDCl₃) δ 5.47-5.49 (dd, 1H, J=3.0, 5.0 Hz), 2.68-2.75 (ddd, 1H, J=6.7, 12.7, 15.9 Hz), 2.39-2.44 (ddd, 1H, J=3.0, 5.7, 15.9 Hz), 1.84-2.14 (m, 7H), 1.72-1.78 (td, 1H, J=6.0, 12.7 Hz), 1.54-1.66 (m, 2H), 1.47 (s, 3H), 1.31-1.38 (m, 2H), 1.23-1.29 (td, 1H, J=3.5, 13.0 Hz), 1.11 (s, 3H), 1.08 (s, 3H), 0.14 (s, 9H); $^{13}$C NMR (CDCl₃) δ 217.3, 147.2, 120.1, 115.1, 85.3, 54.2, 47.9, 42.5, 40.7, 40.2, 37.4, 36.3, 34.9, 26.3, 26.1, 22.7, 22.0, 20.7, 19.2, 0.3.

Synthesis of A4.

To a solution of A3 (589 mg, 1.69 mmol) in i-propanol (20 mL) was added aluminum i-propoxide (2.89 g, 14.2 mmol). The mixture was heated under reflux overnight. To the reaction mixture was added 5% aqueous HCl solution (25 mL). The aqueous mixture was extracted with methylene chloride (25 mL ×4). The extract was washed with saturated aqueous sodium bicarbonate (35 mL ×1) and brine (35 mL ×1), dried over MgSO₄, and filtered. The filtrate was evaporated in vacuo to give a crystalline solid (570 mg). The solid was purified by flash chromatography [hexanes-ethyl acetate (10: 1, 7:1, and 5:1)] to give A4 as a crystalline solid (190 mg, 32%): $^1$H NMR (CDCl₃) δ 5.48 (1H, t, J=3.6 Hz), 3.43 (1H, d, J=3.3 Hz), 1.32, 0.97, 0.92 (each 3H, s), 0.13 (9H, s).

Synthesis of A5.

To a solution of A4 (308 mg, 0.89 mmol) in dry methylene chloride (12 mL) was added 2-(trimethylsilyl)ethoxymethyl chloride (SEMCl, 480 μL, 2.7 mmol). Subsequently, N,N-diisopropylethylamine (DIEA, 740 μL, 4.48 mmol) was slowly added. The mixture was stirred at room temperature overnight. The reaction mixture was diluted with methylene chloride (35 mL) and water (10 mL). The organic layer was separated and washed with brine (10 mL ×1), dried over MgSO₄, and filtered. The filtrate was evaporated in vacuo to give a crystalline solid (733 mg). The solid was purified by flash chromatography [hexanes-ethyl acetate (10:1)] to give A5 as an oil (424 mg, 100%): $^1$H NMR (CDCl$_3$) δ 5.45 (1H, dd, J=2.5 and 4.5 Hz), 4.74 (1H, d, J=7.3 Hz), 4.64 (1H, d, J=7.3 Hz), 3.65 (2H, m), 3.27 (1H, s), 1.31, 0.94, 0.92 (each 3H, s), 0.13, 0.02 (each 9H, s); $^{13}$C NMR (CDCl$_3$) δ 148.6, 118.4, 94.0, 91.8, 84.5, 82.1, 65.2, 48.6, 43.1, 41.0, 40.6, 38.3, 36.4, 32.0, 28.9, 26.3, 23.3, 22.7, 22.6, 19.4, 19.2, 18.3, 0.4, −1.2

Synthesis of A6.

To a solution of A5 (424 mg, 0.89 mmol) in methylene chloride (9 mL) was added t-butyl hydroperoxide (70% in water, 1.28 mL, 8.93 mmol), followed by chromium trioxide (115 mg, 1.15 mmol) in an ice bath. The mixture was stirred at room temperature for 3 h. The reaction mixture was diluted with methylene chloride/ether (1:2, 30 mL) and water (5 mL). The mixture was washed with 5% aqueous NaOH solution (15 mL ×1), 5% aqueous HCl solution (15 mL ×1), saturated aqueous sodium bicarbonate solution (15 mL ×1), and brine (15 mL ×1), dried over MgSO$_4$, and filtered. The filtrate was evaporated in vacuo to give a brown residue (529 mg). The residue was purified by flash chromatography [hexanes-ethyl acetate (7:1)] to give A6 as an amorphous solid (236 mg, 54%): $^1$H NMR (CDCl$_3$) δ 5.87 (1H, s), 4.72 (1H, d, J=7.3 Hz), 4.63 (1H, d, J=7.3 Hz), 3.65 (2H, m), 3.29 (1H, s), 2.81, 2.37, 2.18, 2.07 (each 1H, m), 1.37, 0.98, 0.96 (each 3H, s), 0.13, 0.02 (each 9H, s); $^{13}$C NMR (CDCl$_3$) δ 201.2, 173.2, 122.2, 109.3, 94.0, 87.0, 81.2, 65.4, 47.2, 42.5, 41.9, 39.4, 38.6, 37.0, 34.8, 31.2, 28.8, 23.2, 22.8, 22.3, 18.9, 18.3, 0.1, −1.2

Synthesis of A7.

To a solution of A6 (49 mg, 0.10 mmol) in dry THF (325 μL) was added LDA (2M solution in THF/n-heptane/ethylbenzene, 60 μL, 0.12 mmol) at −78° C. (in a dry ice/1-propanol bath). The reaction mixture was stirred at room temperature for 20 min. To the mixture was slowly added a cloudy solution of p-TsCN (95%, 31.3 mg, 0.17 mmol) in dry THF (490 μL) at −78° C. The mixture was stirred at −78° C. for 45 min, and then saturated aqueous ammonia solution (490 μL) was slowly added. The mixture was allowed to reach room temperature, and additional saturated aqueous ammonia solution (2 mL) was added. The mixture was extracted with ethyl acetate (6 mL ×3). The extract was washed with saturated aqueous sodium bicarbonate solution (8 mL ×1) and brine (8 mL ×1), dried over MgSO$_4$, and filtered. The filtrate was evaporated in vacuo to give a residue (51 mg).

The mixture of the residue and DDQ (28 mg, 0.122 mmol) in dry benzene (2.3 mL) was heated under reflux for 30 min. After removal of insoluble matter, the filtrate was evaporated in vacuo to give a residual oil (76 mg). The residue was purified by flash chromatography [methylene chloride-acetone (130:1)] to give A7 as a crystalline solid (20 mg, 40%): $^1$H NMR (CDCl$_3$) δ 7.33 (1H, s), 6.25 (1H, s), 4.71 (1H, d, J=7.3 Hz), 4.61 (1H, d, J=7.3 Hz), 3.62 (2H, m), 3.30 (1H, brs), 1.46, 0.99, 0.97 (each 3H, s), 0.16, 0.02 (each 9H, s).

Synthesis of A8.

A suspension of A7 (38 mg, 0.074 mmol) in 48% aqueous HF solution/CH$_3$CN (1:10, 2.7 mL) was stirred at room temperature for 24 h. The reaction mixture was diluted with methylene chloride/ether (1:2, 10 mL), washed with water (5 mL ×3), saturated aqueous sodium bicarbonate solution (5 mL ×1), and brine (5 mL ×1), dried over MgSO$_4$, and filtered. The filtrate was evaporated in vacuo to give A8 as a crystalline solid (25 mg, 88%): $^1$H NMR (CDCl$_3$) δ 7.33 (1H, s), 6.26 (1H, s), 3.48 (1H, brs), 2.30 (1H, m), 2.01 (4H, m), 1.45, 0.99, 0.98 (each 3H, s), 0.16 (9H, s); $^{13}$C NMR (CDCl$_3$) δ 180.5, 169.3, 160.9, 121.4, 114.0, 109.9, 101.4, 92.3, 75.4, 47.5, 42.6, 40.9, 40.3, 38.8, 30.7, 28.7, 25.6, 22.4, 21.4, 18.8, −0.2. This material was used for the next step without further purification.

Synthesis of MCE-12.

A mixture of A8 (25 mg, 0.065 mmol) and tetra-(n-butyl)ammonium fluoride (TBAF, 52 mg, 0.20 mmol) in THF (500 μM) was stirred at room temperature for 30 min. The mixture was diluted with ethyl acetate (8 mL), and washed with saturated aqueous sodium bicarbonate solution (4 mL ×2). The aqueous basic washings were extracted with ethyl acetate (4 mL ×2). The extract and the original organic solution were combined. The combined organic solution was washed with brine (8 mL ×1), dried over MgSO$_4$, and filtered. The filtrate was evaporated in vacuo to give an amorphous solid (19 mg). The solid was purified by flash chromatography [hexanes-ethyl acetate (1:1)] to give MCE-12 as a crystalline solid (14 mg, 70%): $^1$H NMR (CDCl$_3$) δ 7.36 (1H, s), 6.29 (1H, s), 3.49 (1H, t, J=2.5 Hz), 2.46 (1H, s), 2.35 (1H, m), 2.08 (2H, m), 1.96 (1H, m), 1.78 (2H, m), 1.48, 1.00, 0.98 (each 3H, s); $^{13}$C NMR (CDCl$_3$) δ 180.2, 168.8, 160.7, 121.5, 114.3, 113.7, 80.9, 75.4, 75.1, 47.5, 42.6, 40.2, 39.7, 38.7, 30.7, 28.6, 25.6, 22.3, 21.4, 18.8.

Example 8

Synthesis and Characterization of MCE-8, MCE-9, MCE-10 and MCE-11

MCE-8-11 were synthesized as described below and summarized in Scheme 8.

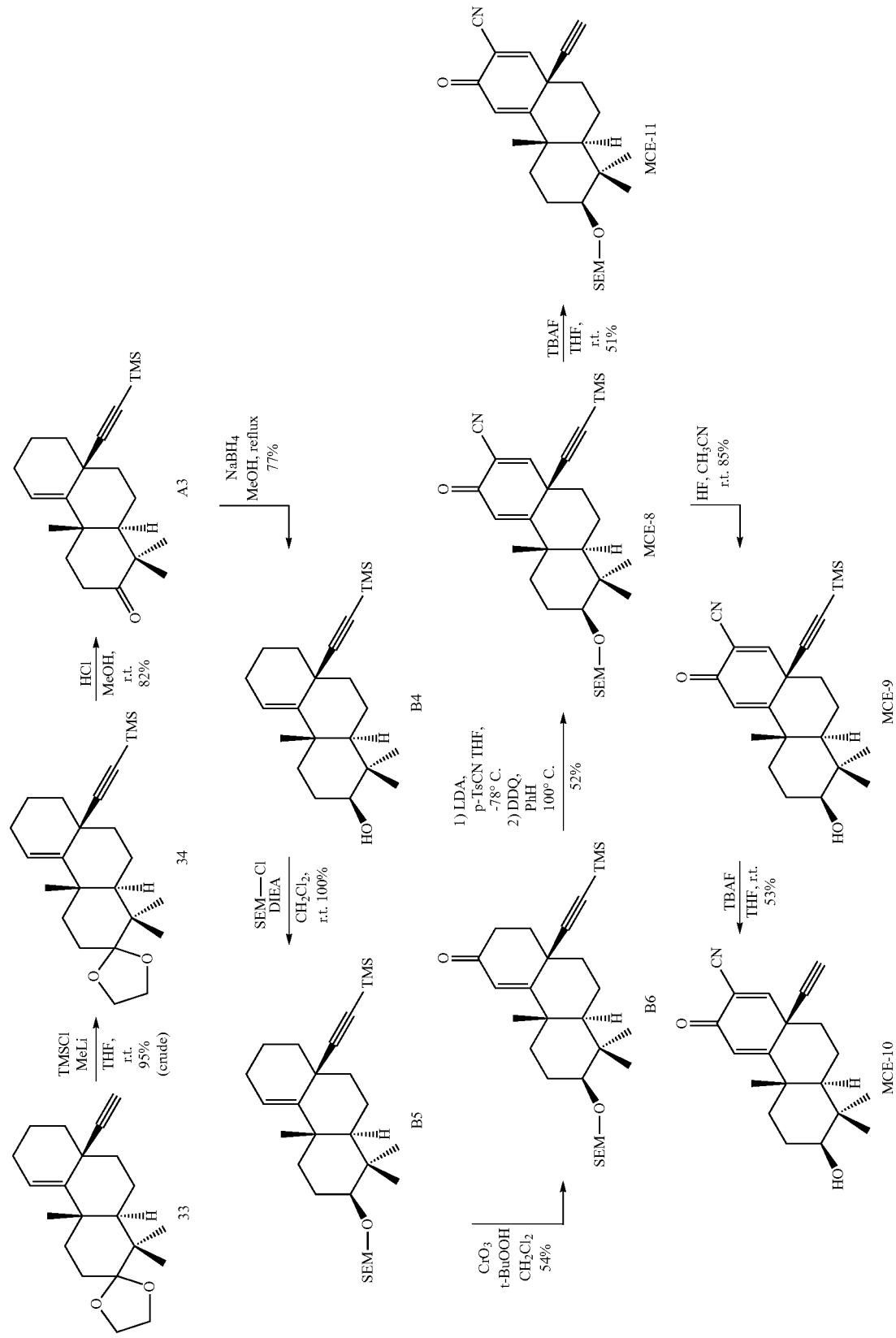

Protocol for the Synthesis of B4:

To a stirred solution of A3 (1.57 mmol, 537 mg) in dry MeOH (25 mL) was added NaBH$_4$ (98%, 2 eq, 3.14 mmol, 121 mg). The mixture was refluxed for 15 min under N$_2$. After cooling to room temperature, the mixture was concentrated in vacuo to get a white residue. The residue was diluted in CH$_2$Cl$_2$ (35 mL) and wash with H$_2$O (2×15 mL). The combined organic layers were extracted with CH$_2$Cl$_2$ (2×10 mL). The combined organic layers were washed with brine (1×15 mL), dried over MgSO$_4$ and filtered. The filtrate was concentrated under reduced pressure to give 560 mg of crude as a pale brown solid. The crude was purified by flash column chromatography (Hexanes/EtOAc:5/1) to afford B4 (420 mg, 77%) as a white amorphous solid. $^1$H NMR (CDCl$_3$) δ 5.43-5.44 (dd, 1H, J=2.5, 5.0 Hz), 3.17-3.24 (m, 1H), 1.30 (s, 3H), 0.99 (s, 3H), 0.85 (s, 3H), 0.13 (s, 9H); $^{13}$C NMR (CDCl$_3$) δ 148.6, 118.7, 115.5, 84.8, 79.0, 53.7, 43.2, 40.9, 40.6, 39.4, 36.9, 36.3, 28.5, 27.9, 26.3, 23.4, 19.6, 19.2, 15.8, 0.3.

Protocol for the Synthesis of B5:

To a stirred solution of B4 (0.725 mmol, 250 mg) in dry CH$_2$Cl$_2$ (10 mL) were successively added SEM-Cl (90%, 3 eq, 2.175 mmol, 430 μL) and DIEA (5 eq, 3.625 mmol, 600 μL). The mixture was stirred under nitrogen at room temperature overnight. It turned into slightly yellow. After diluting with CH$_2$Cl$_2$ (30 mL), the organic phase was washed with H$_2$O (2×15 mL) and with brine (1×15 mL), dried over MgSO4 and filtered. The filtrate was concentrated under reduced pressure to give 538 mg of crude as a yellow oil/solid mix. The crude was purified by flash column chromatography (Hexanes/EtOAc:10/1) to afford B5 (384 mg) as a colorless oil. A SEM-Cl residue reminded after purification. We considered the reaction was quantitative (344 mg, 100%) for the next step. $^1$H NMR (CDCl$_3$) δ 5.41-5.43 (1H, dd, J=3.0, 4.5 Hz), 4.80 (d, 1H, J=7.0 Hz), 4.67 (D, 1H, J=7.0 Hz), 3.60-3.68 (M, 2H), 3.07-3.12 (dd, 1H, J=4.2, 11.7 Hz), 1.30 (s, 3H), 0.95 (s, 3H), 0.87 (s, 3H), 0.13 (s, 9H), 0.02 (s, 9H); $^{13}$C NMR (CDCl$_3$) δ 148.7, 118.6, 115.6, 94.2, 84.7, 84.6, 65.2, 54.1, 43.3, 40.9, 40.5, 39.2, 36.8, 36.3, 28.5, 26.3, 24.5, 23.4, 19.6, 19.3, 18.3, 16.7, 0.3, -1.2.

Protocol for the Synthesis of B6:

To a stirred solution of B5 (0.725 mmol, 344 mg) in CH$_2$Cl$_2$ at 0° C. were successively added t-BuOOH (70% in water, 5 eq, 3.625 mmol, 500 μL) and CrO$_3$ (0.7 eq, 0.508 mmol, 51 mg). The ice bath was removed and the red purple mixture stirred at room temperature for 1 hour. Then, t-BuOOH (70% in water, 5 eq, 3.625 mmol, 500 μL) and CrO$_3$ (0.7 eq, 0.508 mmol, 51 mg) were successively added at 0° C. and the mixture was stirred for an additional hour. After diluting with Et$_2$O/CH$_2$Cl$_2$: 2/1 (50 mL), the organic layer was successively washed with 10% NaOH aqueous solution (1×20 mL), with a 5% HCl aqueous solution (1×20 mL), with a saturated NaHCO$_3$ aqueous solution (1×20 mL) and with brine (lx 20 mL), dried over MgSO$_4$ and filtered. The filtrate was concentrated under reduced pressure to give 410 mg of crude as a red purple oil. The crude was purified by flash column chromatography (Hexanes/EtOAc:7/1) to afford B6 (191 mg, 54%) as a white solid. $^1$H NMR (CDCl$_3$) δ 5.84 (s, 1H), 4.79 (d, 1H, J=7 Hz), 4.66 (d, 1H, J=7 Hz), 3.65 (t, 2H, J=8.5 Hz), 3.08-3.12 (dd, 1H, J=4.0, 12.0 Hz), 2.78-2.85 (ddd, 1H, J=4.7, 15.0, 17.1 Hz), 2.36-2.40 (dt, 1H, J=3.0, 17.0 Hz), 2.19-2.23 (dt, 1H, J=3.0, 12.8 Hz), 2.07-2.11 (ddd, 1H, J=3.1, 4.6, 12.8 Hz), 1.81-1.97 (m, 4H), 1.63-1.74 (m, 2H), 1.35-1.44 (m, 1H), 1.37 (s, 3H), 1.25-1.28 (m, 1H), 0.98-1.03 (m, 1H), 0.99 (s, 3H), 0.86-0.96 (m, 2H), 0.91 (s, 3H), 0.13 (s, 9H), 0.02 (s, 9H); $^{13}$C NMR (CDCl$_3$) δ 201.1, 172.8, 122.4, 109.3, 94.3, 87.2, 83.9, 63.4, 52.9, 42.7, 41.8, 39.5, 39.3, 36.9, 36.0, 34.9, 28.4, 24.2, 23.2, 19.2, 18.3, 16.9, 0.1, -1.2.

Protocol for the Synthesis of MCE-8:

A stirred solution of B6 (0.333 mmol, 163 mg) in dry THF (1.4 mL) was cooled to -78° C. and LDA (2M in THF/heptane, 1.4 eq, 0.466 mmol, 230 μL) was added. The brown mixture was stirred at room temperature for 20 min and then cooled back to -78° C. A cloudy solution of p-TsCN (95%, 1.7 eq, 0.556 mmol, 108 mg) in dry THF (1.3 mL) was added and the mixture was stirred at -78° C. for 45 min. A saturated NH$_4$OH aqueous solution (1.6 mL) was then added and the mixture was let to reach room temperature. It was extracted with EtOAc (3×10 mL). The combined organic layers were washed with a saturated NaHCO$_3$ aqueous solution (1×8 mL) and with brine (1×8 mL), dried over MgSO$_4$ and filtered. The filtrate was concentrated under reduced pressure to give 198 mg of a crude product as an orange oil. This reaction was considered to be complete and the crude was directly dissolved under N$_2$ in dry benzene (10 mL). DDQ (98%, 1.0 eq, 0.460 mmol, 77 mg) was added and the brown suspension was refluxed at 100° C. for 30 min. After cooling to room temperature, the suspension was filtered and the filtrate was concentrated under reduced pressure to give 220 mg of crude as a brown oil. The crude was purified by flash column chromatography (CH$_2$Cl$_2$/Acetone: 140/1) to afford MCE-8 (89 mg, 52%) as a pale pink solid. $^1$H NMR (CDCl$_3$) δ 7.34 (s, 1H), 6.21 (s, 1H), 4.79 (d, 1H, J=7.0 Hz), 4.66 (d, 1H, J=7.0 Hz), 3.63-3.67 (m, 2H), 3.08-3.11 (dd, 1H, J=4.5, 11.5 Hz), 2.30-2.33 (dt, 1H, J=3.0, 12.5 Hz), 1.46 (s, 3H), 1.0 (s, 3H), 0.94 (s, 3H), 0.16 (s, 9H), 0.02 (s, 9H); $^{13}$C NMR (CDCl$_3$) δ 180.4, 169.1, 160.7, 121.4, 114.0, 113.9, 101.1, 94.3, 92.4, 83.6, 65.4, 54.0, 42.3, 40.7, 40.2, 39.8, 36.0, 28.4, 24.1, 21.6, 18.9, 18.3, 16.7, -0.3, -1.2.

Overall yield of MCE-8 (from 33): 32%

Protocol for the Synthesis of MCE-9:

A suspension of MCE-8 (0.09 mmol, 46 mg) in HF (48% aqueous)/CH$_3$CN: 1/10 (3.15 mL) was stirred at room temperature overnight. The mixture was diluted with Et$_2$O/CH$_2$Cl$_2$: 2/1 (15 mL) and washed with water (3×8 mL), with a saturated NaHCO$_3$ aqueous solution (3×8 mL), dried over MgSO$_4$ and filtered. The filtrate was concentrated under reduced pressure to afford 37 mg of crude product as a white solid. The crude product was purified by flash column chromatography (Hexanes/EtOAc: 1.5/1) to afford MCE-9 (29 mg, 85%) as a white solid. $^1$H NMR (CDCl$_3$) δ 7.35 (s, 1H), 6.21 (s, 1H), 3.21-3.23 (m, 1H), 2.30-2.34 (dt, 1H, J=3.2, 12.5 Hz), 2.04-2.12 (m, 1H), 1.72-0.1-90 (m, 4H), 1.65 (bs, 1H), 1.47-1.58 (m, 2H), 1.45 (s, 3H), 1.03 (s, 3H), 0.91-0.94 (m, 1H), 0.93 (s, 3H), 0.16 (s, 9H); $^{13}$C NMR (CDCl$_3$) δ 180.4, 167.0, 160.7, 121.4, 114.0, 113.9, 101.1, 92.5, 78.0, 53.6, 42.4, 40.7, 40.2, 39.9, 36.1, 28.4, 27.3, 21.6, 18.9, 15.8, -0.3.

Overall yield of MCE-9 (from 33): 27%.

Protocol for the Synthesis of MCE-10:

A solution of TBAF (98%, 3 eq, 0.150 mmol, 40 mg) in THF (380 μL) was added to MCE-9 (0.0497 mmol, 19 mg) and the yellow mixture was stirred at room temperature for 15 min. The mixture was then diluted with EtOAc (8 mL) and washed with a saturated NaHCO$_3$ aqueous solution (2×4 mL). The combined aqueous layers were combined and extracted with EtOAc (2×4 mL). The organic layers were combined, washed with brine (1×8 mL), dried over MgSO$_4$ and filtered. The filtrate was concentrated under reduced pressure to give 19 mg of crude product as yellow oil/solid residue. The crude product was purified by flash column chromatography (Hexanes/EtOAc: 1/1) followed by a preparative TLC (Hexanes/EtOAc:1/1) to afford MCE-10 (8 mg, 53%) as white crystals. $^1$H NMR (CDCl$_3$) δ 7.38 (s, 1H), 6.24 (s, 1H), 2.22-2.25 (dd, 1H, J=5.0, 11.0 Hz), 2.48 (s, 1H), 2.34-2.38 (dt, 1H, J=3.2, 12.7 Hz), 2.05-2.15 (m, 1H), 1.73-1.93 (m, 4H), 1.60 (bs, 1H), 1.45-1.58 (m, 2H), 1.48 (s, 3H), 1.03 (s, 3H), 0.93-0.96 (m, 1H), 0.93 (s, 3H); $^{13}$C NMR (CDCl$_3$) δ 180.1, 168.6, 160.6, 121.7, 114.4, 113.7, 80.7, 78.1, 75.3, 53.6, 42.5, 40.2, 40.0, 39.6, 36.1, 28.5, 27.4, 21.7, 19.0, 15.9.

Overall yield of MCE-10 (from 33): 14%.

Protocol for the Synthesis of MCE-11:

A mixture of MCE-8 (27 mg, 0.053 mmol) and TBAF (40 mg, 0.15 mmol, 2.9 equiv.) in THF (405 µL) was stirred at room temperature for 45 min. The reaction mixture was diluted with EtOAc (8 mL) and washed with saturated aqueous sodium bicarbonate solution (4 mL ×4). The washes were extracted with EtOAc (4 mL ×2). The extract and the original organic solution were combined, and then washed with brine (8 mL ×1), dried over MgSO$_4$, and filtered. The filtrate was evaporated in vacuo to give a yellow oil (24 mg). The oil was purified by flash chromatography [hexanes-ethyl acetate (4:1)] to give MCE-11 as an amorphous solid (12 mg, 51%): $^1$H NMR (CDCl$_3$) δ 7.37 (s, 1H), 6.23 (s, 1H), 4.80 (d, 1H, J=7.3 Hz), 4.56 (d, 1H, J=7.3 Hz), 3.65 (dd, 2H, J=7.0, 9.7 Hz), 0.10 (dd, 1H, J=4.5, 11.5 Hz), 2.47 (s, 1H), 2.35 (dt, 1H, J=3.2, 12.7 Hz), 2.10 (m, 1H), 1.68-1.99 (m, 4H), 1.61 (bs, 1H), 1.48 (s, 3H), 1.03 (s, 3H), 0.93 (s, 3H), 0.02 (s, 9H); $^{13}$C NMR (CDCl$_3$) δ 180.1, 168.7, 160.6, 121.6, 114.4, 113.7, 94.3, 83.6, 80.7, 75.2, 65.4, 53.9, 42.3, 40.1, 40.0, 39.8, 39.6, 36.0, 28.4, 24.1, 21.7, 18.9, 18.3, 16.7, −1.2.

Example 9

Proposed Synthesis of Compounds 38 and 39

Compound 38 may be synthesized as described below and summarized in Scheme 9.

Scheme 9

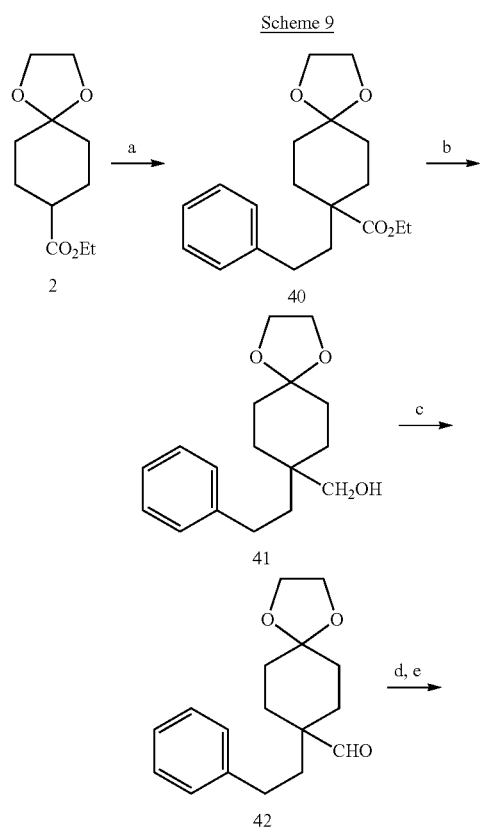

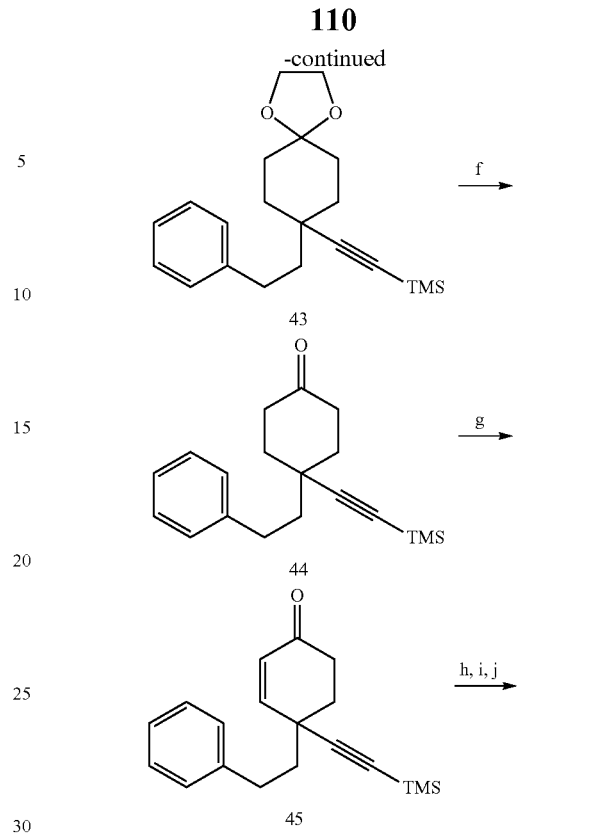

(a) LDA, PhCH$_2$CH$_2$Br; (b) LiAlH$_4$, Et$_2$O (c) CrO$_3$, pyr. CH$_2$Cl$_2$; (d) Ph$_3$PCH$_2$Cl(Cl), n-BuLi, THF; (e) MeLi, THF; TMSCl; (f) aq. HCl, acetone; (g) LDA, PhSeCl; 30% H$_2$O$_2$, CH$_2$Cl$_2$; (h) p-TsCN, LDA, THF; (i) DDQ, PhH; (j) aq. HCl, MeOH.

For example, compound 38 may be synthesized from the known compound 2 (Phansavath et al., 1998) by the sequence shown in Scheme 9. Nucleophilic addition of enolate of 2 to homobenzyl bromide would give 40. Reduction of 40 with LiAlH$_4$, followed by oxidation with CrO$_3$ would give 42. Wittig reaction of 42 with (chloromethyl)triphenylphosphonium chloride (Mella et al., 1988, which is incorporated herein by reference), followed by dehydrochlorination with MeLi and subsequent treatment with chlorotrimethylsilane (TMSCl) (Corey et al., 1973, which is incorporated herein by reference) would afford 43. The ketal of 43 would be removed under acidic conditions to yield 44. Enone 45 would be prepared by addition of phenylselenyl group to lithium enolate of 44 and subsequent oxidation/elimination with 30% aqueous hydrogen peroxide. A target compound 38 would be obtained by cyanation of 45 with p-toluenesulfonyl cyanide (p-TsCN), followed by DDQ oxidation and subsequent removal of TMS group under acidic conditions.

Similarly compound 39 (shown below) may be synthesized using 1-bromo-2,2-diphenylethane, which is prepared from commercially available 2,2-diphenylethanol (Ohno et al., 2005, which is incorporated) in place of homobenzyl bromide in Scheme 9 above.

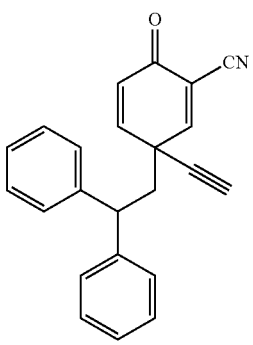

Example 10

Proposed Synthesis of Compound 46

Compound 46 may be synthesized as described below and summarized in Scheme 10.

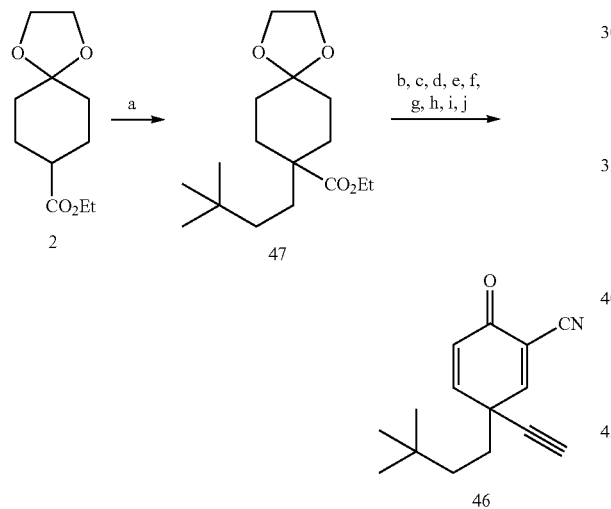

(a) LDA, (CH₃)₃CCH₂CH₂Br; (b) LiAlH₄, Et₂O (c) CrO₃, pyr. CH₂Cl₂;
(d) Ph₃PCH₂Cl(Cl), n-BuLi, THF; (e) MeLi, THF; TMSCl; (f) aq. HCl, acetone;
(g) LDA, PhSeCl; 30% H₂O₂, CH₂Cl₂; (h) p-TsCN, LDA, THF; (i) DDQ, PhH;
(j) aq. HCl, MeOH.

Compound 46 having t-butyl group has been designed as a compound with a typical hydrophobic group. Compound 46 would be synthesized from 2 using 1-bromo-3,3-dimethylbutane (Hsiao et al, 1988, which is incorporated herein by reference) in place of homobenzyl bromide in Scheme 9 above.

Example 11

Proposed Synthesis of Compound 48

Compound 48 may be synthesized as described below and summarized in Scheme 11.

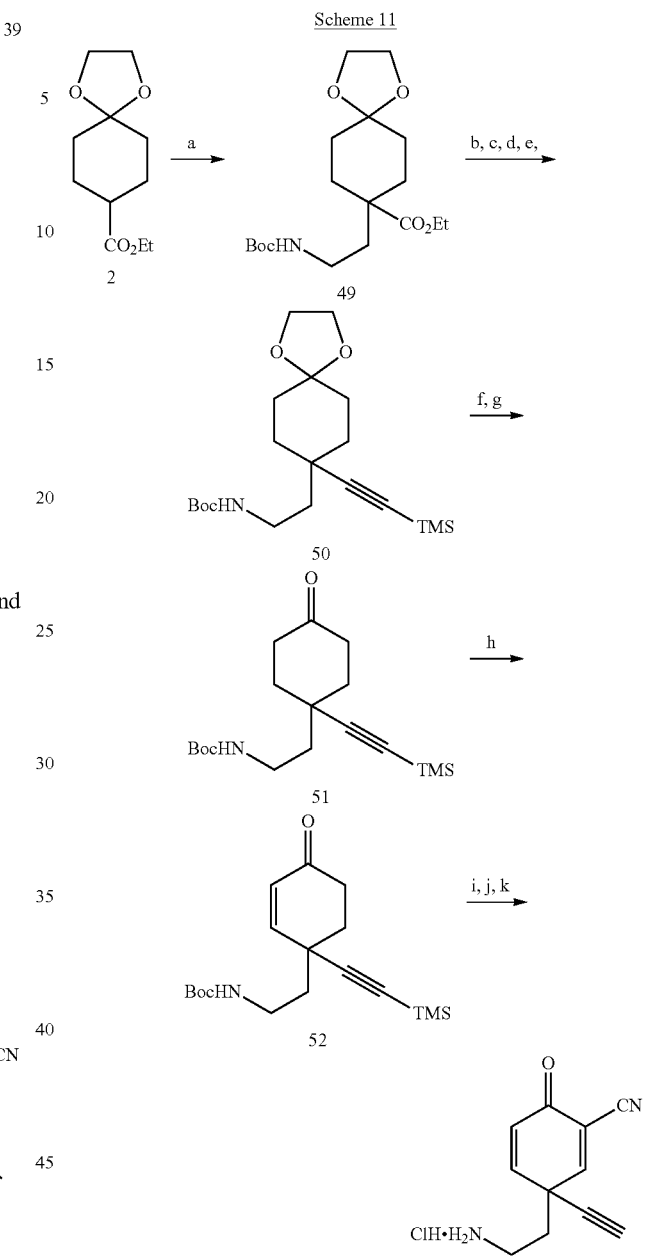

(a) LDA, Br(CH₂)₂NHBoc; (b) LiAlH₄, Et₂O (c) CrO₃, pyr. CH₂Cl₂;
(d) Ph₃PCH₂Cl(Cl), n-BuLi, THF; (e) MeLi, THF; TMSCl; (f) aq. HCl, acetone;
(g) Boc₂O; (h) LDA, PhSeCl; 30% H₂O₂, CH₂Cl₂; (i) p-TsCN, LDA, THF; (j) DDQ, PhH; (k) aq. HCl, MeOH.

Compound 48, having a dimethylene amino group, would be synthesized from 2 by the sequence shown in Scheme 11. Compound 49 would be prepared by nucleophilic addition of the enolate of 2 to commercially available Br(CH₂)₂NHBoc. Compound 50 would be obtained from 49 by the same sequence as for 43 from 40 (see Scheme 9). The ketal of 50 would be removed under acidic conditions, and subsequent reprotection with Boc₂O would give 51. Enone 52 would be prepared by addition of phenylselenyl group to lithium enolate of 51 and subsequent oxidation/elimination with 30% aqueous hydrogen peroxide. Compound 48 (hydrochloride salt) would be obtained by cyanation of 52 with p-TsCN, followed by DDQ oxidation and subsequent treatment with HCl in methanol.

Example 12

Proposed Synthesis of Compound 53

Compound 53 may be synthesized as described below and summarized in Scheme 12.

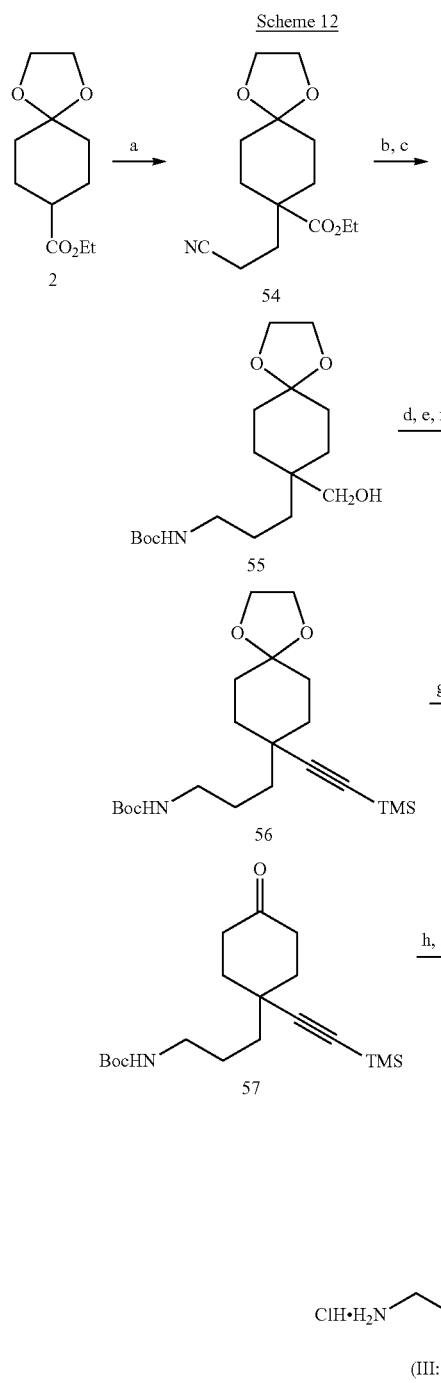

(a) LDA, (or KH, 18-crown-6), Br(CH$_2$)$_2$CN; (b) LiAlH$_4$, Et$_2$O (c) Boc$_2$O (d) CrO$_3$, pyr. CH$_2$Cl$_2$; (e) Ph$_3$PCH$_2$Cl(Cl), n-BuLi, THF; (f) MeLi, THF; TMSCl; (g) aq. HCl, acetone; (h) LDA, PhSeCl; 30% H$_2$O$_2$, CH$_2$Cl$_2$; (i) p-TsCN, LDA, THF; (j) DDQ, PhH; (k) aq. HCl, MeOH.

Compound 53, having a trimethylene amino group, would be synthesized from 2 as shown in Scheme 12 above. Nucleophilic addition of the enolate of 2 to commercially available 3-bromopropionitrile (Shuman et al., 1995, which is incorporated herein by reference) would give 54. Reduction of 54, followed by protection with Boc$_2$O, would produce 55. The ketone 57 would be obtained via 56 from 55 by the same sequence as for 51. A target amine hydrochloride 53 would be prepared from 57 by the same sequence as for 48 from 51.

Example 13

Proposed Synthesis of Compounds 58 and 59

Compounds 58 and 59 may be synthesized as described below and summarized in Scheme 13.

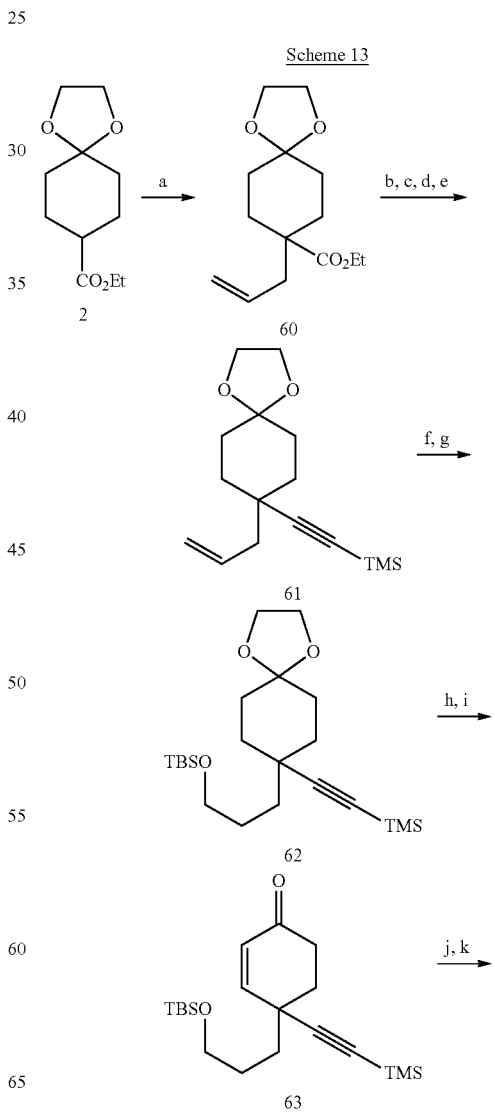

-continued

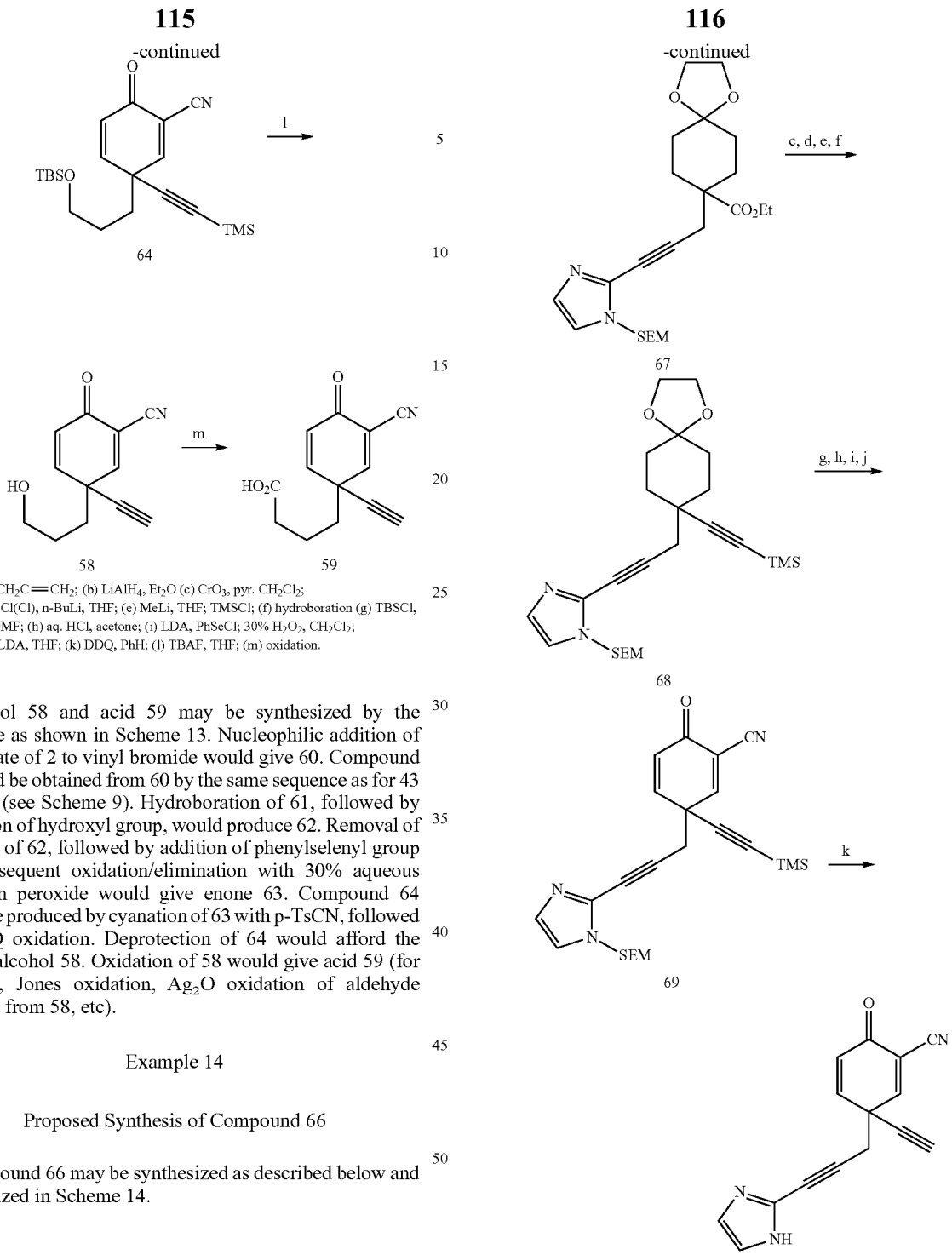

(a) LDA, BrCH₂C═CH₂; (b) LiAlH₄, Et₂O (c) CrO₃, pyr. CH₂Cl₂;
(d) Ph₃PCH₂Cl(Cl), n-BuLi, THF; (e) MeLi, THF; TMSCl; (f) hydroboration (g) TBSCl, imidazole, DMF; (h) aq. HCl, acetone; (i) LDA, PhSeCl; 30% H₂O₂, CH₂Cl₂;
(j) p-TsCN, LDA, THF; (k) DDQ, PhH; (l) TBAF, THF; (m) oxidation.

Alcohol 58 and acid 59 may be synthesized by the sequence as shown in Scheme 13. Nucleophilic addition of the enolate of 2 to vinyl bromide would give 60. Compound 61 would be obtained from 60 by the same sequence as for 43 from 40 (see Scheme 9). Hydroboration of 61, followed by protection of hydroxyl group, would produce 62. Removal of the ketal of 62, followed by addition of phenylselenyl group and subsequent oxidation/elimination with 30% aqueous hydrogen peroxide would give enone 63. Compound 64 would be produced by cyanation of 63 with p-TsCN, followed by DDQ oxidation. Deprotection of 64 would afford the desired alcohol 58. Oxidation of 58 would give acid 59 (for example, Jones oxidation, Ag₂O oxidation of aldehyde obtained from 58, etc).

Example 14

Proposed Synthesis of Compound 66

Compound 66 may be synthesized as described below and summarized in Scheme 14.

Scheme 14

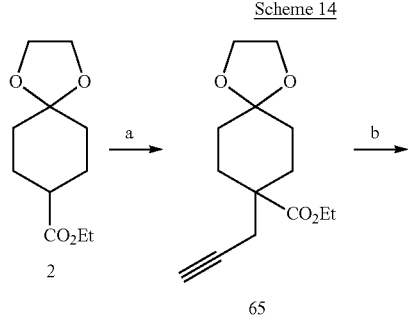

(a) LDA, HCCCH₂Br; (b) 2-Iodo-SEM-imidazole, CuI, Pd(PPh₃)₂Cl₂, Et₃N;
(c) LiAlH₄, Et₂O; (d) CrO₃, pyr. CH₂Cl₂; (e) Ph₃PCH₂Cl(Cl), n-BuLi, THF; (f) MeLi, THF; TMSCl; (g) aq. HCl, acetone; (h) LDA, PhSeCl; 30% H₂O₂, CH₂Cl₂; (i) p-TsCN, LDA, THF; (j) DDQ, PhH; (k) TFA, THF.

For example, compound 66 would be synthesized from 2 by the sequence shown in Scheme 14. Known compound 65 is prepared by nucleophilic addition of the enolate of 2 to propargyl bromide. Sonogashira coupling between 65 and 2-iodo-1-(trimethylsilylethoxymethoxy)imidazole (Paul et al. 2002, which is incorporated herein by reference) would give 67. Compound 68 would be obtained from 67 by the same sequence as for 43 from 40 (see Scheme 9). Usual methods (removal of a ketal, insertion of a double bond by addition of phenylselenyl group and oxidative elimination, cyanation, and DDQ oxidation) would give 69. Removal of the SEM and TMS groups of 69 under trifluoroacetic acid (TFA) in THF would give 66, whose hydrochloride salt is water-soluble.

Example 15

Proposed Synthesis of Compounds of Formula VI

Compounds of formula VI, (for example, R=-Ph. —CH$_2$Ph, and —N=CHCH$_2$Ph) may be synthesized as described below and summarized in Scheme 15.

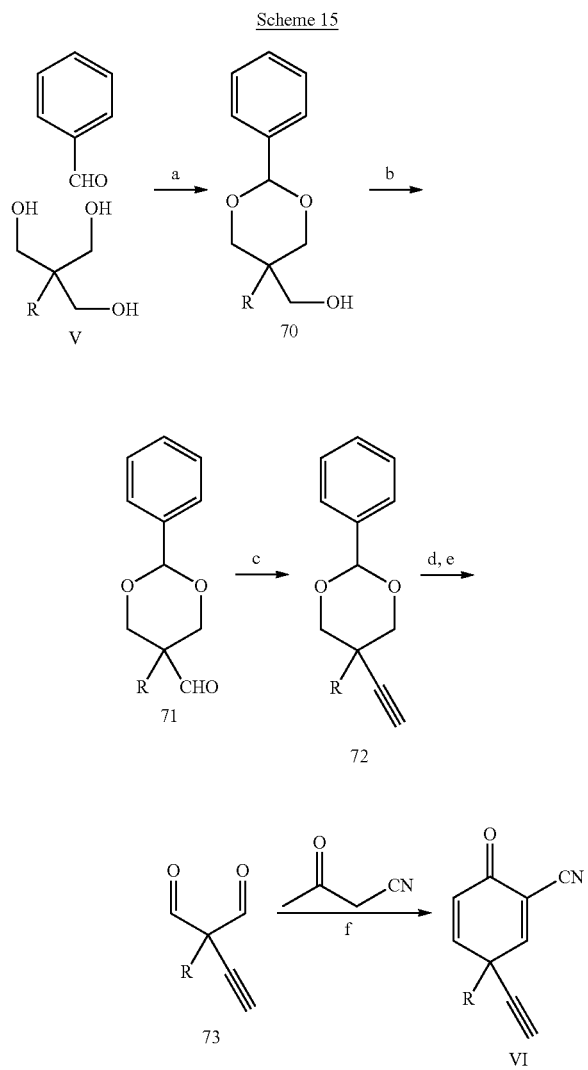

(a) PPTS, toluene; (b) Swern oxidation; (c) (MeO)$_2$POCN$_2$COCH$_3$; (d) H$^+$; (e) Dess-Martin oxidation; (f) basic conditions.

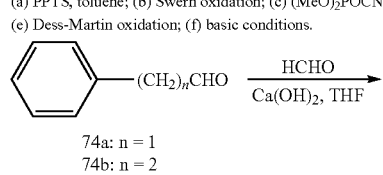

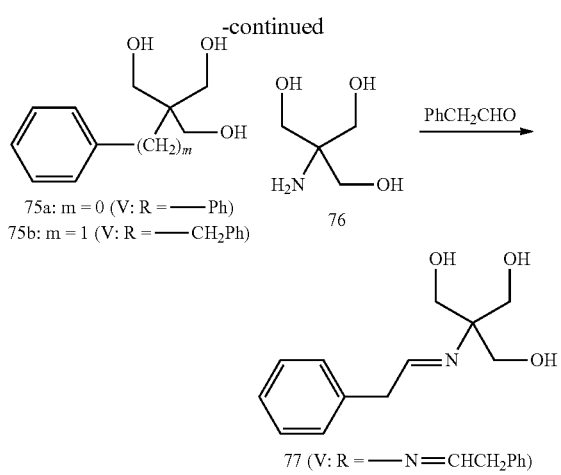

A facile synthetic sequence to compounds of formula VI is shown in Scheme 13. Starting material V would be protected by benzaldehyde (Clarke et al., 2004, which is incorporated herein by reference) to give 70. Swern oxidation of 70 would yield aldehyde 71. The treatment of 71 with the Bestmann-Ohira reagent (Pietruszka et al., 2006, which is incorporated herein by reference) would produce acetylene 72. Deprotection of 72, followed by Dess-Martin oxidation, would afford 73. Desired compound VI would be obtained by aldol condensation between cyanoacetone (Sauers et al., 2003, which is incorporated herein by reference) and 73. Applicants note that they are unaware of any previous reports of a six membered ring by this method. Starting materials V would be easily obtained or prepared. For example, known compounds 75a (V: R=phenyl) and 75b (V: R=benzyl) are prepared by condensation between formaldehyde and 2-phenylethanal (74a) and 3-phenylpropanal (74b) under basic conditions, respectively (Rockendorf et al., 2002). Also, compound 77 (V: R=—N=CHCH$_2$Ph) would be synthesized by condensation between 2-phenylethanal (74a) and commercially available 76.

Example 16

Proposed Syntheses of Further Monocyclic Cyanoenones

Further monocyclic cyanoenones and intermediates thereof may be synthesized as described below and summarized in Schemes 16-18.

In Scheme 16, compounds C16 and C17 may be synthesized from C3 as follows. Grignard reaction of methylmagnesium bromide with C3 would give ten-alcohol C32. C16 would be obtained from C32 via enone C33 by the same sequence as for MCE-15 from 19 (see Scheme 4). Dehydroxylation of C16 would afford C17.

Compound C18 would be synthesized from C35 via C36 by the same sequence as for MCE-15 from 19 (see Scheme 4). The precursor C35 would be obtained from 5 via C34 by Grignard reaction of phenylmagnesium bromide, followed by modified Barton's dehydroxylation method.

Compound C19 would be synthesized from C3 by the same sequence as for MCE-15 from 19 (see Scheme 4). Alkali hydrolysis of C19 would give C20. Compound C21 would be obtained by treatment of C20 with oxalyl chloride, followed by amidation with ammonia.

C22 would be synthesized from 5 as follows. Condensation of 5 with hydroxylamine would give oxime C38. Dehydration of oxime C38 would produce nitrile C39. Protected amine C40 would be prepared by reduction of C39 with NaBH$_4$—CoCl$_2$ and subsequent work-up with acidic conditions, followed by protection with Boc$_2$O. Enone C41 would be obtained by removal of the ketal of C40 and subsequent protection of amino group with Boc$_2$O, followed by addition of phenylselenyl group and subsequent oxidation/elimination with 30% aqueous hydrogen peroxide. Compound C22 would be produced by cyanation with p-TsCN and subsequent DDQ oxidation, followed by deprotection under hydrochloric acid-MeOH conditions.

Compound C23 would be synthesized from C39 via C42 by the same sequence as for MCE-15 from 19 (see Scheme 4).

Compound C24 would be obtained from C43 by the same sequence as for MCE-15 from 19 (see Scheme 4). The precursor C43 would be prepared by protection of the hydroxyl group of C4 with t-butylchlorodimethyl-silane (TBSCl). Removal of the TBS group of C24 with TBAF would give C25.

Compound C26 would be synthesized from C46 by the same sequence as for MCE-15 from 19 (see Scheme 4). The precursor C46 would be prepared by Grignard reaction of methylmagnesium bromide with aldehyde 5, followed by protection with TBSCl. Deprotection of C26 would give C27. Oxidation of C27 with chromium trioxide-pyridine would give C28.

Compounds C48-C53 would be synthesized from C2 according to the same sequence as shown in Scheme 17. For example, C48 would be synthesized in nine steps from C56, which would be obtained by alkylation of the lithium ester enolate C2 with iodoethane (reduction, oxidation, Wittig reaction, dehydrochlorination and trapping with TMSCl, deketalization, insertion of double bond with PhSeCl and subsequent oxidation/elimination, cyanation with p-TsCN, DDQ oxidation, and deprotection with TBAF).

Compounds C54 and C55 would be synthesized as follows. Cyanation of the lithium ester enolate C2 with PhOCN or p-TsCN would give C61. Compound C62 would be obtained from C61 in 4 steps (reduction, oxidation, Wittig reaction, and dehydrochlorination). Alkaline hydrolysis of C62, followed by treatment with iodomethane would afford methyl ester C63. Enone C64 would be produced by removal of the ketal of C63, followed by addition of phenylselenyl group and subsequent oxidation/elimination. Compound C54 would be prepared by cyanation of C64 with p-TsCN and subsequent DDQ oxidation, followed by deprotection. Alkaline hydrolysis of C54 would yield C55.

Compounds C65-C68 and C70 would be synthesized from 5 by the same sequence as shown in Scheme 18. For example, C65 would be synthesized as follows. Wittig reaction of 5 with (chloromethyl)-triphenylphosphonium chloride, followed by dehydrochlorination with MeLi and subsequent treatment with aqueous NH$_4$Cl solution would give C71. Methylation of the acetylide C71 with iodomethane would afford C72. C65 would be obtained in 4 steps from C72 (deketalization, insertion of double bond, cyanation with p-TsCN, DDQ oxidation). C69 would be synthesized from C68 by alkaline hydrolysis.

Scheme 16

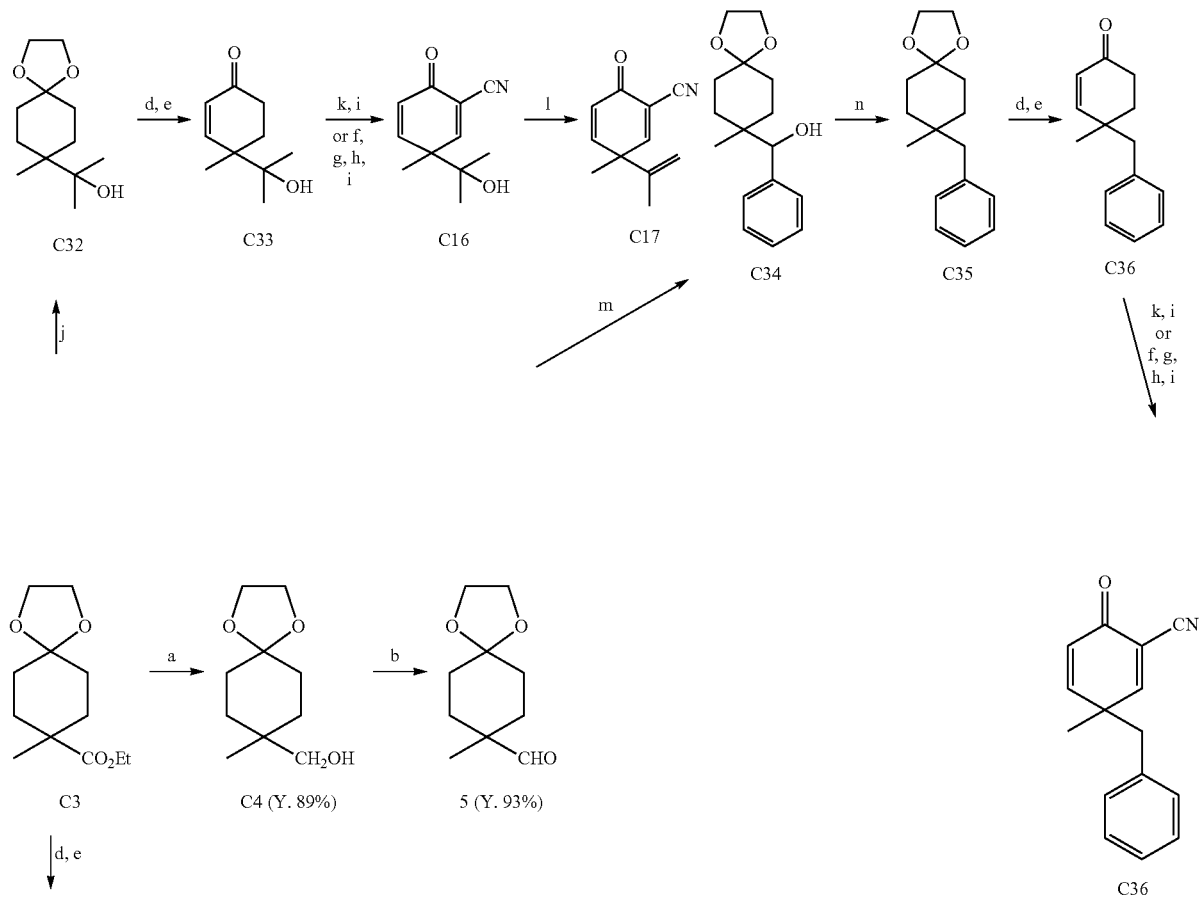

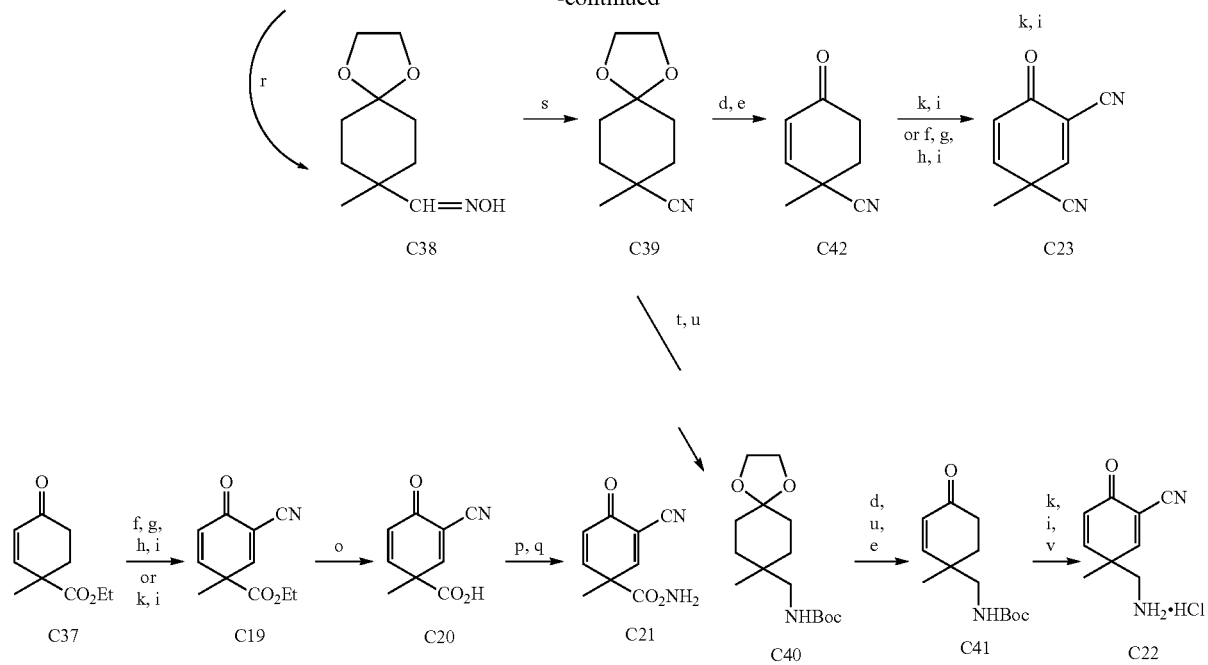

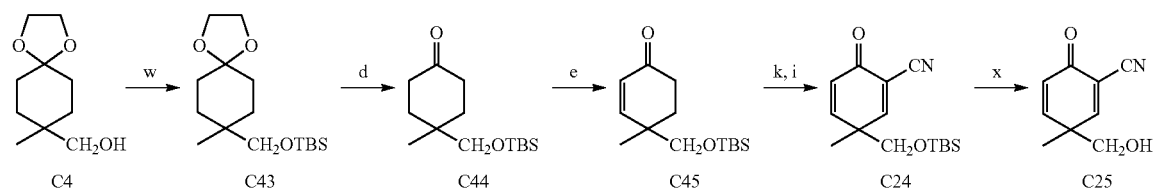

(a) LiAlH$_4$, Et$_2$O; (b) CrO$_3$, pyr. CH$_2$Cl$_2$; (c) Ph$_3$PMeI, t-BuOK, THF; (d) aq. HCl, acetone; (e) LDA, PhSeCl; 30% H$_2$O$_2$, CH$_2$Cl$_2$; (f) HCO$_2$Et, NaOMe, NaOMe, PhH; (g) NH$_2$Cl•HCl, aqueous EtOH; (h) NaOMe, MeOH, Et$_2$O; (i) DDQ, PhH; (j) MeMgBr, Et$_2$O; (k) p-TsCN, LDA, THF; (l) POCl$_3$, pyridine; (m) PhMgBr, Et$_2$O; (n) N,N-thiocarbonyldiimidazole, THF; (r Bu)$_3$SnH, toluene; (o) aq. NaOH, MeOH; (p) (COCl)$_2$, CH$_2$Cl$_2$; (q) NH$_3$, MeOH; (r) NH$_2$OH•HCl, NaOAc; (s) N,N-carbonyldiimidazole CH$_2$Cl$_2$; (t) NaBH$_4$, CoCl$_2$, MeOH; aq. HCl; (u) Boc$_2$O; (v) aq. HCl, MeOH; (w) TBSCl, imidazole, DMF; (x) TBAF, THF; (y) CrO$_3$, pyridine, CH$_2$Cl$_2$.

Scheme 17

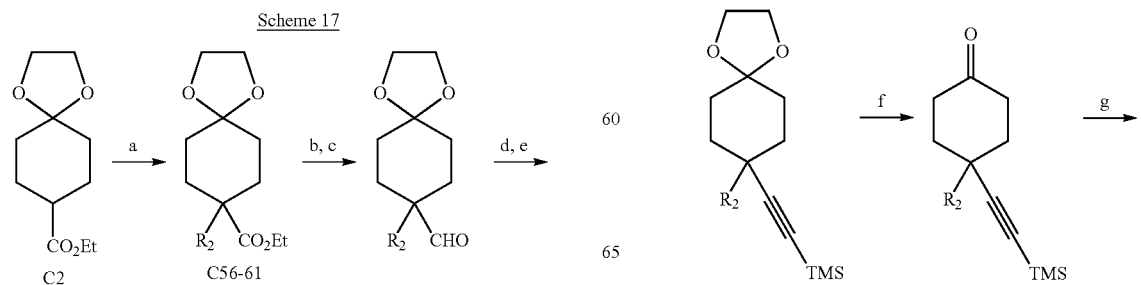

123

-continued

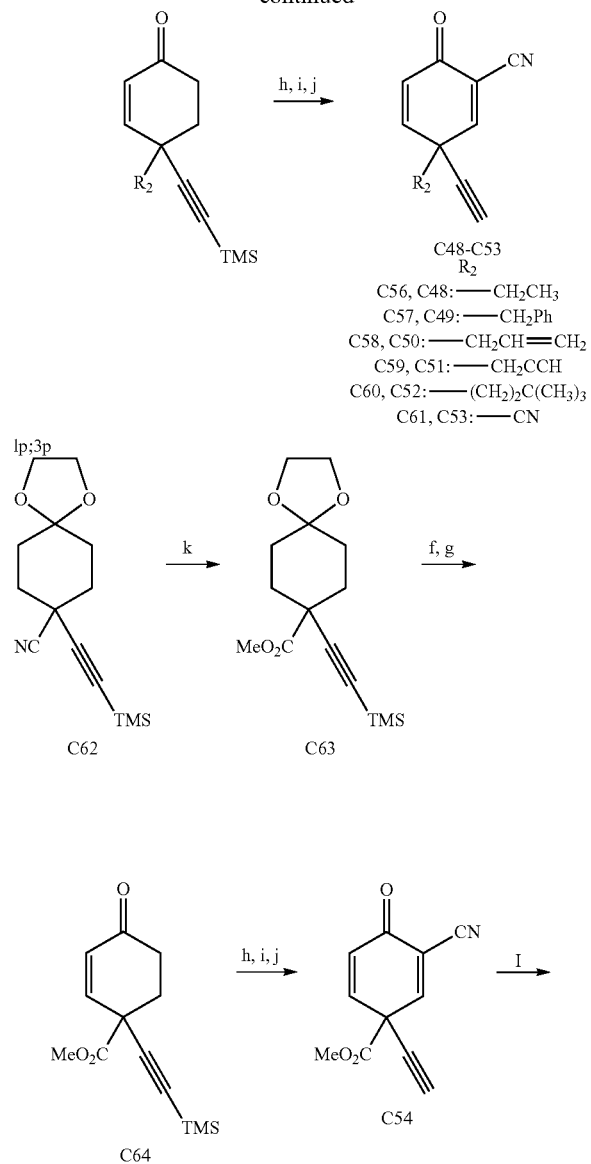

C48-C53
R₂
C56, C48: —CH₂CH₃
C57, C49: —CH₂Ph
C58, C50: —CH₂CH=CH₂
C59, C51: —CH₂CCH
C60, C52: —(CH₂)₂C(CH₃)₃
C61, C53: —CN (a) LDA, EtI for C56, PhCH₂Br for C57, allyl bromide for C58, propargyl bromide for C59, t-Bu(CH₂)₂Br for C60, PhOCN or p-TsCN for C61; (b) LiAlH₄, Et₂O; (c) CrO₃, pyr. CH₂Cl₂; (d) Ph₃PCH₂Cl(Cl), n-BuLi, THF; (e) MeLi, THF; TMSCl; (f) aq. HCl, acetone; (g) LDA, PhSeCl; 30% H₂O₂, CH₂Cl₂; (h) p-TsCN, LDA, THF; (i) DDQ, PhH; (j) TBAF, THF; (k) NaOH, MeOH; MeI; (l) aq. KOH, MeOH.

124

Scheme 18

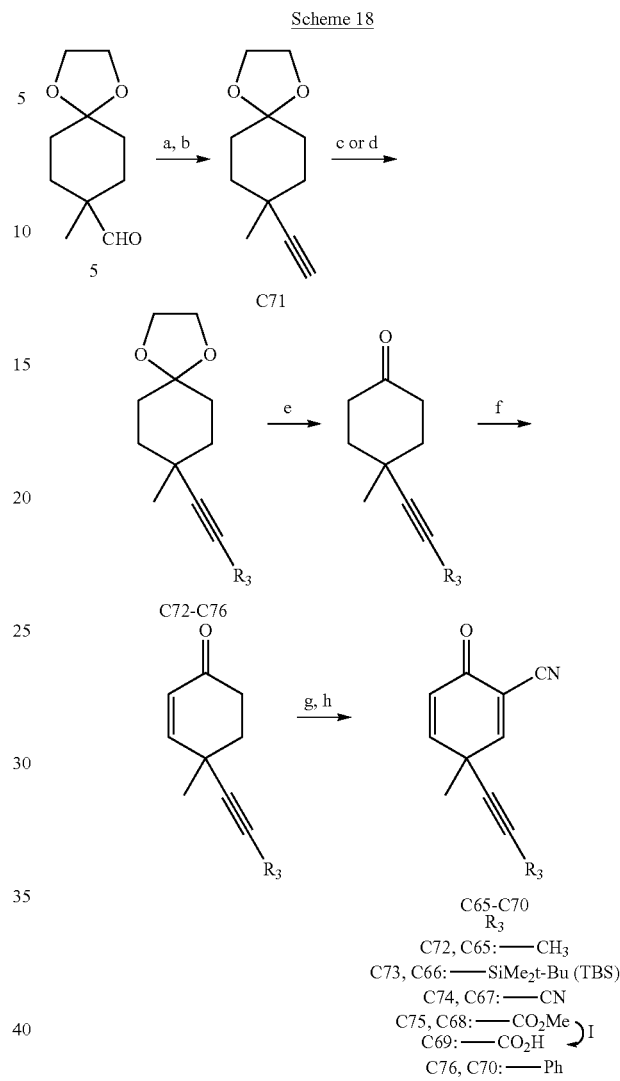

C72-C76

C65-C70
R₃
C72, C65: —CH₃
C73, C66: —SiMe₂t-Bu (TBS)
C74, C67: —CN
C75, C68: —CO₂Me
C69: —CO₂H  } l
C76, C70: —Ph (a) Ph₃PCH₂Cl(Cl), n-BuLi, THF; (b) MeLi, THF; aq. NH₄Cl (c) MeLi or n-BuLi, THF, MeI for C72, TBSCl for C73, PhOCN for C74, ClCO₂Me for C75; (d) PhI, Pd(PPh₃)₂Cl₂, CuI, Et₃N for C76; (e) aq. HCl, acetone; (f) LDA, PhSeCl; 30% H₂O₂, CH₂Cl₂; (g) p-TsCN, LDA, THF; (h) DDQ, PhH; (i) aq. KOH, MeOH Example 17

Proposed Synthesis of Compounds of Formula VII

Compounds of formula VII, (for example, R=—CH₂NH₂ and —CO₂H) may be synthesized as described below and summarized in Schemes 19 or 20.

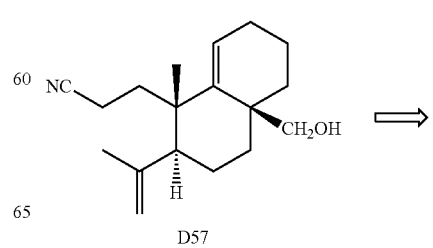

D57

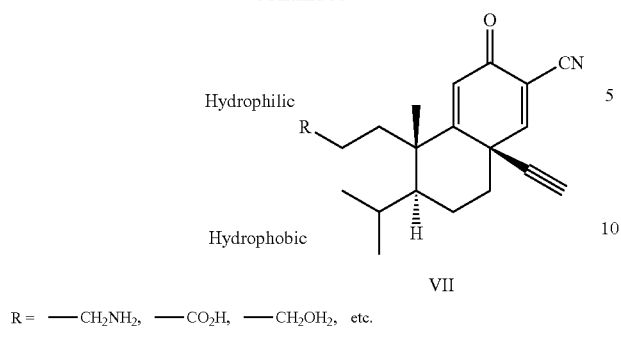

VII

R = —CH₂NH₂, —CO₂H, —CH₂OH₂, etc.

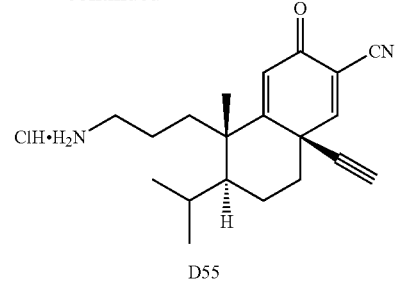

D55
(VII: R = CH₂NH₂)

(a) NaN₃, AcOH, H₂SO₄; (b) H₂,Pd—C; (c) Boc₂O; (d) CrO₃, pyr., CH₂Cl₂; (e) Ph₃PCH₂Cl(Cl), n-BuLi, THF; (f) MeLi, THF; TMSCl; (g) CrO₃, t-BuOOH, CH₂Cl₂; (h) p-TsCN, LDA, THF; (i) DDQ, PhH; (j) aq. HCl, MeOH.

Compound D55 (VII: R=—CH₂NH₂) would be synthesized from a known compound D56 (Honda et al., 2005, which is incorporated herein by reference) by the sequence shown in Scheme 19. Schmidt reaction on D56 would give D57 along with the lactam (Finlay et al., 1997, which is incorporated herein by reference). Hydrogenolysis of D57, followed by protection with Boc₂O, would produce D58. Compound D59 would be prepared by oxidation of D58, followed by a Wittig reaction and subsequent trapping of acetylide with TMSCl. Chromium-mediated allylic oxidation of D59 would produce D60. The desired compound D55 would be obtained by cyanation of D60, followed by DDQ oxidation and subsequent removal of Boc and TMS groups under acidic conditions.

Scheme 19

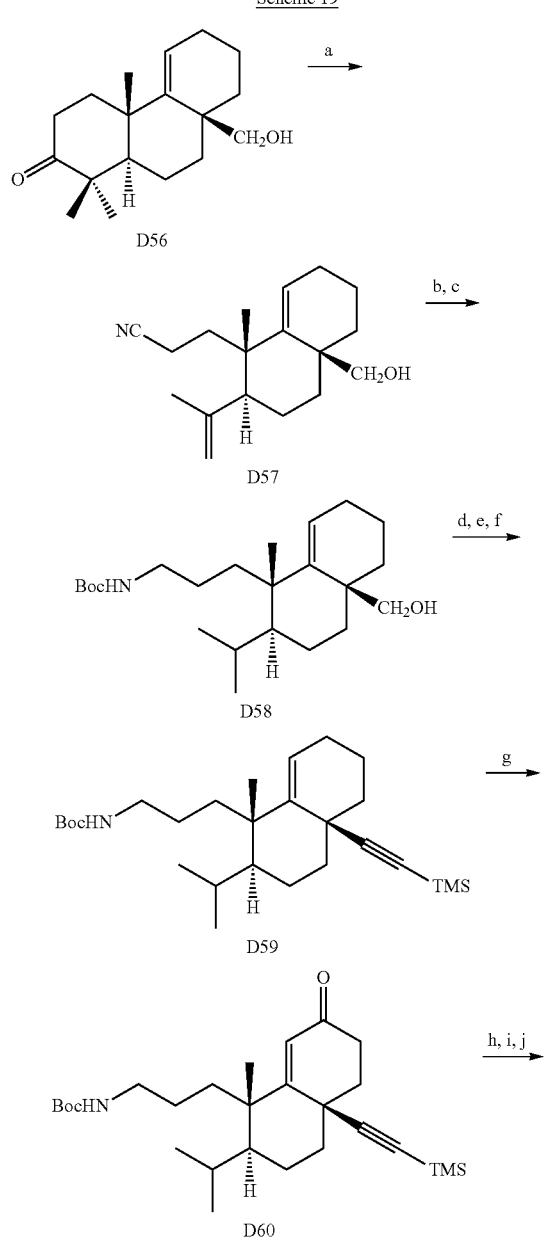

Scheme 20

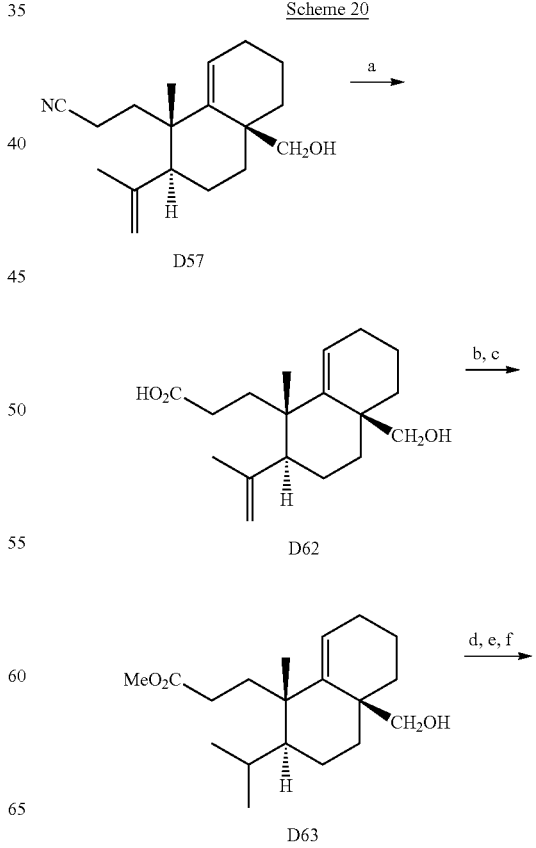

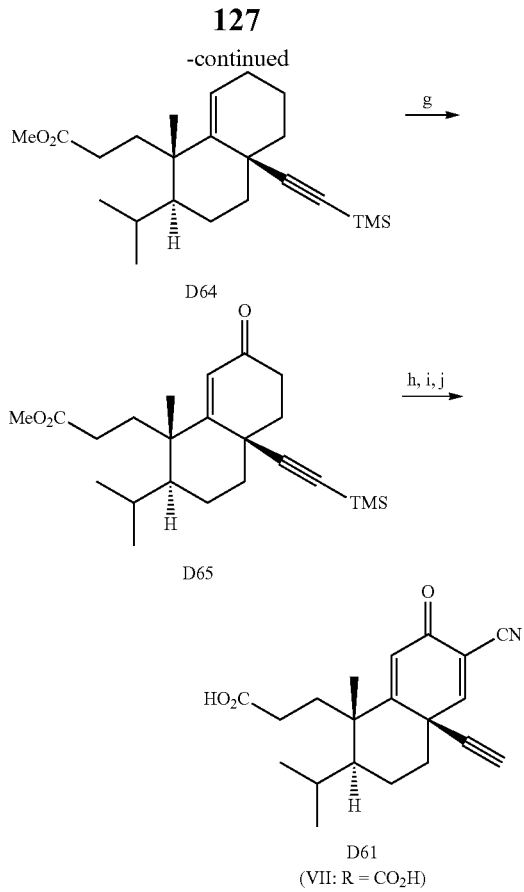

D64

D65

D61
(VII: R = CO₂H)

(a) H⁺, H₂O; (b) H₂, Pd—C; (c) CH₂N₂; (d) CrO₃, pyr., CH₂Cl₂; (e) Ph₃PCH₂Cl(Cl), n-BuLi, THF; (f) MeLi, THF; TMSCl; (g) CrO₃, t-BuOOH, CH₂Cl₂; (h) p-TsCN, LDA, THF; (i) DDQ, PhH; (j) aq. NaOH, MeOH.

Similarly, compound D61 (VII: R=—CO₂H) would be synthesized from D57 by the sequence shown in Scheme 20. Hydrolysis of nitrile of D57 under acidic conditions would give acid D62. Hydrogenolysis of D62, followed by methylation, would yield methyl ester D63. Compound D65 would be prepared via D64 from D63 by the same sequence as for D60. The desired compound D61 would be obtained by cyanation of D65, followed by DDQ oxidation and subsequent removal of methyl and TMS groups under basic conditions.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

U.S. Pat. No. 5,443,826
U.S. Pat. No. 5,599,795
U.S. Pat. No. 6,025,395
U.S. patent Appln. Ser. No. 12/352,473
U.S. Patent Publn. 2009/0060873
Abraham and Kappas, *Free Radical Biol. Med.*, 39:1-25, 2005.
Ahmad et al., *Cancer Res.*, 68:2920-2926, 2008.
Ahmad et al., *J. Biol. Chem.*, 281:35764-35769, 2006.
Akiyama et al., *Alzheimer Dis. Assoc. Disord.*, 14(1):547-53, 2000.
Angulo et al., *Eur. J. Immunol.*, 30:1263-1271, 2000.
Araujo et al., *J. Immunol.*, 171(3):1572-1580, 2003.
Arend and Dayer, *Arthritis Rheum.*, 38:151-160, 1995.
Arend et al., *Annu. Rev. Immunol.*, 16:27-55, 1998.
Autenrieth et al., *Infect. Immun.*, 62:2590-2599, 1994.
Bach, *Hum. Immunol.*, 67(6):430-432, 2006.
Bagasra et al., *Proc. Natl. Acad. Sci. USA*, 92(26):12041-12045, 1995.
Ball, *Ann. Rheum. Dis.*, 30:213-223, 1971.
Beal, *Curr. Opin. Neurobiol.*, 6:661-666, 1996.
Berendsen et al., *Comp. Phys. Comm.*, 95: 43-56, 1995
Blumberg et al., *Arthritis Rheum.*, 7:93-97, 1964.
Botoman et al., *Am. Fam. Physician*, 57(1):57-68, 1998.
Brandt et al., *Arthritis Rheum.*, 43:1346-1352, 2000.
Braun et al., *Arthritis Rheum.*, 42:2039-2044, 1999.
Brewerton et al., *Lancet.*, 1:904-907, 1973a.
Brewerton et al., *Lancet.*, 1:956-957, 1973b.
Bronte et al., *Trends Immunol.*, 24:302-306, 2003.
Brown and DuBois, *Clin. Cancer Res.*, 10:4266s-4269s, 2005.
Brynskov et al., *N Engl. J. Med.*, 321(13):845-850, 1989.
Burger and Dayer, *Neurology*, 45(6S-6):S39-43, 1995.
Cai et al., *Nat. Med.*, 11(2):183-190, 2005.
Calin and Taurog, In: *The Spondylarthritides*, Calin et al. (Eds.), Oxford, UK. Oxford University Press, 179, 1998.
Cann et al., *Gut.*, 24(12):1135-1140, 1983.
Chauhan and Chauhan, *Pathophysiology*, 13(3):171-181 2006.
Chomarat et al., *Arthritis Rheum.*, 38:1046-1054, 1995.
Clarke et al., *Tetrahedron*, 60:3625-3636, 2004.
Corey et al., *Tetrahedron Lett.*, 1495-1499, 1973.
Couch et al., *Bioorg. Med. Chem. Lett.*, 15: 2215-2219, 2005.
Coyle and Puttfarcken, *Science*, 262(5134):689-695, 1993.
Crowell et al., *Mol. Cancer Ther.*, 2:815-823, 2003.
de Waal et al., *J. Exp. Med.*, 174:1209-1220, 1991.
Dickerson et al., *Prog Neuropsychopharmacol Biol. Psychiatry*, Mar. 6, 2007.
Dinarello, *Int. Rev. Immunol.*, 16:457-499, 1998.
Dinkova-Kostova et al. *Proc. Natl. Acad. Sci. USA*, 99(18): 11908-11913, 2002.
Dinkova-Kostova et al., *Proc. Natl. Acad. Sci. USA*, 102(12): 4584-4589, 2005.
Dionne et al., *Clin. Exp. Immunol.*, 112(3):435-442, 1998.
Doran et al., *J. Rheumatol.*, 30(2):316-320, 2003.
Drossman et al., *Dig. Dis. Sci.*, 38(9):1569-1580, 1993.
Drossman et al., *Gastroenterol.*, 112(6):2120-2137, 1997.
Dudhgaonkar et al., *Eur. J. Pain*, 10(7):573-9, 2006.
Eastgate et al., *Lancet*, 2:706-709, 1988.
Eikelenboom et al., *Glia*, 40(2):232-239, 2002.
Ettehadi et al., *Clin. Exp. Immunol.*, 96(1):146-151, 1994.
Everhart et al., *Gastroenterol.*, 100(4):998-1005, 1991.
Favaloro et al., *J. Med. Chem.*, 45:4801-4805, 2002.
Fearon and Locksley, *Science*, 272(5258):50-53, 1996.
Feldtkeller et al., *Rheumatol. Int.*, 23(2):61-66, 2003.
Firestein et al., *Arthritis Rheum.*, 37:644-652, 1994.
Forstermann, *Biol. Chem.*, 387:1521, 2006.

Fujikawa et al., *Ann. Rheum. Dis.*, 54:318-320, 1995.
Funakoshi et al., *Digestion*, 59(1):73-78, 1998.
Galley and Webster, *Br. J. Anaesth.*, 77:11-16, 1996.
Gehrmann et al., *Glia*, 15(2):141-151, 1995.
Genain and Nauser, *J. Mol. Med.*, 75:187-197, 1997.
Gladman et al., *Br. J. Rheumatol.*, 22:675-679, 1995.
Gladman et al., *J. Med.*, 62:127-141, 1987.
Gladman, *Rheum. Dis. Clin. North Am.*, 18:247-256, 1992.
Goodman et al., *Kidney Int.*, 72(8):945-953, 2007.
Graeber et al., *Glia*, 40(2):252-259, 2002.
Greten et al., *Cell*, 118:285-296, 2004.
Griffin et al., *Proc. Natl. Acad. Sci. USA*, 86(19):7611-7615, 1989.
Guilherme et al., *Nat. Rev. Mol. Cell Biol.*, 9(5):367-77, 2008.
Gwee et al., *Gut.*, 44(3):400-406., 1999.
Hahn and Tsao, In: *Dubois' Lupus Erythematosus*, 4th Ed, Wallace and Hahn (Eds.), Lea and Febiger, Philadelphia, 195-201, 1993.
*Handbook of Pharmaceutical Salts: Properties, and Use* (Stahl and Wermuth Eds., Verlag Helvetica Chimica Acta, 2002.
Hannum et al., *Nature*, 343:336-340, 1990.
Hanson et al., *BMC Medical Genetics*, 6(7), 2005.
Hansson and Anton, *Annu. Rev. Entomol.*, 45, 203-231, 2006.
Harrison et al., *J. Rheumatol.*, 25(12):2324-2330, 1998.
Hart et al., *Immunology*, 84:536-542, 1995.
Honda et al. *Bioorg. Med. Chem. Lett.*, 12:1027-1030, 2002.
Honda et al., *Bioorg Med Chem Lett.*, 16(24):6306-6309, 2006.
Honda et al., *Bioorg. Med. Chem. Lett.*, 7:1623-1628, 1997.
Honda et al., *Bioorg. Med. Chem. Lett.*, 8(19):2711-2714, 1998.
Honda et al., *Bioorg. Med. Chem. Lett.*, 9(24):3429-3434, 1999.
Honda et al., *J. Med. Chem.*, 43:4233-4246, 2000a.
Honda et al., *J. Med. Chem.*, 50:1731-1734, 2007.
Honda et al., *Org. Biomol. Chem.*, 1:4384-4391, 2003.
Honda, et al., *J. Med. Chem.*, 43:1866-1877, 2000b.
Horwitz and Fisher, *N. Engl. J. Med.*, 344(24):1846-1850, 2001.
Hotamisligil, *Nature*, 444(7121):860-7, 2006.
Hsiao et al., *J. Org. Chem.*, 53:2688-2699, 1988.
Ishikawa et al., *Circulation*, 104(15):1831-1836, 2001.
Ishizawa and Dickson, *J. Neuropathol. Exp. Neurol.*, 60(6): 647-657, 2001.
Jailwala et al., *Ann. Intern. Med.*, 133(2):136-147, 2000.
Jarvis, *Curr. Opin. Rheumatol.*, 10(5):459-467, 1998.
Jarvis, *Pediatr. Ann.*, 31(7):437-446, 2002.
Jones et al., *Br. J. Rheumatol.*, 33:834-839, 1994.
Jonsson et al., *Br. J. Rheumatol.*, 32(7):578-581 1993.
Jonsson et al., *Oral Dis.*, 8(3):130-140, 2002.
Jonsson et al., *Trends Immunol.*, 22(12):653-654, 2001.
Kahle et al., *Ann. Rheum. Dis.*, 51:731-734, 1992.
Kaltschmidt et al. *Proc. Natl. Acad. Sci. USA*, 94:2642-2647, 1997.
Karin et al., *Nature Reviews, Drug Discovery.* 3: 17-26, 2004.
Kawakami et al., *Brain Dev.*, 28(4):243-246, 2006.
Kellow and Phillips, *Gastroenterol.*, 92(6):1885-1893, 1987.
Kendall-Tackett, *Trauma Violence Abuse*, 8(2):117-126, 2007.
Khan, *Clin. Exp. Rheumatol.*, 20(6):6-10, 1998.
Khan, In: *Ankylosing spondylitis and related spondyloarthropathies*, Spine, State of the Art Reviews, 1990.
Kortylewski et al., *Cancer Metastasis Rev.*, 24:315-327, 2005.
Kotake et al., *Infect. Immun.*, 67:2682-2686, 1999.
Kotzin and O'Dell, In: *Samler's Immunologic Diseases*, 5th Ed., Frank et al. (Eds.), Little Brown & Co., Boston, 667-697, 1995.
Kotzin, *Cell*, 85:303-306, 1996.
Kruger et al., *J. Pharmacol. Exp. Ther.*, 319(3):1144-1152, 2006.
Kuboyama, *Kurume Med. J.*, 45(1):33-37, 1998.
Lahesmaa et al., *J. Immunol.*, 148:3079-3085, 1992.
Laskowski et al., *J. Biomolecular NMR* 8:477-486, 1996.
Lee et al., *Glia*, 55(7):712-22, 2007.
Lencz et al., *Mol. Psychiatry*, 12(6):572-80, 2007.
Liby et al., *Cancer Res.*, 65:4789-4798, 2005.
Liby et al., *Cancer Res.*, 68:6727-6733, 2008.
Liby et al., *Mol. Cancer Ther.*, 6(7), 2007b.
Liby et al., *Nat. Rev. Cancer*, 7(5):357-69, 2007a.
Lipsky, In: *Harrison's principles of internal medicine*, Fauci et al. (Eds.), 14th Ed., NY, McGraw-Hill, 1880-1888, 1998.
Liu et al., *FASEB J.*, 20(2):207-216, 2006.
Liu et al., *Synlett*, 1119-1122, 2000.
Lo et al., *Curr. Dir. Autoimmun.*, 1:226-246, 1999.
Lugering et al., *Ital. J. Gastroenterol. Hepatol.*, 30(3):338-344, 1998.
Lynn and Friedman, *N. Engl. J. Med.*, 329(26):1940-1945, 1993.
Macatonia et al., *J. Immunol.*, 150:3755-3765, 1993.
*March's Advanced Organic Chemistry: Reactions, Mechanisms, and Structure*, 2007.
Marsal et al., *Rheumatology*, 38:332-337, 1999.
Mazur et al., *Cell Microbiol.*, 9(7):1683-94, 2007.
Mazzoni et al., *J. Immunol.*, 168:689-695, 2002.
McAlindon et al., *Gut*, 42(2):214-219, 1998.
McGeer and McGeer, *Brain Res. Brain Res. Rev.*, 21(2):195-218, 1995.
McGeer et al., *Neurology*, 19:331-338, 1996.
McGonagle et al., *Arthritis Rheum.*, 41:694-700, 1998.
McGonagle et al., *Curr. Opin. Rheumatol.*, 11:244-250, 1999.
McIver et al., *Pain*, 120(1-2):161-9, 2005.
Mease et al., *Lancet*, 356:385-390, 2000.
Mella et al., *Tetrahedron*, 44:1673-1678, 1988.
Merrill and Benvenist, *Trends Neurosci.*, 19:331-338, 1996.
Mertz et al., *Gastroenterol.*, 118(5):842-848, 2000.
Moll and Wright, *Ann. Rheum. Dis.*, 32:181-201, 1973.
Morris et al., *J. Mol. Med.*, 80(2):96-104, 2002.
Morse and Choi, *Am. J. Respir. Crit. Care Med.*, 172(6):660-670, 2005.
Morse and Choi, *Am. J. Respir. Crit. Care Med.*, 27(1):8-16, 2002.
Müller et al., *Synlett*, 521-522, 1996.
Muzart, *Tetrahedron Lett.*, 28:4665-4668, 1987.
Nath et al., *Neurology*, 66(1):149-150, 2006.
Neal et al., *BMJ.*, 314(7083):779-782, 1997.
Nichols, *Drug News Perspect.*, 17(2):99-104, 2004.
Nielen et al., *Arthritis Rheum.*, 50(2):380-386, 2004.
Ohnishi et al., *Int. Immunol.*, 6:817-830, 1994.
Ohno et al., *J. Med. Chem.*, 48:5279-5294, 2005.
Pall, *Med. Hypoth.*, 69:821-825, 2007.
Paquette et al., *Tetrahedron*, 45:107-124, 1989.
Partsch et al., *Br. I Rheumatol.*, 24:518-523, 1997.
Paul et al., *Inorg. Chem.*, 41:3699-3704, 2002.
Phansavath et al., *Synthesis*, 436-443, 1998.
Pica et al., *Antimicrob A,gents Chemother.*, 44(1):200-204, 2000.
Pietruszka et al., *Synthesis*, 4266-4268, 2006.
Pimentel et al., *Am. J. Gastroenterol.*, 95(12):3503-3506, 2000.
Place et al., *Clin. Cancer. Res.*, 9:2798-2806, 2003.
Prieur et al., *Lancet.*, 2:1240-1242, 1987.

Rajakariar et al., *Proc. Natl. Acad. Sci. USA*, 104(52):20979-84, 2007.
Rantapaa-Dahlqvist et al., *Arthritis Rheum.*, 48(10):2741-2749, 2003.
Reimund et al., *Eur. I Clin. Invest.*, 28(2):145-150, 1998.
Ribbens et al., *Eur. Cytokine Netw.*, 11:669-676, 2000.
Rockendorf et al., *Aust. I Chem.*, 55:87-93., 2002.
Rogers et al., *Neurobiol Aging*, 9(4):339-349, 1988.
Rogler and Andus, *World J. Surg.*, 22(4):382-389, 1998.
Rooney et al., *Rheumatol. Int.*, 10:217-219, 1990.
Ross et al., *Am. I Clin. Pathol.*, 120(Suppl):S53-71, 2003.
Ross et al., *Expert Rev. Mol. Diagn.*, 3(5):573-585, 2003.
Rostom et al., *Ann. Intern. Med.*, 146, 376-389, 2007.
Rothstein, *Med. Clin. North Am.*, 84(5):1247-1257, 2000.
Ruster et al., *Scand. J. Rheumatol.*, 34(6):460-3, 2005.
Sacerdoti et al., *Curr Neurovasc Res.* 2(2):103-111, 2005.
Saiki et al., *Scand. I Gastroenterol.*, 33(6):616-622, 1998.
Salomonsson and Jonsson, *Arthritis Rheum.*, 48(11):3187-3201, 2003.
Salomonsson et al., *Scand. J. Immunol.*, 55(4):336-342, 2002.
Salvarani et al., *Curr. Opin. Rheumatol.* 1998; 10:299-305, 1998.
Salvemini et al., *J. Clin. Invest.*, 93(5):1940-1947, 1994.
Sandler, *Gastroenterol.*, 99(2):409-415, 1990.
Sarchielli et al., *Cephalalgia*, 26(9):1071-1079, 2006.
Satoh et al., *Proc. Natl. Acad. Sci. USA*, 103(3):768-773, 2006.
Sauers et al., *J. Heterocyclic Chem.*, 40:655-658, 2003,
Schlaak et al., *Clin. Exp. Rheumatol.*, 14:155-162, 1996.
Schlaak et al., *Eur. I Immunol.*, 22:2771-2776, 1992.
Schlosstein et al., *NE I Medicine*, 288:704-706, 1973.
Schreiber, *Neth. J. Med.*, 53(6):S24-31, 1998.
Schulz et ah, *Antioxid. Redox. Sig.*, 10:115, 2008.
Shuman et al., *J. Med. Chem.*, 38:4446-4152, 1995.
Sieper and Braun, *Arthritis Rheum.*, 38:1547-1554, 1995.
Simon et al., *Clin. Exp. Immunol.*, 94:122-126, 1993.
Simon et al., *Proc. Natl. Acad. Sci. USA*, 91:8562-85666, 1994.
Simonian and Coyle, *Annu. Rev. Pharmacol. Toxicol.*, 36:83-106, 1996.
Sinha et al., *Cancer Res.*, 67:4507-4513, 2007.
Smith et al., *J. Org. Chem.*, 32:2851-2856, 1967.
Sonogashira et al., *Tetrahedron Lett.*, 4467-4470, 1975
Stack et al., *Lancet*, 349(9051):521-524, 1997.
Stewart et al., *Neurology*, 48:626-632, 1997.
Strejan et al., *J. Neuroimmunol.*, 7:27, 1984.
Suh, et al., *Cancer. Res.*, 58:717-723, 1998.
Suh, et al., *Cancer. Res.*, 59:336-341, 1999.
Szabo et al., *Nature Rev. Drug Disc.*, 6:662-680, 2007.
Takahashi et al., *Cancer Res.*, 57:1233-1237, 1997.
Talley et al., *Gastroenterol.*, 109(6):1736-1741, 1995.
Tamir and Tannenbaum, *Biochim. Biophys. Acta.*, 1288:F31-F36, 1996.
Targan et al., *N. Engl. J. Med.*, 337(15):1029-1035, 1997.
Third Report of the National Cholesterol Education Program Expert Panel on Detection, Evaluation and Treatment of High Blood Cholesterol in Adults (Adult Treatment Panel III, or ATP III), National Institutes of Health, NIH Publication No. 01-3670, 2001.
Touzani et al., *J. Neuroimmunol.*, 100(1-2):203-215, 1999.
Tumlin et al., *Am. J. Cardiol.*, 98(6A):14K-20K, 2006.
van den Berg, *Semin. Arthritis Rheum.*, 30(5S-2):7-16, 2001.
van Dullemen et al., *Gastroenterol.*, 109(1):129-135, 1995.
van Hogezand and Verspaget, *Drugs*, 56(3):299-305, 1998.
Vazquez et al., *J. Virol.*, 79(7):4479-91, 2005.
Vodovotz et al., In; *Handbook of Experimental Immunology*, Volumes I-IV, 1996.
Vriend, *J. Mol. Graph.*, 8:52-56, 1990
Wardle, *Nephrol. Dial. Transplant.*, 16(9):1764-8, 2001.
Warrington et al., *Arthritis and Rheumatism*, 44:13-20, 2001.
Weyand and Goronzy, *Ann. NY Acad. Sci.*, 987:140-149, 2003.
Whitehead et al., *Gastroenterol.*, 98(5 Pt 1):1187-1192, 1990.
Williams et al., *Clin. Neurosci.*, 2(3-4):229-245, 1994.
Wordsworth, In: *Genes and Arthritis*, Brit. Medical Bulletin, 51:249-266, 1995.
Wright, *Ann. Rheum. Dis.*, 15:348-356, 1956.
Wright, *Clin. Orthop. Related Res.*, 143:8-14, 1979.
Xanthou et al., *Arthritis Rheum.*, 44(2):408-418, 2001.
Yin et al., *Arthritis Rheum.*, 40:1788-1797, 1997.
Yin et al., *Rheumatology*, 38:1058-1067, 1999.
Yoh et al., *Kidney Int.*, 60(4):1343-1353, 2001.
Yu et al., *Nat. Rev. Immunol.*, 7:41-51, 2007.
Zhou et al., *Am. J. Pathol.*, 166(1):27-37, 2005.
Zhou et al., *Cancer Sci.*, 98:882-889, 2007.
Zingarelli et al., *J. Immunol.*, 171(12):6827-6837, 2003.

The invention claimed is:

1. A pharmaceutical composition comprising a compound of the formula or a pharmaceutically acceptable salt or tautomer thereof:

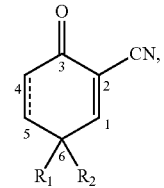

wherein:
$R_1$ is:
hydroxy, amino, cyano, or
alkyl$_{(C \leq 8)}$, alkenyl$_{(C \leq 18)}$, alkynyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, acyl$_{(C \leq 18)}$, alkoxy$_{(C \leq 18)}$, alkenyloxy$_{(C \leq 18)}$, alkynyloxy$_{(C \leq 18)}$, aryloxy$_{(C \leq 18)}$, aralkoxy$_{(C \leq 18)}$, heteroaryloxy$_{(C \leq 18)}$, heteroaralkoxy$_{(C \leq 18)}$, acyloxy$_{(C \leq 18)}$, alkyl-amino$_{(C \leq 18)}$, dialkyl amino$_{(C \leq 18)}$, alkoxyamino$_{(C \leq 18)}$, alkenylamino$_{(C \leq 18)}$, alkynylamino$_{(C \leq 18)}$, arylamino$_{(C \leq 18)}$, aralkylamino$_{(C \leq 18)}$, heteroarylamino$_{(C \leq 18)}$, heteroaralkylamino$_{(C \leq 18)}$, alkylsulphonyl-amino$_{(C \leq 18)}$, amido$_{(C \leq 18)}$, alkylideneamino$_{(C \leq 18)}$, aralkylidene-amino$_{(C \leq 18)}$, or a substituted version of any of these groups; and
$R_2$ is cyano, alkynyl$_{(C \leq 8)}$, substituted alkynyl$_{(C \leq 8)}$, or —C≡C—$R_9$,
wherein $R_9$ is:
hydrogen or cyano; or
alkyl$_{(C \leq 6)}$, aryl$_{(C \leq 6)}$, acyl$_{(C \leq 6)}$, alkylsilyl$_{(C \leq 6)}$ or a substituted version of any of these groups;
and a pharmaceutically acceptable carrier.

2. The pharmaceutical composition of claim 1, wherein the bond between atoms 4 and 5 is a double bond.

3. The pharmaceutical composition of claim 2, wherein $R_2$ is alkynyl$_{(C \leq 8)}$ or substituted alkynyl$_{(C \leq 8)}$.

4. The pharmaceutical composition of claim 2, wherein $R_2$ is —C≡C—$R_9$, wherein R₉ is:
  hydrogen or cyano; or
  alkyl$_{(C≤6)}$, aryl$_{(C≤6)}$, acyl$_{(C≤6)}$, alkylsilyl$_{(C≤6)}$ or a substituted version of any of these groups.

5. The pharmaceutical composition of claim 4, wherein R₉ is hydrogen.

6. The pharmaceutical composition of claim 4, wherein R₉ is —Si(CH₃)₂C(CH₃)₃.

7. The pharmaceutical composition of claim 1, wherein R₂ is cyano.

8. The pharmaceutical composition of claim 2, wherein R₁ is alkyl$_{(C≤8)}$ or substituted alkyl$_{(C≤8)}$.

9. The pharmaceutical composition of claim 8, wherein R₁ is methyl or ethyl.

10. The pharmaceutical composition of claim 2, wherein R₁ is aralkyl$_{(C≤18)}$, substituted aralkyl$_{(C≤18)}$, heteroaralkyl$_{(C≤18)}$ or substituted heteroaralkyl$_{(C≤18)}$.

11. The pharmaceutical composition of claim 2, wherein R₁ is cyano.

12. The pharmaceutical composition of claim 2, wherein the compound is further defined by the formula:

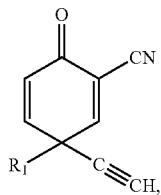

wherein R₁ is:
  cyano, or
  alkyl$_{(C≤18)}$, alkenyl$_{(C≤18)}$, alkynyl$_{(C≤18)}$, aryl$_{(C≤18)}$, aralkyl$_{(C≤18)}$, heteroaryl$_{(C≤18)}$, heteroaralkyl$_{(C≤18)}$, acyl$_{(C≤18)}$, alkoxy$_{(C≤18)}$, alkenyloxy$_{(C≤18)}$, alkynyloxy$_{(C≤18)}$, aryloxy$_{(C≤18)}$, aralkoxy$_{(C≤18)}$, heteroaryloxy$_{(C≤18)}$, heteroaralkoxy$_{(C≤18)}$, acyloxy$_{(C≤18)}$, alkylamino$_{(C≤18)}$, dialkylamino$_{(C≤18)}$, alkoxyamino$_{(C≤18)}$, alkenylamino$_{(C≤18)}$, alkynylamino$_{(C≤18)}$, arylamino$_{(C≤18)}$, aralkylamino$_{(C≤18)}$, heteroarylamino$_{(C≤18)}$, heteroaralkylamino$_{(C≤18)}$, alkyl-sulfonylamino$_{(C≤18)}$, amido$_{(C≤18)}$, alkylideneamino$_{(C≤18)}$, aralkylideneamino$_{(C≤18)}$, or a substituted version of any of these groups;
or a pharmaceutically acceptable salt or tautomer of the formula.

13. The pharmaceutical composition of claim 1, wherein the compound is selected from the group consisting of:

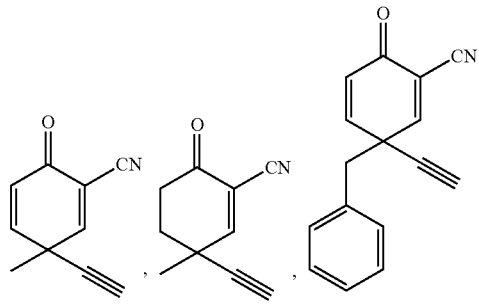

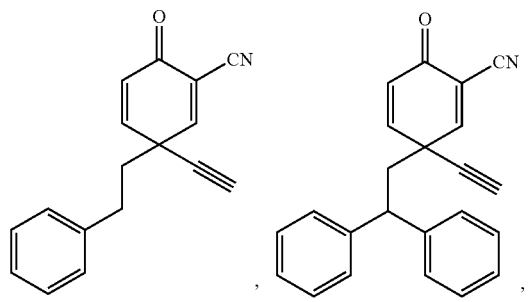

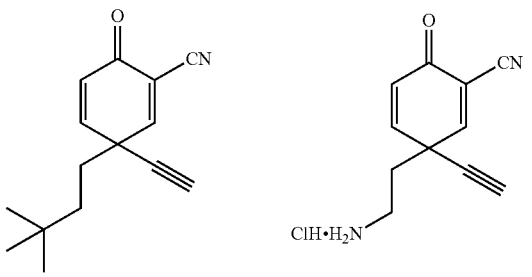

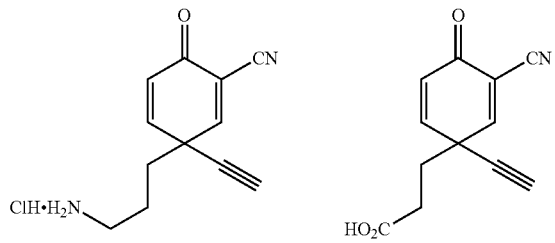

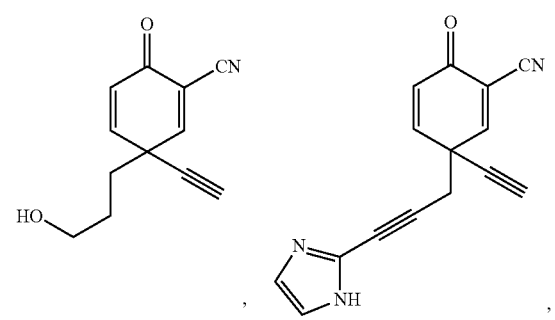

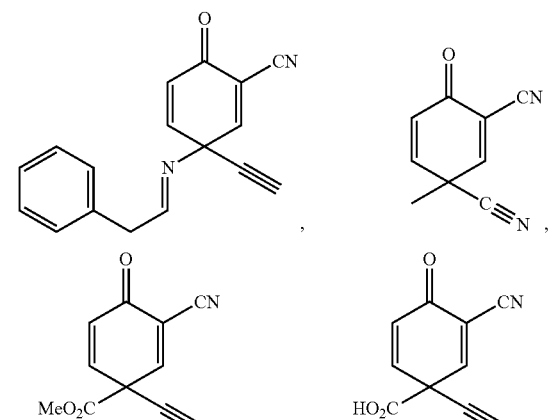

14. A pharmaceutical composition, comprising a compound of the formula:
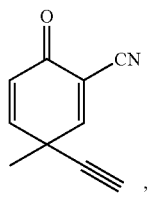
and a pharmaceutically acceptable carrier.
* * * * *

UNITED STATES PATENT AND TRADEMARK OFFICE
CERTIFICATE OF CORRECTION

Page 1 of 1

PATENT NO. : 9,000,188 B2
APPLICATION NO. : 13/645187
DATED : April 7, 2015
INVENTOR(S) : Tadashi Honda et al.

It is certified that error appears in the above-identified patent and that said Letters Patent is hereby corrected as shown below:

In the Claims

In claim 1, column 132, line 41, delete "alkyl$_{(C \leq 8)}$," and insert -- alkyl$_{(C \leq 18)}$, -- therefor.

Signed and Sealed this
Fourteenth Day of July, 2015

Michelle K. Lee
*Director of the United States Patent and Trademark Office*